US011472864B2

(12) United States Patent
Hayden-Ledbetter et al.

(10) Patent No.: US 11,472,864 B2
(45) Date of Patent: Oct. 18, 2022

(54) POLYNUCLEOTIDES ENCODING APOA1-PON1 FUSION POLYPEPTIDES

(71) Applicant: Theripion, Inc., Shoreline, WA (US)

(72) Inventors: Martha S. Hayden-Ledbetter, Shoreline, WA (US); Jeffrey A. Ledbetter, Shoreline, WA (US)

(73) Assignee: Theripion, Inc., Shoreline, WA (US)

( * ) Notice: Subject to any disclaimer, the term of this patent is extended or adjusted under 35 U.S.C. 154(b) by 0 days.

(21) Appl. No.: 17/542,181

(22) Filed: Dec. 3, 2021

(65) Prior Publication Data

US 2022/0089687 A1   Mar. 24, 2022

Related U.S. Application Data

(60) Division of application No. 15/909,314, filed on Mar. 1, 2018, which is a continuation-in-part of application No. PCT/US2016/050405, filed on Sep. 6, 2016.

(60) Provisional application No. 62/215,256, filed on Sep. 8, 2015.

(51) Int. Cl.
| C07K 14/775 | (2006.01) |
| C12N 9/18 | (2006.01) |
| C12N 9/22 | (2006.01) |
| C12N 15/62 | (2006.01) |
| A61K 38/00 | (2006.01) |

(52) U.S. Cl.
CPC ........... *C07K 14/775* (2013.01); *C12N 9/18* (2013.01); *C12N 9/22* (2013.01); *C12N 15/62* (2013.01); *C12Y 301/01002* (2013.01); *C12Y 301/01047* (2013.01); *C12Y 301/08001* (2013.01); *C07K 2319/30* (2013.01); *C12Y 301/27005* (2013.01)

(58) Field of Classification Search
CPC ................................................ C07K 16/18
See application file for complete search history.

(56) References Cited

U.S. PATENT DOCUMENTS

| 5,447,851 | A | 9/1995 | Beutler et al. | |
|---|---|---|---|---|
| 5,795,572 | A | 8/1998 | Diegel et al. | |
| 6,258,596 | B1 | 7/2001 | Benoit et al. | |
| 8,569,457 | B2 | 10/2013 | Raines et al. | |
| 8,937,157 | B2 | 1/2015 | Ledbetter et al. | |
| 9,416,188 | B2 | 8/2016 | Chaplin et al. | |
| 2003/0008373 | A1* | 1/2003 | Bartel ................. | C07K 14/775 435/7.1 |
| 2004/0115183 | A1 | 6/2004 | Rabinkov et al. | |
| 2005/0202532 | A1 | 9/2005 | Bielicki et al. | |
| 2006/0286632 | A1 | 12/2006 | Bielicki | |
| 2007/0111281 | A1 | 5/2007 | Sondermann et al. | |
| 2009/0042787 | A1* | 2/2009 | Metzner ............... | C07K 14/745 536/23.4 |
| 2009/0318346 | A1 | 12/2009 | Bacus et al. | |
| 2010/0098693 | A1* | 4/2010 | Pardridge ............... | A61P 25/28 530/387.3 |
| 2010/0105619 | A1* | 4/2010 | Bielicki ............... | C07K 14/775 530/324 |
| 2011/0178029 | A1 | 7/2011 | Knudsen et al. | |
| 2012/0121585 | A1 | 5/2012 | Huesser et al. | |
| 2014/0112914 | A1 | 4/2014 | Nezu et al. | |
| 2014/0120091 | A1 | 5/2014 | Ledbetter et al. | |
| 2014/0363428 | A1 | 12/2014 | Igawa et al. | |
| 2015/0353626 | A1 | 12/2015 | Lagerstedt et al. | |
| 2016/0009776 | A1* | 1/2016 | Linden .................. | C07K 14/49 424/134.1 |
| 2016/0108413 | A1 | 4/2016 | Meulewaeter et al. | |

(Continued)

FOREIGN PATENT DOCUMENTS

| WO | 2002038609 | A2 | 5/2002 |
| WO | 2005018572 | A2 | 3/2005 |
| WO | 2005047327 | A2 | 5/2005 |

(Continued)

OTHER PUBLICATIONS

White, C.R., et al., "Anti-infl ammatory and cholesterol-reducing properties of apolipoprotein mimetics: a review," J. Lipid. Res. 55:2007-2021, 2014; published, JLR Papers in Press, Aug. 25, 2014; DOI:10.1194/jlr.R051367.

Zamanian-Daryoush, M., "The Cardioprotective Protein Apolipoprotein A1 Promotes Potent Anti-tumorigenic Effects,"J. Biol. Chem., 288:21237-21252, Jul. 19, 2013; published, JBC Papers In Press, May 17, 2013; DOI:10.1074/jbc.M113.468967.

Aharoni, A., et al., "Directed evolution of mammalian paraoxonases PON1 and PON3 for bacterial expression and catalytic specialization," Proc. Natl. Acad. Sci. USA 101:482-487, Jan. 13, 2004, DOI:10.1073/pnas.2536901100.

(Continued)

*Primary Examiner* — Manjunath N Rao
*Assistant Examiner* — Samuel W Liu
(74) *Attorney, Agent, or Firm* — Sherbina Intellectual Property Law, PLLC; Nicholas V. Sherbina

(57) ABSTRACT

Compositions and methods relating to ApoA-1 fusion polypeptides are disclosed. The fusion polypeptides include a first polypeptide segment corresponding to an ApoA-1 polypeptide or ApoA-1 mimetic, and may also include a dimerizing domain such as, e.g., an Fc region, which is typically linked carboxyl-terminal to the first polypeptide segment via a flexible linker. In some embodiments, the fusion polypeptide further includes a second polypeptide segment located carboxyl-terminal to the first polypeptide segment and which confers a second biological activity (e.g., an RNase, paraoxonase, platelet-activating factor acetylhydrolase, cholesterol ester transfer protein, lecithin-cholesterol acyltransferase, polypeptide that specifically binds to proprotein convertase subtilisin/kexin type 9, or polypeptide that specifically binds to amyloid beta). Also disclosed are dimeric proteins comprising first and second ApoA-1 fusion polypeptides as disclosed herein. The fusion polypeptides and dimeric proteins are useful in methods for therapy.

16 Claims, 21 Drawing Sheets
Specification includes a Sequence Listing.

(56) References Cited

U.S. PATENT DOCUMENTS

2016/0251638 A1* 9/2016 Posada ........... C12Y 301/21001
424/94.6

FOREIGN PATENT DOCUMENTS

| WO | 2005063815 A2 | 7/2005 |
|---|---|---|
| WO | 2013127752 A1 | 9/2013 |

OTHER PUBLICATIONS

Bedoya, V.I., et al., "Ribonucleases in HIV Type 1 Inhibition: Effect of Recombinant RNases on Infection of Primary T Cells and Immune Activation-Induced RNase Gene and Protein Expression," AIDS Research and Human Retroviruses 22:897-907, 2006.

Berisha, S.Z., et al., "HDL from apoA1 transgenic mice expressing the 4WF isoform is resistant to oxidative loss of function," J. Lipid Res. 56:653-664, 2015; published, JLR Papers in Press, Jan. 5, 2015; DOI:10.1194/jlr.M056754.

Bernard, M.A., et al., "HIV-Derived ssRNA Binds to TLR8 to Induce Inflammation-Driven Macrophage Foam Cell Formation," PLoS ONE 9:e104039, Aug. 14, 2014, DOI:10.1371/journal.pone.0104039.

Brill, A., et al., "Extrahepatic HDL Receptor SR-BI and apoA-I Protect against Deep Vein Thrombosis in Mice," Arterioscler. Thromb. Vasc. Biol. Author manuscript; available in PMC Aug. 1, 2013; published in final edited form as Arterioscler. Thromb. Vasc. Biol. 32:1841-1847, Aug. 2012, DOI:10.1161/ATVBAHA.112.252130.

Ceron, J.J., et al., "Serum paraoxonase 1 (PON1) measurement: an update," BMC Vet. Res. 10:74, 2014, DOI:10.1186/1746-6148-10-74.

Charles-Schoeman, C., et al., "Cholesterol efflux by high density lipoproteins is impaired in patients with active rheumatoid arthritis," Ann. Rheum. Dis. Author manuscript; available in PMC Aug. 27, 2012; published in final edited form as Ann. Rheum. Dis. 71:1157-1162, Jul. 2012, DOI:10.1136/annrheumdis-2011-200493.

Chen, C., et al., "Role of Extracellular RNA and TLR3-Trif Signaling in Myocardial Ischemia-Reperfusion Injury," J. Am. Heart Assoc. 3:e000683, 2014, DOI:10.1161/JAHA.113.000683.

Chen, C., et al., "Protective Effect of RNase on Unilateral Nephrectomy-Induced Postoperative Cognitive Dysfunction in Aged Mice," PLoS ONE 10:e0134307, Jul. 30, 2015, DOI:10.1371/journal.pone.0134307.

Cho, K., and Kim, J., "A reconstituted HDL containing V156K or R173C apoA-I exhibited anti-inflammatory activity in apo-E deficient mice and showed enhanced resistance to myeloperoxidase-mediated oxidation," Exp. Mol. Med. 41:417-428, Jun. 2009, DOI:10.3858/emm.2009.41.6.047.

Dias, C.G., et al., "Quantification of the arylesterase activity of paraoxonase-1 in human blood," Anal. Methods 6:289-294, 2014, DOI:10.1039/c3ay41527a.

Drew, B.G., et al., "The emerging role of HDL in glucose metabolism," Nat. Rev. Endocrinol. 8:237-245, 2012; published online Jan. 24, 2012; DOI:10.1038/nrendo.2011.235.

Feng, Y., et al., "Cardiac RNA Induces Inflammatory Responses in Cardiomyocytes and Immune Cells via Toll-like Receptor 7 Signaling," J. Biol. Chem. 290:26688-26698, Oct. 30, 2015; published, JBC Papers in Press, Sep. 11, 2015; DOI:10.1074/jbc.M115.661835.

Goldsmith, M., et al., "Evolved Stereoselective Hydrolases for Broad-Spectrum G-Type Nerve Agent Detoxification," Chemistry & Biology 19:456-466, Apr. 20, 2012, DOI:10.1016/j.chembiol.2012.01.017.

Graverson, J.H., et al., "Trimerization of Apolipoprotein A-I Retards Plasma Clearance and Preserves Antiatherosclerotic Properties," J. Cardiovasc. Pharmacol. 51:170-177, Feb. 2008.

Gugliucci, A., et al., "Enzymatic assessment of paraoxonase 1 activity on HDL subclasses: A practical zymogram method to assess HDL function," Clin. Chim. Acta 415:162-168, 2013; available online Oct. 30, 2012; DOI:10.1016/j.cca.2012.10.044.

Hewing, B., et al., "Effects of native and myeloperoxidase-modified apolipoprotein A-I on reverse cholesterol transport and atherosclerosis in mice," Arterioscler. Thromb. Vasc. Biol. Author manuscript; available in PMC Apr. 1, 2015; published in final edited form as Arterioscler. Thromb. Vasc. Biol. 34:779-789, Apr. 2014; DOI:10.1161/ATVBAHA.113.303044.

Ito, A., et al., "Cholesterol Accumulation in CD11c+ Immune Cells Is a Causal and Targetable Factor in Autoimmune Disease," Immunity 45:1311-1326, Dec. 20, 2016, DOI:10.1016/j.immuni.2016.11.008.

Jafri, H., et al., "Baseline and On-Treatment High-Density Lipoprotein Cholesterol and the Risk of Cancer in Randomized Controlled Trials of Lipid-Altering Therapy," J. Am. Coll. Cardiol. 55:2846-2854, 2010, DOI:10.1016/j.jacc.2009.12.069.

Kirby, S.D., et al., "Human paraoxonase double mutants hydrolyze V and G class organophosphorus nerve agents," Chem. Biol. Interact 203:181-185, 2013; available online Nov. 15, 2012; DOI:10.1016/j.cbi.2012.10.023.

Lewis, T.L., et al., "Overexpression of Human Apolipoprotein A-I Preserves Cognitive Function and Attenuates Neuroinflammation and Cerebral Amyloid Angiopathy in a Mouse Model of Alzheimer Disease," J. Biol. Chem. 285:36958-36968, Nov. 19, 2010; published, JBC Papers in Press, Sep. 16, 2010; DOI:10.1074/jbc.M110.127829.

Medina-Echeverz, J., et al., "Harnessing High Density Lipoproteins to Block Transforming Growth Factor Beta and to Inhibit the Growth of Liver Tumor Metastases," PLoS ONE 9:e96799, May 5, 2014, DOI:10.1371/journal.pone.0096799.

Moreira, R.S., et al., "Apolipoprotein A-I mimetic peptide 4F attenuates kidney injury, heart injury, and endothelial dysfunction in sepsis," Am. J. Physiol. Regul. Integr. Comp. Physiol. 307:R514-R524, 2014; first published Jun. 11, 2014; DOI:10.1152/ajpregu.00445.2013.

Navab, M., et al., "Oral Administration of an Apo A-I Mimetic Peptide Synthesized From D-Amino Acids Dramatically Reduces Atherosclerosis in Mice Independent of Plasma Cholesterol," Circulation 105:290-292, 2002.

Ory, D.S., and Schaffer, J.E., "ApoA-1 in Diabetes: Damaged Goods," Diabetes 59:2358-2359, Oct. 2010, DOI:10.2337/db10-1040.

Otto, T.C., et al., "Dramatic Differences in Organophosphorus Hydrolase Activity between Human and Chimeric Recombinant Mammalian Paraoxonase-1 Enzymes," Biochemistry 48:10416-10422, 2009, DOI:10.1021/bi901161b.

Shao, B., et al., "Myeloperoxidase Impairs ABCA1-dependent Cholesterol Efflux through Methionine Oxidation and Site-specific Tyrosine Chlorination of Apolipoprotein A-I," J. Biol. Chem. 281:9001-9004, Apr. 7, 2006; published, JBC Papers in Press, Feb. 22, 2006; DOI:10.1074/jbc.C600011200.

Shao, B., et al., "Humans with Atherosclerosis have Impaired ABCA1 Cholesterol Efflux and Enhanced HDL Oxidation by Myeloperoxidase," Circ. Res. Author manuscript; available in PMC May 23, 2015; published in final edited form as Circ. Res. 114:1733-1742, May 23, 2014, DOI:10.1161/CIRCRESAHA.114.303454.

Skaggs, B.J., et al. "Dysfunctional, pro-inflammatory HDL directly upregulate monocyte PDGFRβ, chemotaxis and TNFα production," Clin. Immunol. Author manuscript; available in PMC Oct. 1, 2011; published in final edited form as Clin. Immunol. 137:147-156, Oct. 2010, DOI:10.1016/j.clim.2010.06.014.

Smith, C.K., et al., "Lupus high-density lipoprotein induces proinflammatory responses in macrophages by binding lectin-like oxidised low-density lipoprotein receptor 1 and failing to promote activating transcription factor 3 activity," Ann. Rheum. Dis. 0:1-10, 2016, DOI:10.1136/annrheumdis-2016-209683.

Stevens, R.C., et al., "Engineered recombinant human paraoxonase 1 (rHuPON1) purified from *Escherichia coli* protects against organophosphate poisoning," Proc. Natl. Acad. Sci. USA 105:12780-12784, Sep. 2, 2008, DOI:10.1073/pnas.0805865105.

Suzuki, M., et al., "HDL suppresses the type I interferon response, a family of potent antiviral immunoregulators, in macrophages challenged with lipopolysaccharide," Circulation. Author manu-

(56) References Cited

OTHER PUBLICATIONS script; available in PMC Nov. 9, 2011; published in final edited form as Circulation 122:1919-1927, Nov. 9, 2010, DOI:10.1161/CIRCULATIONAHA.110.961193.
Tardy, C., et al., "CER-001, a HDL-mimetic, stimulates the reverse lipid transport and atherosclerosis regression in high cholesterol diet-fed LDL-receptor deficient mice," Atherosclerosis 232:110-118, 2014; available online Nov. 8, 2013; DOI:10.1016/j.atherosclerosis.2013.10.018.
Yamashita, J., et al., Paraoxonase-1 Suppresses Experimental Colitis via the Inhibition of IFN-gamma Production from CD4 T Cells, J Immunol.191:949-960, 2013; prepublished Jun. 14, 2013; DOI:10.4049/jimmunol.1201828.
Xianglan, Y., et al., "5A, an Apolipoprotein A-I Mimetic Peptide, Attenuates the Induction of House Dust Mite-induced Asthma," J. Immunol. Author manuscript; available in PMC Jan. 1, 2012; published in final edited form as J. Immunol. 186:576-583, Jan. 1, 2011, DOI:10.4049/jimmunol.1001534.
Bojic, S., et al., "Low Paraoxonase 1 Activity Predicts Mortality in Surgical Patients with Sepsis," Disease Markers, vol. 2014, Article ID 427378, pp. 1-8, Feb. 9, 2014, DOI:10.1155/2014/427378.
Inal, V., et al., "Paraoxonase 1 Activity and Survival in Sepsis Patients," Balkan Med. J. 32:183-8, Apr. 2015, DOI:10.5152/balkanmedj.2015.15674.
Monigari, N., et al., "Study of Serum HDL Levels in Severe Sepsis Patients in Medical Intensive Care Unit," International Journal of Scientific and Research Publications, vol. 5, Issue 7, pp. 1-13, Jul. 2015.
Morin, E.E., et al., "HDL in sepsis—risk factor and therapeutic approach," Front. Pharmacol. 6:244, pp. 1-9, Oct. 23, 2015, DOI:10.3389/fphar.2015.00244.
Tanaka, S., et al., "Low HDL levels in sepsis versus trauma patients in intensive care unit," Ann. Intensive Care 7:60, 2017; published online Jun. 6, 2017; DOI:10.1186/s13613-017-0284-3.
Communication pursuant to Article 94(3) EPC dated May 30, 2018, issued in corresponding European Application No. 16770394.1, 5 pages.
Segrest, J.P., et al., "Structure and function of apolipoprotein A-I and high density lipoprotein," Curr. Opin. Lipidol. 11:105-115, 2000.
Lu, S., et al., "An apoA-I mimetic peptibody generates HDL-like particles and increases alpha-1 HDL subfraction in mice," J. Lipid Res. 53:643-652, 2012; published, JLR Papers in Press, Jan. 27, 2012, DOI:10.1194/jlr.M020438.
Rosenblat, M., et al., "Paraoxonase 1 (PON1) enhances HDL-mediated macrophage cholesterol efflux via the ABCA1 transporter in association with increased HDL binding to the cells: a possible role for lysophosphatidylcholine," Atherosclerosis 179:69-77, 2005.
Noelle, R.J., et al., "A 39-kDa protein on activated helper T cells binds CD40 and transduces the signal for cognate activation of B cells," Proc. Natl. Acad. Sci. USA 89:6550-6554, Jul. 1992.
Peach, R.J., et al., "Complementarity Determining Region 1 (CDR1)- and CDR3-analogous Regions in CTLA-4 and CD28 Determine the Binding to B7-1," J. Exp. Med. 180:2049-2058, Dec. 1994, DOI:10.1084/jem.180.6.2049.
Peach, R.J., et al., "Both Extracellular Immunoglobin-like Domains of CD80 Contain Residues Critical for Binding T Cell Surface Receptors CTLA-4 and CD28," J. Biol. Chem. 270:21181-21187, Sep. 8, 1995.
Peters, R.T., et al., "Prolonged activity of factor IX as a monomeric Fc fusion protein," Blood 115:2057-2064, 2010, DOI:10.1182/blood-2009-08-239665.
Pollock, K.E., et al., "Inducible T Cell Antigen 4-1 BB," J. Immunol. 150:771-781, Feb. 1, 1993.
Salas, J., et al., "Enhanced Pharmacokinetics of Factor VIIa as a Monomeric Fc Fusion," Thromb. Res. 135:970-976, 2015; available online Jan. 3, 2015.
Sgroi, D., et al., "Regulation of CD45 engagement by the B-cell receptor CD22," Proc. Natl. Acad. Sci. USA 92:4026-4030, Apr. 1995.
Traunecker, A., et al., "Highly efficient neutralization of HIV with recombinant CD4-immunoglobulin molecules," Nature 339:68-70, May 4, 1989.
Wang, S., et al., "Costimulation of T cells by B7-H2, a B7-like molecule that binds ICOS," Blood 96:2808-2813, Oct. 15, 2000.
Zhang, N., et al., "Targeted and Untargeted CD137L Fusion Proteins for the Immunotherapy of Experimental Solid Tumors," Clin. Cancer Res. 13:2758-2767, May 1, 2007.
Dwyer, M.A., et al., "Expression and Characterization of a DNase I-Fc Fusion Enzyme," J. Biol. Chem. 274:9738-9743, Apr. 2, 1999.
Bagley, R.G., et al., "sFLT01: A Novel Fusion Protein with Antiangiogenic Activity," Mol. Cancer Ther. 10:404-415, Mar. 2011; published OnlineFirst Jan. 20, 2011; DOI:10.1158/1535-7163.MCT-10-0813.
De Beer, M.C., et al., "Apolipoprotein A-I conformation markedly influences HDL interaction with scavenger receptor BI," J. Lipid. Res. 42:309-313, 2001.
Jazayeri, J.A., et al., "Generation of mutant leukaemia inhibitory factor (LIF)—IgG heavy chain fusion proteins as bivalent antagonists of LIF," J. Immunol. Methods 323:1-10, 2007; available online Mar. 28, 2007; DOI:10.1016/j.jim.2007.02.011.
Jones, T.D., et al.,"The Development of a Modified Human IFN-a2b Linked to the Fc Portion of Human IgG1 as a Novel Potential Therapeutic for the Treatment of Hepatitis C Virus Infection," J. Interferon Cytokine Res. 24:560-572, 2004.
Lewis, V.A., et al., "Human Nerve Growth Factor Receptor and Cytosine Deaminase Fusion Genes," Hum. Gene Ther. 14:1009-1016, Jul. 1, 2003.
Mezo, A.R., et al., "Atrial Natriuretic Peptide-Fc, ANP-Fc, Fusion Proteins: Semisynthesis, In Vitro Activity and Pharmacokinetics in Rats," Bioconjugate Chem. 23:518-526, Jan. 22, 2012, DOI:10.1021/bc200592c.
Spahr, C., et al., "Recombinant human lecithin-cholesterol acyltransferase Fc fusion: Analysis of N- and O-linked glycans and identification and elimination of a xylose-based O-linked tetrasaccharide core in the linker region," Protein Sci. 22:1739-1753, 2013; published online Oct. 1, 2013: DOI:10.1002/pro.2373.
Hu, S., et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res. 56:3055-3061, Jul. 1, 1996.
Loffler, A., et al., "A recombinant bispecific single-chain antibody, CD19xCD3, induces rapid and high lymphoma-directed cytotoxicity by unstimulated T lymphocytes," Blood 95:2098-2013, Mar. 15, 2000.
Mack, M., et al., "A small bispecific antibody construct expressed as a functional single-chain molecule with high tumor cell cytotoxicity," Proc. Natl. Acad. Sci. USA 92:7021-7025, Jul. 1995.
Boado, R.J., et al., "IgG-Paraoxonase-1 Fusion Protein for Targeted Drug Delivery Across the Human Blood-Brain Barrier," Mol. Pharm. Author manuscript; available in PMC Nov. 9, 2009; published in final edited form as Mol. Pharm. 5:1037-1043, 2008.
Boado, R.J., et al., "CHO Cell Expression, Long-Term Stability, and Primate Pharmacokinetics and Brain Uptake of an IgG-Paraoxonase-1 Fusion Protein," Biotechnology and Bioengineering 108:186-196, Jan. 1, 2011; published online Aug. 27, 2010, DOI:10.1002/bit.22907.
Linderholm, A.L., and Chamow, S.M., "Immunoglobulin Fc-Fusion Proteins Part 1: Their Design and Manufacture," BioProcess International 12:30-35, Oct. 2014.
PCT International Search Report & Written Opinion for PCT/US2016/050405, dated Jan. 13, 2017, 19 pages.
Hiatt, W.R., et al., "Atherosclerotic Peripheral Vascular Disease Symposium II, Nomenclature for Vascular Diseases," Circulation 118:2826-2829, 2008.
Kim, D.S., et al. "Pharmacogenetics of paraoxonase activity: elucidating the role of high-density lipoprotein in disease," Pharmacogenomics Author Manuscript; available in PMC Jul. 1, 2014; published in final edited form as Pharmacogenomics 14:1495-1515, Sep. 2013.
Koyama, M., et al., "Interaction between the N- and C-terminal Domain Modulates the Stability and Lipid Binding of Apolipoprotein A-I," Biochemistry 48:2529-2537, Feb. 24, 2009.

(56) References Cited

OTHER PUBLICATIONS

Lund-Katz, S., and Phillips, M.C., "High Density Lipoprotein Structure-Function and Role in Reverse Cholesterol Transport," Subcell Biochem. Author manuscript; available in PMC Nov. 14, 2011; published in final edited form as Subcell Biochem. 51:183-227, Feb. 2010.

Mineo, C., and Shaul, P.W., "Novel Biological Functions of High-Density Lipoprotein Cholesterol," Circulation Research 111:1079-1090, Sep. 28, 2012.

Ochoa, M.C., et al., "Liver Gene Transfer of Interleukin-15 Constructs That Become Part of Circulating High Density Lipoproteins for Immunotherapy," PLOS One 7:e52370, Dec. 21, 2012, DOI:10.1371/journal.pone.0052370.

Phillips, M.C., et al., "New insights into the determination of HDL structure by apolipoproteins," Journal of Lipid Research 54:2034-2048, 2013; published, JLR Papers in Press, Dec. 10, 2012.

Reimers, G.J., et al., "Inhibition of rupture of established atherosclerotic plaques by treatment with apolipoprotein A-I," Cardiovascular Research 91:37-44, Feb. 24, 2011, DOI:10.1093/cvr/cvr057.

Rocco, A.G., et al., "Structural features and dynamics properties of human apolipoprotein A-I in a model of synthetic HDL," Journal of Molecular Graphics and Modelling 28:305-312, Aug. 27, 2009, DOI:10.1016/j.jmgm.2009.08.008.

Sena, A., et al., "Plasma Lipoproteins in Brain Inflammatory and Neurodegenerative Diseases," Lipoproteins—Role in Health and Diseases, Prof. Gerhard Kostner (Ed.), InTech, 2012, DOI:10.5772/51268.

Sorenson, R.C., et al., "Human Serum Paraoxonase/Arylesterase's Retained Hydrophobic N-Terminal Leader Sequence Associates with HDLs by Binding Phospholipids—Apolipoprotein A-I Stabilizes Activity," Thromb. Vasc. Biol. 19:2214-2225, 1999.

Stevens, R.C., et al., "Engineered recombinants human paraoxonase 1 (rHuPON1) purified from *Escherichia coli* protects against organophosphate poisoning," Proc Natl. Acad. Sci. USA 105:12780-12784, Sep. 2, 2008.

Safety Data Sheet, APOA1 (APOAI), Human Prot, Recomb (hIgG1-Fc Tag), Life Technologies, Dec. 4, 2012.

Bielicki, J.K., "ABCA1 Agonist Peptides for the Treatment of Disease," Curr. Opin. Lipidol. Author manuscript; available in PMC Feb. 1, 2017; published in final edited form as Curr. Opin. Lipidol. 27:40-46, Feb. 2016, DOI:10.1097/MOL.0000000000000258.

Crosby, N.M., et al., "Anti-CD20 single chain variable antibody fragment-apolipoprotein A-I chimera containing nanodisks promote targeted bioactive agent delivery to CD20-positive lymphomas," Biochem. Cell Biol. Author manuscript; available in PMC Aug. 1, 2015; published in final edited form as Biochem. Cell Biol. 93:343-350, Aug. 2017, DOI:10.1139/bcb-2015-0009.

Das, M., et al. "Structural Stability and Local Dynamics in Disease-Causing Mutants of Human Apolipoprotein A-I: What Makes the Protein Amyloidogenic?," J. Mol. Biol. 2015, DOI:10.1016/j.jmb.2015.10.029.

Eren, E., et al., "Functionally Defective High-Density Lipoprotein and Paraoxonase: A Couple for Endothelial Dysfunction in Atherosclerosis," Cholesterol 2013, Article ID 792090, DOI:10.1155/2013/792090.

Fioravanti, J., et al., "The Fusion Protein of IFN-α and Apolipoprotein A-I Crosses the Blood-Brain Barrier by a Saturable Transport Mechanism," J. Immunol. 188:3988-3992, 2012, prepublished online Mar. 14, 2012, DOI:10.4049/jimmunol.1101598.

Fisher, S., et al., "Extracellular RNA promotes leukocyte recruitment in the vascular system by mobilising proinflammatory cytokines," Thromb. Haemost. 108:730-741, 2012, DOI:10.1160/TH12-03-0186.

Jun, M., et al., "Effects of fibrates on cardiovascular outcomes: a systematic review and meta-analysis," Lancet 375:1875-1884, May 29, 2010, DOI:10.1016/S0140-6736(10)60656-3.

Keeney, J.T.R., et al., "Apolipoprotein A-I: Insights from redox proteomics for its role in neurodegeneration," Proteomics Clin. Appl. 7:109-122, 2013, DOI:10.1002/prca.201200087.

Kempen, H.J., et al., "Effect of repeated apoA-IMilano/POPC infusion on lipids, (apo)lipoproteins, and serum cholesterol effl ux capacity in cynomolgus monkeys," J. Lipid Res. 54:2341-2353, 2013, DOI:10.1194/jlr.M033779.

Kim, M.J., et al., "Transduced PEP-1-PON1 proteins regulate microglial activation and dopaminergic neuronal death in a Parkinson's disease model," Biomaterials 64:45-56, 2015, available online Jun. 14, 2015.

Kingwell, B.A., and Chapman, M.J., "Future of High-Density Lipoprotein Infusion Therapies—Potential for Clinical Management of Vascular Disease," Circulation 128:1112-1121, 2013, DOI:10.1161/CIRCULATIONAHA.113.002683.

Kingwell, B.A., et al., "HDL-targeted therapies: progress, failures and future," Nat. Rev. Drug Discov. 13:445-464, Jun. 2014, DOI:10.1038/nrd4279.

Koldamova, R.P., et al., "Apolipoprotein A-I Directly Interacts with Amyloid Precursor Protein and Inhibits Aβ Aggregation and Toxicity," Biochemistry 40:3553-3560, 2001, published on Web Feb. 27, 2001, DOI:10.1021/bi002186k.

Koren-Gluzer, M., et al., "The antioxidant HDL-associated paraoxonase-1 (PON1) attenuates diabetes development and stimulates β-cell insulin release," Atherosclerosis 219:510-518, 2011, available online Aug. 4, 2011, DOI:10.1016/j.atherosclerosis.2011.07.119.

Koutsis, G., et al., "An APOA1 promoter polymorphism is associated with cognitive performance in patients with multiple sclerosis," Multiple Sclerosis 15:174-179, 2009, DOI:10.1177/1352458508097217.

Lehmann, S.M., et al., "Extracellularly Delivered Single-Stranded Viral RNA Causes Neurodegeneration Dependent on TLR7," J. Immunol. 189:1448-1458, 2012, prepublished online Jun. 27, 2012, DOI:10.4049/jimmunol.1201078.

Mackness, B., et al., "Human Paraoxonase-1 Overexpression Inhibits Atherosclerosis in a Mouse Model of Metabolic Syndrome," Arterioscler. Thromb. Vasc. Biol. 26:1545-1550, 2006, DOI:10.1161/01.ATV.0000222924.62641.aa.

Mackness, M., and Mackness, B., "Human paraoxonase-1 (PON1): Gene structure and expression, promiscuous activities and multiple physiological roles," Gene 567:12-21, 2015, available online May 9, 2015, DOI:10.1016/j.gene.2015.04.088.

Menini, T., and Gugliucci, A., "Paraoxonase 1 in neurological disorders," Redox Report, 19:49-58, 2014, DOI:10.1179/1351000213Y.0000000071.

Meyers, L., et al., "A role for Apolipoprotein A-I in the pathogenesis of multiple sclerosis," J. Neuroimmunol. 277:176-185, 2014, DOI:10.1016/j.neuraim.2014.10.010.

Mizuguchi, C., et al., "Amyloidogenic Mutation Promotes Fibril Formation of the N-terminal Apolipoprotein A-I on Lipid Membranes," J. Biol. Chem. 290:20947-20959, Aug. 21, 2015.

Nanjee, M.N., et al., "Effects of Intravenous Infusion of Lipid-Free Apo A-I in Humans," Arterioscler. Thromb. Vasc. Biol. 16:1203-1214, Sep. 1996, DOI:10.1161/01.ATV.16.9.1203.

Newton, D.L., et al., "Potent and specific antitumor effects of an anti-CD22-targeted cytotoxic ribonuclease: potential for the treatment of non-Hodgkin lymphoma," Blood 97:528-535, Jan. 15, 2001, DOI:10.1182/blood.V97.2.528.

Nissen, S.E., et al., Effect of Recombinant ApoA-I Milano on Coronary Atherosclerosis in Patients with Acute Coronary Syndromes—A Randomized Controlled Trial, JAMA 290:2292-2300, Nov. 5, 2003.

Obici, L., et al., "Structure, function and amyloidogenic propensity of apolipoprotein A-I," Amyloid 13:191-205, Dec. 2006, DOI:10.1080/13506120600960288.

Paula-Lima, A.C., et al., "Human apolipoprotein A-I binds amyloid-β and prevents Aβ-induced neurotoxicity," Int. J. Biochem. Cell Biol. 41:1361-1370, 2009, available online Dec. 14, 2008, DOI:10.1016/j.biocel.2008.12.003.

Peng, W., et al., "Comparative evaluation of the protective potentials of human paraoxonase 1 and 3 against CCl4-induced liver injury," Toxicol. Lett. 193:159-166, 2010, available online Jan. 15, 2010, DOI:10.1016/j.toxlet.2010.01.003.

(56) References Cited

OTHER PUBLICATIONS

Prieto, E.D., et al., "Characterization of a Human Apolipoprotein A-I Construct Expressed in a Bacterial System," Protein J. 31:681-688, 2012, published online Sep. 18, 2012, DOI:10.1007/s10930-012-9448-z.
Reddy, S.T., et al., "Apolipoprotein A-I mimetics," Curr. Opin. Lipidol. 25:304-308, Aug. 2014, DOI:10.1097/MOL.0000000000000092.
Regenass-Lechner, F., et al., "Immunogenicity, Inflammation, and Lipid Accumulation in Cynomolgus Monkeys Infused with a Lipidated Tetranectin-ApoA-I Fusion Protein," Toxicol. Sci. 150:378-389, 2016; Advance Access Publication Date: Jan. 18, 2016; DOI:10.1093/toxsci/kfw004.
Rosenblat, M., et al., "Injection of paraoxonase 1 (PON1) to mice stimulates their HDL and macrophage antiatherogenicity," Biofactors 37:462-467, 2011, published online Dec. 8, 2011, DOI:10.1002/biof.188.
Ryan, R., et al., "Optimized bacterial expression of human apolipoprotein A-I," Protein Expr. Purif. 27:98-103, 2003.
Simsekyilmaz, S., et al., "Role of Extracellular RNA in Atherosclerotic Plaque Formation in Mice," Circulation 129:598-606, 2014, DOI:10.1161/CIRCULATIONAHA.113.002562.
Su, F., et al., "Apolipoprotein A-I (apoA-I) and apoA-I mimetic peptides inhibit tumor development in a mouse model of ovarian cancer," Proc. Natl. Acad. Sci. USA 107:19997-20002, Nov. 16, 2010.
Sun, X., et al., "Increased Ribonuclease Expression Reduces Inflammation and Prolongs Survival in TLR7 Transgenic Mice," J. Immunol. 190:2536-2543, 2013, prepublished online Feb. 4, 2013, DOI:10.4049/jimmunol.1202689.
Aicher, A., et al., "Characterization of Human Inducible Costimulator Ligand Expression and Function," J. Immunol. 164:4689-4696, 2000, DOI:10.4049/jimmunol.164.9.4689.
Arrigoni, C., et al., "The voltage-sensing domain of a phosphatase gates the pore of a potassium channel," J. Gen. Physiol. 141:389-395, 2013, DOI:10.1085/jgp.201210940.
Belsare, K.D., et al., "P-LinK: A method for generating multicomponent cytochrome P450 fusions with variable linker length," BioTechniques 57:13-20, Jul. 2014, DOI:10.2144/000114187.
Chen, X., "Fusion Protein Linkers: Property, Design and Functionality," Adv. Drug Deliv. Rev. Author manuscript; available in PMC Oct. 15, 2014; published in final edited form as Adv. Drug Deliv. Rev. 65:1357-1369, Oct. 15, 2013, DOI:10.1016/j.addr.2012.09.039.
Connelly, R.S., et al., "Mitogenic properties of a bispecific single-chain Fv-Ig fusion generated from CD2-specific mAb to distinct epitopes," Int. Immunol. 10:1863-1872, 1998.
Contarino, M., et al., "Chimeric Cyanovirin-MPER Recombinantly Engineered Proteins Cause Cell-Free Virolysis of HIV-1," Antimicrob. Agents Chemother. 57:4743-4750, Oct. 2013, published ahead of print Jul. 15, 2013, DOI:10.1128/AAC.00309-13.
Evers, T.H., et al., "Quantitative Understanding of the Energy Transfer between Fluorescent Proteins Connected via Flexible Peptide Linkers," Biochemistry 45:13183-13192, 2006, published on Web Oct. 12, 2006, DOI:10.1021/bi061288t.
Fan, G., et al., "Bispecific antibodies and their applications," J. Hematol. Oncol. 8:130, 2015, DOI:10.1186/s13045-015-0227-0.
Gilliland, L.K., et al., "Rapid and reliable cloning of antibody variable regions and generation of recombinant single chain antibody fragments," Tissue Antigens 47:1-20, 1996.
Guo, H., et al., "Effect of flexible linker length on the activity of fusion protein 4-coumaroyl-CoA ligase::stilbene synthase," Mol. BioSyst. 13:598-606, 2017, DOI:10.1039/c6mb00563b.
Hayden, M.S., et al., "Single-chain mono- and bispecific antibody derivatives with novel biological properties and antitumour activity from a COS cell transient expression system," Ther. Immunol. 1:3-15, 1994.
Hayden, M.S., et al., "Costimulation by CD28 sFv expressed on the tumor cell surface or as a soluble bispecific molecule targeted to the L6 carcinoma antigen," Tissue Antigens 48:242-254, 1996.

Hayden-Ledbetter, M.S., et al., "CD20-Directed Small Modular Immunopharmaceutical, TRU-015, Depletes Normal and Malignant B Cells," Clin. Cancer Res. 15:2739-2746, 2009.
Hellstrom, I., et al., "The HE4 (WFDC2) Protein Is a Biomarker for Ovarian Carcinoma," Cancer Res. 63:3695-3700, Jul. 1, 2003.
Hudson, P.J., and Kortt, A.A., "High avidity scFv multimers; diabodies and triabodies," J. Immunol. Methods 231:177-189, 1999.
Jung, A., et al., "Linker length and fusion site composition improve the optical signal of genetically encoded fluorescent voltage sensors," Neurophotonics 2:021012, Apr.-Jun. 2015, DOI:10.1117/1.NPh.2.2.021012.
Klement, M., et al., "Effect of linker flexibility and length on the functionality of a cytotoxic engineered antibody fragment," J. Biotechnol. 199:90-97, 2015, DOI:10.1016/j.jbiotec.2015.02.008.
Kong, Y., et al., "Linker engineering for fusion protein construction: Improvement and characterization of a GLP-1 fusion protein," Enzyme Microb. Technol. 82:105-109, 2016, DOI:10.1016/j.enzmictec.2015.09.001.
Law, C., et al., "Linker engineering for fusion protein construction: Improvement and characterization of a GLP-1 fusion protein," Int. Immunol. 14:389-400, Apr. 2002.
Linsley, P.S., et al., "CTLA-4 Is a Second Receptor for the B Cell Activation Antigen B7," J. Exp. Med. 174:561-569, Sep. 1991.
Linsley, P.S., et al., "Binding of the B Cell Activation Antigen B7 to CD28 Costimulates T Cell Proliferation and Interleukin 2 mRNA Accumulation," J. Exp. Med. 173:721-730, Mar. 1991.
Mack, E.T., "Dependence of Avidity on Linker Length for a Bivalent Ligand-Bivalent Receptor Model System," J. Am. Chem. Soc. Author manuscript; available in PMC Jan. 11, 2013; published in final edited form as J. Am. Chem. Soc. 134:333-345, Jan. 11, 2012, DOI:10.1021/ja2073033.
Robinson-Mosher, A., et al., "Designing Cell-Targeted Therapeutic Proteins Reveals the Interplay between Domain Connectivity and Cell Binding," Biophysical J. 107:2456-2466, Nov. 2014, DOI:10.1016/j.bpj.2014.10.007.
Scholler, N., et al., "Cutting Edge: CD83 Regulates the Development of Cellular Immunity," J. Immunol. 168:2599-2602, 2002.
Shan, D., et al., "Characterization of scFv-Ig Constructs Generated from the Anti-CD20 mAb 1F5 Using Linker Peptides of Varying Lengths," J. Immunol. 162:6589-6595, 1999.
Shastry, S., and Hancock, W.O., "Neck Linker Length Determines the Degree of Processivity in Kinesin-1 and Kinesin-2 Motors," Curr. Biol. Author manuscript; available in PMC May 25, 2011; published in final edited form as Curr. Biol. 20:939-943, May 25, 2010, DOI:110.1016/j.cub.2010.03.065.
Silacci, M., et al., "Linker Length Matters, Fynomer-Fc Fusion with an Optimized Linker Displaying Picomolar IL-17A Inhibition Potency," J. Biol. Chem. 289:14392-14398, May 16, 2014; published, JBC Papers in Press, Apr. 1, 2014, DOI:10.1074/jbc.M113.534578.
Wittenberg, G., et al., "Accelerated electron transport from photosystem I to redox partners by covalently linked ferredoxin," Phys. Chem. Chem. Phys. 15:19608-19614, 2013, DOI:10.1039/c3cp53264j.
Human ApoAI Protein (Fc Tag), Catalog No. 10686-H02H, Sino Biological, product information downloaded from manufacturer's website on Apr. 4, 2019.
Recombinant Human APOA1, Fc tagged, APOA1-33H Human, Creative BioMart, product information downloaded from manufacturer's website on Apr. 4, 2019.
Aruffo, A., et al., "CD44 Is the Principal Cell Surface Receptor for Hyaluronate," Cell 61:1303-1313, Jun. 29, 1990.
Bitonti, A.J., et al., "Pulmonary delivery of an erythropoietin Fc fusion protein in non-human primates through an immunoglobulin transport pathway," Proc. Natl. Acad. Sci. USA 101:9763-9768, Jun. 29, 2004, DOI:10.1073/pnas.0403235101.
Byrn, R.A., et al., "Biological properties of a CD4 immunoadhesin," Nature 344:667-670, Apr. 12, 1990.
Dapon, D.J., et al., "Designing CD4 immunoadhesins for AIDS therapy," Nature 337:525-531, Feb. 9, 1989.
Chalupny, N.J., et al., "T-cell activation molecule 4-1BB binds to extracellular matrix proteins," Proc. Natl. Acad. Sci. USA 89:10360-10364, Nov. 1992.
Chapoval, A.I., et al., "Immunoglobulin Fusion Proteins as a Tool for Evaluation of T-Cell Costimulatory Molecules," in Methods in

(56) References Cited

OTHER PUBLICATIONS

Molecular Medicine, vol. 45: Hepatocellular Carcinoma Methods and Protocols, 247-255 (N.A. Habib ed., 2000).

Chapoval, A.I., et al., "B7-H3:A costimulatory molecule for T cell activation and IFN-γ production," Nat. Immunol. 2:269-274, Mar. 2001.

Cox, G.N., et al., "Enhanced circulating half-life and hematopoietic properties of a human granulocyte colony-stimulating factor/immunoglobulin fusion protein," Exp. Hematol. 32:441-449, 2004, DOI:10.1016/j.exphem.2004.01.012.

Dong, H., et al., "B7-H1, a third member of the B7 family, co-stimulates T-cell proliferation and interleukin-10 secretion," Nat. Med. 5:1365-1369, Dec. 1999.

Godfrey, W.R., et al., "Identification of a Human OX-40 Ligand, a Costimulator of CD4+ T Cells with Homology to Tumor Necrosis Factor," J. Exp. Med. 180:757-762, Aug. 1994.

Hollenbaugh, D., et al., "The human T cell antigen gp39, a member of the TNF gene family, is a ligand for the CD40 receptor: expression of a soluble form of gp39 with B cell co-stimulatory activity," EMBO J. 11:4313-4321, 1992.

Hollenbaugh, D., et al., "Cleavable CD40Ig fusion proteins and the binding to sgp39," J. Immunol. Methods 188:1-7, 1995.

Hu, P., et al., "Construction and Preclinical Characterization of Fc-mGITRL for the Immunotherapy of Cancer," Clin. Cancer Res. 14:579-588, Jan. 15, 2008.

Kelm, S., et al., "Sialoadhesin, myelin-associated glycoprotein and CD22 define a new family of sialic acid-dependent adhesion molecules of the immunoglobulin superfamily," Curr. Biol. 4:965-972, 1994.

Kelm, S., et al., "The Ligand-binding Domain of CD22 Is Needed for Inhibition of the B Cell Receptor Signal, as Demonstrated by a Novel Human CD22-specific Inhibitor Compound," J. Exp. Med. 195:1207-1213, May 6, 2002, DOI:10.1084/jem.20011783.

Lane, P., et al., "Expression and functional properties of mouse B7/BB1 using a fusion protein between mouse CTLA4 and human γ1," Immunology 80:56-61, 1993.

Mahlangu, J., et al., "Phase 3 study of recombinant factor VIII Fc fusion protein in severe hemophilia A," Blood 123:317-325, Jan. 16, 2014.

Mancuso, M.E., and Mannucci, P.M., "Fc-fusion technology and recombinant FVIII and FIX in the management of the hemophilias," Drug Des. Dev. Ther. 8:365-371, Mar. 28, 2014, DOI:10.2147/DDDT.S47312.

Miller, G.T., et al., "Specific Interaction of Lymphocyte Function-associated Antigen 3 with CD2 Can Inhibit T Cell Responses," J Exp. Med 178:211-222, Jul. 1993, DOI:10.1084/jem.178.1.211.

Murphy, K.A., et al., "An In Vivo Immunotherapy Screen of Costimulatory Molecules Identifies Fc-OX40L as a Potent Reagent for the Treatment of Established Murine Gliomas," Clin. Cancer Res. 18:4657-4668, 2012; Published OnlineFirst Jul. 10, 2012; DOI:10.1158/1078-0432.CCR-12-0990.

Walberer, M., et al., "RNase therapy assessed by magnetic resonance imaging reduces cerebral edema and infarction size in acute stroke," Curr. Neurovasc. Res. 6:12-19, 2009, PMID 19355922, Abstract.

\* cited by examiner

POLYNUCLEOTIDES ENCODING APOA1-PON1 FUSION POLYPEPTIDES

CROSS-REFERENCE TO RELATED APPLICATIONS

This application is a divisional of U.S. application Ser. No. 15/909,314, filed Mar. 1, 2018, which is a continuation-in-part of International Application No. PCT/US2016/050405, filed Sep. 6, 2016, which claims the benefit of U.S. Provisional Application No. 62/215,256, filed Sep. 8, 2015. Each of the foregoing applications is incorporated by reference herein in its entirety.

REFERENCE TO SEQUENCE LISTING

The instant application contains a Sequence Listing which has been submitted in ASCII format via EFS-Web and is hereby incorporated by reference in its entirety. Said ASCII Copy, created on Nov. 26, 2021, is named "TRP_0130 US_20211126_Seq_Listing_ST25" and is 177,536 bytes in size.

BACKGROUND OF THE INVENTION

Apolipoprotein A-I (ApoA-1) and High Density Lipoprotein (HDL)

Cardiovascular disease is the leading cause of mortality in many nations, accounting for approximately 16.7 million deaths each year world-wide. The most common consequences of cardiovascular disease are myocardial infarction and stroke, which have a common underlying etiology of atherosclerosis.

Epidemiological studies since the 1970's have shown that low levels of high density lipoprotein (HDL) is associated with increased risk for myocardial infarction. This has led to multiple approaches to new therapies targeting HDL (see Kingwell et al., *Nature Reviews Drug Discovery* 13:445-64, 2014) and to a consensus view that the process of reverse cholesterol transport (RCT) is central to beneficial HDL activity rather than simply an increase in HDL without RCT. For example, in clinical trials so far, drugs that increase HDL by inhibition of RCT with inhibitors of cholesterol ester transfer protein (CETP) have not been efficacious. Further, it has more recently been realized that measuring levels of HDL is not sufficient to determine its function in patients because HDL is damaged by oxidation and glycation, including during chemotherapy and in patients with neurodegenerative disorders. See Keeney et al., *Proteomics Clin Appl.* 7:109-122, 2013.

Apolipoprotein A-1 (ApoA-1) is the principal protein component of HDL. Phillips, *Journal of Lipid Research* 54:2034-2048, 2013. Human ApoA-1 is a 243 amino acid protein, with a series of eight 22-mer and two 11-mer amphipathic α-helices spanning residues 44-243. Lund-Katz and Phillips, *Subcell Biochem.* 51:183-227, 2010. The helices in the amino-terminal two-thirds of the molecule form a helix bundle structure, whereas the carboxyl-terminal region forms a separate, relatively disorganized domain important for lipid binding. The interaction of the C-terminal segment with lipids induces conformational changes in the ApoA-1 structure, increasing the α-helix content of the molecule and allowing subsequent opening of the N-terminal helix bundle. See id. The lipid affinity of ApoA-1 confers detergent-like properties, and it can solubilize phospholipids to form discoidal HDL particles containing a segment of phospholipid bilayer and two ApoA-1 molecules arranged in an anti-parallel, double-belt conformation around the edge of the disc. Phillips, supra. The conformational adaptability ApoA-1 also confers stability to HDL particles, including discoidal particles of different sizes as well as spherical HDL particles. See id. These characteristics allow ApoA-1 to partner with ABCA1 in mediating efflux of cellular phospholipid and cholesterol and the production of stable HDL particles. See Phillips, supra; Lund-Katz and Phillips, supra.

Due to its important role in HDL particle formation and function, ApoA-1 has become the focus for several HDL-targeted therapeutic strategies. Drugs including niacin and fibrates that increase synthesis of ApoA-1, however, also decrease the concentration of very low density lipoproteins (VLDL) and are thus not specific for HDL. Clinical trials of niacin were halted due to lack of efficacy, whereas fibrates that activate peroxisome proliferator activated receptors (PPARs) were found to cause a 10% reduction in major cardiovascular events (p<0.05) and a 13% reduction in coronary events (p<0.0001) in a meta-analysis. See Jun et al., *Lancet* 375:1875, 2010. Because more effective therapies are needed, there are several other orally active drugs that increase ApoA-1 in preclinical development. See Kingwell et al., supra.

An alternative approach to increasing ApoA-1 is by direct injection of the purified protein. See, e.g., Kingwell et al., *Circulation* 128:1112, 2013. ApoA-1 has been purified from human plasma (reconstituted HDL) and tested in clinical trials. Recombinant ApoA-1 has also been expressed in both bacterial and mammalian expression systems and tested in clinical trials. These studies have shown that infusion of ApoA-1, reconstituted with phospholipids into pre-β HDL, causes reduction of plaque volume and improvement in plaque morphology as measured by intravascular ultrasound (IVUS) after small (47-60 patients) clinical trials. While promising, use of natural or recombinant ApoA-1 has several limitations, including a requirement for weekly administration due to a short ApoA-1 half-life and a high cost of manufacturing.

Recombinant ApoA-1 Milano, a highly active ApoA-1 mutant, was expressed in bacterial cells and tested in clinical trials in patients with acute coronary syndromes (see Nissen et al., *JAMA* 290:2292, 2003), where reduction in plaque volume was seen. While this study is considered the first to directly test and confirm the HDL hypothesis, ApoA-1 produced in bacterial systems has not progressed due to low expression levels and high manufacturing costs. Recombinant ApoA-1 produced in mammalian cells has progressed further in clinical trials, including recently completed phase II studies. CER-001, in development by Cerenis Therapeutics, is a recombinant ApoA-1 produced by mammalian cells and formulated with specific lipids to form pre-β-like HDL particles. According to Cerenis, CER-001 met its primary end point of a reduction in carotid plaque volume measured by MRI in patients with familial hypercholesterolaemia in the MODE trial (NCT01412034). In the CHI-SQUARE trial (NCT01201837), Cerenis announced that CER-001 reduced plaque volume versus baseline in patients with acute coronary syndrome, but the reduction was not significant versus placebo.

In another study in macaques, ApoA-1 Milano, reconstituted with lipids (POPC), was infused at relatively high doses (30, 100, and 300 mg/kg) given every second day for 21 infusions. Kempen et al., *J. Lipid. Res.* 54:2341-2353, 2013. Drug infusion quickly decreased the endogenous cholesterol esterification rate, increased the formation of large ApoE-rich particles due to lack of LCAT activation, and caused a large increase in free cholesterol due to sustained stimulation of ABCA1-mediated efflux. See id. These results show that infusion of large amounts of reconstituted ApoA-1 Milano disrupt HDL metabolism by enhancing cholesterol efflux without the ability to process it through the normal metabolic pathways.

While the prospects for HDL infusion therapy are very promising, there is a need for improved recombinant ApoA-1 molecules that overcome some of the limitations of current approaches. Several recombinant ApoA-1 fusion proteins have been produced, including ApoA-1 produced in bacteria with a His tag to simplify purification. See, e.g., Prieto et al., *Protein J.* 31:681-688, 2012; Ryan et al., *Protein Expr. Purif.* 27:98-103, 2003. In another example, IFNα was attached to the amino terminus of ApoA-1 through a 3aa (Gly Ala Pro) linker. See Fioravanti et al., *J. Immunol.* 188:3988-3992, 2012. The linker in this construct was created by the choice of restriction enzymes, and the fusion protein was tested by adenovirus delivery to target to the liver and reduce the toxicity of IFNα therapy. ApoA-1 has also been fused with an Fc domain (ApoA-1-Ig) and is available commercially from Creative Biomart (cat. No. APOA-1-33H) and from Life Technologies (Cat #10686-HO2H-5). However, this ApoA-1-Ig molecule has very low functional activity (see Example 1).

Additional recombinant ApoA-1 fusion proteins include anti-CD20 scFv-ApoA-1 (Crosby et al., *Biochem. Cell Biol.* 10:1139/bcb, 2015), IL-15-ApoA-1 (Ochoa et al., *Cancer Res.* 73:139-149, 2013), and a trimeric ApoA-1 fusion protein made by the addition of the trimerization domain of human tetranectin (Graversen et al., *J. Cardiovascular Pharmacol.* 51:170-77, 2008). In these examples, the fusion was at the N-terminus of ApoA-1.

The trimeric tetranectin-ApoA-1 (TN-ApoA-1) was effective in reverse cholesterol efflux and its half-life in mice was increased to 12 hours versus three hours for monomeric ApoA-1. See Gaversen et al., supra. In an aggressive model of atherosclerosis (LDLR −/− mice fed a high-fat diet), trimeric TN-ApoA-1 slowed progression of lesions in the aortic roots. See id. Recent studies in nonhuman primates, however, showed that multiple infusions of lipidated TN-ApoA-1 were not well tolerated and resulted in high immunogenicity and lipid accumulation. See Regeness-Lechner et al., *Toxilogical Sciences* 150:378-89, 2016. The trimer fusion protein was complexed with phospholipids and injected at concentrations of 100 mg/kg and 400 mg/kg every four days for three weeks, followed by a six week recovery period. After multiple infusions of lipidated TN-ApoA-1, clinical condition deteriorated and was accompanied by changes indicative of a progressive inflammatory response, increased levels of cytokines, C-reactive protein and vascular/perivascular infiltrates in multiple tissues. Rapid formation of antidrug antibodies occurred in all animals receiving lipidated TN-ApoA-1. See id. The accumulation of trimeric TN-ApoA-1 in tissues of the treated animals resembles fibril formation and deposition of ApoA-1 in patients who have mutations near the N-terminus. See Mizuguchi et al., *J. Biol. Chem.* 290:20947-20959, 2015; Das et al., *J. Mol. Biol.* 2015.10.029; Obici et al., *Amyloid* 13:191-205, 2006.

Current forms of ApoA-1 in clinical development require formulation with specific lipids into preβ-like HDL particles prior to infusion, because the half-life of ApoA-1 in the absence of lipids is very short. See Nanjee et al, *Arterioscler Thromb Vasc Biol* 16:1203-1214, 1996 (showing that lipid-free ApoA-1 has a half-life of only 2-2.3 hours after either bolus or slow infusion in humans). After lipid formulation, half-life increases to about 48 hours, so frequent (weekly) administration is still required.

ApoA-1 therapy has also shown significant benefit in improving insulin sensitivity and glucose uptake (see Drew et al., *Nature Reviews Endocrinology* 8:237, 2012), and may be useful in patients with diabetes and with NASH (non-alcoholic steatohepatitis). In addition, ApoA-1 binds amyloid-beta and prevents neurotoxicity in cultured hippocampal neuronal cells. See Koldamova et al., *Biochemistry* 40:3553, 2001; Paula-Lima et al., *Int. J. Biochem. Cell Biol.* 41:1361, 2009. Further, ApoA-1 polymorphisms are linked to risk for Alzheimer's disease and ApoA-1 is found at decreased levels in patients with neurodegenerative disorders. See Keeney et al., *Proteomics Clin. Appl.* 7: 109-122, 2013).

Efficacy of ApoA-1 therapy has also been demonstrated in animal models of cancer. One study examined the effect of ApoA-1 infusion on growth of tumors in mice. See Zamanian-Daryoush et al., *J. Biol. Chem.* 288:21237-21252, 2013. Zamanian-Daryoush et al. found that ApoA-1 potently suppresses tumor growth and metastasis in multiple syngeneic tumor models, including B16F10L malignant melanoma and Lewis Lung carcinoma. The effect of ApoA-1 was due to modulation of the immune response. Recruitment and expansion of myeloid-derived suppressor cells (MDSC) in the tumors was inhibited. There was also inhibition of tumor angiogenesis and the matrix-degrading protease MMP-9. In contrast, ApoA-1 therapy increased CD11b macrophages and increased amounts of IFNγ, IL-12b, and CXCL10, markers of a Th1 response supporting T cell activation. The authors showed that T cells were required for the potent suppressive effect of ApoA-1 on tumor growth, and ApoA-1 therapy caused a specific increase in $CD8^+$ T cells in the tumors. See id. While the results of Zamanian-Daryoush et al. are promising, the study used high doses of lipid-free ApoA-1 to achieve the observed effects (15 mg every second day per mouse), see id., which was likely required because of the short half-life of ApoA-1.

Another cancer study showed that ApoA-1 and mimetic peptides (L-4F, D-4F, L-5F) inhibit tumor development in a murine model of ovarian carcinoma. See Su et al., *Proc. Natl. Acad. Sci. USA* 107:19997-20002, 2010. Su et al. found that ApoA-1 overexpression in transgenic mice, or peptide mimetic administration, reduced stimulatory phospholipids, implicating an additional mechanism for inhibition of tumor growth. See id.

Studies have also suggested a role for ApoA-1 in the pathogenesis of multiple sclerosis (MS). In particular, ApoA-1 expression was shown to be lower in MS patients compared to healthy controls, and primary progressive MS patients had less plasma ApoA-1 than patients with other forms of MS. See Meyers et al., *J. Neuroimmunol.* 277:176-185, 2014. Using experimental allergic encephalomyelitis (EAE) as a model for MS, mice deficient in ApoA-1 exhibited worse clinical disease and more neurodegeneration compared to wild-type animals. The authors suggest that agents that increase ApoA-1 levels are possible therapies for MS. See id. Another MS study found that the ApoA-1 promoter polymorphism A-allele, associated with elevated ApoA-1 levels, is correlated with improved cognitive performance in patients with MS; A-allele carriers displayed overall superior cognitive performance and had a three-fold decreased overall risk of cognitive impairment. See Koutsis et al., *Mult. Scler.* 15:174-179, 2009.

Peptide Mimetics

ApoA-1 mimetic peptides have shown efficacy in a number of animal models of disease and have properties that make them attractive as potential therapeutic agents. See, e.g., Reddy et al., *Curr. Opin. Lipidol.* 25:304-308, 2014 and White et al., *J. Lipid. Res.* 55:2007-2021, 2014. Peptide 4F has been tested in high risk patients with coronary artery disease. Several ApoA-1 mimetic peptides that are resistant to oxidation have been described in the past several years. While these α-helical peptides show activity in animal models, they require daily dosing because of their short half-life. In addition, toxicity, including muscle toxicity and hypertriglyceridemia, have been seen in peptide-treated animals (these toxicities have been seen in mice treated with ApoA-1). Advances to reduce toxicity by sequence design and to reduce cost of peptide production were described. See, e.g., Bielicki, *Curr. Opin. Lipidol.* 27:40-46, 2016. Another approach has been to synthesize D-peptides, including the highly studied D-4F peptide. These have a longer half-life and can be given orally, but the high cost of manufacturing and accumulation of D-peptides in tissues may be preventing these peptides from moving past initial clinical testing.

RNase

RNase has been studied as a therapy for cancer and autoimmune disease. For cancer therapy, both natural (onconase, frog RNase), and recombinant human RNase1 resistant to inhibition by cytoplasmic inhibitor (see U.S. Pat. No. 8,569,457) have been reported. In addition, targeting of RNase to tumor cells by conjugation of cytotoxic RNase (onconase) to anti-tumor antibodies has been reported. See Lui et al., *Mol. Cancer* 13:1186, 2014; Newton et al., *Blood* 97:528-535, 2001.

RNase therapy has also been studied in a mouse model of cardiovascular disease. See Simsekyilmaz et al., *Circulation* 129:598-606, 2014. They and others show that extracellular RNA accumulates at sites of vascular injury and that extracellular RNA causes production of inflammatory cytokines. See Fischer et al., *Thromb. Haemost.* 108:730-741, 2012. RNase therapy reduced neointima formation in a mouse model of accelerated cardiovascular disease, reduced plaque macrophage content, and inhibited leukocyte recruitment to injured carotid arteries in vivo. See Simsekyilmaz et al., supra.

RNase therapy has also been studied in models of acute stroke, where it was found to reduce infarction size. See Walberer et al., *Curr. Neurovasc. Res.* 6:12-19, 2009. Thus systemic treatment with RNase 1 rescued mice from arterial thrombotic occlusion to limit cerebral edema and to serve as a potent anti-inflammatory regimen in vivo. In these RNase therapy studies, the RNase was given by continuous infusion using osmotic minipumps implanted subcutaneously because the half-life of RNase 1 is very short.

RNase therapy has also been studied in a mouse model of systemic lupus erythematosus (SLE). See Sun et al., *J. Immunol.* 190:2536-2543, 2013. Overexpression of TLR7, an RNA sensor, causes a lupus-like disease with autoantibodies, kidney disease, and early mortality. Crossing these mice with mice that overexpress RNase A as a transgene resulted in progeny with increased survival, reduced lymphocyte activation, reduced kidney deposits of IgG and C3, and reduced hepatic inflammation and necrosis.

Extracellular single stranded viral RNA caused widespread neurodegeneration after intrathecal administration to mice, and the neuronal damage was mediated by TLR7. See Lehmann et al., *J. Immunol.* 189: 1448-58, 2012.

RNase-Ig wherein human RNase 1 is fused to a mutated human IgG1 Fc domain comprising p238s and p331s mutations (see U.S. Pat. No. 8,937,157) is in clinical development by Resolve Therapeutics in patients with systemic lupus erythematosus (SLE).

Paraoxonase

Human Paraoxonase 1 (PON1) is a lipolactonase with efficient esterase activity and capable of hydrolyzing organophosphates. PON1 prevents LDL and cell membrane oxidation and is considered to be atheroprotective. PON1 is exclusively associated with HDL and contributes to the antioxidative function of HDL. See, e.g., Mackness et al., *Gene* 567:12-21, 2015. Reductions in HDL-PON1 activity are present in a wide variety of inflammatory diseases where loss of PON1 activity leads to dysfunctional HDL which can promote inflammation and atherosclerosis. See, e.g., Eren et al., *Cholesterol.* 792090 doi 10.1155/2013/792090, 2013. PON1 activity is also decreased in patients with Alzheimer's disease and other dementias, suggesting a possible neuroprotective role of PON1. See Menini et al., *Redox Rep.* 19:49-58, 2014.

PON1 has shown protective activity in multiple animal models. Overexpression of human PON1 inhibited the development of atherosclerosis in mice with combined leptin and LDL receptor deficiency, a model of metabolic syndrome. See Mackness et al., *Arterioscler. Thromb. Vasc. Biol.* 26:1545-50, 2006.

In another study, injection of recombinant PON1 to mice prior to STZ-induced diabetes resulted in reduced incidence of diabetes and higher serum insulin levels. Addition of HDL simultaneously with PON1 had an additive effect on insulin secretion. See Koren-Gluser et al., *Atherosclerosis* 219:510-518, 2011.

In another study, a PON1 fusion protein containing a protein transduction domain (PTD) was used to transduce PON1 into cells and tissues. PON1 transduction protected microglial cells in vitro from oxidative stress-induced inflammatory responses and protected against dopaminergic neuronal cell death in a Parkinsons disease model. See Kim et al., *Biomaterials* 64:45-56, 2015.

In another study, recombinant PON1 was administered to mice where there was a significant reduction in cholesterol mass and an inhibition in the cholesterol biosynthesis rate, effects that could probably lead to attenuation of atherosclerosis. See Rosenblat et al., *Biofactors* 37:462-467, 2011.

In another study, mice were given recombinant adenovirus PON1 or PON3 and either was shown to protect against CCl(4)-induced liver injury. Overexpression of either human PON1 or human PON3 reduced hepatic oxidative stress and strengthened the antioxidant capabilities in the liver. See Peng et al., *Toxicol. Lett.* 193:159-166, 2010.

In another study, PON1 was fused to the C-terminus of an Fc domain, and expressed as a bispecific molecule using an antibody to human insulin receptor (HIR). This molecule, termed HIRMAb-PON1, was stable after expression in CHO cells, and was shown in Rhesus monkeys to have a high blood brain barrier permeation but was rapidly cleared by the liver. See Boado et al., *Biotechnol. Bioeng.* 108: 186-196, 2011.

Platelet-Activating Factor Acetylhydrolase

Platelet-activating factor acetylhydrolase (PAF-AH) is an LDL and HDL-associated enzyme that hydrolyzes short chain acyl groups of phospholipids such as platelet-activating factor and oxidized phospholipids to reduce their inflammatory properties. See Watson et al., *J. Clin. Invest.* 95:774-782, 1995; Stafforini, *Cardiovasc. Drugs Ther.* 23:73-83, 2009. Therapy with PAF-AH through adenovirus-mediated gene delivery has been reported to ameliorate proteinuria and glomerulosclerosis in a rat model. See Iso-O et al.,

*Molecular Therapy* 13:118-126, 2006. PAF-AH also enhanced liver recovery after paracetamol intoxication in the rat, and PAF is associated with liver toxicity from high doses of acetaminophen. See Grypioti et al., *Dig. Dis. Sci.* 52:2580-2590, 2007; Grypioti et al., *Dig. Dis. Sci.* 53:1054-1062, 2008. A mutation in PAF-AH that causes a loss of function is present in 4% of Japanese, and PAF-AH was found to be an independent risk factor for cardiovascular disease and stroke in these individuals. See Blankenberg et al., *J. Lipid Res.* 44:1381-1386, 2003. Recombinant PAF-AH was tested in phase III clinical trials in patients with acute respiratory distress syndrome (ARDS) and in patients with sepsis. See Karabina et al., *Biochim. Biophys. Acta* 1761:1351-1358, 2006.

Cholesteryl Ester Transfer Protein

Cholesteryl ester transfer protein (CETP) transports cholesteryl ester from high-density lipoproteins (HDL) to low density and very low density lipoproteins (LDL and VLDL). Many CETP inhibitors have been developed and tested in clinical trials. Torcetrapib was the first CETP inhibitor to advance to late stage clinical trials, and showed a significant effect on plasma lipoprotein levels, raising antiatherogenic HDL cholesterol levels while lowering proatherogenic LDL cholesterol levels. Torcetrapib binds deeply within CETP and shifts the bound cholesteryl ester in the N-terminal pocket of the hydrophobic tunnel and displaces phospholipid from the pocket. See Liu et al., *J. Biol. Chem.* 287: 37321-37329, 2012. Initial hopes that CETP inhibitors would be useful for therapy of cardiovascular disease have not been fulfilled; four inhibitors have reached late stage clinical trials but have failed to show a reduction in cardiovascular events. See Kosmas et al., *Clinical Medical Insights: Cardiology* 2016: 10 37-42 doi: 10.4137/CMC.S32667).

Alternative views of CETP inhibitors and cardiovascular disease have emerged. See, e.g., Miller, *F100Research* 3:124, 2014. There is mounting evidence for a protective role of CETP. For example, multiple studies in man now show that cardiovascular disease is related inversely to CETP levels. In addition, CETP alleles that have reduced hepatic secretion are associated with increased risk of myocardial infarction. See Miller, supra. The original idea, that CETP inhibitors increase HDL cholesterol levels and would therefore be beneficial in reducing cardiovascular disease, may not be correct. It is likely that HDL cholesterol is beneficial because of its lipid transport function, and the CETP-mediated transfer of cholesteryl ester from HDL to LDL and VLDL is an important component of this function.

SUMMARY OF THE INVENTION

In one aspect, the present invention provides a fusion polypeptide comprising, from an amino-terminal position to a carboxyl-terminal position, ApoA1-L1-D, where ApoA1 is a first polypeptide segment having cholesterol efflux activity and which is selected from (i) a polypeptide comprising an amino acid sequence having at least 90% or at least 95% identity with amino acid residues 19-267, 25-267, or 1-267 of SEQ ID NO:2 and (ii) an ApoA-1 mimetic; L1 is a first polypeptide linker; and D is a dimerizing domain. In certain embodiments, L1 comprises at least two amino acid residues, at least three amino acid residues, or at least 16 amino acid residues. For example, in particular variations, L1 consists of from two to 60 amino acid residues, from three to 60 amino acid residues, from five to 40 amino acid residues, from 15 to 40 amino acid residues, or from 16 to 36 amino acid residues. In more specific variations, L1 consists of 16 amino acid residues, 21 amino acid residues, 26 amino acid residues, 31 amino acid residues, or 36 amino acid residues; in some such embodiments, L1 has the amino acid sequence shown in residues 268-283 of SEQ ID NO:22, residues 268-288 of SEQ ID NO:26, residues 268-293 of SEQ ID NO:2, SEQ ID NO:54, or residues 268-303 of SEQ ID NO:24. In certain embodiments, the first polypeptide segment comprises the amino acid sequence shown in residues 19-267 or 25-267 of SEQ ID NO:2.

In some embodiments of a fusion polypeptide as above, the first polypeptide segment comprises an amino acid sequence having at least 90% or at least 95% identity with amino acid residues 19-267, 25-267, or 1-267 of SEQ ID NO:2, where the first polypeptide segment comprises at least one amino acid substitution (relative to SEQ ID NO:2) selected from (a) valine at the amino acid position corresponding to position 180 of SEQ ID NO:2 replaced with glutamate or lysine ("V156[E/K]"); (b) tyrosine at the amino acid position corresponding to position 216 of SEQ ID NO:2 replaced with serine, glutamine, asparagine, histidine, or phenylalanine ("Y192[S/Q/N/H/F]"); (c) methionine at the amino acid position corresponding to position 110 of SEQ ID NO:2 replaced with leucine, isoleucine, or valine ("M86 [L/I/V]"); (d) methionine at the amino acid position corresponding to position 136 of SEQ ID NO:2 replaced with leucine, isoleucine, or valine ("M112[L/I/V]"); (e) methionine at the amino acid position corresponding to position 172 of SEQ ID NO:2 replaced with leucine, isoleucine, or valine ("M148[L/I/V]"); (f) tryptophan at the amino acid position corresponding to position 32 of SEQ ID NO:2 replaced with phenylalanine ("W8F"); (g) tryptophan at the amino acid position corresponding to position 74 of SEQ ID NO:2 replaced with phenylalanine ("W50F"); (h) tryptophan at the amino acid position corresponding to position 96 of SEQ ID NO:2 replaced with phenylalanine ("W72F"); and (i) tryptophan at the amino acid position corresponding to position 132 of SEQ ID NO:2 replaced with phenylalanine ("W132F"). In some such embodiments, the first polypeptide segment comprises the V156[E/K] or Y192[S/Q/N/H/F] substitution, and optionally further comprises at least one substitution selected from M86[L/I/V], M112[L/I/V], and M148[L/I/V]. In another variation, the first polypeptide segment comprises the both the V156[E/K] and Y192[S/Q/N/H/F] substitutions, and optionally further comprises at least one substitution selected from M86[L/I/V], M112[L/I/V], and M148[L/I/V]. In another variation, the first polypeptide segment comprises the W8F, W50F, W72F, and W132F substitutions. In certain embodiments, the first polypeptide segment comprises one or more of the substitutions selected from V156[E/K], Y192[S/Q/N/H/F], M86[L/I/V], M112[L/I/V], M148[L/I/V], W8F, W50F, W72F, and W132F (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F) but comprises an amino acid sequence that is otherwise 100% identical to residues 19-267, 25-267, or 1-267 of SEQ ID NO:2. In some variations, the first polypeptide segment comprises an amino acid sequence having at least 90% or at least 95% identity with amino acid residues 19-267, 25-267, or 1-267 of SEQ ID NO:2, where the first polypeptide segment comprises the specific V156[E/K] and/or Y192[S/Q/N/H/F] substitution(s) of any one of variant combinations A1-A17 as shown in Table 3 herein; in some such embodiments, the first polypeptide segment comprises an amino acid sequence that is otherwise 100% identical to residues 19-267, 25-267, or 1-267 of SEQ ID NO:2.

In some embodiments of a fusion polypeptide as above, D is an immunoglobulin heavy chain constant region such as, for example, an immunoglobulin Fc region. In certain embodiments where the dimerizing domain is an immunoglobulin Fc region, the Fc region is a human Fc region such as, e.g., a human Fc variant comprising one or more amino acid substitutions relative to the wild-type human sequence. Particularly suitable Fc regions include human γ1 and γ3 Fc regions. In some variations, the Fc region is a human γ1 Fc variant in which Eu residue C220 is replaced by serine; in some such embodiments Eu residues C226 and C229 are each replaced by serine, and/or Eu residue P238 is replaced by serine. In further variations comprising an Fc region as above, the Fc region is a human γ1 Fc variant in which Eu residue P331 is replaced by serine. Fc variants may include an amino acid substitution that reduces glycosylation relative to the wild-type human sequence; in some such embodiments, Eu residue N297 is replaced with another amino acid. In further variations comprising an Fc region as above, the Fc region is an Fc variant comprising an amino acid substitution that increases or reduces binding affinity for an Fc receptor (e.g., an amino acid substitution that increases or reduces binding affinity for at least one of FcγRI, FcγRII, and FcγRIII). In certain embodiments, an Fc variant includes an amino acid substitution that increases or reduces binding affinity for the neonatal Fc receptor (FcRn). Suitable Fc regions include (i) an Fc region comprising the amino acid sequence shown in residues 294-525 or 294-524 of SEQ ID NO:2 and (ii) an Fc region comprising the amino acid sequence shown in residues 294-525 or 294-524 of SEQ ID NO:13.

In certain embodiments of a fusion polypeptide as above, the fusion polypeptide comprises an amino acid sequence having at least 90% or at least 95% identity with (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24. In more specific variations, the fusion polypeptide comprises the amino acid sequence shown in (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24. In some embodiments, the fusion polypeptide comprises an amino acid sequence having at least 90% or at least 95% identity with (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24, where the fusion polypeptide comprises one or more amino acid substitutions in the first polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24.

In some embodiments of a fusion polypeptide as above, the fusion polypeptide further includes a second polypeptide segment located carboxyl-terminal to the dimerizing domain. In particular variations, the second polypeptide segment is an RNase, a paraoxonase, a platelet-activating factor acetylhydrolase (PAF-AH), a cholesterol ester transfer protein (CETP), a lecithin-cholesterol acyltransferase (LCAT), or a polypeptide that specifically binds to amyloid beta (Aβ) such as, e.g., an Aβ-specific scFv. A fusion polypeptide comprising a second polypeptide segment as above may be represented by the formula ApoA1-L1-D-L2-P (from an amino-terminal position to a carboxyl-terminal position), where ApoA1, L1, and D are each defined as above, where L2 is a second polypeptide linker and is optionally present, and where P is the second polypeptide segment. In some embodiments of a fusion polypeptide where L2 is present, L2 has the amino acid sequence shown in residues 526-543 of SEQ ID NO:4.

In another aspect, the present invention provides a fusion polypeptide comprising a first polypeptide segment having cholesterol efflux activity and which is selected from (i) a polypeptide comprising an amino acid sequence having at least 90% or at least 95% identity with amino acid residues 19-267 or 25-267 of SEQ ID NO:2 and (ii) an ApoA-1 mimetic, and a second polypeptide segment located carboxyl-terminal to the first polypeptide segment, where the second polypeptide segment is selected from an RNase, a paraoxonase, a platelet-activating factor acetylhydrolase (PAF-AH), a cholesterol ester transfer protein (CETP), a lecithin-cholesterol acyltransferase (LCAT), and a polypeptide that specifically binds to amyloid beta such as, e.g., an Aβ-specific scFv. In some embodiments, the first polypeptide segment has the amino acid sequence shown in residues 19-267 or 25-267 of SEQ ID NO:2. In some variations, the fusion polypeptide further includes a linker polypeptide located carboxyl-terminal to the first polypeptide segment and amino-terminal to the second polypeptide segment. In some embodiments, the fusion polypeptide further includes a dimerizing domain.

In some embodiments of a fusion polypeptide as above comprising an RNase as a second polypeptide segment, the RNase is human RNAse 1 or a functional variant or fragment thereof. In certain embodiments, the RNase has at least 90% or at least 95% identity with amino acid residues 544-675 or 548-675 of SEQ ID NO:4. In a specific variation, the RNase has the amino acid sequence shown in residues 544-675 or 548-675 of SEQ ID NO:4. In particular embodiments of a fusion polypeptide comprising an RNase and having the formula ApoA1-L1-D-L2-P as above, the fusion polypeptide comprises an amino acid sequence having at least 90% or at least 95% identity with (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59; in some such embodiments, the fusion polypeptide comprises the amino acid sequence shown in (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59. In some embodiments, the fusion polypeptide comprises an amino acid sequence having at least 90% or at least 95% identity with (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59, where the fusion polypeptide comprises one or more amino acid substitutions in the first polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59.

In some embodiments of a fusion polypeptide as above comprising a paraoxonase as a second polypeptide segment, the paraoxonase is human paraoxonase 1 (PON1) or a functional variant thereof. In certain embodiments, the paraoxonase has at least 90% or at least 95% identity with amino acid residues 16-355 of SEQ ID NO:12, amino acid residues 16-355 of SEQ ID NO:42, or amino acid residues 16-355 of SEQ ID NO:44. In specific variations, the paraoxonase comprises the amino acid sequence shown in residues 16-355 of SEQ ID NO:12, residues 16-355 of SEQ ID NO:42, or residues 16-355 of SEQ ID NO:44. In particular embodiments of a fusion polypeptide comprising an paraoxonase and having the formula ApoA1-L1-D-L2-P as above, the fusion polypeptide comprises an amino acid sequence having at least 90% or at least 95% identity with (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48; in some such embodiments, the fusion polypeptide comprises the amino acid sequence shown in (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48. In some embodiments of a fusion polypeptide as above comprising a paraoxonase as a second polypeptide segment, the second polypeptide segment comprises an amino acid sequence having at least 90% or at least 95% identity with amino acid residues 16-355 of SEQ ID NO:12, amino acid residues 16-355 of SEQ ID NO:42, or amino acid residues 16-355 of SEQ ID NO:44, where (a) tyrosine at the amino acid position corresponding to position 185 of SEQ ID NO:12, SEQ ID NO:42, or SEQ ID NO:44 is replaced with histidine, glutamine, or serine ("Y185[H/Q/S]" substitution) and/or phenylalanine at the amino acid position corresponding to position 293 of SEQ ID NO:12, SEQ ID NO:42, or SEQ ID NO:44 is replaced with histidine, glutamine, or asparagine ("F293[H/Q/N]" substitution); in some such embodiments, the second polypeptide segment comprises the Y185[H/Q/S] substitution and/or the F293[H/Q/S] substitution but comprises an amino acid sequence that is otherwise 100% identical to residues 16-355 of SEQ ID NO:12, residues 16-355 of SEQ ID NO:42, or residues 16-355 of SEQ ID NO:44. In some variations, the second polypeptide segment comprises an amino acid sequence having at least 90% or at least 95% identity with amino acid residues 16-355 of SEQ ID NO:12, amino acid residues 16-355 of SEQ ID NO:42, or amino acid residues 16-355 of SEQ ID NO:44, where the second polypeptide segment comprises the specific Y185[H/Q/S] and/or F293[H/Q/N] substitution(s) of any one of variant combinations P1-P15 as shown in Table 4 herein; in some such embodiments, the second polypeptide segment comprises an amino acid sequence that is otherwise 100% identical to residues 16-355 of SEQ ID NO:12, residues 16-355 of SEQ ID NO:42, or residues 16-355 of SEQ ID NO:44. In some embodiments, the fusion polypeptide comprises an amino acid sequence having at least 90% or at least 95% identity with (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48, where the fusion polypeptide comprises (A) at least one amino acid substitution in the first polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F), and/or (B) at least one substitution in the second polypeptide segment selected from Y185[H/Q/S] and F293[H/Q/N] as described herein; in some such embodiments, the fusion polypeptide comprises an amino acid sequence that is otherwise 100% identical to (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48; in particular variations, the fusion polypeptide comprises substitutions of both (A) and (B) as above (e.g., V156[E/K] and/or Y192[S/Q/N/H/F] and optionally at least one of M86[L/I/V], M112[L/I/V], and M148[L/I/V] in the first polypeptide segment and Y185[H/Q/S] and optionally F293[H/Q/N] in the second polypeptide segment).

In some embodiments of a fusion polypeptide as above comprising a platelet-activating factor acetylhydrolase (PAF-AH) as a second polypeptide segment, the platelet-activating factor acetylhydrolase is a human PAF-AH or a functional variant thereof. In certain embodiments, the platelet-activating factor acetylhydrolase has at least 90% or at least 95% identity with amino acid residues 22-441 of SEQ ID NO:32. In a specific variation, the platelet-activating factor acetylhydrolase comprises the amino acid sequence shown in residues 22-441 of SEQ ID NO:32. In particular embodiments of a fusion polypeptide comprising a platelet-activating factor acetylhydrolase and having the formula ApoA1-L1-D-L2-P as above, the fusion polypeptide comprises an amino acid sequence having at least 90% or at least 95% identity with residues 19-963 or 25-963 of SEQ ID NO:34; in some such embodiments, the fusion polypeptide comprises the amino acid sequence shown in residues 19-963 or 25-963 of SEQ ID NO:34. In some embodiments, the fusion polypeptide comprises an amino acid sequence having at least 90% or at least 95% identity with residues 19-963 or 25-963 of SEQ ID NO:34, where the fusion polypeptide comprises one or more amino acid substitutions in the first polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to residues 19-963 or 25-963 of SEQ ID NO:34.

In some embodiments of a fusion polypeptide as above comprising a cholesterol ester transfer protein (CETP) as a second polypeptide segment, the cholesterol ester transfer protein is human CETP or a functional variant thereof. In certain embodiments, the cholesterol ester transfer protein has at least 90% or at least 95% identity with amino acid residues 18-493 of SEQ ID NO:30. In a specific variation, the cholesterol ester transfer protein comprises the amino acid sequence shown in residues 18-493 of SEQ ID NO:30. In particular embodiments of a fusion polypeptide comprising a cholesterol ester transfer protein and having the formula ApoA1-L1-D-L2-P as above, the fusion polypeptide comprises an amino acid sequence having at least 90% or at least 95% identity with residues 19-1019 or 25-1019 of SEQ ID NO:40; in some such embodiments, the fusion polypeptide comprises the amino acid sequence shown in residues 19-1019 or 25-1019 of SEQ ID NO:40. In some embodiments, the fusion polypeptide comprises an amino acid sequence having at least 90% or at least 95% identity with residues 19-1019 or 25-1019 of SEQ ID NO:40, where the fusion polypeptide comprises one or more amino acid substitutions in the first polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to residues 19-1019 or 25-1019 of SEQ ID NO:40.

In certain embodiments of a fusion polypeptide as above, the fusion polypeptide is linked to a myeloperoxidase (MPO) inhibitor.

In another aspect, the present invention provides a dimeric protein comprising a first fusion polypeptide and a second fusion polypeptide, where each of said first and second fusion polypeptides is a fusion polypeptide comprising a dimerizing domain, as described above.

In another aspect, the present invention provides a polynucleotide encoding a fusion polypeptide as described above.

In still another aspect, the present invention provides an expression vector comprising the following operably linked elements: a transcription promoter, a DNA segment encoding a fusion polypeptide as described above, and a transcription terminator. Also provided is a cultured cell into which has been introduced an expression vector as above, wherein the cell expresses the DNA segment.

In another aspect, the present invention provides a method of making a fusion polypeptide. The method generally includes culturing a cell into which has been introduced an expression vector as described above, where the cell expresses the DNA segment and the encoded fusion polypeptide is produced, and recovering the fusion polypeptide.

In yet another aspect, the present invention provides a method of making a dimeric protein. The method generally includes culturing a cell into which has been introduced an expression vector as described above, where the cell expresses the DNA segment and the encoded fusion polypeptide is produced as a dimeric protein, and recovering the dimeric protein.

In another aspect, the present invention provides a composition comprising a fusion polypeptide as described above and a pharmaceutically acceptable carrier.

In another aspect, the present invention provides a composition comprising a dimeric protein as described above and a pharmaceutically acceptable carrier.

In still another aspect, the present invention provides a method for treating a cardiovascular disease characterized by atherosclerosis. The method generally includes administering to a subject having the cardiovascular disease an effective amount of a fusion polypeptide or dimeric fusion protein as described above. In some embodiments, the cardiovascular disease is selected from the group consisting of coronary heart disease and stroke. In certain variations, the coronary heart disease is characterized by acute coronary syndrome.

In another aspect, the present invention provides a method for treating a neurodegenerative disease. The method generally includes administering to a subject having the neurodegenerative disease an effective amount of a fusion polypeptide or dimeric fusion protein as described above. In some embodiments, the neurodegenerative disease is selected from the group consisting of Alzheimer's disease and multiple sclerosis. In certain embodiments, the neurodegenerative disease is characterized by dementia; in some such variations, the neurodegenerative disease is Alzheimer's disease.

In another aspect, the present invention provides a method for treating a disease characterized by amyloid deposit. The method generally includes administering to a subject having the disease characterized by amyloid deposit an effective amount of a fusion polypeptide or dimeric fusion protein as described above. In some embodiments, the disease is Alzheimer's disease.

In another aspect, the present invention provides a method for treating an autoimmune disease. The method generally includes administering to a subject having the autoimmune disease an effective amount of a fusion polypeptide or dimeric fusion protein as described above. In some embodiments, the autoimmune disease is selected from the group consisting of rheumatoid arthritis, systemic lupus erythematosus, multiple sclerosis, and type 1 diabetes.

In yet another aspect, the present invention provides a method for treating an inflammatory disease. The method generally includes administering to a subject having the inflammatory disease an effective amount of a fusion polypeptide or dimeric fusion protein as described above. In some embodiments, the inflammatory disease is selected from the group consisting of rheumatoid arthritis, systemic lupus erythematosus, multiple sclerosis, type 1 diabetes, type 2 diabetes, obesity, non-alcoholic steatohepatitis, coronary heart disease, and stroke. In other embodiments, the inflammatory disease is an inflammatory lung disease such as, for example, asthma, chronic obstructive pulmonary disease (COPD), bronchiectasis, idiopathic pulmonary fibrosis, hyperoxia, hypoxia, or acute respiratory distress syndrome.

In still another aspect, the present invention provides a method for treating an infectious disease. The method generally includes administering to a subject having the infectious disease an effective amount of a fusion polypeptide or dimeric fusion protein as described above. In certain embodiments, the infectious disease is characterized by a bacterial infection; in some such embodiments, the bacterial infection is a *Pseudomonas aeruginosa* infection.

In another aspect, the present invention provides a method for treating nephrotic syndrome (NS). The method generally includes administering to a subject having nephrotic syndrome an effective amount of a fusion polypeptide or dimeric fusion protein as described above. In specific variations, the subject's nephrotic syndrome is associated with a disease selected from the group consisting of a primary kidney disease (e g, minimal-change nephropathy, focal glomerulosclerosis, membranous nephropathy, or IgA nephropathy), amyloidosis, systemic lupus erythematosus, type 1 diabetes, and type 2 diabetes.

In yet another aspect, the present invention provides a method for treating exposure to sulfur mustard gas or to an organophosphate. The method generally includes administering to a subject exposed to the sulfur mustard gas or to the organophosphate an effective amount of a fusion polypeptide or dimeric fusion protein as described above.

In still another aspect, the present invention provides a method for treating cancer. The method generally includes administering to a subject having cancer an effective amount of a fusion polypeptide or dimeric fusion protein as described above. In some embodiments, the cancer is selected from the group consisting of malignant melanoma, renal cell carcinoma, non-small cell lung cancer, bladder cancer, and head and neck cancer. In certain variations, the cancer treatment is a combination therapy. In some combination therapy embodiments, the combination therapy includes a non-ApoA1-mediated immunomodulatory therapy such as, e.g., an immunomodulatory therapy comprising an anti-PD-1/PD-L1 therapy, an anti-CTLA-4 therapy, or both. In other combination therapy embodiments, the combination therapy includes radiation therapy or chemotherapy. In some combination therapy embodiments, the combination therapy includes a targeted therapy; in some such embodiments, the targeted therapy includes (i) a therapeutic monoclonal antibody targeting a specific cell-surface or extracellular antigen (e.g., VEGF, EGFR, CTLA-4, PD-1, or PD-L1) or (ii) a small molecule targeting an intracellular protein such as, for example, an intracellular enzyme (e.g., a proteasome, a tyrosine kinase, a cyclin-dependent kinase, serine/threonine-protein kinase B-Raf (BRAF), or a MEK kinase).

These and other aspects of the invention will become evident upon reference to the following detailed description of the invention.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" (or "N-terminal") and "carboxyl-terminal" (or "C-terminal") are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The terms "polynucleotide" and "nucleic acid" are used synonymously herein and refer to a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment that, when read from the 5' to the 3' direction, encodes the sequence of amino acids of the specified polypeptide. Also, in the context of a fusion polypeptide in accordance with the present invention, a polypeptide segment "having cholesterol efflux activity" and "comprising an amino acid sequence having at least 90% or at least 95% identity with amino acid residue 19-267 or 25-267 of SEQ ID NO:2" is a portion of the longer polypeptide fusion molecule that, in addition to the specified polypeptide segment having cholesterol efflux activity, includes other polypeptide segments (e.g., linker(s), dimerizing domain) as described herein.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all. By the term "recombinant nucleic acid" herein is meant nucleic acid, originally formed in vitro, in general, by the manipulation of nucleic acid using, e.g., polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, i.e., through the expression of a recombinant nucleic acid as depicted above.

The term "heterologous," when used with reference to portions of a nucleic acid, indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, "heterologous," when used in reference to portions of a protein, indicates that the protein comprises two or more subsequences that are not found in the same relationship to each other in nature (e.g., two or segments of a fusion polypeptide).

An "immunoglobulin" is a serum protein which functions as an antibody in a vertebrate organism. Five classes of "immunoglobulin," or antibody, protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3) that are essentially invariant for a given subclass in a species. DNA sequences encoding human and non-human immunoglobulin chains are known in the art. See, e.g., Ellison et al., *DNA* 1:11-18, 1981; Ellison et al., *Nuc. Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228. For a review of immunoglobulin structure and function, see Putnam, *The Plasma Proteins, Vol V*, Academic Press, Inc., 49-140, 1987; and Padlan, *Mol. Immunol.* 31:169-217, 1994.

An "immunoglobulin hinge" is that portion of an immunoglobulin heavy chain connecting the CH1 and CH2 domains. The hinge region of human γ1 corresponds approximately to Eu residues 216-230.

The terms "Fc fragment," "Fc region," or "Fc domain," as used herein, are synonymous and refer to the portion of an immunoglobulin that is responsible for binding to antibody receptors on cells and the C1q component of complement (in the absence of any amino acid changes, relative to the naturally occurring sequence, to remove such binding activity). Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. As used herein, the term also refers to a single chain consisting of CH3, CH2, and at least a portion of the hinge sufficient to form a disulfide-linked dimer with a second such chain. As used herein, the term Fc region further includes variants of naturally occurring sequences, where the variants are capable of forming dimers and including such variants that have increased or decreased Fc receptor-binding or complement-binding activity.

"Dimerizing domain," as used herein, refers to a polypeptide having affinity for a second polypeptide, such that the two polypeptides associate under physiological conditions to form a dimer. Typically, the second polypeptide is the same polypeptide, although in some variations the second polypeptide is different. The polypeptides may interact with each other through covalent and/or non-covalent association(s). Examples of dimerizing domains include an Fc region; a hinge region; a CH3 domain; a CH4 domain; a CH1 or CL domain; a leucine zipper domain (e.g., a jun/fos leucine zipper domain, see, e.g., Kostelney et al., *J. Immunol.*, 148:1547-1553, 1992; or a yeast GCN4 leucine zipper domain); an isoleucine zipper domain; a dimerizing region of a dimerizing cell-surface receptor (e.g., interleukin-8 receptor (IL-8R); or an integrin heterodimer such as LFA-1 or GPIIIb/IIIa); a dimerizing region of a secreted, dimerizing ligand (e.g., nerve growth factor (NGF), neurotrophin-3 (NT-3), interleukin-8 (IL-8), vascular endothelial growth factor (VEGF), or brain-derived neurotrophic factor (BDNF); see, e.g., Arakawa et al., *J. Biol. Chem.* 269:27833-27839, 1994, and Radziejewski et al., *Biochem.* 32:1350, 1993); and a polypeptide comprising at least one cysteine residue (e.g., from about one, two, or three to about ten cysteine residues) such that disulfide bond(s) can form between the polypeptide and a second polypeptide comprising at least one cysteine residue (hereinafter "a synthetic hinge"). A preferred dimerizing domain in accordance with the present invention is an Fc region.

The term "dimer" or "dimeric protein" as used herein, refers to a multimer of two ("first" and "second") fusion polypeptides as disclosed herein linked together via a dimerizing domain. Unless the context clearly indicates otherwise, a "dimer" or "dimeric protein" includes reference to such dimerized first and second fusion polypeptides in the context of higher order multimers that may form in spherical HDL particles (e.g., trimers), such as through an interaction of dimerized first and second fusion polypeptides with another ApoA-1 polypeptide that may be present (e.g., through interaction with a naturally occurring, endogenous ApoA-1 protein). The term also includes reference to dimerized first and second fusion polypeptides in the context of higher order multimers that may be created by inclusion of an additional dimerizing domain in a first or second fusion polypeptide (e.g., a first fusion polypeptide comprising an immunoglobulin light chain and a second fusion polypeptide comprising an immunoglobulin heavy chain can heterodimerize via the interaction between the CH1 and CL domains, and two such heterodimers may further dimerize via the Fc region of the immunoglobulin heavy chain, thereby forming a tetramer).

The term "linker" or "polypeptide linker" is used herein to indicate two or more amino acids joined by peptide bond(s) and linking two discrete, separate polypeptide regions. The linker is typically designed to allow the separate polypeptide regions to perform their separate functions (such as, e.g., where a dimerizing domain, linked to other polypeptide regions, associates with another, corresponding dimerization domain to form a dimer). The linker can be a portion of a native sequence, a variant thereof, or a synthetic sequence. Linkers are also referred to herein using the abbreviation "L." The use of a subscript (e.g., "1" or "2") with "L" is used herein to differentiate among multiple linkers within a polypeptide chain, which linkers may be the same or different with respect to amino acid sequence.

Unless the context clearly indicates otherwise, reference herein to "ApoA-1" is understood to include naturally occurring ApoA-1 polypeptides as well as functional variants, functional fragments, and mimetics thereof. "ApoA1," Apo A-1," "apoA-1," and "apo A-1" are used herein synonymously with "ApoA-1."

Unless the context clearly indicates otherwise, reference herein "RNase" (e.g., "RNase 1"), "paraoxonase" (e.g., "PON1"), "platelet-activating factor acetylhydrolase" ("PAF-AH"), "cholesterol ester transfer protein" ("CETP"), or "lecithin-cholesterol acyltransferase" ("LCAT") is understood to include naturally occurring polypeptides of any of the foregoing, as well as functional variants and functional fragments thereof.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

ApoA-1 fusion polypeptides of the present disclosure may be referred to herein by formulae such as, for example, "ApoA1-L1-D," "ApoA1-L1-D-L2-P," "ApoA1-L1-[Fc region]," "ApoA1-L1-D-L2-RNase," "ApoA1-L1-[Fc region]-L2-RNase1," "ApoA1-L1-D-L2-paraoxonase," or "ApoA1-L1-[Fc region]-L2-PON1." In each such case, unless the context clearly dictates otherwise, a term referring to a particular segment of a fusion polypeptide (e.g., "ApoA1," "D" (for dimerizing domain), "L1" (for a first polypeptide linker), "Fc region," "RNase," "paraoxonase," etc.) is understood to have the meaning ascribed to such term herein and is inclusive of the various embodiments as described herein.

The term "effective amount," in the context of treatment of a disease by administration of a soluble fusion polypeptide or dimeric protein to a subject as described herein, refers to an amount of such molecule that is sufficient to inhibit the occurrence or ameliorate one or more symptoms of the disease. For example, in the specific context of treatment of an autoimmune disease by administration of a dimeric ApoA1 fusion protein to a subject as described herein, the term "effective amount" refers to an amount of such molecule that is sufficient to modulate an autoimmune response in the subject so as to inhibit the occurrence or ameliorate one or more symptoms of the autoimmune disease. An effective amount of an agent is administered according to the methods of the present invention in an "effective regime." The term "effective regime" refers to a combination of amount of the agent being administered and dosage frequency adequate to accomplish treatment or prevention of the disease.

The term "patient" or "subject," in the context of treating a disease or disorder as described herein, includes mammals such as, for example, humans and other primates. The term also includes domesticated animals such as, e.g., cows, hogs, sheep, horses, dogs, and cats.

The term "combination therapy" refers to a therapeutic regimen that involves the provision of at least two distinct therapies to achieve an indicated therapeutic effect. For example, a combination therapy may involve the administration of two or more chemically distinct active ingredients, or agents, for example, a soluble ApoA1 fusion polypeptide or dimeric protein according to the present invention and another agent such as, e.g., another anti-inflammatory or immunomodulatory agent. Alternatively, a combination therapy may involve the administration of a soluble ApoA1 fusion polypeptide or dimeric protein according to the present invention, alone or in conjunction with another agent, as well as the delivery of another therapy (e.g., radiation therapy). The distinct therapies constituting a combination therapy may be delivered, e.g., as simultaneous, overlapping, or sequential dosing regimens. In the context of the administration of two or more chemically distinct agents, it is understood that the active ingredients may be administered as part of the same composition or as different compositions. When administered as separate compositions, the compositions comprising the different active ingredients may be administered at the same or different times, by the same or different routes, using the same or different dosing regimens, all as the particular context requires and as determined by the attending physician.

The term "non-ApoA1-mediated immunomodulatory therapy," in the context of treating cancer, means an immunomodulatory therapy that does not specifically target ApoA-1 or ApoA-1-mediated signaling pathways.

The term "targeted therapy," in the context of treating cancer, refers to a type of treatment that uses a therapeutic agent to identify and attack a specific type of cancer cell, typically with less harm to normal cells. In some embodiments, a targeted therapy blocks the action of an enzyme or other molecule involved in the growth and spread of cancer cells. In other embodiments, a targeted therapy either helps the immune system to attack cancer cells or delivers a toxic substance directly to cancer cells. In certain variations, a targeted therapy uses a small molecule drug or a monoclonal antibody as a therapeutic agent.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 90%, or at least 95% sequence identity relative to each other.

Percent sequence identity is determined by conventional methods. See, e.g., Altschul et al., *Bull. Math. Bio.* 48:603, 1986, and Henikoff and Henikoff, *Proc. Natl. Acad. Sci. USA* 89:10915, 1992. For example, two amino acid sequences can be aligned to optimize the alignment scores using a gap opening penalty of 10, a gap extension penalty of 1, and the "BLOSUM62" scoring matrix of Henikoff and Henikoff, supra, as shown in Table 1 (amino acids are indicated by the standard one-letter codes). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and a second amino acid sequence. The FASTA algorithm is described by Pearson and Lipman, *Proc. Nat'l Acad. Sci. USA* 85:2444, 1988, and by Pearson, *Meth. Enzymol.* 183:63, 1990. Briefly, FASTA first characterizes sequence similarity by identifying regions shared by the query sequence (e.g., residues 19-267 or 25-267 of SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

When such a value is expressed as "about" X or "approximately" X, the stated value of X will be understood to be accurate to ±10%.

TABLE 1

BLOSUM62 Scoring Matrix

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

1-Fc fusion protein containing a 26 amino acid linker between ApoA-1 and the Fc region (ApoA-1(26)Fc) demonstrated increased cholesterol efflux as compared to either an ApoA-1-Fc fusion protein with a two amino acid linker (ApoA-1(2)Fc (Theripion)) or an ApoA-1-Fc fusion protein without a linker (ApoA-1(0)Fc (Sino Biol)) and had activity similar to wild-type human ApoA-1 (Control ApoA-1). ApoA-1 molecules were incubated for 2 hours with H3-cholesterol labeled BHK cells induced for ABCA1 expression. The Fc proteins were predicted to be dimers; however, the concentrations shown were calculated and normalized based on the mass of ApoA-1 per molecule.

Figure 2A:
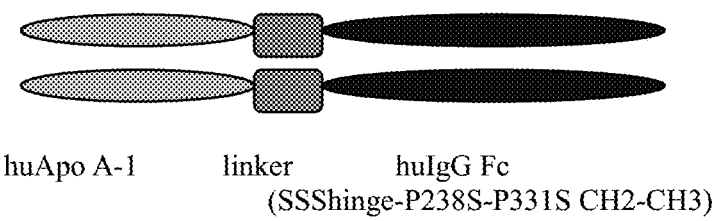
Figure 2B:
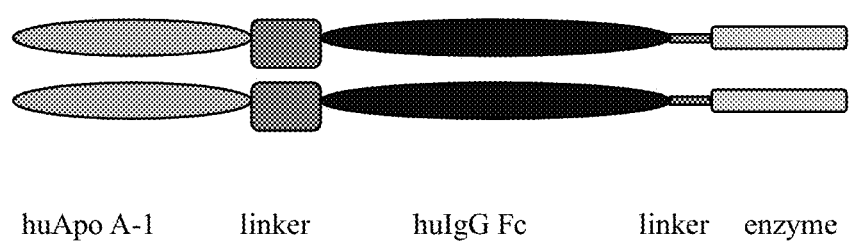

FIGS. 2A and 2B show schematic diagrams of certain embodiments of fusion proteins in accordance with the present disclosure, including component functional domains. FIG. 2A depicts a schematic representation of a human ApoA-1 joined at the carboxyl terminus, via a linker, to a human IgG Fc region (also referred to herein as a "THER fusion protein" or "THER molecule"). FIG. 2B depicts a schematic representation of a THER fusion protein further joined at the carboxyl terminus, via a linker, to an enzyme region (these fusions are also referred to herein a "Bifunctional Enzyme Lipid Transport" or "BELT" molecule; a BELT molecule may also be generally referred to herein as a THER fusion protein or molecule). The linker sequence and the domain present at the carboxyl terminus of the fusion protein varies depending on the construct.

Figure 3:
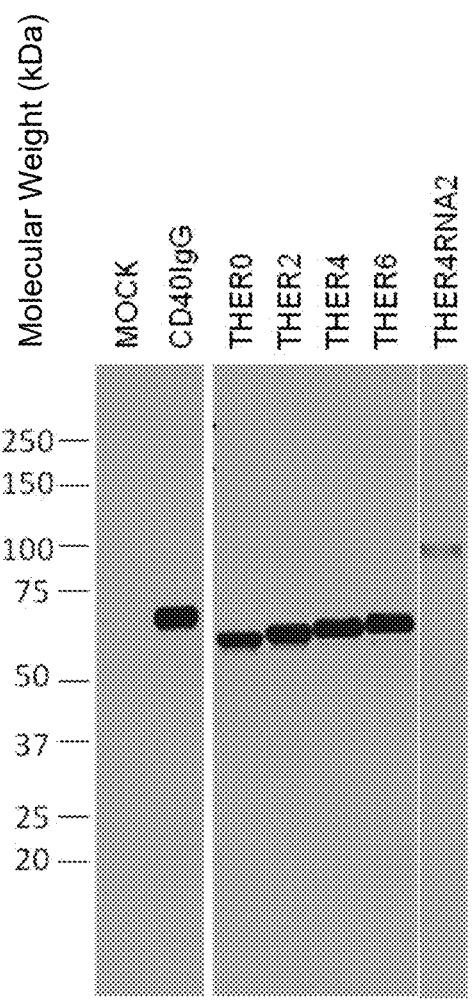
Figure 4A:
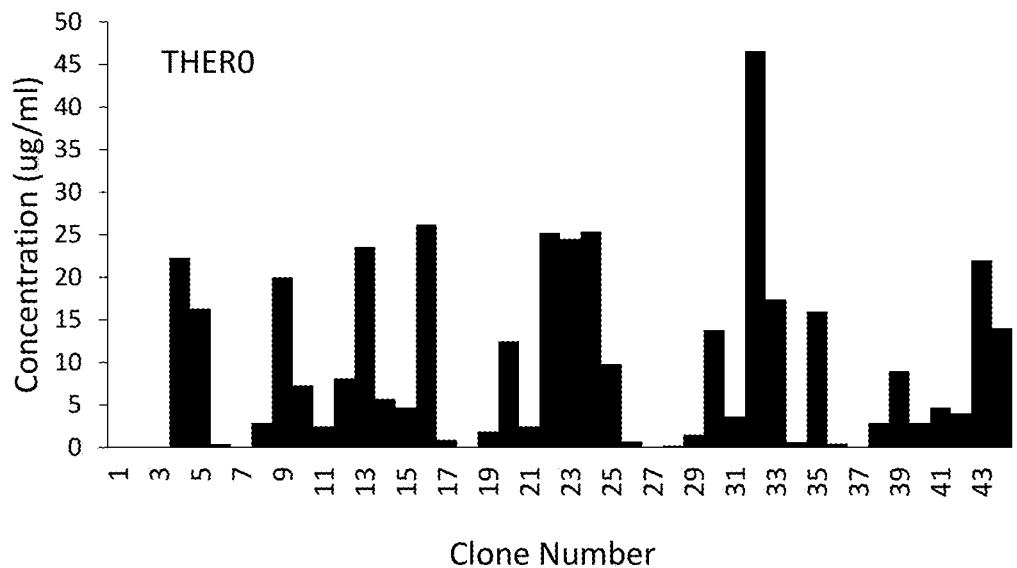
Figure 4B:
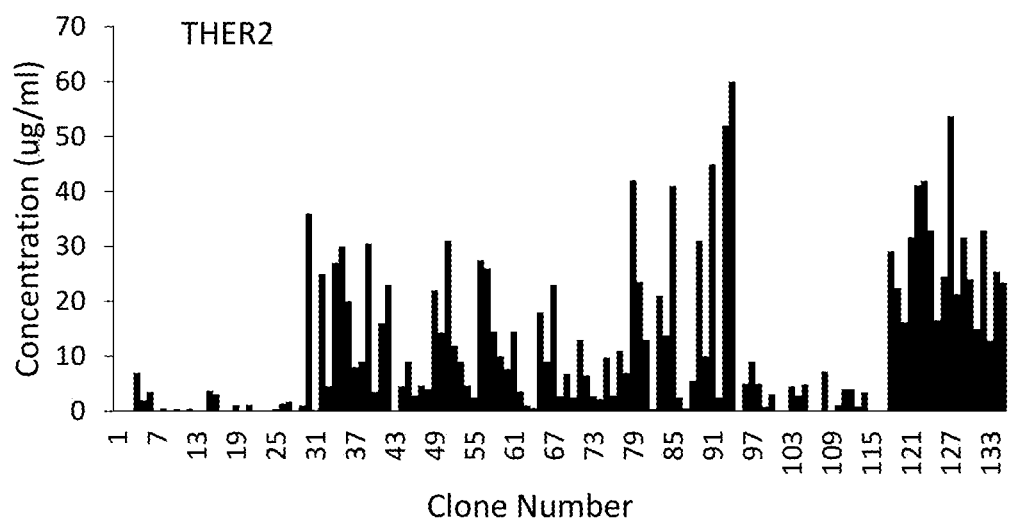
Figure 4C:
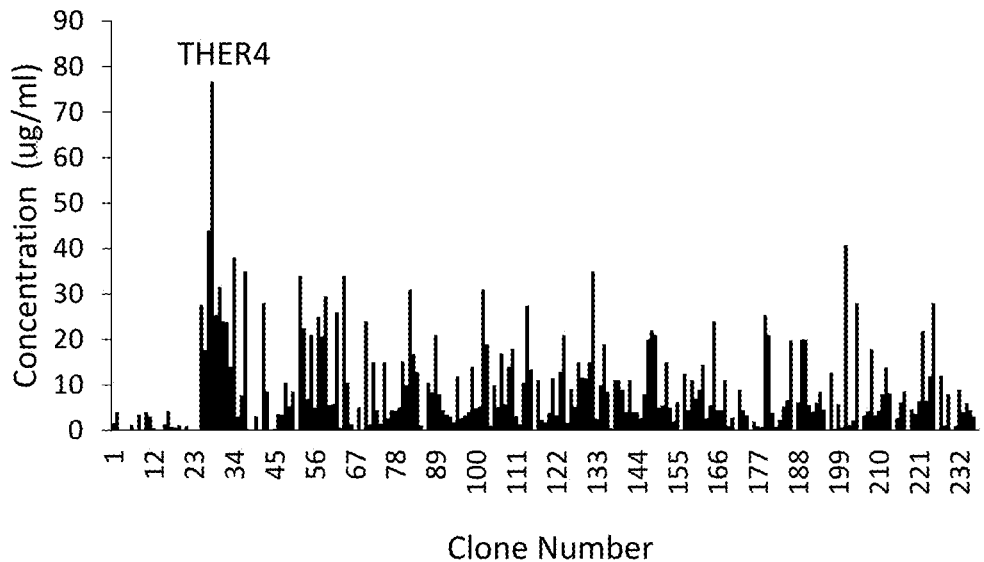
Figure 4D:
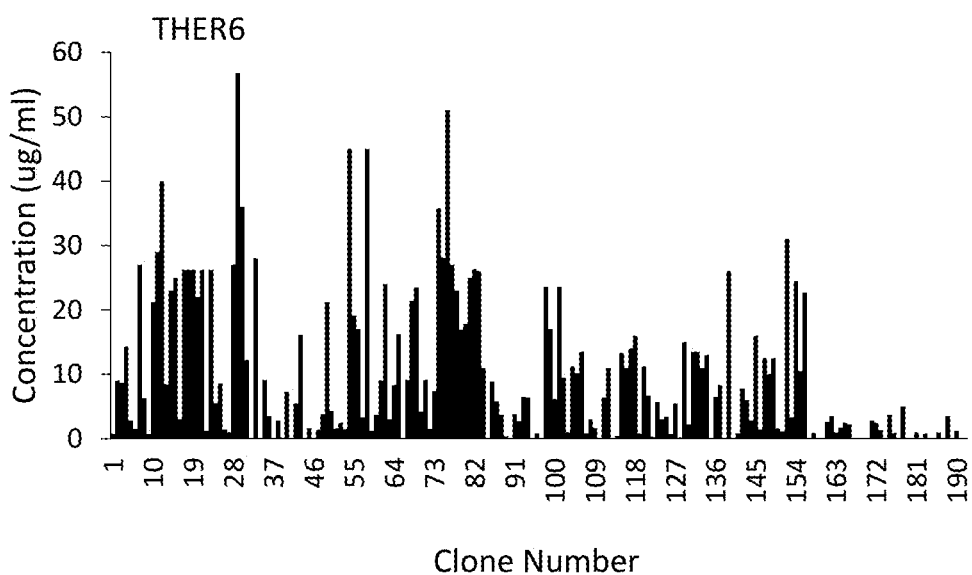
Figure 4E:
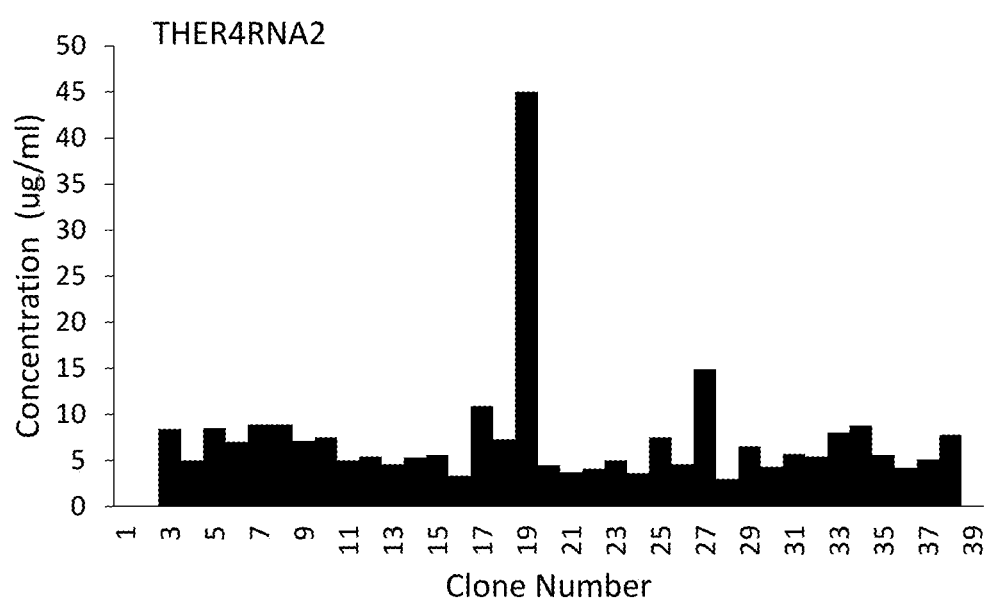

FIG. 3 shows a Western blot of culture supernatants (serum free) from transiently transfected 293T cells expressing five different THER molecules. Transfections and Western blot analysis were performed as described in Example 3, infra. From left to right: MOCK-mock transfection negative control; CD40IgG-CD40IgG DNA transfection positive control; THER0-ApoA1-IgG fusion protein with a linker of two amino acids; THER2-ApoA1-IgG fusion protein with a linker of 16 amino acids; THER4-ApoA1-IgG fusion protein with a linker of 26 amino acids; THER6-ApoA1-IgG fusion protein with a linker of 36 amino acids; THER4RNA-ApoA1-IgG fusion protein with a linker of 36 amino acids, further linked via a second 18 amino acid linker to human RNase1.

FIGS. 4A-4E show columnar graphs summarizing the initial screening of stable CHO clones expressing THER0 (FIG. 4A), THER2 (FIG. 4B), THER4 (FIG. 4C), THER6 (FIG. 4D), and THER4RNA2 (FIG. 4E) ApoA-1 fusion proteins and relative expression levels of the fusion proteins from 96 well culture supernatants (see Example 4, infra).

Figure 5A:
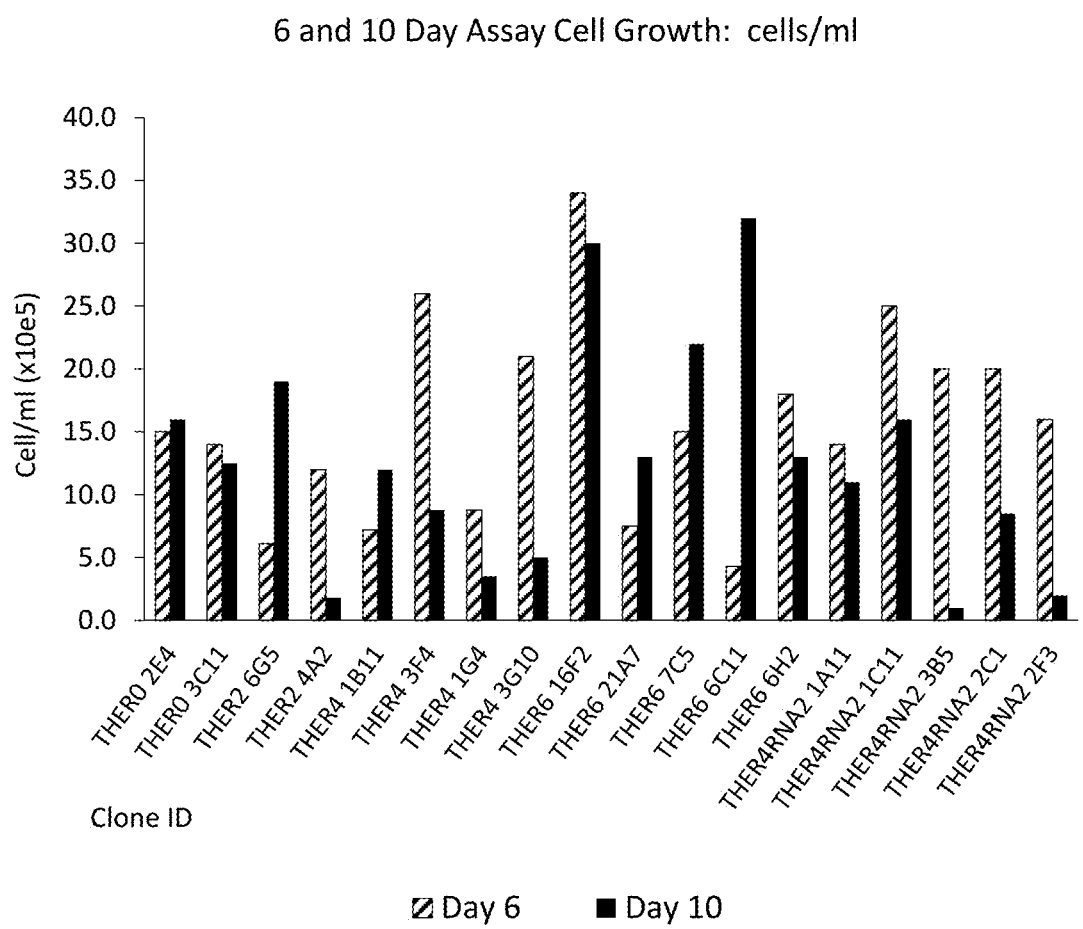
Figure 5B:
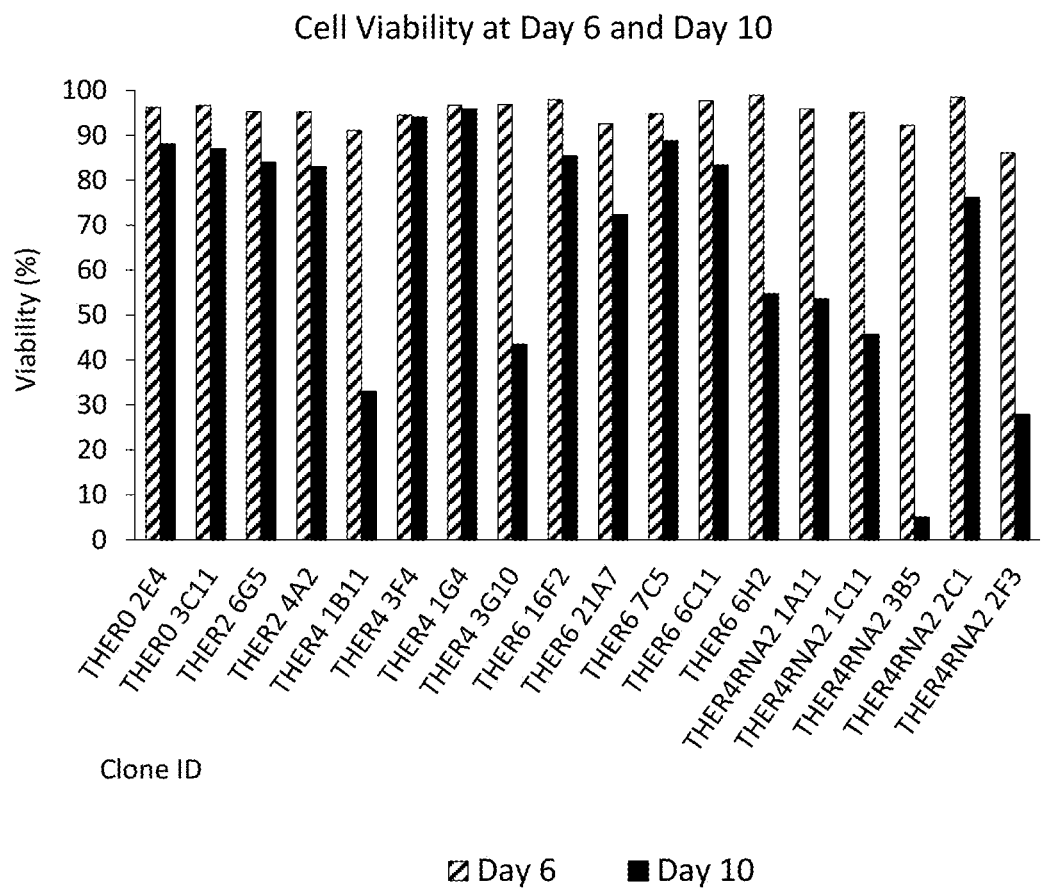
Figure 5C:
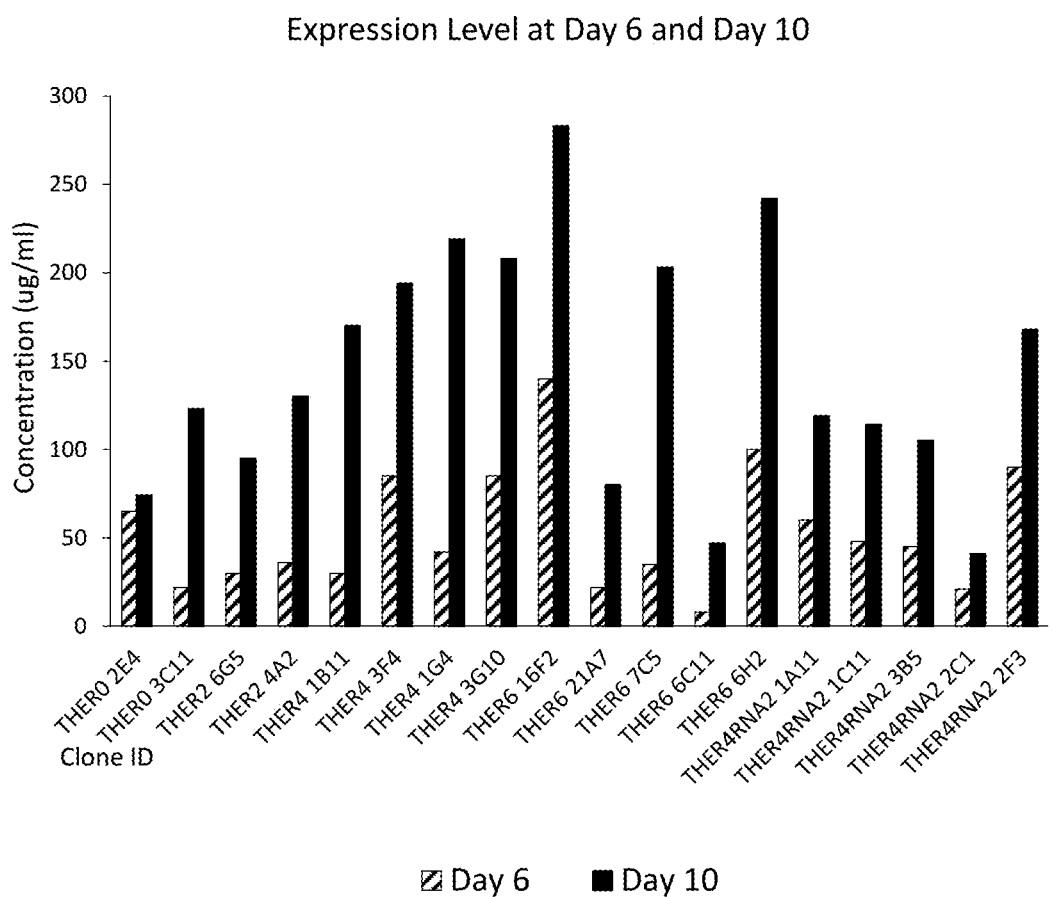

FIGS. 5A-5C show results from analysis of a subset of THER clones that expressed higher levels of fusion protein, assessing their cell growth pattern (FIG. 5A), relative cell viability (FIG. 5B), and expression of fusion protein (FIG. 5C) after six and ten days of culture (see Example 4, infra).

Figures 6A, 6B:
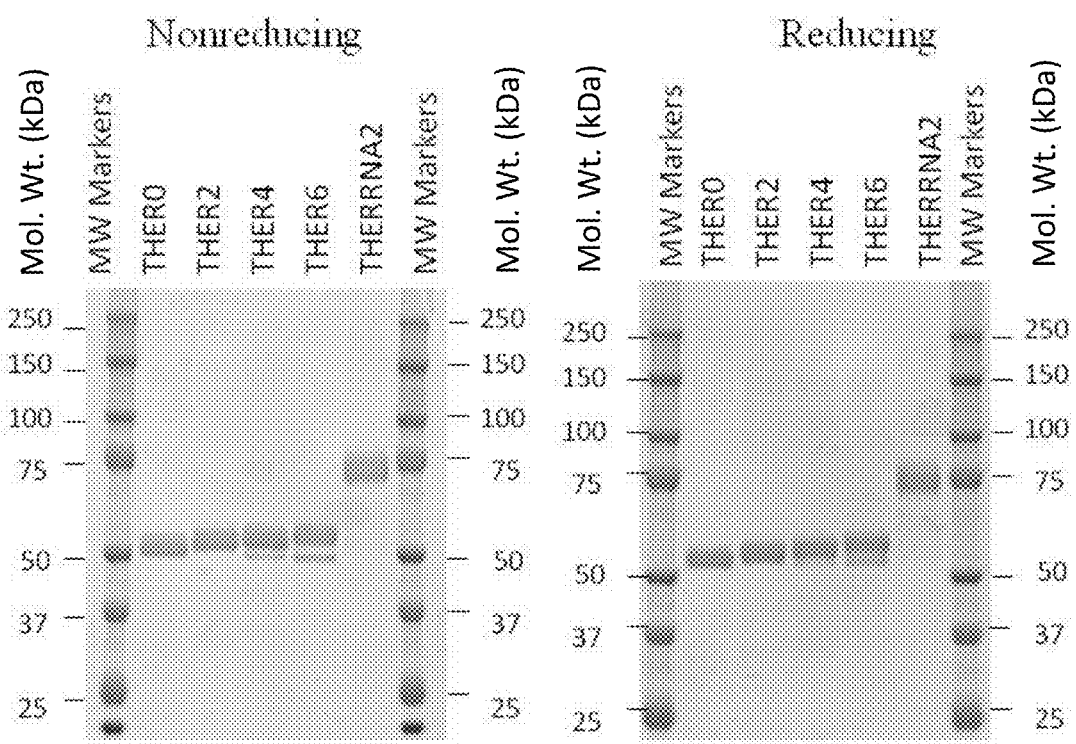

FIGS. 6A and 6B show nonreducing (FIG. 6A) and reducing (FIG. 6B) SDS-PAGE analysis of THER fusion proteins purified from CHO clone spent culture supernatants (see Example 4, infra).

Figure 7:
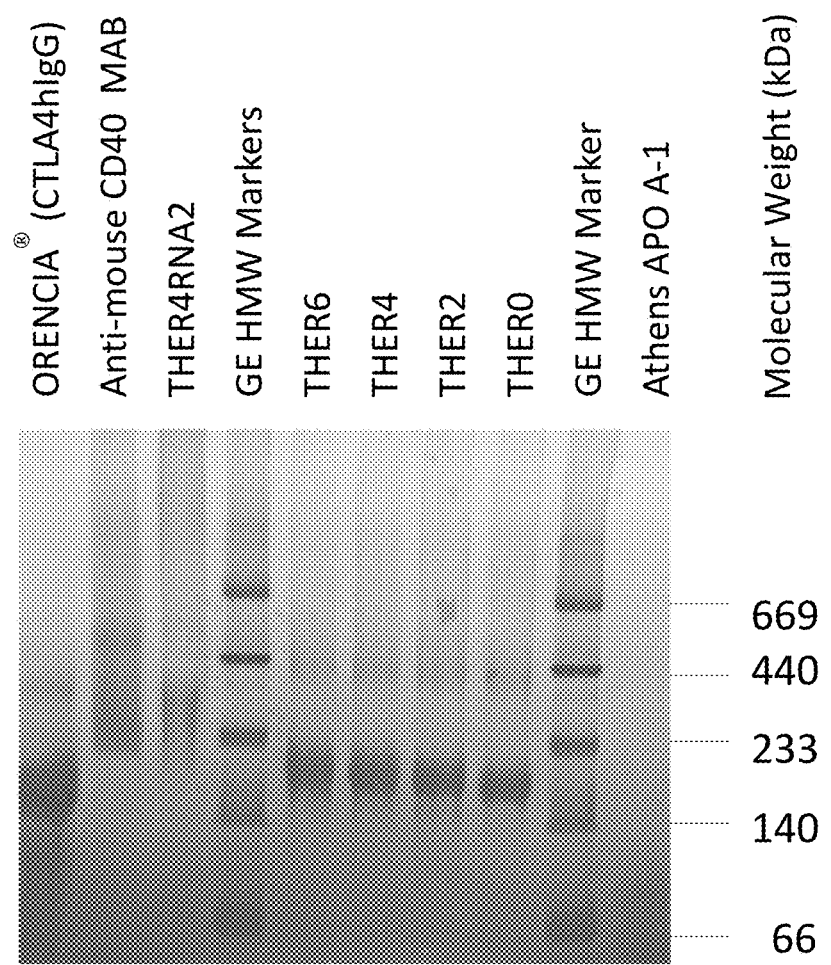

FIG. 7 shows Native PAGE gel analysis of the purified THER fusion proteins. Samples were prepared and BLUE Native PAGE gels were run and stained as described in Example 4, infra.

Figure 8:
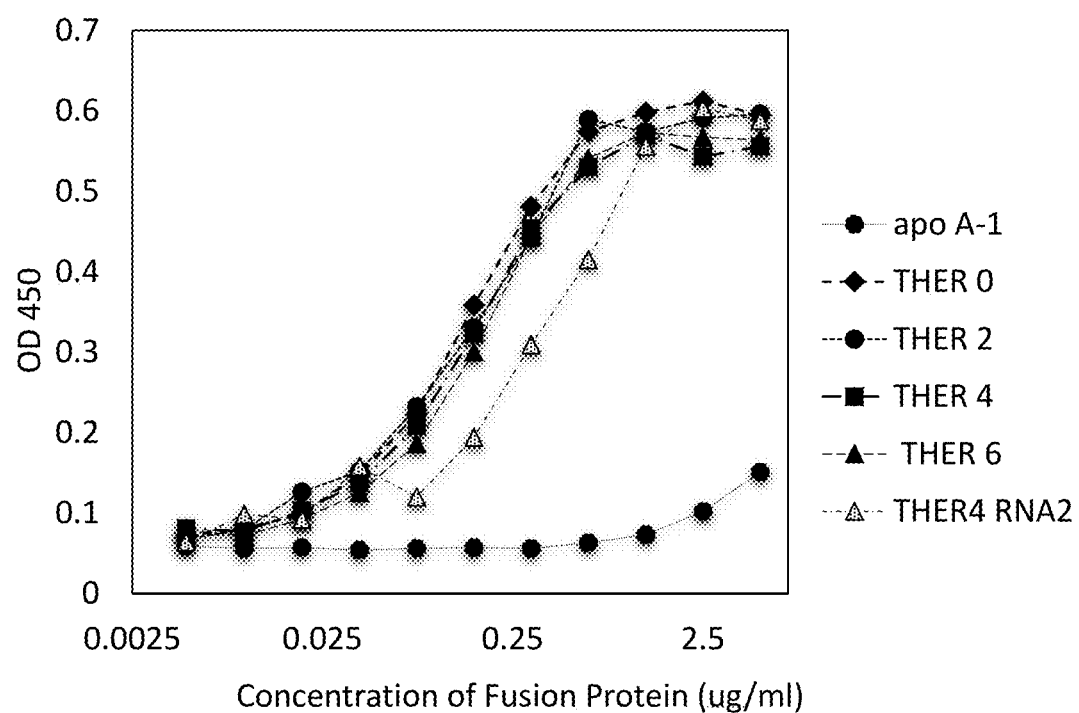

FIG. 8 shows a graph summarizing the relative binding of the different fusion proteins in a sandwich ELISA, using an anti-IgG capture of fusion proteins and detection step with an HRP-conjugated anti-ApoA-1 antibody (see Example 5, infra).

Figure 9:
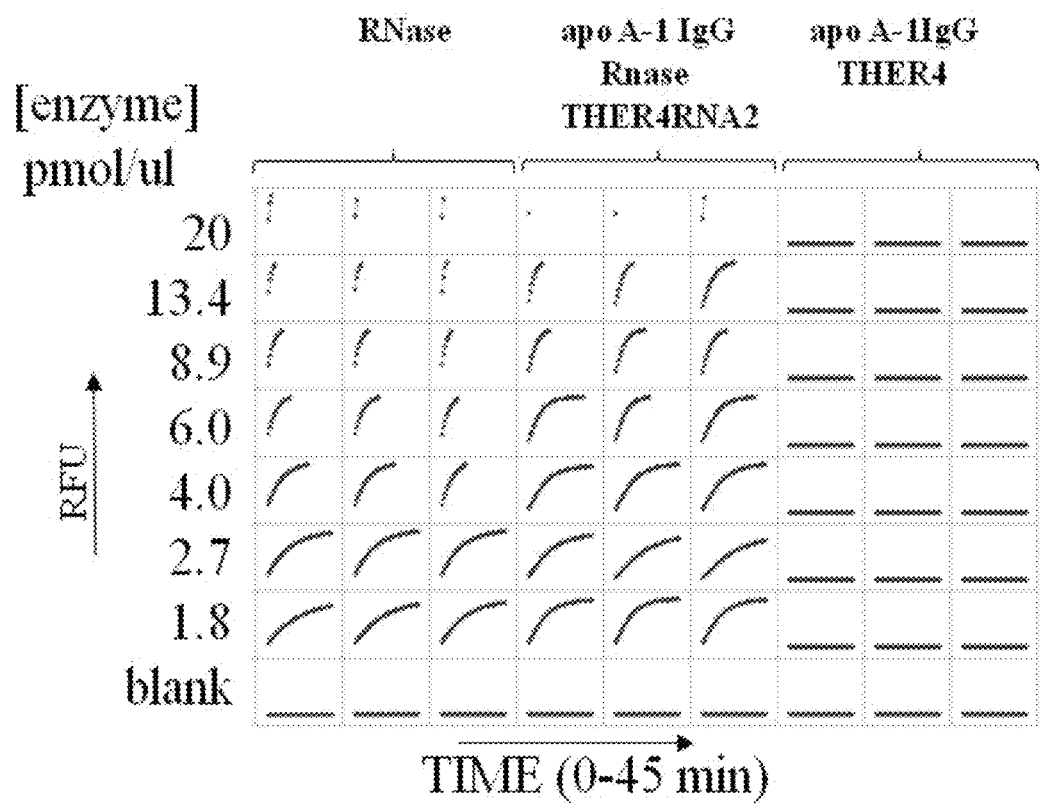

FIG. 9 shows results from a kinetic enzyme assay measuring the RNase activity present in samples of serial dilutions of purified ApoA1-IgG-RNase bispecific fusion protein (THER4RNA2). An RNASEALERT™ assay (IDT, Coralville, Iowa) was performed as described in Example 6, infra, using RNase A ("RNase") as a positive control and ApoA-1-lnk26-hIgG ("THER4") as a negative control. Each box displays the relative fluorescence units observed as a function of time during the course of a 45 minute assay, with a fixed concentration of a non-fluorescent RNA substrate that generates a fluorescent signal upon digestion of the RNA.

Figure 10:
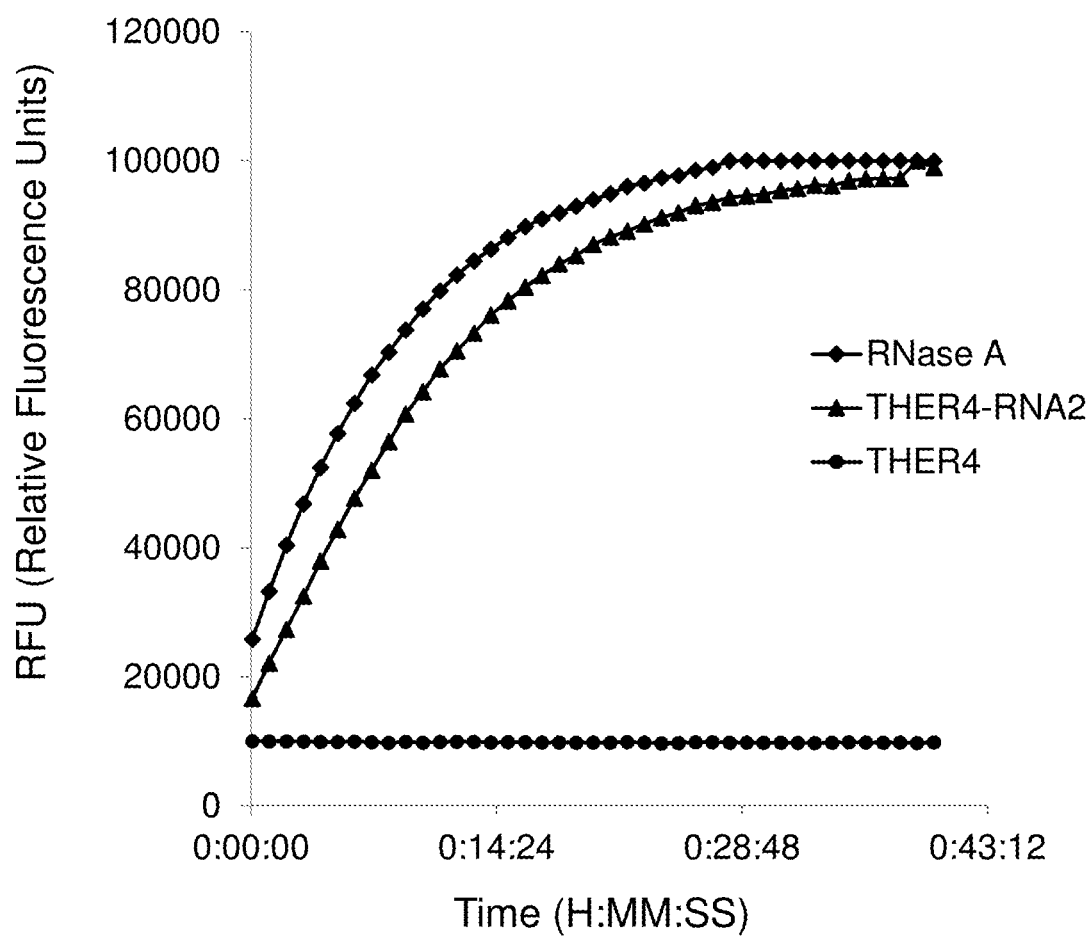

FIG. 10 shows a subset of the data shown in FIG. 9, comparing the RNase enzyme activity at the 4 pmol/µl protein dilution.

Figure 11:
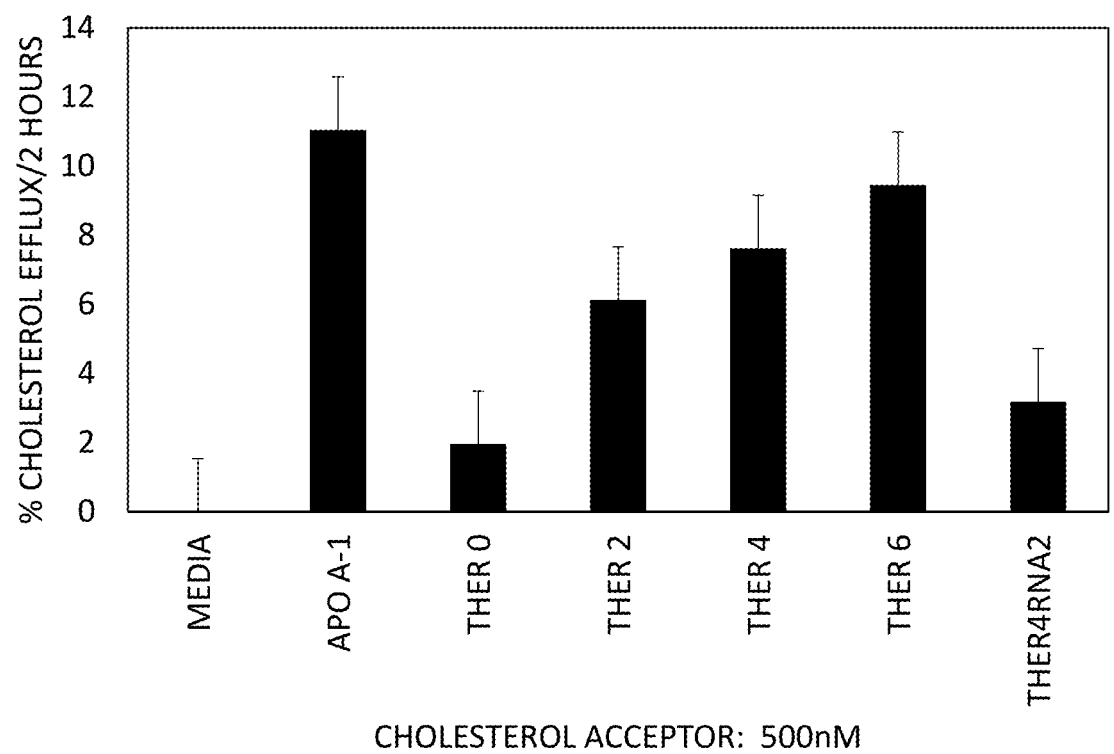

FIG. 11 shows the results of a BODIPY-cholesterol efflux assay using purified fusion proteins and differentiated human monocytic cell line, THP-1. Assays were performed in a 96 well plate format as described in Example 7, infra, and data are displayed as the mean efflux observed from 5 replicates, with baseline efflux (media alone) subtracted from all samples.

Figure 12:
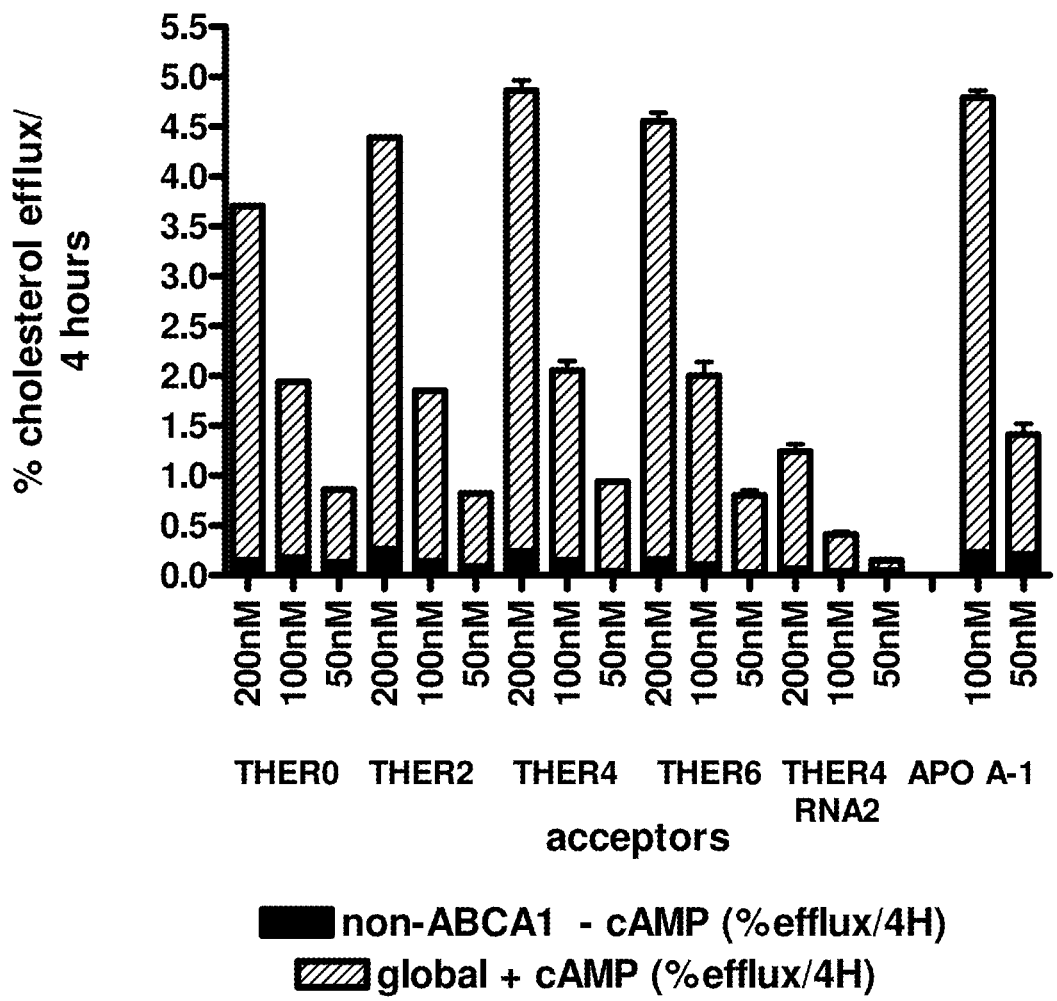

FIG. 12 shows the results of a cholesterol efflux assay using the mouse monocyte-macrophage cell line J774 A.1 (ATCC, Manassas, Va.). Both baseline and cAMP-stimulated efflux were assessed as described in Example 7, infra.

Figure 13:
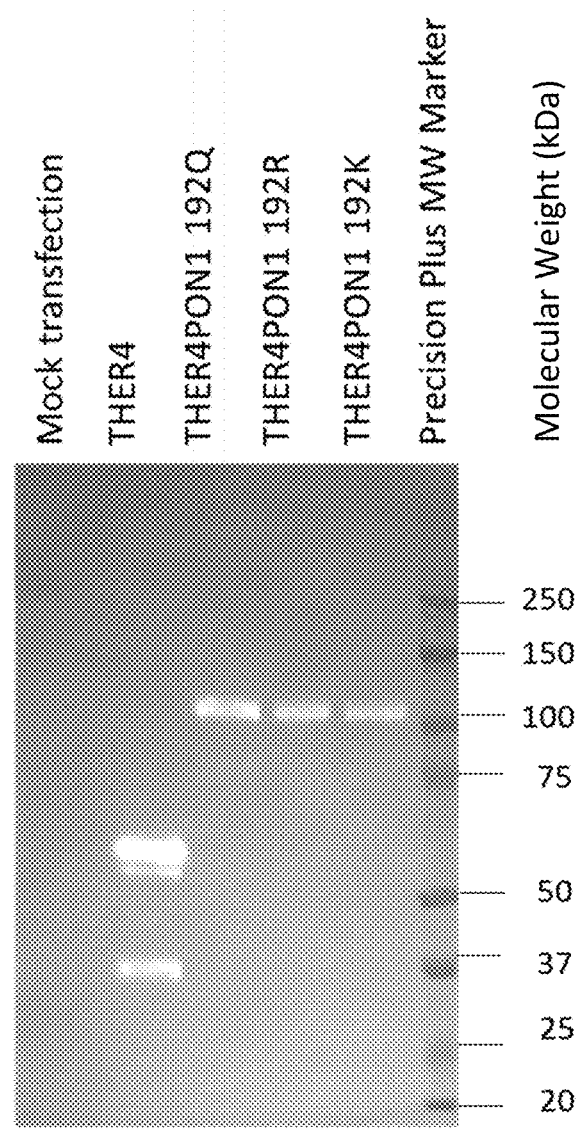

FIG. 13 shows a Western blot of culture supernatants (serum free) from transiently transfected 293T cells expressing three THER4PON1 sequence variants (192Q, 192R, 192K) or THER4. Supernatant from mock transfected cells (Mock transfection) was used as a negative control. Transfections and Western blot analysis were performed as described in Example 10, infra.

Figure 14:
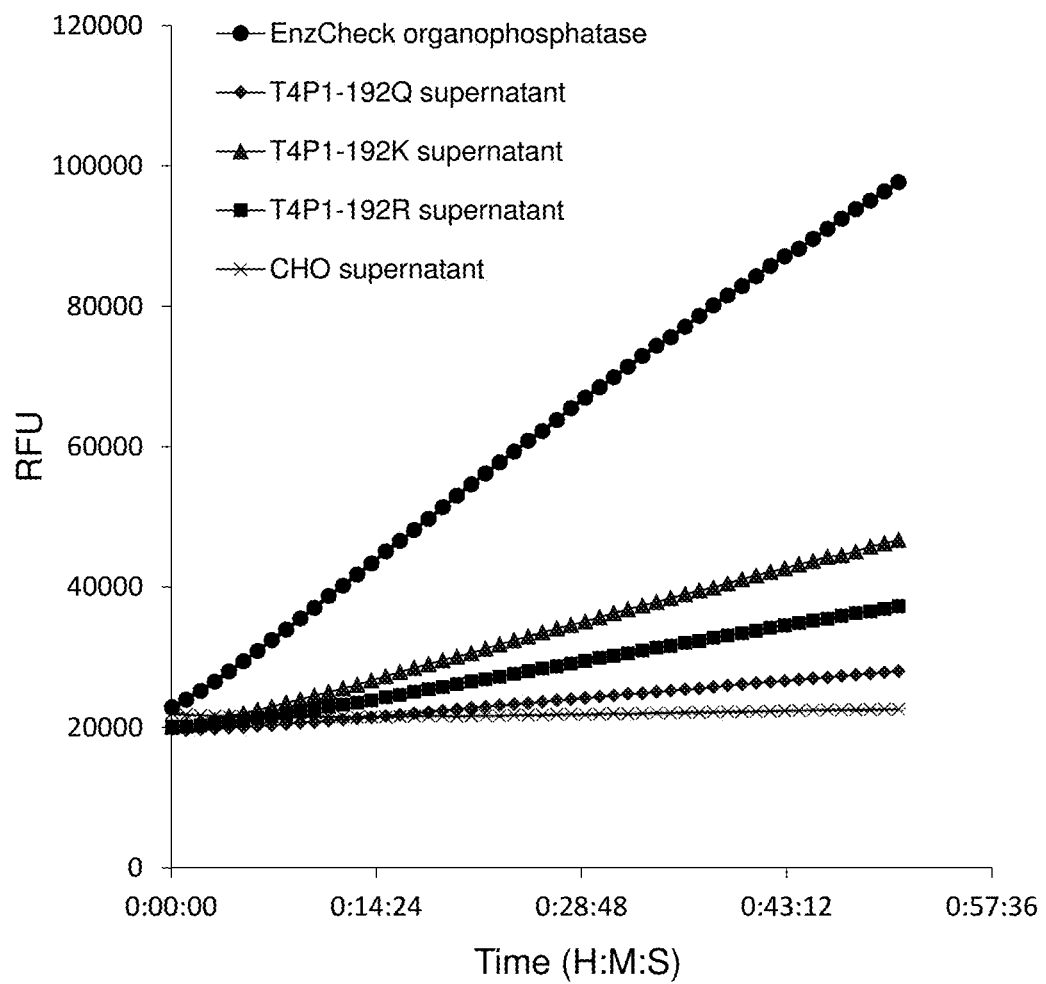

FIG. 14 shows results of an assay measuring the PON1 organophosphatase activity in samples of dialyzed culture supernatants from transfected clones of three THER4PON1 sequence variants (T4P1-192Q, T4P1-192K, T4P1192R). PON1 enzyme (EnzCheck organophosphatase) and untransfected CHO supernatant were used as positive and negative controls, respectively. Organophosphatase enzyme assays were performed as described in Example 11, infra.

Figure 15:
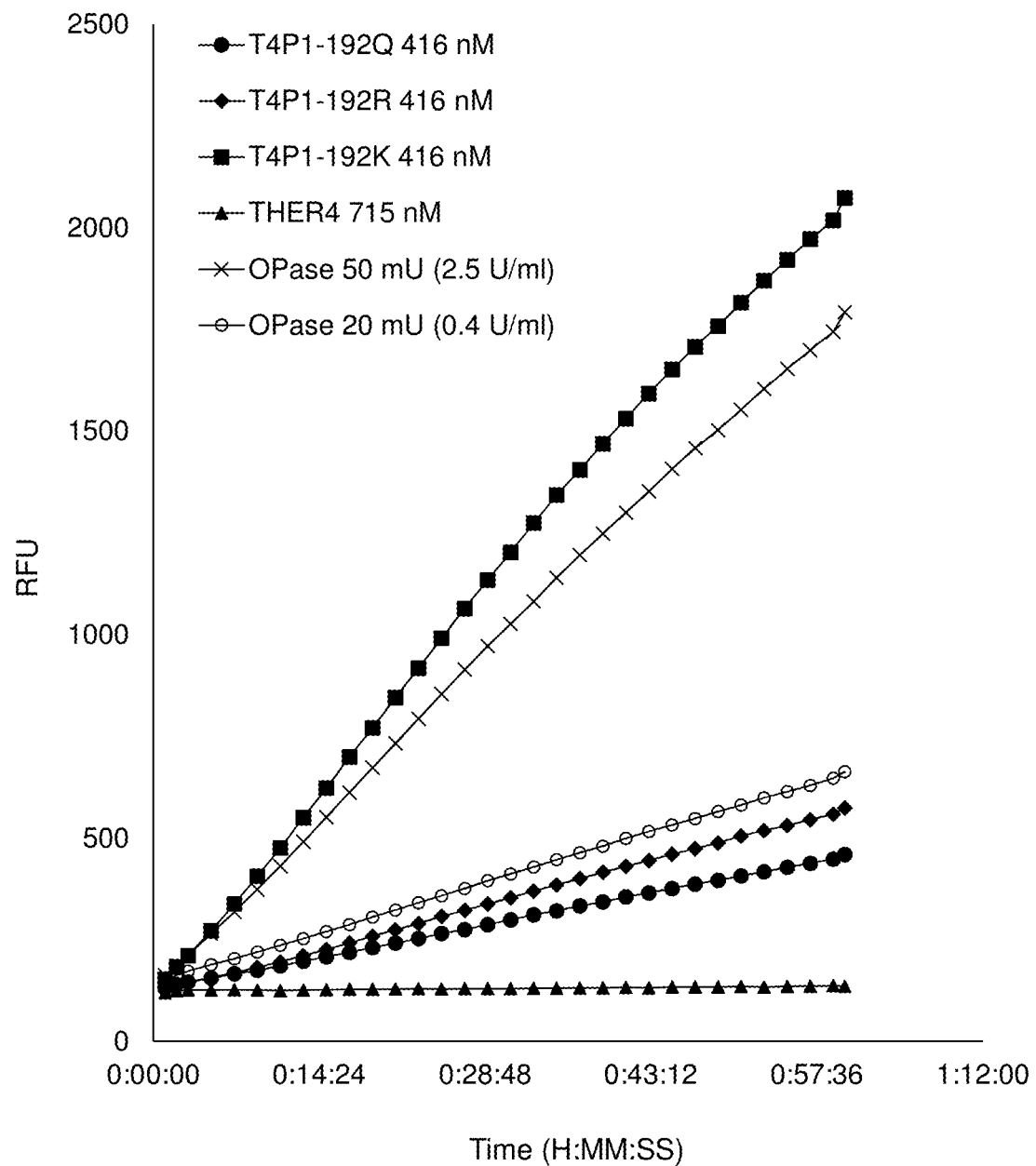

FIG. 15 shows results of an assay measuring the PON1 organophosphatase activity of THER4PON1 sequence variants (T4P1-192Q, T4P1-192R, T4P1-192K) purified from spent CHO culture supernatants. PON1 enzyme (OPase) and THER4 fusion protein were used as positive and negative controls, respectively. Control paraoxonse enzyme was used at two different dilutions (50 mU and 20 mU). Purification of fusion protein was performed as described in Example 10, infra, and organophosphatase enzyme assays were performed as described in Example 11, infra.

Figure 16:
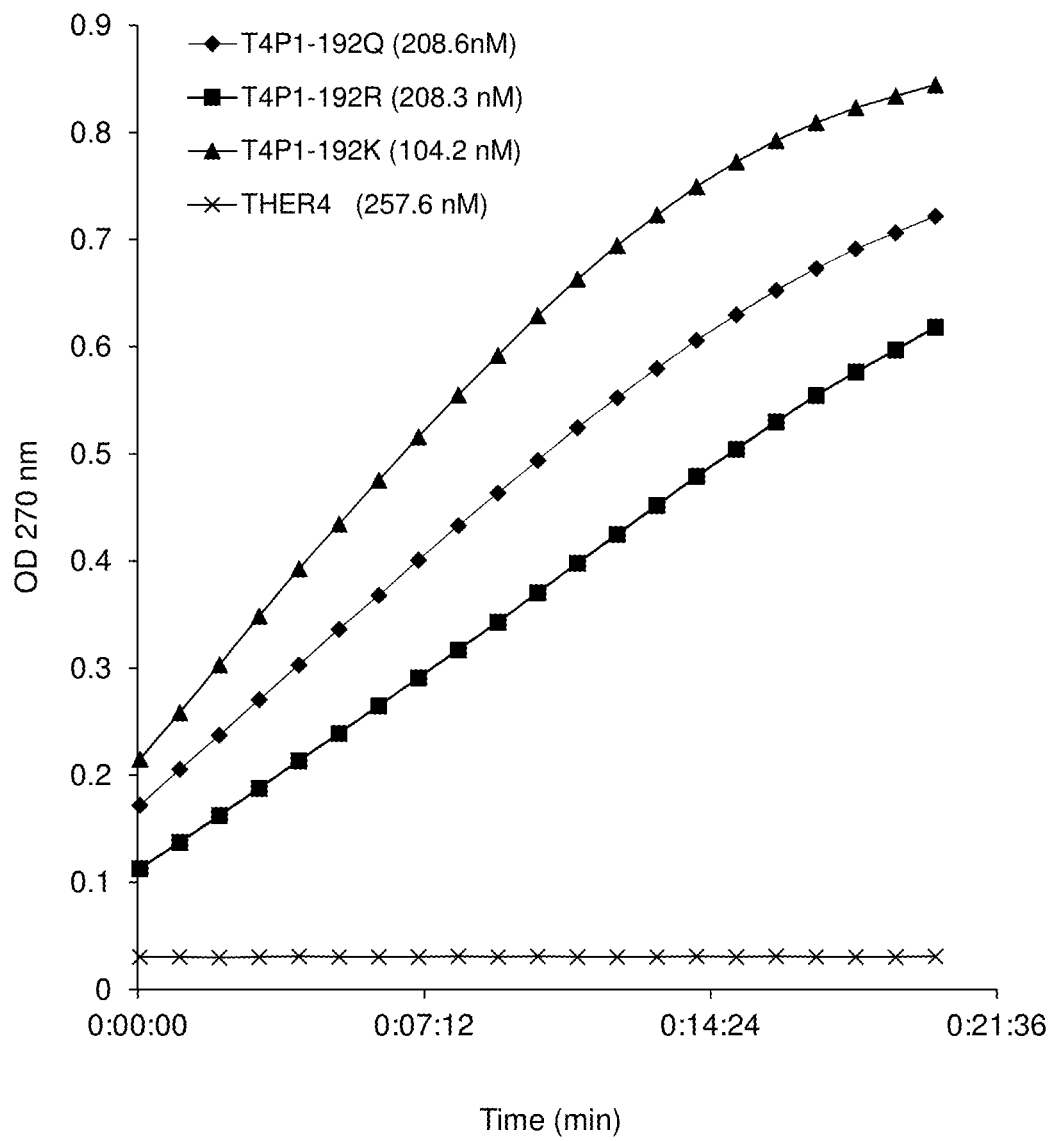

FIG. 16 shows results of an assay measuring arylesterase activity of THER4PON1 sequence variants (T4P1-192Q, T4P1-192R, T4P1-192K) purified from spent CHO culture supernatants. THER4 fusion protein was used as a negative control. Purification of fusion protein was performed as described in Example 10, infra, and arylesterase activity was measured as described in Example 11, infra.

Figure 17:
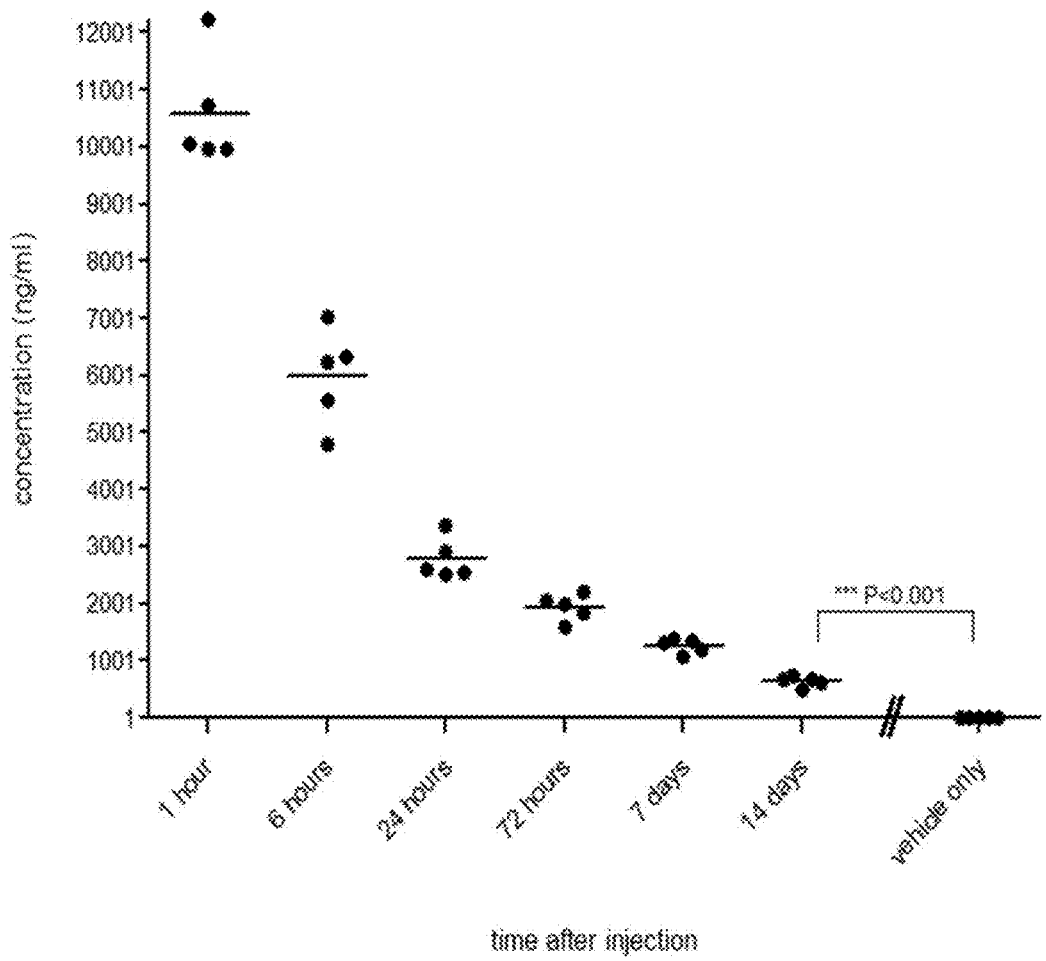

FIG. 17 shows results of PK analysis of purified ApoA1-lnk-hIgG-PON1 fusion protein after injection into wild-type mice. See Example 12, infra. The data shown summarize plasma concentrations (ng/ml) of THER4PON1 192R at different time points following injection.

DESCRIPTION OF THE INVENTION

I. Overview

The present invention provides compositions and methods relating to fusion polypeptides comprising a first polypeptide segment having cholesterol efflux activity and which is either an ApoA1 polypeptide or functional variant or fragment thereof or, alternatively, an ApoA-1 mimetic. In some aspects, the fusion polypeptide further includes a dimerizing domain with a peptide linker between the amino-terminal end of the dimerizing domain and the carboxyl-terminal end of the ApoA-1 polypeptide, variant, fragment, or mimetic, thereby allowing the fusion polypeptide to form stable dimers. In other, non-mutually exclusive aspects, the fusion polypeptides are bispecific constructs further comprising a second polypeptide segment carboxyl-terminal to the ApoA-1 polypeptide, variant, fragment, or mimetic and which confers a second biological activity. Exemplary second polypeptides include RNases, paraoxonases, platelet-activating factor acetylhydrolases (PAF-AHs), cholesterol ester transfer proteins (CETPs), lecithin-cholesterol acyl-transferases (LCATs), polypeptides that specifically bind to proprotein convertase subtilisin/kexin type 9 (PCSK9) and inhibit PCSK9 activity, and polypeptides that specifically bind to amyloid beta, any of which may be a naturally occurring protein or a functional variant or fragment thereof.

The fusion molecules of the present invention can be used, for example, to increase reverse cholesterol transport in a subject and provide therapeutic benefit in the treatment of various diseases. ApoA-1, the major protein of HDL, has already shown beneficial activity in clinical trials in patients with acute coronary syndrome. The ApoA-1 fusion molecules of the present invention can be used to treat coronary heart disease, acute coronary syndrome, and other cardiovascular diseases characterized by atherosclerosis such as, e.g., stroke. Fusion molecules of the present invention are also useful, for example, for the treatment of autoimmune diseases (e.g., rheumatoid arthritis, systemic lupus erythematosus), inflammatory diseases, type 2 diabetes, obesity, and neurodegenerative diseases (e.g., Alzheimer's disease). In some embodiments, fusion proteins of the present invention are used to replace defective ApoA-1 such as, for example, in the treatment of type 1 diabetes and dementia. In certain variations, fusion proteins as disclosed herein are used to treat multiple sclerosis (MS). ApoA-1 levels have been shown to be low in patients with MS, and ApoA-1 deficient mice have been shown to exhibit more neurodegeneration and worse disease in experimental allergic encephalomyelitis (EAE), a model for MS, than wild-type animals. See Meyers et al., *J. Neuroimmunol.* 277: 176-185, 2014. Data further suggests a positive neuroprotective effect of ApoA-1 on the central nervous system. See Gardner et al., *Frontiers in Pharmacology:* 20 Nov. 2015 doi: 10.3389/fphar.2015.00278.

Several studies support the use of ApoA-1 therapy for autoimmune disease. For example, patients with systemic lupus erythematosus (SLE) have low HDL-cholesterol levels and the HDL that is present is often damaged by myeloperoxidase-mediated methionine oxidation and tyrosine chlorination of ApoA-1, resulting in loss of ABCA1-dependent cholesterol efflux activity. See Shao et al., *J. Biol. Chem.* 281:9001-4, 2006; Hewing et al., *Arterioscler. Thromb. Vasc. Biol.* 34:779-89, 2014. This promotes loss of anti-inflammatory properties and generation of proinflammatory HDL seen in patients with SLE. See Skaggs et al., *Clin. Immunol.* 137:147-156, 2010; McMahon et al., *Arthritis Rheum.* 60:2428-2437, 2009. Autoantibodies to ApoA-1 are present in many patients with SLE, and SLE-disease activity assessed by SLEDAI and SLE disease related organ damage assessed by SLICC/ACR damage index are positively correlated with anti-ApoA-1 antibodies. See Batukla et al., *Ann. NY Acad. Sci.* 1108:137-146, 2007; Ahmed et al., *EXCLI Journal* 12:719-732, 2013. Further, increased ApoA-1 concentration attenuated autoimmunity and glomerulonephritis in lupus prone SLE 1, 2, 3 mice. See Black et al., *J. Immunol.* 195:4685-4698, 2015.

Cholesterol efflux capacity of HDL is also impaired in rheumatoid arthritis patients with high disease activity and is correlated with systemic inflammation and loss of HDL antioxidant activity. See Charles-Schoeman et al., *Arthritis Rheum.* 60:2870-2879, 2009; Charles-Schoeman et al., *Ann. Rheum. Dis.* 71:1157-1162, 2012. Treatment of arthritis in the Lewis rat by ApoA-1 and reconstituted HDL reduced acute and chronic joint inflammation, and decreased macrophage TLR2 expression and activation. See Wu et al., *Arterioscler. Thromb. Basc. Biol.* 34:543-551, 2014. Therapy of collagen-induced arthritis in rats with ApoA-1 mimetic peptide D-4F in combination with pravastatin significantly reduced disease activity. See Charles-Schoeman et al., *Clin. Immunol.* 127:234-244, 2008.

Fusion molecules of the present invention may also be used in the treatment of infectious disease. During infection and endotoxemia, significant alterations in lipid metabolism and lipoprotein composition occur, including a reduction in ApoA-1 and changes in HDL composition and size. HDL can bind and neutralize Gram-negative LPS and Gram-positive lipoteichoic acid, promoting clearance of these inflammatory products. Pharmacological studies support the benefit of recombinant ApoA-1 during bacterial infection. See, e.g., Pirillo et al., *Handb Exp Pharmacol.* 224:483-508, 2015.

Fusion molecules of the present invention may be used to treat sepsis. Low levels of HDL have been associated with higher mortality in sepsis patients. See Morin et al., *Front. Pharmacol.* 6:244, 2015; Monigari et al., *International Journal of Scientific and Research Publications*, Vol. 5, Issue 7, 2015; Tanaka et al., *Ann. Intensive Care* 7:60, 2017. In addition, low levels of PON1 have been reported in sepsis patients and are associated with higher mortality. See Bojic et al., *Disease Markers*, Vol. 2014, Article ID 427378, 2014; Inal et al., *Balkan Med. J.* 32:183-188, 2015. Supplementation with molecules of the present invention, including, for example, bifunctional ApoA-1 fusion molecules that contain a paraoxonase (e.g., PON1), can promote anti-inflammatory processes in the recipient that improve clinical outcome.

Bifunctional ApoA-1 fusion molecules of the present invention that contain a paraoxonase (e.g., PON1) are particularly useful for therapy of patients infected with *Pseudomonas aeruginosa*, a gram negative bacterium. This is particularly important for immunocompromised patients, where infections with *P. aeruginosa* are common. *P. aeruginosa* secrete virulence factors and form biofilm in response to small signaling molecules called acyl-homoserine lactones in a concentration-dependent process called quorum sensing (QS). Paraoxonase 1 degrades acyl-homoserine lactones and was shown to protect from lethality from *P. aeruginosa* in a transgenic in vivo model in *Drosophila melanogaster* where there are no endogenous PON homologs. See Estin et al., *Adv. Exp. Med. Biol.* 660:183-193, 2010.

Fusion molecules of the present invention may also be used in the treatment of inflammatory disease. For example, ApoA-1 fusion polypeptides and dimeric proteins as described herein may alter the phenotype of neutrophils, macrophages, and/or antigen-presenting cells to reduce proinflammatory responses. Molecules of the present invention cause efflux of cholesterol from cell membranes, mediated by transporter molecules such as, e.g., ABCA1. Efflux of cholesterol from antigen-presenting cells, including macrophages and dendritic cells, can inhibit proinflammatory responses mediated by these cells, resulting in reduced production of inflammatory cytokines. Studies support the benefit of ApoA-1 in mediating anti-inflammatory effects. For example, treatment with ApoA-1 was shown to inhibit the proinflammatory signaling in macrophages after stimulation of CD40 by altering the composition of lipid rafts. See Yin et al., *J. Atherosclerosis and Thrombosis* 19:923-36, 2012. ApoA-1 was also shown to cause a decrease in TRAF-6 recruitment to lipid rafts, and a decrease in activation of NF-kB. See id. Another study showed that treatment of human monocytes and macrophages with ApoA-1 or ApoA-1 mimetic 4F altered their response to LPS, resulting in decreased production of inflammatory cytokines MCP-1, MIP-1, RANTES, IL-6, and TNFα, but increased the production of IL-10. See Smythies et al., *Am. J. Physiol. Cell Physiol.* 298:C1538-48, 2010. doi:1152/ajpcell.00467.2009. Another study showed that treatment with ApoA-1 significantly decreased LPS-induced MCP-1 release from THP-1 cells, and inhibited expression of CD11b and VCAM-1. See Wang et al., *Cytokine* 49:194-2000, 2010. Thus ApoA-1 inhibits activation and adhesion of human monocytes and macrophages, and induces profound functional changes due to a differentiation to an anti-inflammatory phenotype.

Inflammatory lung diseases are among inflammatory diseases that may be treated with ApoA-1 fusion molecules as described herein. Serum ApoA-1 was found to be positively correlated with FEV1 in patients with combined atopy and asthma, but not in atopic and nonatopic subjects without asthma. See Barochia et al., *Am. J. Respir. Crit. Care Med.* 191:990-1000, 2015. In another study, patients with idiopathic pulmonary fibrosis had low levels of ApoA-1 in bronchiolar lavage fluid compared to controls (P<0.01). See Kim et al., *Am. J. Respir. Crit. Care Med.* 182:633-642, 2010. Further, intranasal treatment with ApoA-1 in mice treated with bleomycin was very effective in reducing the number of inflammatory cells and collagen deposition in the lungs. See id.

Obesity is another inflammatory disease amenable to treatment with ApoA-1 fusion molecules in accordance with the present invention. Evidence supports the use of ApoA-1 and HDL to combat obesity. See, e.g., Mineo et al., *Circ. Res.* 111:1079-1090, 2012. For example, overexpression of ApoA-1 or administration of the ApoA-1 mimetic peptide D-4F has been shown to decrease white adipose mass and insulin resistance and increase energy expenditure in mice fed a high-fat diet. Further, in ob/ob mice, the ApoA-1 mimetic L-4F was shown to lower adiposity and inflammation and improve glucose tolerance. Id.

Yet another disorder that may be treated with ApoA-1 fusion molecules in accordance with the present invention is nephrotic syndrome (NS), which is associated with a higher risk for cardiovascular disease in patients. Urinary wastage of filterable HDL (i.e., HDL3) and lipid-poor apo A1 is a common feature of patients with nephrotic syndrome. This is typically due to decreased reuptake of these molecules via cubulin/megalin receptors in the renal proximal tubule. See Barth et al., *Trends Cardiovasc. Med.* 11:26-31, 2001. ApoA-1 fusion molecules comprising an Fc region as described herein would bypass the need for reuptake in this usual manner, since the molecules are being recycled via FcRn due to the presence of the Fc domain.

Fusion molecules as described herein may also be used for therapy of patients with cancer. It is expected that ApoA-1 fusion polypeptides and dimeric proteins of the present invention, while reducing proinflammatory responses, enhance activation and tumor infiltration of $CD8^+$ T-cells. Studies support the efficacy of ApoA-1 therapy in animal models of cancer and have shown that ApoA-1 therapy can cause a specific increase in $CD8^+$ T cells in tumors. See, e.g., Zamanian-Daryoush et al., *J. Biol. Chem.* 288:21237-21252, 2013. In some aspects, ApoA-1 fusion molecules of the present invention are useful in combination with one or more other anti-cancer therapies such as, for example, an anti-cancer immunotherapy.

In certain aspects, the present invention provides a way to stabilize an active ApoA-1 dimer while also controlling the maturation from pre-beta particles to discoid particles and spherical particles by providing a flexible linker between a dimerizing domain (e.g., an Fc domain) and the C-terminus of the ApoA-1 polypeptide, or functional variant, fragment, or mimetic thereof. A previous ApoA-1-Ig molecule not containing a linker exhibits low activity in cholesterol efflux assays compared to wild-type ApoA1. In contrast, dimerizing fusion polypeptides of the present invention retain ApoA-1 activity in cholesterol efflux assays and also allow for further improvements such as, e.g., fusion of an RNase (e.g., RNase 1) or other polypeptide segments C-terminal to the dimerizing domain. In certain preferred embodiments, the use of an Fc region as the dimerizing domain also allows for increased half-life of the dimer.

While not intending to be bound by theory, it is believed that the length of the linker controls the ability of the stable ApoA-1 dimer to expand as it takes up cholesterol. The invention provides ApoA-1 fusion molecules containing flexible linkers between the C-terminus of an ApoA-1 polypeptide, or variant, fragment, or mimetic thereof, and the N-terminus of a dimerizing domain such as, e.g., an Fc domain. Linkers are of sufficient length to allow ApoA-1, or the functional variant, fragment, or mimetic thereof, to mediate cholesterol efflux from cells, an initial and critical step in Reverse Cholesterol Transport (RCT). Linkers are typically between 2 and 60 amino acids in length. It is believed that ApoA-1 fusion molecules with alternative linker lengths have distinct functional properties by controlling the maturation of the HDL particle by constraining the C-terminus of ApoA-1. HDL discoid particles of intermediate size may have improved atheroprotective properties, and may have improved CNS transport properties. The molecules of this invention may change the progress of HDL maturation at these intermediate discoid stages, thereby improving efficacy of the fusion proteins of the invention relative to wild type ApoA-1 proteins. The molecules of this invention are likely to affect the structure and composition of spherical HDL particles which are composed of trimeric ApoA-1 particles (see Silva et al., *Natl. Acad. Sci. USA* 105:12176-12181, 2008). It is likely that molecules of this invention will interact with natural ApoA-1 in the formation of larger spherical HDL particles.

In certain embodiments, the dimerizing domain is a immunoglobulin Fc region. ApoA-1-Fc fusion molecules of the present invention extend ApoA-1 half-life while retaining ApoA-1 reverse cholesterol efflux and eliminating the requirement for extensive lipid formulation. In addition, the presence of the Fc region allows purification using immobilized Protein A according to standard practices in and antibody and Fc fusion protein manufacturing.

Structural studies of ApoA-1 (see, e.g., Gogonea, *Frontiers Pharmacol.* 6:318, 2016) show that ApoA-1 assumes multiple conformations as it matures from lipid-free monomer to higher order forms. Recent data derived from small angle neutron scattering (SANS) show low resolution structures of ApoA-1 dimers in an open configuration around a lipid core, called the super double helix (DSH) model. Other structures from SANS studies show ApoA-1 in different open configurations depending on the composition of the lipid core; in these structures, the C-terminus of the ApoA-1 monomers are in different positions relative to each other. Similarly, spherical ApoA-1 particles that incorporate a third ApoA-1 monomer show the C-terminus of each monomer in a different position compared to the positions in dimeric discoid ApoA-1. See, e.g., Gogonea, supra. The flexible linkers of the present disclosure are of sufficient length to allow ApoA-1 to assume these positions without conformational constraint.

In certain embodiments, ApoA-1-[linker]-[dimerizing domain] molecules of the present invention include an additional polypeptide segment fused carboxyl-terminal to the dimerizing domain. Such variations allow for the creation of bispecific molecules with ApoA-1 functional activity and a second biological activity.

In some aspects of the present invention, bispecific fusion molecules are provided comprising a (i) first polypeptide segment with reverse cholesterol transport activity and which is either an ApoA1 polypeptide or functional variant or fragment thereof or, alternatively, an ApoA1 mimetic and (ii) a second polypeptide segment carboxyl-terminal to the first polypeptide segment, wherein the second polypeptide segment is selected from an RNase, a paraoxonase, a platelet-activating factor acetylhydrolase (PAF-AH), a cholesterol ester transfer protein (CETP), a lecithin-cholesterol acyltransferase (LCAT), a polypeptide that specifically binds to proprotein convertase subtilisin/kexin type 9 (PCSK9) and inhibits PCSK9 activity, and a polypeptide that specifically binds to amyloid beta. Such second polypeptides may be a naturally occurring protein or a functional variant or fragment thereof. In some embodiments, a linker and dimerizing domain is included between the first and second polypeptides as summarized above. In alternative embodiments, the fusion polypeptide lacks a dimerizing domain.

In some embodiments of the present ApoA-1 fusion molecules that lack an Fc region, the fusion molecule may be conjugated to PEG to provide extended half-life. Such variations may include bispecific molecules as described herein, such as, e.g., fusion molecules comprising an RNase, a paraoxonase, a platelet-activating factor acetylhydrolase (PAF-AH), a cholesterol ester transfer protein (CETP), a lecithin-cholesterol acyltransferase (LCAT), a polypeptide that specifically binds to proprotein convertase subtilisin/kexin type 9 (PCSK9) and inhibits PCSK9 activity, or a polypeptide that specifically binds to amyloid beta.

In some embodiments of a bispecific molecule as summarized above, the second polypeptide segment is an RNase. A preferred RNase is human RNase 1 or a functional variant or fragment thereof. In particular variations, the RNase retains its sensitivity to inhibition by cytoplasmic inhibitor and has very low toxicity to cells, but is highly active extracellularly. RNase has anti-inflammatory properties by digestion of inflammatory extracellular RNA and provides additional therapeutic benefit for treatment of various diseases, including cardiovascular diseases (e.g., coronary artery disease, stroke), autoimmune diseases, inflammatory diseases, type 2 diabetes, infectious disease, and neurodegenerative diseases (e.g., Alzheimer' disease).

For example, a bispecific ApoA-1 fusion molecule comprising an RNase segment as described herein may be used, e.g., for treatment of an inflammatory disease such as, for example, an inflammatory lung disease. One study has shown that TLR3, an RNA sensor, has a major role in the development of ARDS-like pathology in the absence of a viral pathogen. See Murray et al., *Am. J. Respir. Crit. Care Med.* 178:1227-1237, 2008. Oxygen therapy is a major therapeutic intervention in ARDS, but contributes to further lung damage and susceptibility to viral infection. Oxygen therapy was a major stimulus for increased TLR3 expression and activation in cultured human epithelial cells, and absence or blockade of TLR3 protected mice from lung injury and inflammation after exposure to hyperoxic conditions. See Murray et al., supra. Another study has shown that TLR3 activation by extracellular RNA occurs in response to acute hypoxia, and that therapy in mice with RNaseA diminished lung inflammation after acute hypoxia. See Biswas et al., *Eur. J. Immunol.* 45: 3158-3173, 2015. A bispecific ApoA-1 fusion molecule comprising an RNase segment as described herein may also be used, e.g., for treatment of an autoimmune disease such as, for example, systemic lupus erythematosus (SLE). Studies show, for example, a role of RNA immune complexes and RNA receptors, including TLR7, in SLE disease pathogenesis, as well as a protective effect of RNase overexpression in mouse models of SLE. See, e.g., Sun et al., *J. Immunol.* 190:2536-2543, 2013.

In other embodiments of a bispecific molecule as summarized above, the second polypeptide segment is a paraoxonase. A preferred paraoxonase is human paraoxonase 1 (PON1) or a functional variant or fragment thereof. Paraoxonase has multiple activities including organophosphatase, phosphotriesterase, arylesterase, and thiolactonase. The organophosphatase activity confers protection against toxic organophosphates including insecticides such as paraoxon. Paraoxonase bispecific fusion molecules provide additional therapeutic benefit for the treatment of diseases amenable to ApoA-1-mediated therapy, including, for example, through its atheroprotective, antioxidant, anti-inflammatory, and/or neuroprotective properties. In some alternative embodiments, PON1 may attached to an ApoA-1 fusion molecule of the present invention through its natural, high affinity binding to ApoA-1, which binding is mediated by Tyr71 of PON1 (see Huang et al., *J. Clin. Invest.* 123:3815-3828, 2013). Incubating an ApoA-1 fusion molecule with recombinant or natural PON1 prior to administration will be sufficient to "load" PON1 onto the ApoA-1 fusion molecule.

A bispecific ApoA-1 fusion molecule comprising a paraoxonase segment as described herein may be used, e.g., for treatment of an autoimmune disease or an inflammatory disease. For example, studies support use of a paraoxonase for treatment of autoimmune disease such as systemic lupus erythematosus (SLE). The autoantibody titer in many patients with systemic lupus erythematosus (SLE) is correlated with loss of activity of PON1 (see Batukla et al., *Ann. NY Acad. Sci.* 1108:137-146, 2007), and SLE-disease activity assessed by SLEDAI and SLE disease related organ damage assessed by SLICC/ACR damage index are negatively correlated with PON1 activity (see Ahmed et al., *EXCLI Journal* 12:719-732, 2013). PON1 activity is significantly reduced in patients with SLE, and is a risk factor for atherosclerosis. See Kiss et al., *Ann. NY Acad. Sci.* 108:83-91, 2007. In addition, other studies support use of a paraoxonase for treatment of inflammatory disease such as inflammatory lung diseases. One study showed that patients with late lung diseases long after exposure to sulfur mustard gas (SM), including asthma, chronic obstructive pulmonary disease (COPD) and bronchiectasis, have significantly reduced levels of PON1 in bronchiolar lavage fluid (p<0.0001). See Golmanesh et al., *Immunopharmacol. Immunotoxical.* 35:419-425, 2013. Another study showed that Iranian veterans exposed to SM twenty years ago still have significantly low serum levels of PON1 activity, and low PON1 was correlated with lung disease severity. See Taravati et al., *Immunopharmacol. Immunotoxicol.* 34:706-713, 2012.

Bispecific ApoA-1 fusion molecules comprising either an RNase segment or a paraoxonase segment as described herein may also be used, e.g., for treatment of a neurological disease. Such bispecific molecules are transported to the brain where they deliver a protective paraoxonase or RNase enzyme. For example, PON1 is protective in the brain because of its antioxidant properties, and RNase is protective by digesting extracellular RNA that promotes inflammation via stimulation of TLR7 and other RNA receptors. Exemplary neurological diseases amenable to treatment using an ApoA-1/paraoxonase or ApoA1/RNase bispecific molecule of the present invention include multiple sclerosis, Parkinson's disease, and Alzheimer's disease.

Attachment of myeloperoxidase (MPO) inhibitors to ApoA-1 fusion molecules of the present invention may be particularly desirable as a way to protect ApoA-1 from inactivation due to oxidation mediated by MPO, and can also similarly protect paraoxonase from MPO-mediated oxidation and inactivation in the context of a bispecific fusion polypeptide comprising a paraoxonase such as PON1. Myeloperoxidase-mediated oxidation of ApoA-1 promotes crosslinking of ApoA-1, and may be implicated in the mechanism that leads to amyloid deposition in atherosclerotic plaques in vivo. See Chan et al., *J. Biol. Chem.* 290: 10958-71, 2015. For a review of MPO inhibitors, see Malle et al., *Br J Pharmacol.* 152: 838-854, 2007. The attachment of a MPO inhibitor to a molecule of the present invention can also localize the MPO inhibition to selectively protect ApoA-1 from oxidation while preserving MPO activity important in anti-microbial activity.

In other embodiments of a bispecific molecule as summarized above, the second polypeptide segment is selected from a cholesterol ester transfer protein (CETP), and a lecithin-cholesterol acyltransferase (LCAT). CETP is involved in one of the major mechanisms by which HDL particles can deliver cholesterol to the liver during the process of reverse cholesterol transport (RCT), specifically, through unloading and transferring of cholesterol to LDL, which then transports cholesterol back to the liver via LDL receptors. This process of unloading requires CETP. By improving the initial part of the RCT pathway through the delivery of improved ApoA-1 molecules such as provided herein, then adding other RCT components can provide an attractive and potentially synergistic therapeutic approach. Providing more exogenous CETP in the form of a bispecific fusion molecule containing ApoA-1 can enhance CETP activity and overall reverse cholesterol transport.

Bispecific fusions containing LCAT can provide an alternative means of enhancing endogenous CETP. Lecithin-cholesterol acyltransferase (LCAT) is an enzyme that is associated with HDL and converts free cholesterol to cholesteryl esters, which is then sequestered into the HDL particle and allows for its spherical shape formation. A human recombinant LCAT given to mice lacking LCAT significantly improved HDL-C levels, and when given to human ApoA-1 transgenic mice, the increase in HDL-C was eight-fold, suggesting synergy. See Rousset et al., *J Pharmacol Exp Ther.* 335:140-8, 2010. A recombinant human LCAT fusion to Fc has been reported (see Spahr et al., *Protein Sci.* 22:1739-53, 2013), and a bispecific molecule containing both ApoA-1 and LCAT may also improve RCT more efficiently than a mono-specific protein of either alone.

In other embodiments of a bispecific molecule as summarized above, the second polypeptide segment is a polypeptide that specifically binds to proprotein convertase subtilisin/kexin type 9 (PCSK9) and inhibits PCSK9 activity. In some variations, a PCSK9-binding polypeptide inhibits PCSK9 activity by inhibiting its binding to the LDL receptor. In some variations, a PCSK9-binding polypeptide is a PCSK9-specific single chain antibody such as, for example, a PCSK9-specific scFv. Anti-PCSK9 antibodies that inhibit PCSK9 activity are generally known in the art (see, e.g., International PCT Publication Nos. WO 2008/057459, WO 2010/077854, and WO 2012/109530; US Patent Application Publication No. 2011/0142849), and anti-PCSK9 monoclonal antibodies have been approved by FDA for treatment of hypercholesterolemia. A bispecific molecule that mediates cholesterol efflux and inhibits PCSK9 is expected to be a potent therapy for vascular disease because it would reduce inflammation through multiple pathways. Cholesterol efflux from macrophages and neutrophils reduces inflammatory cytokines and myeloperoxidase production and provides the beneficial effects of HDL, while inhibition of PCSK9 increases expression of the LDL receptor, thus reducing inflammatory LDL.

In other embodiments of a bispecific molecule as summarized above, the second polypeptide segment is a polypeptide that specifically binds to amyloid beta (Aβ). In a specific variation, the second polypeptide is a Aβ-specific single chain antibody such as, for example, an Aβ-specific scFv. A scFv specific for amyloid beta peptide is described, for example, by Cattepoel et al., *PLoS One* 6:e18296, 2011. In such embodiments, the Aβ-binding polypeptide is typically fused C-terminal to ApoA-1, or C-terminal to the dimerizing domain, if present. This bispecific fusion molecule has improved properties for therapy of patients with Alzheimer's disease.

II. Fusion Polypeptides and Dimeric Proteins

Accordingly, in one aspect, the present invention provides a fusion polypeptide comprising, from an amino-terminal position to a carboxyl-terminal position, ApoA1-L1-D, where ApoA1 is a first polypeptide segment having cholesterol efflux activity and which is selected from (i) a naturally occurring ApoA-1 polypeptide or a functional variant or fragment thereof and (ii) an ApoA-1 mimetic; L1 is a first polypeptide linker; and D is a dimerizing domain. In some embodiments, the fusion polypeptide further includes a second polypeptide segment located carboxyl-terminal to the dimerizing domain. In particular variations, the second polypeptide segment is (a) a naturally occurring RNase, paraoxonase, platelet-activating factor acetylhydrolase (PAF-AH), cholesterol ester transfer protein (CETP), or lecithin-cholesterol acyltransferase (LCAT); (b) a functional variant or fragment of any of the naturally occurring proteins specified in (a); or (c) a polypeptide that specifically binds to amyloid beta (Aβ) such as, e.g., an Aβ-specific scFv. Such a fusion polypeptide comprising a second polypeptide segment may be represented by the formula ApoA1-L1-D-L2-P (from an amino-terminal position to a carboxyl-terminal position), where ApoA1, L1, and D are each as previously defined, where L2 is a second polypeptide linker and is optionally present, and where P is the second polypeptide segment.

In another aspect, the present invention provides a fusion polypeptide comprising a first polypeptide segment having cholesterol efflux activity and which is selected from (i) a naturally occurring ApoA-1 polypeptide or a functional variant or fragment thereof and (ii) an ApoA-1 mimetic, and a second polypeptide segment located carboxyl-terminal to the first polypeptide segment, where the second polypeptide segment is (a) a naturally occurring RNase, paraoxonase, platelet-activating factor acetylhydrolase (PAF-AH), cholesterol ester transfer protein (CETP), or lecithin-cholesterol acyltransferase (LCAT); (b) a functional variant or fragment of any of the naturally occurring proteins specified in (a); (c) a polypeptide that specifically binds to proprotein convertase subtilisin/kexin type 9 (PCSK9) and inhibits PCSK9 activity such as, e.g., a PCSK9-specific scFv; or (d) a polypeptide that specifically binds to amyloid beta (Aβ) such as, e.g., an Aβ-specific scFv. In some variations, the fusion polypeptide further includes a linker polypeptide located carboxyl-terminal to the first polypeptide segment and amino-terminal to the second polypeptide segment. In some embodiments, the fusion polypeptide further includes a dimerizing domain, which can be located, for example, carboxyl-terminal to the first polypeptide segment and amino-terminal to the second polypeptide segment.

Functional variants of a particular naturally occurring protein specified above can be readily identified using routine assays for assessing the variant for a relevant biological or biochemical activity corresponding to the natural protein. For example, in the case of ApoA-1, variants may be assayed for their ability to induce cholesterol efflux using known cholesterol efflux assays such as described herein. See, e.g., Tang et al., *J Lipid Res.* 47:107-14, 2006. In the case of RNase such as human RNase 1, variants may be assayed for their ability to digest single or double-stranded RNA is known assays to assess ribonuclease activity. See, e.g., Libonati and Sorrentino, *Methods Enzymol.* 341234-248, 2001. Paraoxonase 1 (PON1) variants may be assayed for phosphotriesterase activity using diethyl p-nitrophenol phosphate (paraoxon) as a substrate, or for arylesterase activity using phenyl acetate as a substrate. See, e.g., Graves and Scott, *Curr Chem Genomics* 2:51-61, 2008. In addition to these tests, the EnzChek Paraoxonase Assay Kit (E33702: ThermoFisher) is a highly sensitive, homogeneous fluorometric assay (excitation/emission maxima ~360/450 nm) for the organophosphatase activity of paraoxonase and is based on the hydrolysis of a proprietary, fluorogenic organophosphate analog. This assay has been used in several published studies of PON1 activity in patient sera. See, e.g., Brian et al., *Chemosphere* 120:479-485, 2015; Rector et al., *Am J Physiol Endocrinol Metab* 293:E500-E506, 2007. Assays to assess relevant CETP and LCAT activities are also known. For example, assays for measuring LCAT and CETP enzyme activity are commercially available and include, e.g., Cell Biolabs Cat. No. STA-615, Sigma-Aldrich Cat. No. MAK107, and Roar Biomedical Cat. No. RB-LCAT for LCAT, and Abcam Cat. No. ab65383 and Sigma-Aldrich Cat. No. MAK106 for CETP.

In the case of Aβ-binding or PCSK9-binding activity, polypeptides such as, e.g., single chain antibodies may be assessed for binding activity using any of various known assays. For example, one assay system employs a commercially available biosensor instrument (BIAcore™ Pharmacia Biosensor, Piscataway, N.J.), wherein a binding protein (e.g., Aβ-binding candidate, such as an antibody) is immobilized onto the surface of a sensor chip, and a test sample containing a soluble antigen (e.g., Aβ peptide) is passed through the cell. If the immobilized protein has affinity for the antigen, it will bind to the antigen, causing a change in the refractive index of the medium, which is detected as a change in surface plasmon resonance of the gold film. This system allows the determination of on- and off-rates, from which binding affinity can be calculated, and assessment of stoichiometry of binding. Use of this instrument is disclosed, e.g., by Karlsson (*J. Immunol. Methods* 145:229-240, 1991) and Cunningham and Wells (*J. Mol. Biol.* 234:554-563, 1993). Aβ-binding polypeptides can also be used within other assay systems known in the art. Such systems include Scatchard analysis for determination of binding affinity (see Scatchard, *Ann. NY Acad. Sci.* 51: 660-672, 1949) and calorimetric assays (see Cunningham et al., *Science* 253: 545-548, 1991; Cunningham et al., *Science* 254:821-825, 1991).

Naturally occurring polypeptide segments for use in accordance with the present invention (e.g., a naturally occurring ApoA-1 polypeptide, RNase, paraoxonase, or platelet-activating factor acetylhydrolase) includes naturally occurring variants such as, for example, allelic variants and interspecies homologs consistent with the disclosure.

Functional variants of a particular reference polypeptide (e.g., a wild-type human ApoA-1) are generally characterized as having one or more amino acid substitutions, deletions or additions relative to the reference polypeptide. These changes are preferably of a minor nature, that is conservative amino acid substitutions (see, e.g., Table 2, infra, which lists some exemplary conservative amino acid substitutions) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), or other antigenic epitope or binding domain. (See generally Ford et al., *Protein Expression and Purification* 2:95-107, 1991.) DNAs encoding affinity tags are available from commercial suppliers (e.g., Pharmacia Biotech, Piscataway, N.J.). Conservative substitutions may also be selected from the following: 1) Alanine, Glycine; 2) Aspartate, Glutamate; 3) Asparagine, Glutamine; 4) Arginine, Lysine; 5) Isoleucine, Leucine, Methionine, Valine; 6) Phenylalanine, Tyrosine, Tryptophan; 7) Serine, Threonine; and 8) Cysteine, Methionine (see, e.g., Creighton, *Proteins* (1984)).

TABLE 2

| \multicolumn{6}{c}{Conservative amino acid substitutions} |
| --- | --- | --- | --- | --- | --- |
| Basic | Acidic | Polar | Hydrophobic | Aromatic | Small |
| Arginine | Glutamate | Glutamine | Leucine | Phenylalanine | Glycine |
| Lysine | Aspartate | Asparagine | Isoleucine | Tryptophan | Alanine |
| Histidine | | | Valine | Tyrosine | Serine |
| | | | Methionine | | Threonine |
| | | | | | Methionine |

Essential amino acids in a naturally occurring polypeptide can be identified according to procedures known in the art, such as site-directed mutagenesis or alanine-scanning mutagenesis (Cunningham and Wells, *Science* 244:1081-1085, 1989; Bass et al., *Proc. Natl. Acad. Sci. USA* 88:4498-4502, 1991). In the latter technique, single alanine mutations are introduced at every residue in the molecule, and the resultant mutant molecules are tested for biological activity (e.g., cholesterol efflux for ApoA-1 variants) to identify amino acid residues that are critical to the activity of the molecule. In addition, sites of relevant protein interactions can be determined by analysis of crystal structure as determined by such techniques as nuclear magnetic resonance, crystallography or photoaffinity labeling. The identities of essential amino acids can also be inferred from analysis of homologies with related proteins (e.g., species orthologs retaining the same protein function).

Multiple amino acid substitutions can be made and tested using known methods of mutagenesis and screening, such as those disclosed by Reidhaar-Olson and Sauer *Science* 241: 53-57, 1988 or Bowie and Sauer *Proc. Natl. Acad. Sci. USA* 86:2152-2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Another method that can be used is region-directed mutagenesis (Derbyshire et al., *Gene* 46:145, 1986; Ner et al., *DNA* 7:127, 1988).

Variant nucleotide and polypeptide sequences can also be generated through DNA shuffling. (See, e.g., Stemmer, *Nature* 370:389, 1994; Stemmer, *Proc. Nat'l Acad. Sci. USA* 91:10747, 1994; International Publication No. WO 97/20078.) Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

As previously discussed, a polypeptide fusion in accordance with the present invention can include a polypeptide segment corresponding to a "functional fragment" of a particular polypeptide. Routine deletion analyses of nucleic acid molecules can be performed to obtain functional fragments of a nucleic acid molecule encoding a given polypeptide. As an illustration, ApoA-1-encoding DNA molecules having the nucleotide sequence of residues 70-816 of SEQ ID NO:1 can be digested with Bal31 nuclease to obtain a series of nested deletions. The fragments are then inserted into expression vectors in proper reading frame, and the expressed polypeptides are isolated and tested for the ability to induce cholesterol efflux. One alternative to exonuclease digestion is to use oligonucleotide-directed mutagenesis to introduce deletions or stop codons to specify production of a desired fragment. Alternatively, particular fragments of a gene encoding a polypeptide can be synthesized using the polymerase chain reaction.

Accordingly, using methods such as discussed above, one of ordinary skill in the art can prepare a variety of polypeptides that (i) are substantially identical to a reference polypeptide (e.g., residues 19-267 or 25-267 of SEQ ID NO:2 for a human wild-type ApoA-1 polypeptide) and (ii) retains the desired functional properties of the reference polypeptide.

Polypeptide segments used within the present invention (e.g., polypeptide segments corresponding to ApoA-1, RNase, paraoxonase, platelet-activating factor acetylhydrolase, dimerizing domains such as, e.g., Fc fragments) may be obtained from a variety of species. If the protein is to be used therapeutically in humans, it is preferred that human polypeptide sequences be employed. However, non-human sequences can be used, as can variant sequences. For other uses, including in vitro diagnostic uses and veterinary uses, polypeptide sequences from humans or non-human animals can be employed, although sequences from the same species as the patient may be preferred for in vivo veterinary use or for in vitro uses where species specificity of intermolecular reactions is present. Thus, polypeptide segments for use within the present invention can be, without limitation, human, non-human primate, rodent, canine, feline, equine, bovine, ovine, porcine, lagomorph, and avian polypeptides, as well as variants thereof.

In certain embodiments, the first polypeptide segment is a human wild-type ApoA-1 polypeptide or a functional variant or fragment thereof. For example, in some embodiments, the first polypeptide segment comprises an amino acid sequence having at least 80% identity with amino acid residues 19-267 or 25-267 of SEQ ID NO:2. In more particular embodiments, the first polypeptide segment comprises an amino acid sequence having at least 85%, at least 90%, or at least 95% identity with amino acid residues 19-267 or 25-267 of SEQ ID NO:2. In yet other embodiments, the first polypeptide segment comprises an amino acid sequence having at least 96%, at least 97%, at least 98%, at least 99%, or 100% sequence identity with amino acid residues 19-267 or 25-267 of SEQ ID NO:2. In some embodiments, the first polypeptide segment is a functional variant of human wild-type ApoA-1 comprising one or more amino acid modifications that confer resistance to oxidation by myeloperoxidase (MPO). In specific variations, valine at the amino acid position corresponding to position 156 of mature human wild-type ApoA-1 is replaced by glutamate or lysine, and/or arginine at the amino acid position corresponding to position 173 of mature human wild-type ApoA-1 is replaced by cysteine (also referred to herein, respectively, as V156[E/K] and R173C variants, mutations, or substitutions). Position 156 of the mature human wild-type ApoA-1 corresponds to amino acid position 180 of SEQ ID NO:2, and position 173 of mature human wild-type ApoA-1 corresponds to amino acid position 197 of SEQ ID NO:2. V156K and R173C mutations have improved activity and half-life in atherosclerotic mice compared to wild-type ApoA-1. See Cho et al., *Exp Mol Med* 41:417, 2009. In some variations, tyrosine at the amino acid position corresponding to position 192 of mature human wild-type ApoA-1 is replaced by serine, glutamine, asparagine, histidine, or phenylalanine (also referred to herein as a Y192[S/Q/N/H/F] variant, mutation, or substitution). Position 192 of the mature human wild-type ApoA-1 corresponds to amino acid position 216 of SEQ ID NO:2. In some variations, at least one of the methionine residues at the amino acid positions corresponding to positions 86, 112, and 148 of the mature human wild-type ApoA-1 is replaced with leucine, isoleucine, or valine (also referred to herein as M86[L/I/V], M112[L/I/V], and M148[L/I/V] variants, mutations, or substitutions). Positions 86, 112, and 148 of the mature human wild-type ApoA-1 respectively correspond to amino acid positions 110, 136, and 172 of SEQ ID NO:2. In some variations, at least one of the tryptophan residues at the amino acid positions corresponding to positions 8, 50, 72, and 108 of the mature human wild-type ApoA-1 is replaced with phenylalanine (also referred to herein W8F, W50F, W72F, and W108F variants, mutations, or substitutions); in some such embodiments, all four of these tryptophan residues are replaced with phenylalanine (also referred to herein as a 4WF variant or mutation). Positions 8, 50, 72, and 108 of the mature human wild-type ApoA-1 respectively correspond to amino acid positions 32, 74, 96, and 132 of SEQ ID NO:2. In some embodiments, the first polypeptide segment is an ApoA-1 variant comprising at least one of the V156[E/K] and Y192[S/Q/N/H/F] substitutions, and optionally at least one of the M86[L/I/V], M112[L/I/V], and M148[L/I/V] substitutions; in some such embodiments, the first polypeptide segment is an ApoA-1 variant comprising both of the V156[E/K] and Y192[S/Q/N/H/F] substitutions. In more particular variations, the first polypeptide segment is an ApoA-1 variant comprising the specific V156[E/K] and/or Y192[S/Q/N/H/F] substitution(s) of any one of variant combinations A1-A17 as shown in Table 3, infra.

TABLE 3

Combinations of ApoA-1 V156[E/K] & Y192[S/Q/N/H/F] Variants

| ApoA-1 Variant Combination | Amino Acid at Position No.:† | |
|---|---|---|
| | 156 | 192 |
| A1 | E | S |
| A2 | E | Q |
| A3 | E | N |
| A4 | E | H |
| A5 | E | F |
| A6 | E | Y (wild-type) |
| A7 | K | S |
| A8 | K | Q |
| A9 | K | N |
| A10 | K | H |
| A11 | K | F |
| A12 | K | Y (wild-type) |
| A13 | V (wild-type) | S |
| A14 | V (wild-type) | Q |
| A15 | V (wild-type) | N |
| A16 | V (wild-type) | H |
| A17 | V (wild-type) | F |

†Amino acid positions 156 and 192 are according to the mature human wild-type ApoA-1 and respectively correspond to amino acid positions 180 and 216 of SEQ ID NO: 2.

In other embodiments, the first polypeptide segment is an ApoA-1 mimetic such as, for example, the 4F peptide (see Song et al., *Int. J. Biol. Sci.* 5:637-646, 2009). ApoA-1 mimetics are generally known in the art and are reviewed in Reddy et al., *Curr. Opin. Lipidol.* 25: 304-308, 2014.

In certain embodiments comprising a second polypeptide segment carboxyl-terminal to the first polypeptide segment (e.g., carboxyl-terminal to a dimerizing domain), the second polypeptide segment is an RNase. In some embodiments, the RNase is a human RNAse 1 or a functional variant or fragment thereof. For example, in some embodiments, the second polypeptide segment comprises an amino acid sequence having at least 80% identity with amino acid residues 544-675 or 548-675 of SEQ ID NO:4. In more particular embodiments, the second polypeptide segment comprises an amino acid sequence having at least 85%, at least 90%, or at least 95% identity with amino acid residues 544-675 or 548-675 of SEQ ID NO:4. In yet other embodiments, the second polypeptide segment comprises an amino acid sequence having at least 96%, at least 97%, at least 98%, at least 99%, or 100% sequence identity with amino acid residues 544-675 or 548-675 of SEQ ID NO:4.

In other embodiments comprising a second polypeptide segment carboxyl-terminal to the first polypeptide segment (e.g., carboxyl-terminal to a dimerizing domain), the second polypeptide segment is a paraoxonase. In some embodiments, the paraoxonase is a human paraoxonase 1 (PON1) or a functional variant or fragment thereof. For example, in some embodiments, the second polypeptide segment comprises an amino acid sequence having at least 80% identity with amino acid residues 16-355 of SEQ ID NO:12, amino acid residues 16-355 of SEQ ID NO:42, or amino acid residues 16-355 of SEQ ID NO:44. In more particular embodiments, the second polypeptide segment comprises an amino acid sequence having at least 85%, at least 90%, or at least 95% identity with amino acid residues 16-355 of SEQ ID NO:12, amino acid residues 16-355 of SEQ ID NO:42, or amino acid residues 16-355 of SEQ ID NO:44. In yet other embodiments, the second polypeptide segment comprises an amino acid sequence having at least 96%, at least 97%, at least 98%, at least 99%, or 100% sequence identity with amino acid residues 16-355 of SEQ ID NO:12, amino acid residues 16-355 of SEQ ID NO:42, or amino acid residues 16-355 of SEQ ID NO:44. (SEQ ID NO:12 is a 192Q form, SEQ ID NO:42 is a 192K variant, and SEQ ID NO:44 is a 192R variant of a human paraoxonase molecule, where numbering is based on full length PON1, including the leader peptide.) In some variations where the second polypeptide segment is a variant of a human PON1 polypeptide as above, tyrosine at the amino acid position corresponding to position 185 of full-length human wild-type PON1 is replaced by histidine, glutamine, or serine (also referred to herein as a Y185[H/Q/S] variant, mutation, or substitution) and/or phenylalanine at the amino acid position corresponding to position 293 of full-length human wild-type PON1 is replaced by histidine, glutamine, or asparagine (also referred to herein as a F293[H/Q/N] variant, mutation, or substitution). Positions 185 and 293 of the full-length human wild-type PON1 respectively correspond to amino acid positions 185 and 293 of SEQ ID NO:12, SEQ ID NO:42, or SEQ ID NO:44. In more particular variations where the second polypeptide segment is a variant of a human PON1 polypeptide as above, the second polypeptide segment comprises the specific Y185[H/Q/S] and/or F293 [H/Q/N] substitution(s) of any one of variant combinations P1-P15 as shown in Table 4, infra. Other PON1 amino acid variants that may be incorporated into a paraoxonase polypeptide segment in the context of the present invention are disclosed, e.g., in US Patent Application Publication Nos. 2014/0079682 and 2012/0213834, which are incorporated by reference herein.

TABLE 4

Combinations of PON1 Y185[H/Q/S] & F293[H/Q/N] Variants

| PON1 Variant Combination | Amino Acid at Position No.:† | |
|---|---|---|
| | 185 | 293 |
| P1 | H | H |
| P2 | H | Q |
| P3 | H | N |
| P4 | H | F (wild-type) |
| P5 | Q | H |
| P6 | Q | Q |
| P7 | Q | N |
| P8 | Q | F (wild-type) |
| P9 | S | H |
| P10 | S | Q |
| P11 | S | N |

TABLE 4-continued

Combinations of PON1 Y185[H/Q/S] & F293[H/Q/N] Variants

| PON1 Variant Combination | Amino Acid at Position No.:† | |
|---|---|---|
| | 185 | 293 |
| P12 | S | F (wild-type) |
| P13 | Y (wild-type) | H |
| P14 | Y (wild-type) | Q |
| P15 | Y (wild-type) | N |

†Amino acid positions 185 and 293 are according to the full-length human wild-type PON1 and respectively correspond to amino acid positions 185 and 293 of SEQ ID NO: 12, SEQ ID NO: 42, or SEQ ID NO: 44.

ApoA1 variant combination A3 of Table 3 with PON1 variant combination P2 of Table 4, and represents the specific combination of ApoA1 Y156E and Y192N substitutions together with PON1 Y185H and F293Q substitutions). A fusion polypeptide comprising a paraoxonase carboxyl-terminal to the first polypeptide segment and comprising variants from Tables 3 and 4 herein may be a fusion polypeptide comprising any one of the specific combinations represented by Aβ1-Aβ255 in Table 5; in some such embodiments, the first polypeptide is otherwise 100% identical to residues 19-267 or 25-267 of SEQ ID NO:2 and/or the second polypeptide segment is otherwise 100% identical to residues 16-355 of SEQ ID NO:12, amino acid residues 16-355 of SEQ ID NO:42, or amino acid residues 16-355 of SEQ ID NO:44.

TABLE 5

ApoA-1 V156[E/K]/Y192[S/Q/N/H/F] Variants† in Combination with PON1 Y185[H/Q/S]/F293[H/Q/N] Variants‡

| | P1 | P2 | P3 | P4 | P5 | P6 | P7 | P8 | P9 | P10 | P11 | P12 | P13 | P14 | P15 |
|---|---|---|---|---|---|---|---|---|---|---|---|---|---|---|---|
| A1 | AP1 | AP18 | AP35 | AP52 | AP69 | AP86 | AP103 | AP120 | AP137 | AP154 | AP171 | AP188 | AP205 | AP222 | AP239 |
| A2 | AP2 | AP19 | AP36 | AP53 | AP70 | AP87 | AP104 | AP121 | AP138 | AP155 | AP172 | AP189 | AP206 | AP223 | AP240 |
| A3 | AP3 | AP20 | AP37 | AP54 | AP71 | AP88 | AP105 | AP122 | AP139 | AP156 | AP173 | AP190 | AP207 | AP224 | AP241 |
| A4 | AP4 | AP21 | AP38 | AP55 | AP72 | AP89 | AP106 | AP123 | AP140 | AP157 | AP174 | AP191 | AP208 | AP225 | AP242 |
| A5 | AP5 | AP22 | AP39 | AP56 | AP73 | AP90 | AP107 | AP124 | AP141 | AP158 | AP175 | AP192 | AP209 | AP226 | AP243 |
| A6 | AP6 | AP23 | AP40 | AP57 | AP74 | AP91 | AP108 | AP125 | AP142 | AP159 | AP176 | AP193 | AP210 | AP227 | AP244 |
| A7 | AP7 | AP24 | AP41 | AP58 | AP75 | AP92 | AP109 | AP126 | AP143 | AP160 | AP177 | AP194 | AP211 | AP228 | AP245 |
| A8 | AP8 | AP25 | AP42 | AP59 | AP76 | AP93 | AP110 | AP127 | AP144 | AP161 | AP178 | AP195 | AP212 | AP229 | AP246 |
| A9 | AP9 | AP26 | AP43 | AP60 | AP77 | AP94 | AP111 | AP128 | AP145 | AP162 | AP179 | AP196 | AP213 | AP230 | AP247 |
| A10 | AP10 | AP27 | AP44 | AP61 | AP78 | AP95 | AP112 | AP129 | AP146 | AP163 | AP180 | AP197 | AP214 | AP231 | AP248 |
| A11 | AP11 | AP28 | AP45 | AP62 | AP79 | AP96 | AP113 | AP130 | AP147 | AP164 | AP181 | AP198 | AP215 | AP232 | AP249 |
| A12 | AP12 | AP29 | AP46 | AP63 | AP80 | AP97 | AP114 | AP131 | AP148 | AP165 | AP182 | AP199 | AP216 | AP233 | AP250 |
| A13 | AP13 | AP30 | AP47 | AP64 | AP81 | AP98 | AP115 | AP132 | AP149 | AP166 | AP183 | AP200 | AP217 | AP234 | AP251 |
| A14 | AP14 | AP31 | AP48 | AP65 | AP82 | AP99 | AP116 | AP133 | AP150 | AP167 | AP184 | AP201 | AP218 | AP235 | AP252 |
| A15 | AP15 | AP32 | AP49 | AP66 | AP83 | AP100 | AP117 | AP134 | AP151 | AP168 | AP185 | AP202 | AP219 | AP236 | AP253 |
| A16 | AP16 | AP33 | AP50 | AP67 | AP84 | AP101 | AP118 | AP135 | AP152 | AP169 | AP186 | AP203 | AP220 | AP237 | AP254 |
| A17 | AP17 | AP34 | AP51 | AP68 | AP85 | AP102 | AP119 | AP136 | AP153 | AP170 | AP187 | AP204 | AP221 | AP238 | AP255 |

†ApoA-1 Variant Combinations A1-A17 are shown in Table 3.
‡PON1 Variant Combinations P1-P15 are shown in Table 4.

In some embodiments of a fusion polypeptide comprising a paraoxonase carboxyl-terminal to the first polypeptide segment (e.g., carboxyl-terminal to a dimerizing domain), where the first polypeptide segment comprises an amino acid sequence having at least 80%, at least 85%, at least 90%, or at least 95% identity with amino acid residues 19-267 or 25-267 of SEQ ID NO:2 and the second polypeptide segment comprises an amino acid sequence having at least 80% identity, at least 85%, at least 90%, or at least 95% identity with amino acid residues 16-355 of SEQ ID NO:12, amino acid residues 16-355 of SEQ ID NO:42, or amino acid residues 16-355 of SEQ ID NO:44, the first polypeptide segment is an ApoA-1 variant comprising the specific V156[E/K] and/or Y192[S/Q/N/H/F] substitution(s) of any one of variant combinations A1-A17 as shown in Table 3 herein and the second polypeptide segment is a variant of a human PON1 polypeptide comprising the specific Y185[H/Q/S] and/or F293[H/Q/N] substitution(s) of any one of variant combinations P1-P15 as shown in Table 4 herein. Table 5, infra, shows ApoA-1 variant combinations A1-A17 from Table 3 arrayed against PON1 variant combinations P1-P15 from Table 4, where each "Aβ[44]" designation represents a specific combination of an ApoA-1 V156[E/K]/Y192[S/Q/N/H/F] variant with a PON1 Y185 [H/Q/S]/F293[H/Q/N] variant (for example, "Aβ20" represents a combination of ApoA1/PON1 variants combining In yet other embodiments comprising a second polypeptide segment carboxyl-terminal to the first polypeptide segment (e.g., carboxyl-terminal to a dimerizing domain), the second polypeptide segment is a platelet-activating factor acetylhydrolase (PAF-AH). In some embodiments, the platelet-activating factor acetylhydrolase is a human PAF-AH or a functional variant or fragment thereof. For example, in some embodiments, the second polypeptide segment comprises an amino acid sequence having at least 80% identity with amino acid residues 22-441 of SEQ ID NO:32. In more particular embodiments, the second polypeptide segment comprises an amino acid sequence having at least 85%, at least 90%, or at least 95% identity with amino acid residues 22-441 of SEQ ID NO:32. In yet other embodiments, the second polypeptide segment comprises an amino acid sequence having at least 96%, at least 97%, at least 98%, at least 99%, or 100% sequence identity with amino acid residues 22-441 of SEQ ID NO:32.

In still other embodiments comprising a second polypeptide segment carboxyl-terminal to the first polypeptide segment (e.g., carboxyl-terminal to a dimerizing domain), the second polypeptide segment is a cholesterol ester transfer protein (CETP). In some embodiments, the cholesterol ester transfer protein is a human CETP or a functional variant or fragment thereof. For example, in some embodiments, the second polypeptide segment comprises an amino acid sequence having at least 80% identity with amino acid residues 18-493 of SEQ ID NO:30. In more particular embodiments, the second polypeptide segment comprises an amino acid sequence having at least 85%, at least 90%, or at least 95% identity with amino acid residues 18-493 of SEQ ID NO:30. In yet other embodiments, the second polypeptide segment comprises an amino acid sequence having at least 96%, at least 97%, at least 98%, at least 99%, or 100% sequence identity with amino acid residues 18-493 of SEQ ID NO:30.

Polypeptide linkers for use in accordance with the present invention can be naturally-occurring, synthetic, or a combination of both. The linker joins two separate polypeptide regions (e.g., a dimerizing domain and an ApoA-1 polypeptide) and maintains the linked polypeptide regions as separate and discrete domains of a longer polypeptide. The linker can allow the separate, discrete domains to cooperate yet maintain separate properties (e.g., in the case of an Fc region dimerizing domain linked to an ApoA-1 polypeptide, Fc receptor (e.g., FcRn) binding may be maintained for the Fc region, while functional properties of the ApoA-1 polypeptide (e.g., lipid binding) will be maintained). For examples of the use of naturally occurring as well as artificial peptide linkers to connect heterologous polypeptides, see, e.g., Hallewell et al., *J. Biol. Chem.* 264, 5260-5268, 1989; Alfthan et al., *Protein Eng.* 8, 725-731, 1995; Robinson and Sauer, *Biochemistry* 35, 109-116, 1996; Khandekar et al., *J. Biol. Chem.* 272, 32190-32197, 1997; Fares et al., *Endocrinology* 139, 2459-2464, 1998; Smallshaw et al., *Protein Eng.* 12, 623-630, 1999; U.S. Pat. No. 5,856,456.

Typically, residues within the linker polypeptide are selected to provide an overall hydrophilic character and to be non-immunogenic and flexible. As used herein, a "flexible" linker is one that lacks a substantially stable higher-order conformation in solution, although regions of local stability are permissible. In general, small, polar, and hydrophilic residues are preferred, and bulky and hydrophobic residues are undesirable. Areas of local charge are to be avoided; if the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Pro, Leu, Ile, Lys, and Arg residues will be avoided (unless present within an immunoglobulin hinge region of the linker), Pro residues due to their hydrophobicity and lack of flexibility, and Lys and Arg residues due to potential immunogenicity. The sequence of the linker will also be designed to avoid unwanted proteolysis.

In certain embodiments, linker L1 comprises at least two or at least three amino acid residues. In some embodiments, L1 comprises at least four, at least five, at least six, at least seven, at least eight, at least nine, at least 10, at least 11, at least 12, at least 13, at least 14, at least 15, at least 16, at least 20, at least 26, or at least 36 amino acid residues. In particular variations, L1 consists of from two to 60, from two to 50, from two to 40, from two to 36, from two to 35, from two to 31, from two to 30, from two to 26, from three to 60, from three to 50, from three to 40, from three to 36, from three to 35, from three to 31, from three to 30, from three to 26, from four to 60, from four to 50, from four to 40, from four to 36, from four to 35, from four to 31, from four to 30, or from four to 26 amino acid residues. In other variations, L1 consists of from five to 60, from five to 50, from five to 40, from five to 36, from five to 35, from five to 31, from five to 30, from five to 26, from six to 60, from six to 50, from six to 40, from six to 36, from six to 35, from six to 31, from six to 30, from six to 26, from seven to 60, from seven to 50, from seven to 40, from seven to 36, from seven to 35, from seven to 31, from seven to 30, or from seven to 26 amino acid residues. In other variations, L1 consists of from eight to 60, from eight to 50, from eight to 40, from eight to 36, from eight to 35, from eight to 31, from eight to 30, from eight to 26, from nine to 60, from nine to 50, from nine to 40, from nine to 36, from nine to 35, from nine to 31, from nine to 30, from nine to 26, from 10 to 60, from 10 to 50, from 10 to 40, from 10 to 36, from 10 to 35, from 10 to 31, from 10 to 30, or from 10 to 26 amino acid residues. In other variations, L1 consists of from 11 to 60, from 11 to 50, from 11 to 40, from 11 to 36, from 11 to 35, from 11 to 31, from 11 to 30, from 11 to 26, from 12 to 60, from 12 to 50, from 12 to 40, from 12 to 36, from 12 to 35, from 12 to 31, from 12 to 30, from 12 to 26, from 15 to 60, from 15 to 50, from 15 to 40, from 15 to 36, from 15 to 35, from 15 to 31, from 15 to 30, or from 15 to 26 amino acid residues. In other variations, L1 consists of from 16 to 60, from 16 to 50, from 16 to 40, or from 16 to 36 amino acid residues. In yet other variations, L1 consists of from 20 to 60, from 20 to 50, from 20 to 40, from 20 to 36, from 25 to 60, from 25 to 50, from 25 to 40, or from 25 to 36 amino acid residues. In still other variations, L1 consists of from 26 to 60, from 26 to 50, from 26 to 40, or from 26 to 36 amino acid residues. In more specific variations, L1 consists of 16 amino acid residues, 21 amino acid residues, 26 amino acid residues, 31 amino acid residues, or 36 amino acid residues. In some embodiments, L1 comprises or consists of the amino acid sequence shown in residues 268-293 of SEQ ID NO:2, residues 268-288 of SEQ ID NO:26, residues 268-283 of SEQ ID NO:22, SEQ ID NO:54, or residues 268-303 of SEQ ID NO:24.

Exemplary L2 linkers comprise at least three amino acid residues and are typically up to 60 amino acid residues. In certain variations, L2 linkers have a range of sequence lengths as described above for L1. In a specific embodiment of a polypeptide comprising the formula ApoA1-L1-D-L2-P and where L2 is present and P is an RNase, L2 comprises or consists of the amino acid sequence shown in residues 526-543 of SEQ ID NO:4.

In certain embodiments, polypeptide linkers comprise a plurality of glycine residues. For example, in some embodiments, a polypeptide linker (e.g., L1) comprises a plurality of glycine residues and optionally at least one serine residue. In particular variations, a polypeptide linker (e.g., L1) comprises the sequence Gly-Gly-Gly-Gly-Ser (SEQ ID NO:15), such as, e.g., two or more tandem repeats of the amino acid sequence of SEQ ID NO:15. In some embodiments, a linker comprises the sequence [Gly-Gly-Gly-Gly-Ser]$_n$ ([SEQ ID NO:15]$_n$), where n is a positive integer such as, for example, an integer from 1 to 5, from 2 to 5, from 3 to 5, from 1 to 6, from 2 to 6, from 3 to 6, or from 4 to 6. In a specific variation of a polypeptide linker comprising the formula [Gly-Gly-Gly-Gly-Ser]$_n$, n is 4. In another specific variation of a polypeptide linker comprising the formula [Gly-Gly-Gly-Gly-Ser]$_n$, n is 3. In yet another specific variation of a polypeptide linker comprising the formula [Gly-Gly-Gly-Gly-Ser]$_n$, n is 5. In still another specific variation of a polypeptide linker comprising the formula [Gly-Gly-Gly-Gly-Ser]$_n$, n is 6. In certain embodiments, a polypeptide linker comprises a series of glycine and serine residues (e.g., [Gly-Gly-Gly-Gly-Ser]$_n$, where n is defined as above) inserted between two other sequences of the polypeptide linker (e.g., any of the polypeptide linker sequences described herein). In other embodiments, a polypeptide linker includes glycine and serine residues (e.g., [Gly-Gly-Gly-Gly-Ser]$_n$, where n is defined as above) attached at one or both ends of another sequence of the polypeptide linker (e.g., any of the polypeptide linker sequences described herein). In one embodiment, a polypeptide linker comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of glycine and serine amino acid residues (e.g., [Gly-Gly-Gly-Gly-Ser]$_n$, wherein n is defined as above).

In another embodiment, a polypeptide linker comprises a non-naturally occurring immunoglobulin hinge region, e.g., a hinge region that is not naturally found in an immunoglobulin and/or a hinge region that has been altered so that it differs in amino acid sequence from a naturally occurring immunoglobulin hinge region. In one embodiment, mutations can be made to a hinge region to make a polypeptide linker. In one embodiment, a polypeptide linker comprises a hinge domain that does not comprise a naturally occurring number of cysteines, i.e., the polypeptide linker comprises either fewer cysteines or a greater number of cysteines than a naturally occurring hinge molecule.

Various dimerization domains are suitable for use in accordance with the fusion polypeptides and dimeric fusion proteins as described herein. In certain embodiments, the dimerizing domain is an immunoglobulin heavy chain constant region, such as an Fc region. The Fc region may be a native sequence Fc region or a variant Fc region. In some embodiments, the Fc region lacks one or more effector functions (e.g., one or both of ADCC and CDC effector functions).

In some embodiments, the dimerizing domain is an Fc region of a human antibody with a mutation in the CH2 region so that the molecule is not glycosylated, including but not limited to N297 (EU numbering for human IgG heavy chain constant region) (corresponding to amino acid position 375 of SEQ ID NO:2). In another embodiment, the Fc region is human IgG1 (γ1) with the three cysteines of the hinge region (C220, C226, C229) each changed to serine, and the proline at position 238 of the CH2 domain changed to serine. In another preferred embodiment, the Fc region is human γ1 with N297 changed to any other amino acid. In another embodiment, the Fc region is human γ1 with one or more amino acid substitutions between Eu positions 292 and 300. In another embodiment, the Fc region is human γ1 with one or more amino acid additions or deletions at any position between residues 292 and 300. In another embodiment, the Fc region is human γ1 with an SCC hinge (i.e., with cysteine C220 changed to serine and with a cysteine at each of Eu positions 226 and 229) or an SSS hinge (i.e., each of the three cysteines at Eu positions 220, 226, and 229 changed to serine). In further embodiments, the Fc region is human γ1 with an SCC hinge and a P238 mutation. In another embodiment, the Fc domain is human γ1 with mutations that alter binding by Fc gamma receptors (I, II, III) without affecting FcRn binding important for half-life. In further embodiments, an Fc region is as disclosed in Ehrhardt and Cooper, *Curr. Top. Microbiol. Immunol.* 2010 Aug. 3 (Immunoregulatory Roles for Fc Receptor-Like Molecules); Davis et al., *Ann. Rev. Immunol.* 25:525-60, 2007 (Fc receptor-like molecules); or Swainson et al., *J. Immunol.* 184:3639-47, 2010.

In certain embodiments, an Fc region is a human IgG variant (e.g., a human γ1 variant) in which one or more of the cysteine residues in the hinge region have each been changed to a non-cysteine residue. For example, in some embodiments, the Fc region is a human IgG variant in which all of the cysteine residues in the hinge region have each been changed to a non-cysteine residue. A particularly suitable Fc region is a human γ1 variant in which each of the three cysteines at Eu positions 220, 226, and 229 changed; in some such variations, each cysteine is replaced with serine.

In some embodiments of a fusion polypeptide comprising an Fc dimerizing domain, the Fc region comprises an amino acid substitution that alters the antigen-independent effector functions of the fusion protein. In some such embodiments, the Fc region includes an amino acid substitution that alters the circulating half-life of the resulting molecule. Such antibody derivatives exhibit either increased or decreased binding to FcRn when compared to antibodies lacking these substitutions and, therefore, have an increased or decreased half-life in serum, respectively. Fc variants with improved affinity for FcRn are anticipated to have longer serum half-lives, and such antibodies have useful applications in methods of treating mammals where long half-life of the administered antibody is desired. In contrast, Fc variants with decreased FcRn binding affinity are expected to have shorter half-lives, and such antibodies are also useful, for example, for administration to a mammal where a shortened circulation time may be advantageous, e.g., where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization to the brain, kidney, and/or liver is desired. In one exemplary embodiment, the antibodies of the invention exhibit reduced transport across the epithelium of kidney glomeruli from the vasculature. In another embodiment, the fusion proteins of the invention exhibit reduced transport across the blood brain barrier (BBB) from the brain, into the vascular space. In one embodiment, a fusion protein with altered FcRn binding comprises an Fc region having one or more amino acid substitutions within the "FcRn binding loop" of the Fc domain. Exemplary amino acid substitutions which altered FcRn binding activity are disclosed in International PCT Publication No. WO 05/047327, which is incorporated by reference herein.

In other embodiments, a fusion polypeptide of the present invention comprises an Fc variant comprising an amino acid substitution which alters the antigen-dependent effector functions of the polypeptide, in particular ADCC or complement activation, e.g., as compared to a wild type Fc region. In an exemplary embodiment, such fusion polypeptides exhibit altered binding to an Fc gamma receptor (FcγR, e.g., CD16). Such fusion polypeptides exhibit either increased or decreased binding to FcγR when compared to wild-type polypeptides and, therefore, mediate enhanced or reduced effector function, respectively. Fc variants with improved affinity for FcγRs are anticipated to enhance effector function, and such fusion proteins have useful applications in methods of treating mammals where target molecule destruction is desired. In contrast, Fc variants with decreased FcγR binding affinity are expected to reduce effector function, and such fusion proteins are also useful, for example, for treatment of conditions in which target cell destruction is undesirable, e.g., where normal cells may express target molecules, or where chronic administration of the antibody might result in unwanted immune system activation. In one embodiment, the fusion polypeptide comprising an Fc region exhibits at least one altered antigen-dependent effector function selected from the group consisting of opsonization, phagocytosis, complement dependent cytotoxicity, antigen-dependent cellular cytotoxicity (ADCC), or effector cell modulation as compared to a polypeptide comprising a wild-type Fc region.

In one embodiment, a fusion polypeptide comprising an Fc region exhibits altered binding to an activating FcγR (e.g., FcγI, FcγIIa, or FcγRIIIa). In another embodiment, the fusion protein exhibits altered binding affinity to an inhibitory FcγR (e.g., FcγRIIb). Exemplary amino acid substitutions which altered FcR or complement binding activity are disclosed in International PCT Publication No. WO 05/063815, which is incorporated by reference herein.

A fusion polypeptide comprising an Fc region may also comprise an amino acid substitution that alters the glycosylation of the Fc region. For example, the Fc domain of the fusion protein may have a mutation leading to reduced glycosylation (e.g., N- or O-linked glycosylation) or may comprise an altered glycoform of the wild-type Fc domain (e.g., a low fucose or fucose-free glycan). In another embodiment, the molecule has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO 05/018572 and US Patent Application Publication No. 2007/0111281, which are incorporated by reference herein.

It will be understood by those of skill in the art that various embodiments of Fc variants as described herein can be combined in the fusion polypeptides of the present invention, unless the context clearly indicates otherwise.

In some embodiments, a dimerizing domain is an Fc region comprising an amino acid sequence having at least 80%, at least 85%, at least 90%, or at least 95% identity with an amino acid sequence selected from sequence shown in (i) residues 294-525 or 294-524 of SEQ ID NO:2, or (ii) residues 294-525 or 294-524 of SEQ ID NO:13. In yet other embodiments, the Fc region comprises an amino acid sequence having at least 96%, at least 97%, at least 98%, at least 99%, or 100% sequence identity with the amino acid sequence shown in (i) residues 294-525 or 294-524 of SEQ ID NO:2, or (ii) residues 294-525 or 294-524 of SEQ ID NO:13.

In some embodiments of a fusion polypeptide comprising ApoA1-L1-D as described above, the fusion polypeptide comprises an amino acid sequence having at least 80%, at least 85%, at least 90%, or at least 95% identity with an amino acid sequence selected from sequence shown in (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24. In yet other embodiments, the fusion polypeptide comprises an amino acid sequence having at least 96%, at least 97%, at least 98%, at least 99%, or 100% sequence identity with the amino acid sequence shown in (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24. In some embodiments, the fusion polypeptide comprises an amino acid sequence having at least 80%, at least 85%, at least 90%, or at least 95% identity with (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24, where the fusion polypeptide comprises at least one amino acid substitution in the first ("ApoA1") polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24. In some variations, the fusion polypeptide comprises an amino acid sequence having at least 80%, at least 85%, at least 90%, or at least 95% identity with an amino acid sequence selected from sequence shown in (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24, where the fusion polypeptide comprises, in the ApoA1 polypeptide segment, the specific V156[E/K] and/or Y192[S/Q/N/H/F] substitution(s) of any one of variant combinations A1-A17 as shown in Table 3 herein; in some such embodiments, the fusion polypeptide comprises an amino acid sequence that is otherwise 100% identical to (i) residues 19-525, 19-524, 25-525, or 25-524 of SEQ ID NO:2, (ii) residues 19-525, 19-524, 25-525, or 25-524 of SEQ ID NO:13, (iii) residues 19-501, 19-500, 25-501, or 25-500 of SEQ ID NO:20, (iv) residues 19-515, 19-514, 25-515, or 25-514 of SEQ ID NO:22, (v) residues 19-520, 19-519, 25-520, or 25-519 of SEQ ID NO:26, or (vi) residues 19-535, 19-534, 25-535, or 25-534 of SEQ ID NO:24.

In some embodiments of a fusion polypeptide comprising ApoA1-L1-D-L2-P as described above and where P is an RNase, the fusion polypeptide comprises an amino acid sequence having at least 80%, at least 85%, at least 90%, or at least 95% identity with the amino acid sequence shown in (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59. In yet other embodiments, the fusion polypeptide comprises an amino acid sequence having at least 96%, at least 97%, at least 98%, at least 99%, or 100% sequence identity with the amino acid sequence shown in (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59. In some embodiments, the fusion polypeptide comprises an amino acid sequence having at least 80%, at least 85%, at least 90%, or at least 95% identity with (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59, where the fusion polypeptide comprises at least one amino acid substitution in the first ("ApoA1") polypeptide segment selected from V156[E/K], Y192[S/Q/N/H/F], M86[L/I/V], M112[L/I/V], M148[L/I/V], W8F, W50F, W72F, and W132F as described herein (e.g., V156 [E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59. In some variations, the fusion polypeptide comprises an amino acid sequence having at least 80%, at least 85%, at least 90%, or at least 95% identity with an amino acid sequence selected from sequence shown in (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59, where the fusion polypeptide comprises, in the ApoA1 polypeptide segment, the specific V156[E/K] and/or Y192[S/Q/N/H/F] substitution(s) of any one of variant combinations A1-A17 as shown in Table 3 herein; in some such embodiments, the fusion polypeptide comprises an amino acid sequence that is otherwise 100% identical to (i) residues 19-675 or 25-675 of SEQ ID NO:4, (ii) residues 19-675 or 25-675 of SEQ ID NO:14, (iii) residues 19-671 or 25-671 of SEQ ID NO:58, or (iv) residues 19-671 or 25-671 of SEQ ID NO:59.

In some embodiments of a fusion polypeptide comprising ApoA1-L1-D-L2-P as described above and where P is a paraoxonase, the fusion polypeptide comprises an amino acid sequence having at least 80%, at least 85%, at least 90%, or at least 95% identity with the amino acid sequence shown in (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48. In yet other embodiments, the fusion polypeptide comprises an amino acid sequence having at least 96%, at least 97%, at least 98%, at least 99%, or 100% sequence identity with the amino acid sequence shown in (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48. In some embodiments, the fusion polypeptide comprises an amino acid sequence having at least 80%, at least 85%, at least 90%, or at least 95% identity with (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48, where the fusion polypeptide comprises (A) at least one amino acid substitution in the first ("ApoA1") polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F), and/or (B) at least one substitution in the second ("P") polypeptide segment selected from Y185[H/Q/S] and F293[H/Q/N] as described herein; in some such embodiments, the fusion polypeptide comprises an amino acid sequence that is otherwise 100% identical to (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48; in particular variations, the fusion polypeptide comprises substitutions of both (A) and (B) as above (e.g., V156[E/K] and/or Y192[S/Q/N/H/F] and optionally at least one of M86[L/I/V], M112[L/I/V], and M148[L/I/V] in the first polypeptide segment and Y185[H/Q/S] and optionally F293[H/Q/N] in the second polypeptide segment). In some embodiments, the fusion polypeptide comprises an amino acid sequence having at least 80%, at least 85%, at least 90%, or at least 95% identity with (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48, where the fusion polypeptide comprises (A) in the ApoA1 polypeptide segment, the specific V156[E/K] and/or Y192[S/Q/N/H/F] substitution(s) of any one of variant combinations A1-A17 as shown in Table 3 herein, and/or (B) in the P polypeptide segment, the specific Y185[H/Q/S] and/or F293[H/Q/N] substitution(s) of any one of variant combinations P1-P15 as shown in Table 4 herein (e.g., a fusion polypeptide comprising a specific combination of variants selected from combinations AP1-AP255 as shown in Table 5 herein); in some such embodiments, the fusion polypeptide comprises an amino acid sequence that is otherwise 100% identical to (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48.

In some embodiments of a fusion polypeptide comprising ApoA1-L1-D-L2-P as described above and where P is a platelet-activating factor acetylhydrolase (PAF-AH), the fusion polypeptide comprises an amino acid sequence having at least 80%, at least 85%, at least 90%, or at least 95% identity with the amino acid sequence shown in residues 19-963 or 25-963 of SEQ ID NO:34. In yet other embodiments, the fusion polypeptide comprises an amino acid sequence having at least 96%, at least 97%, at least 98%, at least 99%, or 100% sequence identity with the amino acid sequence shown in residues 19-963 or 25-963 of SEQ ID NO:34. In some embodiments, the fusion polypeptide comprises an amino acid sequence having at least 80%, at least 85%, at least 90%, or at least 95% identity with residues 19-963 or 25-963 of SEQ ID NO:34, where the fusion polypeptide comprises at least one amino acid substitution in the first ("ApoA1") polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to residues 19-963 or 25-963 of SEQ ID NO:34. In some variations, the fusion polypeptide comprises an amino acid sequence having at least 80%, at least 85%, at least 90%, or at least 95% identity with an amino acid sequence selected from sequence shown in residues 19-963 or 25-963 of SEQ ID NO:34, where the fusion polypeptide comprises, in the ApoA1 polypeptide segment, the specific V156[E/K] and/or Y192[S/Q/N/H/F] substitution(s) of any one of variant combinations A1-A17 as shown in Table 3 herein; in some such embodiments, the fusion polypeptide comprises an amino acid sequence that is otherwise 100% identical to residues 19-963 or 25-963 of SEQ ID NO:34.

In some embodiments of a fusion polypeptide comprising ApoA1-L1-D-L2-P as described above and where P is a cholesterol ester transfer protein (CETP), the fusion polypeptide comprises an amino acid sequence having at least 80%, at least 85%, at least 90%, or at least 95% identity with the amino acid sequence shown in residues 19-1019 or 25-1019 of SEQ ID NO:40. In yet other embodiments, the fusion polypeptide comprises an amino acid sequence having at least 96%, at least 97%, at least 98%, at least 99%, or 100% sequence identity with the amino acid sequence shown in residues 19-1019 or 25-1019 of SEQ ID NO:40. In some embodiments, the fusion polypeptide comprises an amino acid sequence having at least 80%, at least 85%, at least 90%, or at least 95% identity with residues 19-1019 or 25-1019 of SEQ ID NO:40, where the fusion polypeptide comprises at least one amino acid substitution in the first ("ApoA1") polypeptide segment selected from V156[E/K], Y192[S/Q/N/H/F], M86[L/I/V], M112[L/I/V], M148[L/I/V], W8F, W50F, W72F, and W132F as described herein (e.g., V156[E/K] or Y192[S/Q/N/H/F] and optionally at least one of M86[L/I/V], M112[L/I/V], and M148[L/I/V]; both V156[E/K] and Y192[S/Q/N/H/F] and optionally at least one of M86[L/I/V], M112[L/I/V], and M148[L/I/V]; or all four of W8F, W50F, W72F, and W132F); in some such embodiments, the fusion polypeptide comprises an amino acid sequence that is otherwise 100% identical to residues 19-1019 or 25-1019 of SEQ ID NO:40. In some variations, the fusion polypeptide comprises an amino acid sequence having at least 80%, at least 85%, at least 90%, or at least 95% identity with an amino acid sequence selected from sequence shown in residues 19-1019 or 25-1019 of SEQ ID NO:40, where the fusion polypeptide comprises, in the ApoA1 polypeptide segment, the specific V156[E/K] and/or Y192[S/Q/N/H/F] substitution(s) of any one of variant combinations A1-A17 as shown in Table 3 herein; in some such embodiments, the fusion polypeptide comprises an amino acid sequence that is otherwise 100% identical to residues 19-1019 or 25-1019 of SEQ ID NO:40.

The present invention also provides dimeric proteins comprising first and second polypeptide fusions as described above. Accordingly, in another aspect, the present invention provides a dimeric protein comprising a first fusion polypeptide and a second fusion polypeptide, where each of the first and second polypeptide fusions comprises, from an amino-terminal position to a carboxyl-terminal position, ApoA1-L1-D, where ApoA1 is a first polypeptide segment having cholesterol efflux activity and which is selected from (i) a naturally occurring ApoA-1 polypeptide or a functional variant or fragment thereof and (ii) an ApoA-1 mimetic; L1 is a first polypeptide linker; and D is a dimerizing domain. In some embodiments, each of the first and second fusion polypeptides further includes a second polypeptide segment located carboxyl-terminal to the dimerizing domain. In particular variations, the second polypeptide segment is (a) a naturally occurring RNase, paraoxonase, platelet-activating factor acetylhydrolase (PAF-AH), cholesterol ester transfer protein (CETP), or lecithin-cholesterol acyltransferase (LCAT); (b) a functional variant or fragment of any of the naturally occurring proteins specified in (a); (c) a polypeptide that specifically binds to proprotein convertase subtilisin/kexin type 9 (PCSK9) and inhibits PCSK9 activity such as, e.g., a PCSK9-specific scFv; or (d) a polypeptide that specifically binds to amyloid beta (Aβ) such as, e.g., an Aβ-specific scFv. Such a fusion polypeptide comprising a second polypeptide segment may be represented by the formula ApoA1-L1-D-L2-P (from an amino-terminal position to a carboxyl-terminal position), where ApoA1, L1, and D are each as previously defined, where L2 is a second polypeptide linker and is optionally present, and where P is the second polypeptide segment.

In another aspect, the present invention provides a dimeric protein comprising a first fusion polypeptide and a second fusion polypeptide, where each of the first and second fusion polypeptides comprises a first polypeptide segment, a second polypeptide segment, and a dimerizing domain, where the first polypeptide segment has cholesterol efflux activity and is selected from (i) a naturally occurring ApoA-1 polypeptide or a functional variant or fragment thereof and (ii) an ApoA-1 mimetic, and where the second polypeptide segment is located carboxyl-terminal to the first polypeptide segment and is (a) a naturally occurring RNase, paraoxonase, platelet-activating factor acetylhydrolase (PAF-AH), cholesterol ester transfer protein (CETP), or lecithin-cholesterol acyltransferase (LCAT), (b) a functional variant or fragment of any of the naturally occurring proteins specified in (a), (c) a polypeptide that specifically binds to proprotein convertase subtilisin/kexin type 9 (PCSK9) and inhibits PCSK9 activity such as, e.g., a PCSK9-specific scFv, or (d) a polypeptide that specifically binds to amyloid beta (Aβ) such as, e.g., an Aβ-specific scFv. In some embodiments, the dimerizing domain is located carboxyl-terminal to the first polypeptide segment and amino-terminal to the second polypeptide segment.

In another aspect, the present invention provides (a) a first fusion polypeptide comprising an immunoglobulin heavy chain linked carboxyl-terminal to an ApoA-1 polypeptide or ApoA-1 mimetic and (b) a second fusion polypeptide comprising an immunoglobulin light chain linked carboxyl-terminal to the ApoA-1 polypeptide or ApoA-1 mimetic. The first and second fusion polypeptides can be co-expressed to create a stable tetramer composed of two double belt ApoA-1 dimers, wherein linkers between ApoA-1 and the heavy chain and between ApoA-1 and the light chain are of sufficient length to allow cholesterol efflux and reverse cholesterol transport.

The fusion polypeptides of the present invention, including dimeric fusion proteins, can further be conjugated to an effector moiety. The effector moiety can be any number of molecules, including, e.g., a labeling moiety such as a radioactive label or fluorescent label, a TLR ligand or binding domain, an enzyme, or a therapeutic moiety. In a particular embodiment, the effector moiety is a myeloperoxidase (MPO) inhibitor. MPO inhibitors are generally known (see, e.g., Malle et al., *Br J Pharmacol.* 152: 838-854, 2007) and may be readily conjugated to fusion polypeptides as described herein. Exemplary MPO inhibitors include inhibitors based on 3-alkylindole derivatives (see Soubhye et al., *J Med Chem* 56:3943-58, 2013; describing studies of 3-alkylindole derivatives as selective and highly potent myeloperoxidase inhibitors, including a compound with high and selective inhibition of MPO (IC50=18 nM));

inhibitors based on 3-(aminoalkyl)-5-fluorindoles (see Soubhye et al., *J Med Chem* 53: 8747-8759, 2010); inhibitors based on 2H-indazoles and 1H-indazolones (see Roth et al., *Bioorg Med Chem* 22: 6422-6429, 2014; describing the evaluation 2H-indazoles and 1H-indazolones and the identification of compounds with IC50 values <1 µM); and benzoic acid hydrazide-containing compounds (see Huang et al., *Arch Biochem Biophys* 570: 14-22, 2015; showing inactivation of MPO by benzoic acid hydrazide-containing compounds, where the light chain subunit of MPO is freed from the larger heavy chain by cleavage of the ester bond).

In another embodiment, the fusion polypeptides of the present invention, including dimeric fusion proteins, are modified to extend half-life, such as, for example, by attaching at least one molecule to the fusion protein for extending serum half-life. Such molecules for attachment may include, e.g., a polyethlyene glycol (PEG) group, serum albumin, transferrin, transferrin receptor or the transferrin-binding portion thereof, or a combination thereof. Methods for such modification are generally well-known in the art. As used herein, the word "attached" refers to a covalently or non-covalently conjugated substance. The conjugation may be by genetic engineering or by chemical means.

III. Materials and Methods for Making Polypeptide Fusions and Dimeric Proteins The present invention also provides polynucleotide molecules, including DNA and RNA molecules, that encode the fusion polypeptides disclosed above. The polynucleotides of the present invention include both single-stranded and double-stranded molecules. Polynucleotides encoding various segments of a fusion polypeptide (e.g., a dimerizing domain such as an Fc fragment; ApoA1 and P polypeptide segments) can be generated and linked together to form a polynucleotide encoding a fusion polypeptide as described herein using known methods for recombinant manipulation of nucleic acids.

DNA sequences encoding ApoA-1, RNases (e.g., RNase 1), paraoxonases (e.g., PON1), platelet-activating factor acetylhydrolase (PAF-AH), cholesterol ester transfer protein (CETP), and lecithin-cholesterol acyltransferase (LCAT) are known in the art. DNA sequences encoding various dimerizing domains (e.g., immunoglobulin heavy chain constant regions such as Fc fragments) are also known. Polynucleotides encoding, e.g., the variable regions of PCSK9-binding or Aβ-binding antibodies, including scFvs, are also readily identifiable using techniques well-known in the art such as screening of recombinant antibody expression libraries (e.g., phage display expression libraries). Additional DNA sequences encoding any of these polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding a given polypeptide. DNA and RNA encoding functional variants and fragments of such polypeptides can also be obtained using known recombinant methods to introduce variation into a polynucleotide sequence, followed by expression of the encoded polypeptide and determination of functional activity (e.g., cholesterol efflux) using an appropriate screening assay.

Methods for preparing DNA and RNA are well known in the art. For example, complementary DNA (cDNA) clones can be prepared from RNA that is isolated from a tissue or cell that produces large amounts of RNA encoding a polypeptide of interest. Total RNA can be prepared using guanidine HCl extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-1412, 1972). Complementary DNA is prepared from poly(A)$^+$ RNA using known methods. In the alternative, genomic DNA can be isolated. Methods for identifying and isolating cDNA and genomic clones are well known and within the level of ordinary skill in the art, and include the use of the sequences disclosed herein, or parts thereof, for probing or priming a library. Polynucleotides encoding polypeptides of interest are identified and isolated by, for example, hybridization or polymerase chain reaction ("PCR," Mullis, U.S. Pat. No. 4,683,202). Expression libraries can be probed with antibodies to the polypeptide of interest, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See generally Glick and Pasternak, *Molecular Biotechnology, Principles & Applications of Recombinant DNA*, ASM Press, Washington, D.C., 1994; Itakura et al., *Ann. Rev. Biochem.* 53:323-356, 1984; and Climie et al., *Proc. Natl. Acad. Sci. USA* 87:633-637, 1990.

In another aspect, materials and methods are provided for producing the polypeptide fusions of the present invention, including dimeric proteins comprising the fusion polypeptides. The fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, N Y, 1993.

In general, a DNA sequence encoding a fusion polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct an ApoA-1 fusion polypeptide into the secretory pathway of a host cell, a secretory signal sequence is provided in the expression vector. The secretory signal sequence may be that of the native ApoA-1 polypeptide, or may be derived from another secreted protein (e.g., t-PA; see U.S. Pat. No. 5,641,655) or synthesized de novo. An engineered cleavage site may be included at the junction between the secretory peptide and the remainder of the polypeptide fusion to optimize proteolytic processing in the host cell. The secretory signal sequence is operably linked to the DNA sequence encoding the polypeptide fusion, i.e., the two sequences are joined in the correct reading frame and positioned to direct the newly synthesized polypeptide fusion into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Secretory signal sequences suitable for use in accordance with the present invention include, for example, polynucleotides encoding amino acid residues 1-18 of SEQ ID NO:2.

Expression of fusion polypeptides comprising a dimerizing domain, via a host cell secretory pathway, is expected to result in the production of dimeric proteins. Accordingly, in another aspect, the present invention provides dimeric proteins comprising first and second fusion polypeptides as described above (e.g., a dimeric protein comprising a first fusion polypeptide and a second fusion polypeptide, where each of the first and second fusion polypeptides comprises, from an amino-terminal position to a carboxyl-terminal position, ApoA1-L1-D or ApoA1-L1-D-L2-P as described herein). Dimers may also be assembled in vitro upon incubation of component polypeptides under suitable conditions. In general, in vitro assembly will include incubating the protein mixture under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g., CHO-K1, ATCC No. CCL 61; CHO-DG44, Urlaub et al., *Proc. Natl. Acad. Sci. USA* 77:4216-4220, 1980) cell lines. Additional suitable cell lines are known in the art and available from public depositories such as the American Type Culture Collection, Manassas, Va. Strong transcription promoters can be used, such as promoters from SV-40, cytomegalovirus, or myeloproliferative sarcoma virus. See, e.g., U.S. Pat. No. 4,956,288 and U.S. Patent Application Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, Va. USA under accession numbers 98669, 98668, and PTA-5266, respectively, and derivatives of these vectors.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used. Cell-surface markers and other phenotypic selection markers can be used to facilitate identification of transfected cells (e.g., by fluorescence-activated cell sorting), and include, for example, CD8, CD4, nerve growth factor receptor, green fluorescent protein, and the like.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide*, Chapman & Hall, London; O'Reilly et al., *Baculovirus Expression Vectors: A Laboratory Manual*, Oxford University Press., New York, 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. Using techniques known in the art, a transfer vector encoding a polypeptide fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the polypeptide fusion is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, supra. See also U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (e.g., King and Possee, supra; O'Reilly et al., supra.; Richardson, supra).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillernondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well-known in the art (see, e.g., Sambrook et al., supra). When expressing a fusion polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine HCl or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) and recovering the protein, thereby obviating the need for denaturation and refolding. See, e.g., Lu et al., *J. Immunol. Meth.* 267:213-226, 2002.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Proteins of the present invention are purified by conventional protein purification methods, typically by a combination of chromatographic techniques. See generally *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising an immunoglobulin heavy chain polypeptide can be purified by affinity chromatography on immobilized protein A. Additional purification steps, such as gel filtration, can be used to obtain the desired level of purity or to provide for desalting, buffer exchange, and the like.

For example, fractionation and/or conventional purification methods can be used to obtain fusion polypeptides and dimeric proteins of the present invention purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well-known and widely used in the art, and are available from commercial suppliers. Selection of a particular method for polypeptide isolation and purification is a matter of routine design and is determined in part by the properties of the chosen support. See, e.g., *Affinity Chromatography: Principles & Methods* (Pharmacia LKB Biotechnology 1988); and Doonan, *Protein Purification Protocols* (The Humana Press 1996).

Additional variations in protein isolation and purification can be devised by those of skill in the art. For example, antibodies that specifically bind a fusion polypeptide or dimeric protein as described herein (e.g., an antibody that specifically binds a polypeptide segment corresponding to ApoA-1) can be used to isolate large quantities of protein by immunoaffinity purification.

The proteins of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (see, e.g., M. Deutscher, (ed.), *Meth. Enzymol.* 182:529, 1990). Within additional embodiments of the invention, a fusion of the polypeptide of interest and an affinity tag (e.g., maltose-binding protein, an immunoglobulin domain) may be constructed to facilitate purification. Moreover, receptor- or ligand-binding properties of a fusion polypeptide or dimer thereof can be exploited for purification. For example, a fusion polypeptide comprising an Aβ-binding polypeptide segment may be isolated by using affinity chromatography wherein amyloid beta (Aβ) peptide is bound to a column and the fusion polypeptide is bound and subsequently eluted using standard chromatography methods.

The polypeptides of the present invention are typically purified to at least about 80% purity, more typically to at least about 90% purity and preferably to at least about 95%, at least about 96%, at least about 97%, at least about 98%, or at least about 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

IV. Methods of Use and Pharmaceutical Compositions

The fusion polypeptides and dimeric proteins of the present invention can be used to provide ApoA-1-mediated therapy for the treatment of various diseases or disorders. In some aspects relating to bispecific fusions further comprising a second polypeptide segment as described herein (e.g., an RNase, paraoxonase, platelet-activating factor acetylhydrolase (PAF-AH), cholesterol ester transfer protein (CETP), or lecithin-cholesterol acyltransferase (LCAT)), the fusion polypeptides and dimeric proteins may further provide one or more additional biological activities for such treatment.

In particular aspects, the present invention provides methods for treating a disease or disorder selected from a cardiovascular disease characterized by atherosclerosis, a neurodegenerative disease, a disease characterized by amyloid deposit, an autoimmune disease, an inflammatory disease, an infectious disease, obesity, metabolic syndrome, nephrotic syndrome, burns, exposure to sulfur mustard gas, exposure to an organophosphate, sepsis, and cancer. The methods generally include administering to a subject having the disease or disorder an effective amount of a fusion polypeptide or dimeric protein as described herein.

Atherosclerotic cardiovascular diseases amenable to treatment in accordance with the present invention include, for example, coronary heart disease and stroke. In some variations of treatment of coronary heart disease, the coronary heart disease is characterized by acute coronary syndrome. In some embodiments, the atherosclerotic cardiovascular disease is selected from cerebral artery disease (e.g., extracranial cerebral artery disease, intracranial cerebral artery disease), arteriosclerotic aortic disease, renal artery disease, mesenteric artery disease, and peripheral artery disease (e.g., aortoiliac occlusive disease).

Neurodegenerative diseases amenable to treatment in accordance with the present invention include, for example, neurodegenerative diseases characterized by amyloid deposit and/or dementia. An exemplary neurodegenerative disease characterized by amyloid deposit is Alzheimer's disease. Exemplary neurodegenerative diseases characterized by dementia include Alzheimer's disease, Parkinson's disease, Huntington's disease, and amylotrophic lateral sclerosis (ALS). In some embodiments, the neurodegenerative disease is an inflammatory disease such as, for example, a demyelinating inflammatory disease of the CNS (e.g., multiple sclerosis (MS), including, for example, spino-optical MS, primary progressive MS (PPMS), and relapsing remitting MS (RRMS)).

In some embodiments of a method for treating a neurodegenerative disease (e.g., Alzheimer's disease or Parkinson's disease), a fusion molecule for the neurodegenerative disease treatment is a polypeptide having the structure ApoA1-L1-D-L2-RNase (e.g., ApoA1-L1-[Fc region]-L2-RNase1) or ApoA1-L1-D-L2-paraoxonase (e.g., ApoA1-L1-[Fc region]-L2-PON1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-675 or 25-675 of SEQ ID NO:4, (ii) amino acid residues 19-657 or 25-675 of SEQ ID NO:14, (iii) amino acid residues 19-671 or 25-671 of SEQ ID NO:58, (iv) amino acid residues 19-671 or 25-671 of SEQ ID NO:59; (v) amino acid residues 19-883 or 25-883 of SEQ ID NO:28, (vi) amino acid residues 19-873 or 25-873 of SEQ ID NO:38, (vii) amino acid residues 19-883 or 25-883 of SEQ ID NO:46, or (viii) amino acid residues 19-883 or 25-883 of SEQ ID NO:48.

Autoimmune diseases amenable to treatment in accordance with the present invention include, for example, rheumatoid arthritis, systemic lupus erythematosus, multiple sclerosis, and type 1 diabetes. In other embodiments, the autoimmune disease is selected from coeliac disease, neuritis, polymyositis, juvenile rheumatoid arthritis, psoriasis, psoriatic arthritis, vitiligo, Sjogren's syndrome, autoimmune pancreatitis, an inflammatory bowel disease (e.g., Crohn's disease, ulcerative colitis), active chronic hepatitis, glomerulonephritis, lupus nephritis, scleroderma, antiphospholipid syndrome, autoimmune vasculitis, sarcoidosis, autoimmune thyroid diseases, Hashimoto's thyroiditis, Graves disease, Wegener's granulomatosis, myasthenia gravis, Addison's disease, autoimmune uveoretinitis, pemphigus vulgaris, primary biliary cirrhosis, pernicious anemia, sympathetic opthalmia, uveitis, autoimmune hemolytic anemia, pulmonary fibrosis, chronic beryllium disease, and idiopathic pulmonary fibrosis. In some variations, the autoimmune disease is selected from rheumatoid arthritis, juvenile rheumatoid arthritis, psoriatic arthritis, systemic lupus erythematosus, lupus nephritis, scleroderma, psoriasis, Sjogren's syndrome, type 1 diabetes, antiphospholipid syndrome, and autoimmune vasculitis.

In some embodiments, a fusion molecule for treatment of an autoimmune disease is a polypeptide having the structure ApoA1-L1-D (e.g., ApoA1-L1-[Fc region]), ApoA1-L1-D-L2-RNase (e.g., ApoA1-L1-[Fc region]-L2-RNase1), or ApoA1-L1-D-L2-paraoxonase (e.g., ApoA1-L1-[Fc region]-L2-PON1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, (v) amino acid residues 19-535, 19-534, 25-535, or 25-534 of SEQ ID NO:24, (vi) amino acid residues 19-675 or 25-675 of SEQ ID NO:4, (vii) amino acid residues 19-657 or 25-675 of SEQ ID NO:14, (viii) amino acid residues 19-671 or 25-671 of SEQ ID NO:58, (ix) amino acid residues 19-671 or 25-671 of SEQ ID NO:59; (x) amino acid residues 19-883 or 25-883 of SEQ ID NO:28, (xi) amino acid residues 19-873 or 25-873 of SEQ ID NO:38, (xii) amino acid residues 19-883 or 25-883 of SEQ ID NO:46, or (xiii) amino acid residues 19-883 or 25-883 of SEQ ID NO:48. In some particular variations of a method for treating rheumatoid arthritis (RA), a fusion molecule for the RA treatment is a polypeptide having the structure ApoA1-L1-D (e.g., ApoA1-L1-[Fc region]), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, or (v) amino acid residues 19-535, 19-534, 25-535, or 25-534 of SEQ ID NO:24. In some particular variations of a method for treating systemic lupus erythematosus (SLE), a fusion molecule for the SLE treatment is a polypeptide having the structure ApoA1-L1-D-L2-RNase (e.g., ApoA1-L1-[Fc region]-L2-RNase1) or ApoA1-L1-D-L2-paraoxonase (e.g., ApoA1-L1-[Fc region]-L2-PON1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-675 or 25-675 of SEQ ID NO:4, (ii) amino acid residues 19-657 or 25-675 of SEQ ID NO:14, (iii) amino acid residues 19-671 or 25-671 of SEQ ID NO:58, (iv) amino acid residues 19-671 or 25-671 of SEQ ID NO:59, (v) amino acid residues 19-883 or 25-883 of SEQ ID NO:28, (vi) amino acid residues 19-873 or 25-873 of SEQ ID NO:38, (vii) amino acid residues 19-883 or 25-883 of SEQ ID NO:46, or (viii) amino acid residues 19-883 or 25-883 of SEQ ID NO:48. In some particular variations of a method for treating multiple sclerosis (MS), a fusion molecule for the MS treatment is a polypeptide having the structure ApoA1-L1-D-L2-paraoxonase (e.g., ApoA1-L1-[Fc region]-L2-PON1), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-883 or 25-883 of SEQ ID NO:28, (ii) amino acid residues 19-873 or 25-873 of SEQ ID NO:38, (iii) amino acid residues 19-883 or 25-883 of SEQ ID NO:46, or (iv) amino acid residues 19-883 or 25-883 of SEQ ID NO:48.

Inflammatory diseases amenable to treatment in accordance with the present invention include, for example, rheumatoid arthritis, systemic lupus erythematosus, multiple sclerosis, type 1 diabetes, type 2 diabetes, and obesity. In some embodiments, the inflammatory disease is a neurodegenerative inflammatory disease such as, for example, multiple sclerosis, Alzheimer's disease, or Parkinson's disease. In other embodiments, the inflammatory disease is an atherosclerotic disease (e.g., coronary heart disease or stroke). In yet other variations, the inflammatory disease is selected from hepatitis (e.g., non-alcoholic steatohepatitis), ankylosing spondylitis, arthritis (e.g., osteoarthritis, rheumatoid arthritis (RA), psoriatic arthritis), Crohn's disease, ulcerative colitis, dermatitis, diverticulitis, fibromyalgia, irritable bowel syndrome (IBS), and nephritis. In other embodiments, the inflammatory disease is an inflammatory lung disease; in some such embodiments, the inflammatory lung disease is selected from asthma, chronic obstructive pulmonary disease (COPD), bronchiectasis, idiopathic pulmonary fibrosis, hyperoxia, hypoxia, and acute respiratory distress syndrome (ARDS). In some variations, a patient having the inflammatory lung disease is a patient that has been exposed to sulfur mustard gas (SM). In other variations, a patient having the inflammatory lung disease is a patient that has been exposed to an organophosphate, such as an insecticide or other neurotoxin.

In some embodiments, a fusion molecule for treatment of an inflammatory disease (e.g., an inflammatory lung disease) is a polypeptide having the structure ApoA1-L1-D (e.g., ApoA1-L1-[Fc region]), ApoA1-L1-D-L2-RNase (e.g., ApoA1-L1-[Fc region]-L2-RNase1), or ApoA1-L1-D-L2-paraoxonase (e.g., ApoA1-L1-[Fc region]-L2-PON1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, (v) amino acid residues 19-535, 19-534, 25-535, or 25-534 of SEQ ID NO:24, (vi) amino acid residues 19-675 or 25-675 of SEQ ID NO:4, (vii) amino acid residues 19-657 or 25-675 of SEQ ID NO:14, (viii) amino acid residues 19-671 or 25-671 of SEQ ID NO:58, (ix) amino acid residues 19-671 or 25-671 of SEQ ID NO:59; (x) amino acid residues 19-883 or 25-883 of SEQ ID NO:28, (xi) amino acid residues 19-873 or 25-873 of SEQ ID NO:38, (xii) amino acid residues 19-883 or 25-883 of SEQ ID NO:46, or (xiii) amino acid residues 19-883 or 25-883 of SEQ ID NO:48. In some particular variations of a method for treating idiopathic pulmonary fibrosis, a fusion molecule for the idiopathic pulmonary fibrosis treatment is a polypeptide having the structure ApoA1-L1-D (e.g., ApoA1-L1-[Fc region]), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, or (v) amino acid residues 19-535, 19-534, 25-535, or 25-534 of SEQ ID NO:24. In some particular variations of a method for treating an inflammatory lung disease in a patient that has been exposed to sulfur mustard gas (SM) or an organophosphate, a fusion molecule for the treatment is a polypeptide having the structure ApoA1-L1-D-L2-paraoxonase (e.g., ApoA1-L1-[Fc region]-L2-PON1), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-883 or 25-883 of SEQ ID NO:28, (ii) amino acid residues 19-873 or 25-873 of SEQ ID NO:38, (iii) amino acid residues 19-883 or 25-883 of SEQ ID NO:46, or (iv) amino acid residues 19-883 or 25-883 of SEQ ID NO:48. In some particular variations of a method for treating acute respiratory distress syndrome (ARDS), hypoxia, or hyperoxia, a fusion molecule for the treatment is a polypeptide having the structure ApoA1-L1-D-L2-RNase (e.g., ApoA1-L1-[Fc region]-L2-RNase1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-675 or 25-675 of SEQ ID NO:4, (ii) amino acid residues 19-657 or 25-675 of SEQ ID NO:14, (iii) amino acid residues 19-671 or 25-671 of SEQ ID NO:58, or (iv) amino acid residues 19-671 or 25-671 of SEQ ID NO:59. In certain embodiments, such ApoA1-L1-D-L2-RNase variations are used to treat premature infants that are treated with oxygen for an extended period of time.

In some embodiments, a fusion molecule for treatment of exposure to sulfur mustard gas (SM) or exposure to an organophosphate is a polypeptide having the structure ApoA1-L1-D-L2-paraoxonase (e.g., ApoA1-L1-[Fc region]-L2-PON1), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-883 or 25-883 of SEQ ID NO:28, (ii) amino acid residues 19-873 or 25-873 of SEQ ID NO:38, (iii) amino acid residues 19-883 or 25-883 of SEQ ID NO:46, or (iv) amino acid residues 19-883 or 25-883 of SEQ ID NO:48.

Infectious diseases amenable to treatment in accordance with the present invention include, for example, bacterial infections and parasitic infections. In some embodiments, the parasitic infection is a *Trypanosoma brucei* or *Leishmania* infection. In other embodiments, the bacterial infection is a *Pseudomonas aeruginosa* infection.

In some embodiments of a method for treating a *Pseudomonas aeruginosa* infection, a fusion molecule for the *Pseudomonas aeruginosa* infection treatment is a polypeptide having the structure ApoA1-L1-D-L2-paraoxonase (e.g., ApoA1-L1-[Fc region]-L2-PON1), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-883 or 25-883 of SEQ ID NO:28, (ii) amino acid residues 19-873 or 25-873 of SEQ ID NO:38, (iii) amino acid residues 19-883 or 25-883 of SEQ ID NO:46, or (iv) amino acid residues 19-883 or 25-883 of SEQ ID NO:48.

In some embodiments, a fusion molecule for treatment of an infectious disease (e.g., an inflammatory lung disease) is a polypeptide having the structure ApoA1-L1-D (e.g., ApoA1-L1-[Fc region]), or a dimeric protein formed by dimerization of the foregoing fusion polypeptide; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, or (v) amino acid residues 19-535, 19-534, 25-535, or 25-534 of SEQ ID NO:24.

In some embodiments, a fusion molecule for treatment of sepsis is a polypeptide having the structure ApoA1-L1-D (e.g., ApoA1-L1-[Fc region]) or ApoA1-L1-D-L2-paraoxonase (e.g., ApoA1-L1-[Fc region]-L2-PON1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, (v) amino acid residues 19-535, 19-534, 25-535, or 25-534 of SEQ ID NO:24, (vi) amino acid residues 19-883 or 25-883 of SEQ ID NO:28, (vii) amino acid residues 19-873 or 25-873 of SEQ ID NO:38, (viii) amino acid residues 19-883 or 25-883 of SEQ ID NO:46, or (ix) amino acid residues 19-883 or 25-883 of SEQ ID NO:48.

Cancers that may be treated in accordance with the present invention include, for example, the following: a cancer of the head and neck (e.g., a cancer of the oral cavity, oropharynx, nasopharynx, hypopharynx, nasal cavity or paranasal sinuses, larynx, lip, or salivary gland); a lung cancer (e.g., non-small cell lung cancer, small cell carcinoma, or mesothelimia); a gastrointestinal tract cancer (e.g., colorectal cancer, gastric cancer, esophageal cancer, or anal cancer); gastrointestinal stromal tumor (GIST); pancreatic adenocarcinoma; pancreatic acinar cell carcinoma; a cancer of the small intestine; a cancer of the liver or biliary tree (e.g., liver cell adenoma, hepatocellular carcinoma, hemangiosarcoma, extrahepatic or intrahepatic cholangiosarcoma, cancer of the ampulla of vater, or gallbladder cancer); a breast cancer (e.g., metastatic breast cancer or inflammatory breast cancer); a gynecologic cancer (e.g., cervical cancer, ovarian cancer, fallopian tube cancer, peritoneal carcinoma, vaginal cancer, vulvar cancer, gestational trophoblastic neoplasia, or uterine cancer, including endometrial cancer or uterine sarcoma); a cancer of the urinary tract (e.g., prostate cancer; bladder cancer; penile cancer; urethral cancer, or kidney cancer such as, for example, renal cell carcinoma or transitional cell carcinoma, including renal pelvis and ureter); testicular cancer; a cancer of the central nervous system (CNS) such as an intracranial tumor (e.g., astrocytoma, anaplastic astrocytoma, glioblastoma, oligodendroglioma, anaplastic oligodendroglioma, ependymoma, primary CNS lymphoma, medulloblastoma, germ cell tumor, pineal gland neoplasm, meningioma, pituitary tumor, tumor of the nerve sheath (e.g., schwannoma), chordoma, craniopharyngioma, a chloroid plexus tumor (e.g., chloroid plexus carcinoma); or other intracranial tumor of neuronal or glial origin) or a tumor of the spinal cord (e.g., schwannoma, meningioma); an endocrine neoplasm (e.g., thyroid cancer such as, for example, thyroid carcinoma, medullary cancer, or thyroid lymphoma; a pancreatic endocrine tumor such as, for example, an insulinoma or glucagonoma; an adrenal carcinoma such as, for example, pheochromocytoma; a carcinoid tumor; or a parathyroid carcinoma); a skin cancer (e.g., squamous cell carcinoma; basal cell carcinoma; Kaposi's sarcoma; or a malignant melanoma such as, for example, an intraocular melanoma); a bone cancer (e.g., a bone sarcoma such as, for example, osteosarcoma, osteochondroma, or Ewing's sarcoma); multiple myeloma; a chloroma; a soft tissue sarcoma (e.g., a fibrous tumor or fibrohistiocytic tumor); a tumor of the smooth muscle or skeletal muscle; a blood or lymph vessel perivascular tumor (e.g., Kaposi's sarcoma); a synovial tumor; a mesothelial tumor; a neural tumor; a paraganglionic tumor; an extraskeletal cartilaginous or osseous tumor; and a pluripotential mesenchymal tumor. In some such embodiments, an ApoA-1 fusion molecule as described herein is administered to a cancer patient as one of the distinct therapies of a combination therapy such as, for example, a combination therapy comprising a non-ApoA1-mediated immunomodulatory therapy (e.g., a therapy comprising an immune checkpoint inhibitor), a radiation therapy, or a chemotherapy.

In certain embodiments, a combination cancer therapy comprises an ApoA-1 fusion molecule as described herein and a targeted therapy such as, e.g., a therapeutic monoclonal antibody targeting a specific cell-surface or extracellular antigen, or a small molecule targeting an intracellular protein (e.g., an intracellular enzyme). Exemplary antibody targeted therapies include anti-VEGF (e.g., bevacizumab), anti-EGFR (e.g., cetuximab), anti-CTLA-4 (e.g., ipilimumab), anti-PD-1 (e.g., nivolumab), and anti-PD-L1 (e.g., pembrolizumab). Exemplary small molecule targeted therapies include proteasome inhibitors (e.g., bortezomib), tyrosine kinase inhibitors (e.g., imatinib), cyclin-dependent kinase inhibitors (e.g., seliciclib); BRAF inhibitors (e.g., vemurafenib or dabrafenib); and MEK kinase inhibitors (e.g., trametnib).

In some cancer combination therapy variations comprising an immune checkpoint inhibitor, the combination therapy includes an anti-PD-1/PD-L1 therapy, an anti-CTLA-4 therapy, or both. In certain aspects, ApoA-1 fusion molecules as described herein can increase the response rate to either anti-CTLA-4 or anti-PD-1/PD-L1 therapy, as well as the response rate to the combination of anti-CTLA-4 plus anti-PD-1/PD-L1 therapy. Fusion molecules of the invention may also be useful for reducing the toxicity associated with anti-CTLA-4, anti-PD-1/PD-L1, or the combination thereof.

In certain variations, a cancer treated in accordance with the present invention is selected from malignant melanoma, renal cell carcinoma, non-small cell lung cancer, bladder cancer, and head and neck cancer. These cancers have shown responses to immune checkpoint inhibitors anti-PD-1/PD-L1 and anti-CTLA-4. See Grimaldi et al., *Expert Opin. Biol. Ther.* 16:433-41, 2016; Gunturi et al., *Curr. Treat. Options Oncol.* 15:137-46, 2014; Topalian et al., *Nat. Rev. Cancer* 16:275-87, 2016. Thus, in some more specific variations, any of these cancers is treated with an ApoA-1 fusion molecule as described herein in combination with an anti-PD-1/PD-L1 therapy, an anti-CTLA-4 therapy, or both.

In some embodiments, a fusion molecule for treatment of a cancer is a polypeptide having the structure ApoA1-L1-D (e.g., ApoA1-L1-[Fc region]), ApoA1-L1-D-L2-RNase (e.g., ApoA1-L1-[Fc region]-L2-RNase1), or ApoA1-L1-D-L2-paraoxonase (e.g., ApoA1-L1-[Fc region]-L2-PON1), or a dimeric protein formed by dimerization of any of the foregoing fusion polypeptides; in some such embodiments, the fusion polypeptide comprises or consists of an amino acid sequence having at least 90%, at least 95%, or 100% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, (v) amino acid residues 19-535, 19-534, 25-535, or 25-534 of SEQ ID NO:24, (vi) amino acid residues 19-675 or 25-675 of SEQ ID NO:4, (vii) amino acid residues 19-657 or 25-675 of SEQ ID NO:14, (viii) amino acid residues 19-671 or 25-671 of SEQ ID NO:58, (ix) amino acid residues 19-671 or 25-671 of SEQ ID NO:59; (x) amino acid residues 19-883 or 25-883 of SEQ ID NO:28, (xi) amino acid residues 19-873 or 25-873 of SEQ ID NO:38, (xii) amino acid residues 19-883 or 25-883 of SEQ ID NO:46, or (xiii) amino acid residues 19-883 or 25-883 of SEQ ID NO:48.

In certain embodiments for treatment of a disease or disorder as described herein, the fusion polypeptide comprises an amino acid sequence having at least 90% or at least 95% identity with (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, (v) amino acid residues 19-535, 19-534, 25-535, or 25-534 of SEQ ID NO:24, (vi) amino acid residues 19-675 or 25-675 of SEQ ID NO:4, (vii) amino acid residues 19-657 or 25-675 of SEQ ID NO:14, (viii) amino acid residues 19-671 or 25-671 of SEQ ID NO:58, (ix) amino acid residues 19-671 or 25-671 of SEQ ID NO:59; (x) amino acid residues 19-883 or 25-883 of SEQ ID NO:28, (xi) amino acid residues 19-873 or 25-873 of SEQ ID NO:38, (xii) amino acid residues 19-883 or 25-883 of SEQ ID NO:46, or (xiii) amino acid residues 19-883 or 25-883 of SEQ ID NO:48, where the fusion polypeptide comprises at least one amino acid substitution in the first ("ApoA1") polypeptide segment selected from V156[E/K], Y192[S/Q/N/H/F], M86[L/I/V], M112[L/I/V], M148[L/I/V], W8F, W50F, W72F, and W132F as described herein. In some treatment embodiments where the fusion polypeptide has the structure ApoA1-L1-D-L2-paraoxonase (e.g., ApoA1-L1-[Fc region]-L2-PON1), the fusion polypeptide comprises an amino acid sequence having at least 90% or at least 95% identity with (i) amino acid residues 19-883 or 25-883 of SEQ ID NO:28, (ii) amino acid residues 19-873 or 25-873 of SEQ ID NO:38, (iii) amino acid residues 19-883 or 25-883 of SEQ ID NO:46, or (iv) amino acid residues 19-883 or 25-883 of SEQ ID NO:48, where the fusion polypeptide comprises a substitution in the second ("P") polypeptide segment selected from Y185[H/Q/S] and F293[H/Q/N] as described herein; in some such variations, the fusion polypeptide comprises at least one of the foregoing substitutions in the ApoA1 segment. In some treatment embodiments where the fusion polypeptide comprises one or more substitutions as above, the fusion polypeptide comprises an amino acid sequence that is otherwise 100% identical to (i) amino acid residues 19-525, 19-524, 25-525, or 25-524 of SEQ ID NO:2, (ii) amino acid residues 19-525, 19-524, 25-525, or 25-524 of SEQ ID NO:13, (iii) amino acid residues 19-501, 19-500, 25-501, or 25-500 of SEQ ID NO:20, (iv) amino acid residues 19-515, 19-514, 25-515, or 25-514 of SEQ ID NO:22, (v) amino acid residues 19-535, 19-534, 25-535, or 25-534 of SEQ ID NO:24, (vi) amino acid residues 19-675 or 25-675 of SEQ ID NO:4, (vii) amino acid residues 19-657 or 25-675 of SEQ ID NO:14, (viii) amino acid residues 19-671 or 25-671 of SEQ ID NO:58, (ix) amino acid residues 19-671 or 25-671 of SEQ ID NO:59; (x) amino acid residues 19-883 or 25-883 of SEQ ID NO:28, (xi) amino acid residues 19-873 or 25-873 of SEQ ID NO:38, (xii) amino acid residues 19-883 or 25-883 of SEQ ID NO:46, or (xiii) amino acid residues 19-883 or 25-883 of SEQ ID NO:48.

In some embodiments, an ApoA-1 fusion molecule as described herein is administered to a patient as one of the distinct therapies of a combination therapy comprising administration of a myeloperoxidase (MPO) inhibitor. MPO can oxidize and inactivate ApoA-1 and PON1, so inhibition of MPO during the period of therapy can protect the fusion molecules of the present invention, including, for example, bispecific fusion molecules further comprising a paraoxonase (e.g., PON1). After therapy with fusion molecules of the present invention, production of MPO is expected to be suppressed, and the treated individual is expected to have recovered redox balance and the ability to regulate MPO production. Because of the importance of myeloperoxidase in killing off bacteria by leukocytes, a combined short term use of MPO inhibitors and fusion molecules of the present invention is preferred over a combined long term use. Inhibitors of MPO are generally known in the art and include, for example, PF-06282999 (see Ruggeri et al., *J. Med. Chem.* 58:8513-8528, 2015) and INV-315 (see Liu et al., *PLoS ONE* 7:e50767, 2012).

For therapeutic use, a fusion polypeptide or dimeric protein as described herein is delivered in a manner consistent with conventional methodologies associated with management of the disease or disorder for which treatment is sought. In accordance with the disclosure herein, an effective amount of the fusion polypeptide or dimeric protein is administered to a subject in need of such treatment for a time and under conditions sufficient to prevent or treat the disease or disorder.

Subjects for administration of fusion polypeptides or dimeric proteins as described herein include patients at high risk for developing a particular disease or disorder as well as patients presenting with an existing disease or disorder. In certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder). Also, in some variations, the subject does not suffer from another disease or disorder requiring treatment that involves administration of an ApoA-1 protein.

In prophylactic applications, pharmaceutical compositions or medicants are administered to a patient susceptible to, or otherwise at risk of, a particular disease in an amount sufficient to eliminate or reduce the risk or delay the onset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is referred to as a therapeutically or pharmaceutically effective dose or amount. In both prophylactic and therapeutic regimes, agents are usually administered in several dosages until a sufficient response (e.g., atherosclerosis regression or stabilization of existing plaques in coronary heart disease) has been achieved. Typically, the response is monitored and repeated dosages are given if the desired response starts to fade.

To identify subject patients for treatment according to the methods of the invention, accepted screening methods may be employed to determine risk factors associated with a specific disease or to determine the status of an existing disease identified in a subject. Such methods can include, for example, determining whether an individual has relatives who have been diagnosed with a particular disease. Screening methods can also include, for example, conventional work-ups to determine familial status for a particular disease known to have a heritable component. Toward this end, nucleotide probes can be routinely employed to identify individuals carrying genetic markers associated with a particular disease of interest. In addition, a wide variety of immunological methods are known in the art that are useful to identify markers for specific diseases. Screening may be implemented as indicated by known patient symptomology, age factors, related risk factors, etc. These methods allow the clinician to routinely select patients in need of the methods described herein for treatment. In accordance with these methods, treatment using a fusion polypeptide or dimeric protein of the present invention may be implemented as an independent treatment program or as a follow-up, adjunct, or coordinate treatment regimen to other treatments.

For administration, a fusion polypeptide or dimeric protein in accordance with the present invention is formulated as a pharmaceutical composition. A pharmaceutical composition comprising a fusion polypeptide or dimeric protein as described herein can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, e.g., Gennaro (ed.), *Remington's Pharmaceutical Sciences* (Mack Publishing Company, 19th ed. 1995). Formulations may further include one or more excipients, preservatives, solubilizers, buffering agents, albumin to prevent protein loss on vial surfaces, etc.

A pharmaceutical composition comprising a fusion polypeptide or dimeric protein of the present invention is administered to a subject in an effective amount. The fusion polypeptide or dimeric protein may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the fusion polypeptide or dimeric protein may be administered to a subject in a single bolus delivery, via continuous delivery (e.g., continuous transdermal delivery)

over an extended time period, or in a repeated administration protocol (e.g., on an hourly, daily, or weekly basis).

Determination of effective dosages in this context is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects (e.g., in the case of treatment of atherosclerotic cardiovascular disease, where any undesired collateral effects are outweighed by any beneficial effects such as increase in HDL, atherosclerosis regression, and/or plaque stabilization). For administration of a fusion polypeptide or dimeric protein of the present invention, a dosage typically ranges from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of clinical symptoms of the disease or disorder and/or monitoring of disease biomarkers or other disease correlates (e.g., HDL levels in the case of atherosclerotic cardiovascular disease).

Particularly suitable animal models for evaluating efficacy of an ApoA-1 composition of the present invention for treatment of atherosclerosis include, for example, known mouse models that are deficient in the low density lipoprotein receptor (LDLR) or ApoE. LDLR deficient mice develop atherosclerotic plaques after eating a high fat diet for 12 weeks, and human ApoA-1 (reconstituted with lipids) is effective in reducing plaques in this model. ApoE deficient mice are also commonly used to study atherosclerosis, and human ApoA-1 (reconstituted with lipids) works rapidly in this model. Rabbits that are transgenic for hepatic lipase are another known atherosclerosis model for testing ApoA-1 compositions.

One model of Alzheimer's disease uses overexpression of mutant amyloid-β precursor protein (APP) and presenilin 1 in mice. In these mice, overexpression of human ApoA-1 prevented memory and learning deficits. See Lewis et al., *J Biol. Chem.* 285: 36958-36968, 2010.

Also known is the collagen-induced arthritis (CIA) model for rheumatoid arthritis (RA). CIA shares similar immunological and pathological features with RA, making it an ideal model for evaluating efficacy of ApoA-1 compositions. See, e.g., Charles-Schoeman et al., *Clin Immunol.* 127:234-44, 2008 (describing studies showing efficacy of the ApoA-1 mimetic peptide, D-4F, in the CIA model). Another known model for RA is PG-polysaccharide (PG-PS)-induced arthritis in female Lewis rats. In these mice, administration of ApoA-1 protein or reconstituted HDLs reduced acute and chronic joint inflammation. Wu et al., *Arterioscler Thromb Vasc Biol* 34:543-551, 2014.

Animal models for multiple sclerosis (MS) include, for example, experimental allergic encephalomyelitis (EAE) models that rely on the induction of an autoimmune response in the CNS by immunization with a CNS antigen (also referred to as an "encephalitogen" in the context of EAE), which leads to inflammation, demyelination, and weakness. ApoA-1 deficient mice have been shown to exhibit more neurodegeneration and worse disease than wild-type animals in this model. See Meyers et al., *J. Neuroimmunol.* 277: 176-185, 2014.

Fusion molecules of the present invention can be evaluated for anti-tumor activity in animal tumor models such as, e.g., B16 melanoma, a poorly immunogenic tumor. Multiple models of tumor immunotherapy have been studied. See Ngiow et al., *Adv. Immunol.* 130:1-24, 2016. The B16 melanoma model has been studied extensively with checkpoint inhibitors anti-CTLA-4, anti-PD-1, and the combination thereof. Anti-CTLA-4 alone has a potent therapeutic effect in this model only when combined with GM-CSF transduced tumor vaccine, or combined with anti-PD-1. See Weber, *Semin. Oncol.* 37:430-439, 2010; Ai et al., *Cancer Immunol. Immunother.* 64:885-92, 2015; Haanen et al., *Prog. Tumor Res.* 42:55-66, 2015. Efficacy of an ApoA-1 fusion molecule for treatment of malignant melanoma is shown, for example, by slowed tumor growth following administration to B16 melanoma mice that have formed palpable subcutaneous tumor nodules. Efficacy of an ApoA-1 fusion molecule can be evaluated in B16 melanoma mice either alone or, alternatively, in combination with another anti-cancer therapy (e.g., anti-CTLA-4, with or without tumor vaccine or with or without anti-PD-1/PD-L1). For example, tumor rejection in B16 melanoma mice using a combination of an ApoA-1 fusion molecule as described herein and anti-CTLA-4, in the absence of tumor vaccine, demonstrates an enhanced response to anti-CTLA-4 using the ApoA-1 therapy. In exemplary studies to evaluate ApoA-1 fusion molecules comprising human protein sequences, which are functionally active in mice but are expected to be immunogenic in these models (and thereby likely to result in formation of neutralizing antibodies after 7-10 days), mice may be administered a fusion molecule of the present invention for a short period (for example, one week, administered in, e.g., two doses of about 40 mg/kg three days apart), and tumor growth then monitored, typically for two to three weeks after injection with the fusion molecule.

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

A pharmaceutical composition comprising a fusion polypeptide or dimeric protein as described herein can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein Delivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117 (Sanders and Hendren, eds., Plenum Press 1997). Other solid forms include creams, pastes, other topological applications, and the like.

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer. See, e.g., Gombotz and Pettit, *Bioconjugate Chem.* 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in *Protein Delivery: Physical Systems* 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998. Polyethylene glycol (PEG)-coated nanospheres can also provide carriers for intravenous administration of therapeutic proteins. See, e.g., Gref et al., *Pharm. Biotechnol.* 10:167, 1997.

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

Pharmaceutical compositions as described herein may also be used in the context of combination therapy. The term "combination therapy" is used herein to denote that a subject is administered at least one therapeutically effective dose of a fusion polypeptide or dimeric protein as described herein and another therapeutic agent.

Pharmaceutical compositions may be supplied as a kit comprising a container that comprises a fusion polypeptide or dimeric protein as described herein. A therapeutic molecule can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a therapeutic protein. Such a kit may further comprise written information on indications and usage of the pharmaceutical composition.

The invention is further illustrated by the following non-limiting examples.

Example 1

Molecule Design and Preparation: Two ApoA-1-Fc cDNA constructs were designed, synthesized, expressed by transient transfection of COST cells, and the expressed proteins then purified by Protein A chromatography. One construct had the nucleotide sequence shown in SEQ ID NO:1 and encoded the fusion polypeptide of SEQ ID NO:2, and is also referred to herein as ApoA-1(26)Fc or THER4. This construct contained a DNA segment encoding a 26 amino acid linker (residues 268-293 of SEQ ID NO:2) between the C-terminal end of human ApoA-1 (residues 1-267 of SEQ ID NO:2) and a human γ1 Fc variant (residues 294-525 of SEQ ID NO:2). Upon expression in mammalian cells and cleavage of the secretory signal peptide (residues 1-18), and any potential cleavage of the propeptide (residues 19-24), this fusion polypeptide had a predicted amino acid sequence corresponding to residues 19-525, 19-524, 25-525, or 25-524 of SEQ ID NO:2 (the C-terminal lysine of the Fc region is known to be frequently cleaved in the production of Fc-containing proteins). The other construct contained ApoA-1 and Fc regions identical to those of the ApoA-1 (26)Fc construct, but lacked a (gly4ser) linker between human ApoA-1 and the Fc regions; this construct is also referred to herein as ApoA-1(2)Fc (Theripion) or as THER0 (for no (gly4ser) repeat units). This construct does contain a two amino acid linker due to insertion of overlapping restriction sites between the ApoA-1 region and the hinge region of human IgG1.

Figure 1:
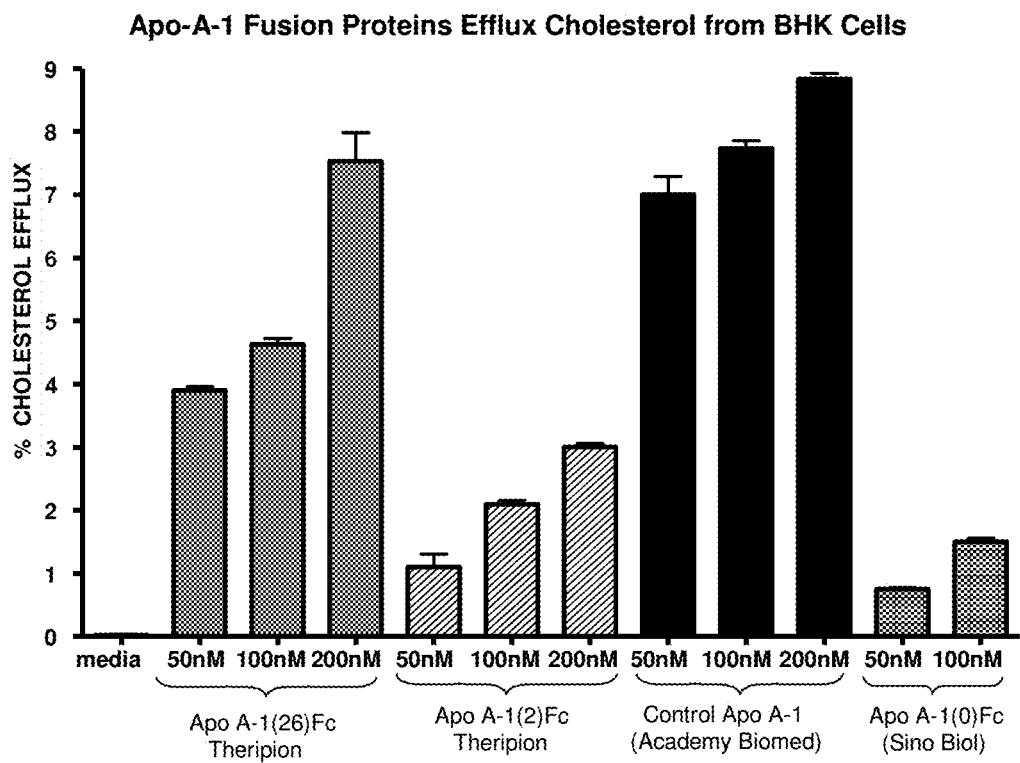
FIG. 1 illustrates cholesterol efflux in BHK cell cultures ApoA-1 molecules and recombinant fusions thereof. ApoA-

Cholesterol efflux: The cholesterol efflux activity of the ApoA-I fusion proteins were measured using an in vitro assay. See Tang et al., *J Lipid Res.* 47:107-14, 2006. In vitro cholesterol efflux assays were performed using radio-labelled cholesterol and BHK cells expressing a mifespristone-inducible human ABCA1. H3-cholesterol was added to growth media in order to label cellular cholesterol 24 hours prior to treatments, and ABCA1 is induced using 10 nM mifepristone for 16-20 hours. Cholesterol efflux was measured by incubating cells with or without the fusion proteins for 2 hours at 37° C., chilled on ice, and medium and cells separated to measure radiolabeled cholesterol. Wild-type human ApoA-1 protein was used as a positive control. A commercially available ApoA-1-Fc protein, linked directly to Fc without any linker between the ApoA-1 and Fc regions (APOA1 Recombinant Human Protein, hIgG1-Fc tag; Sino Biological, Inc.), was also tested and is referred to herein as ApoA-1(0)Fc (Sino Biol). The results of this assay are shown in FIG. 1. Cholesterol efflux was increased in cultures containing ApoA-1-Fc with a 26 amino acid linker (ApoA-1(26)Fc), compared to either ApoA-1-Fc with a two amino acid linker (ApoA-1(2)Fc (Theripion)) or ApoA-1-Fc without a linker (ApoA-1(0)Fc (Sino Biol)). ApoA-1(26)Fc also had activity similar to wild-type human ApoA-1 (Control ApoA-1).

Example 2: Generation of Fusion Constructs and Sequence Verification

Additional ApoA1 fusion constructs were designed and the fusion gene sequences were submitted to Blue Heron (Bothell, Wash.) for gene synthesis. A basic schematic diagramming the position of functional domains is shown in FIGS. 2A and 2B for the design of the ApoA1 fusion proteins. Fusion gene constructs inserted into pUC-based vectors isolated by restriction enzyme digestion, and fragments encoding the fusion genes were subcloned into the mammalian expression vector pDG. Briefly, HindIII+XbaI flanking restriction sites were used for removal of each expression gene from the vector, subfragments isolated by gel electrophoresis, DNA extracted using QIAquick purification columns, and eluted in 30 microliters EB buffer. Fragments were ligated into HindIII+XbaI digested pDG vector, and ligation reactions transformed into NEB 5-alpha, chemically competent bacteria. Clones were inoculated into 3 ml LB broth with 100 µg/ml ampicillin, grown at 37° C. overnight with shaking at 200 rpm, and plasmid DNA prepared using the QIAGEN spin plasmid miniprep kits according to manufacturer's instructions. Sequencing primers were obtained from IDT Integrated DNA Technologies (Coralville, Iowa) and included the following:

```
pdgF-2:
                                    (SEQ ID NO: 16)
5'-ggttttggcagtacatcaatgg-3';

pdgR-2:
                                    (SEQ ID NO: 17)
5'-ctattgtcttcccaatcctccc-3';

higgras:
                                    (SEQ ID NO: 18)
5'-accttgcacttgtactcctt-3'.
```

Plasmid DNA (800 ng) and sequencing primers (25 pmol, or 5 µl of a 5 pmol/µl stock) were mixed and submitted for DNA sequencing by GENEWIZ (South Plainfield, N.J.). Chromatograms were then analyzed, sequences assembled into contigs, and sequence verified using Vector Nti Advance 11.5 software (Life Technologies, Grand Island, N.Y.).

Example 3: Expression of Fusion Proteins in a Transient HEK 293T Transfection System This example illustrates transfection of plasmid constructs and expression of fusion proteins described herein in a mammalian transient transfection system. The Ig fusion gene fragments with correct sequence were inserted into the mammalian expression vector pDG, and DNA from positive clones was amplified using QIAGEN plasmid preparation kits (QIAGEN, Valencia, Calif.). Five different constructs were generated. These each included the native coding sequence of the human ApoA-1 gene (nucleotide sequence shown in SEQ ID NO:35, encoding the amino acid sequence shown in SEQ ID NO:36). Each sequence included the wild-type signal peptide (nucleotides 1-54 of SEQ ID NO:35, encoding amino acids 1-18 of SEQ ID NO:36) and propeptide sequences (nucleotides 55-72 of SEQ ID NO:35, encoding amino acids 19-24 of SEQ ID NO:36) for apolipoprotein A-1. The C-terminal Q (Gln) residues of the ApoA-1 sequence was linked via a variable length linker segment to the human IgG1 hinge, CH2, and CH3 domains to create a single chain (ApoA-1)-lnk-human IgG1 Fc fusion gene/protein. The hinge sequence of the human IgG1 is mutated so that the three cysteines are substituted with serine residues, eliminating disulfide bond formation in this region or unpaired cysteines that might compromise proper folding of the fusion protein. The P238 and P331 residues of CH2 are also mutated to serines to eliminate effector functions such as ADCC and complement fixation. Each construct also included a linker sequence inserted between the carboxyl terminus of apolipoprotein A-1 (ending with the sequence . . . TKKLNTQ (SEQ ID NO:35 residues 261-267)) and the beginning of the hinge sequence of the human Fc (starting with the motif . . . EPKSSDKT . . . (SEQ ID NO:2 residues 294-301). This linker sequence ranged from two amino acids (or four if the overlap with the flanking domains is included) to 36 amino acids in length, depending on the construct.

The shortest linker included only two overlapping restriction sites (BglII and XhoI) with a linker length of six additional nucleotides or two additional non-native amino acids. The restriction sites were incorporated into the coding sequence of the molecule so that only two additional amino acids needed to be added to the amino acid sequence. The BglII site of the linker overlaps with the codon for the C-terminal glutamine of ApoA-1, and three of the nucleotides encoding the XhoI site form the codon for the first amino acid of the hinge (E-glutamic acid). The linker amino acid sequence (including the two overlapping amino acids) is shown in residues 267-270 of SEQ ID NO:20, which is encoded by nucleotides 816-825 of SEQ ID NO:19. The fusion gene and protein for this construct are identified as THER0 (since there are no (gly4ser) repeat units present) or apoA-1-lnk(2)hIgG. The nucleotide and amino acid sequences for THER0 are listed as SEQ ID NO:19 and SEQ ID NO:20. The figures use the THER0 nomenclature to specify this construct.

The second construct included a linker that encodes two (gly4ser) sequences flanked by restriction sites (16 amino acid linker), and the fusion gene and protein for this construct are identified as THER2 (or apoA-1-lnk(16)-hIgG1 or apoA-1-(g4s)2-hIgG1). The nucleotide and amino acid sequences for THER2 are listed as SEQ ID NO:21 and SEQ ID NO:22, respectively. The (gly4ser)2 linker sequence is shown in residues 268-283 of SEQ ID NO:22, and the encoding nucleotide sequence for the (gly4ser)2 linker is shown in residues 817-864 of SEQ ID NO:21.

The third construct included a linker that encodes four (gly4ser) sequences flanked by restriction sites (26 amino acid linker), and the fusion gene and protein for this construct is identified as THER4 (or apoA-1-(g4s)4-mthIgG or apoA-1-lnk(26)-mthIgG), where "4" in "THER4" refers to the number of (gly4ser) repeat units, and the number 26 refers to the total number of amino acids encoded in the non-native, introduced linker sequence. The nucleotide and amino acid sequences for THER4 are listed as SEQ ID NO:1 and SEQ ID NO:2, respectively. The (gly4ser)4 linker sequence is shown in SEQ ID NO:50 (residues 268-293 of SEQ ID NO:2), and the encoding nucleotide sequence for the (gly4ser)4 linker is shown in SEQ ID NO:49 (residues 817-894 of SEQ ID NO:1).

The fourth construct included a linker that encodes six (gly4ser) sequences flanked by restriction sites (36 amino acid linker), and the fusion gene and protein for this construct is identified as THER6 (or apoA-1-(g4s)6-mthIgG or apoA-1-lnk(36)-mthIgG). The nucleotide and amino acid sequences for THER6 are listed as SEQ ID NO:23 and SEQ ID NO:24, respectively. The (gly4ser)6 linker sequence is shown in SEQ ID NO:52 (residues 268-303 of SEQ ID NO:24), and the encoding nucleotide sequence for the (gly4ser)6 linker is shown in SEQ ID NO:51 (residues 817-924 of SEQ ID NO:23).

The fifth construct included a linker that encodes four (gly4ser) sequences flanked by restriction sites (36 amino acid linker), but in addition, the construct included a second linker and an enzyme sequence at the carboxyl terminus of the IgG1 domain. The (gly4ser)4 linker sequence is as described above for THER4 (nucleotide and amino acid sequences shown in SEQ ID NO:49 and SEQ ID NO:50, respectively). The second linker is an 18 amino acid long sequence (VDGASSPVNVSSPSVQDI; amino acid residues 1-18 of SEQ ID NO:8, encoded by nucleotides 1-54 of SEQ ID NO:7) that includes an N-linked glycosylation site, followed by a sequence that encodes human RNase1 enzyme activity. The linker sequence is listed as the first 54 nucleotides of SEQ ID NO 7, or the first 18 amino acids of SEQ ID NO 8, followed by the RNase sequence. The ApoA-1-lnk-hIgG1 segment is fused to the NLG-RNase, and this construct is identified as THER4RNA2. The nucleotide and amino acid sequences are identified as SEQ ID NO:3 and SEQ ID NO:4, respectively.

Miniprep DNA for each of the five constructs was prepared and the concentration checked by Nanodrop analysis.

The day before transfection, approximately $1.2 \times 10^6$ 293 T cells were plated to 60 mm dishes. Mini-plasmid preparations (4.0 µg DNA for 60 mm plates) were used for 293T transfections using the QIAGEN POLYFECT® reagent (Catalog #301105/301107) and following the manufacturer's instructions. Culture supernatants were harvested 48-72 hours after transfection. For most transfections, media was changed to serum-free media 24 hours after transfection, and cultures incubated for a further 48 hours prior to harvest.

Culture supernatants were used directly for further analysis. 7 µl of each serum-free culture supernatant from transiently transfected cells was loaded onto gels with a 4× dilution of 4×LDS sample buffer (Life Technologies, Grand Island, N.Y.) added to each sample to give a final concentration of 1×LDS loading buffer. For reducing gels, sample reducing agent was added to 1/10 final volume. Samples were heated at 72° C. for 10 minutes and loaded on NuPAGE® 4-12% Bis-Tris gels (Life Technologies/ThermoFisher Scientific, Grand Island, N.Y.). Gels were subjected to electrophoresis in 1× NuPAGE® MOPS SDS-PAGE running buffer (NP0001, Life Technologies/ThermoFisher) at 180 volts for 1.5 hours, and proteins transferred to nitrocellulose using the XCell II™ Blot Module (Catalog #EI002/EI9051, Life Technologies/ThermoFisher, Grand Island, N.Y.) at 30 volts for 1 hour. Blots were blocked overnight at 4° C. in PBS containing 5% nonfat milk Blots were incubated with 1:250,000× dilution of horseradish peroxidase conjugated goat anti-human IgG (Jackson Immunoresearch, Catalog #109-036-098, Lot #122301). Blots were washed three times for 30 minutes each in PBS/0.05% Tween 20, and were developed in ThermoScientific ECL reagent (Catalog #32106) for 1 minute. Blots were exposed to autoradiograph film for 30 seconds to 2 minutes, depending on the blot. FIG. 3 shows Western Blot analysis of culture supernatants from representative 293T transient transfections. Positive and negative controls (CD40IgG and mock transfection/no DNA, respectively) were included in each transfection series. Transfected samples are as indicated in FIG. 3; lanes from left to right are as follows: Lane #1—mock transfection; Lane #2—CD40IgG; Lane #3—MW markers; Lane #4—THER0; Lane #5—THER2; Lane #6—THER4; Lane #7—THER6; Lane #8—MW marker; Lane #9—THER4RNA2.

The THER0, THER2, THER4, and THER6 fusion proteins run at a position above the 50 kDa molecular weight marker. The predicted molecular weight for these fusion proteins should be approximately 55, 56, 56.6, and 57 kDa, respectively. The increasing linker length is evident by altered mobility for each fusion protein. The THER4RNA2 molecule is predicted to be approximately 73.2 kDa, while ApoA-1 is predicted to run at 28.6 kDa. The CD40IgG control is expected to run at approximately 55 kDa.

Example 4: Expression of THERmthIgG and Multi-SubunitIg Fusion Constructs and Fusion Proteins in Stable CHO Cell Lines This example illustrates expression of the different Ig fusion genes described herein in eukaryotic cell lines and characterization of the expressed fusion proteins by SDS-PAGE and by IgG sandwich ELISA.

Transfection and Selection of Stable Cell Lines Expressing Fusion Proteins

Stable production of the Ig fusion protein was achieved by electroporation of a selectable, amplifiable plasmid, pDG, containing the THER-mthIgG cDNAs (human apo A-1 forms separated from the hinge and Fc domain of human IgG1 by linkers of varying lengths) under the control of the CMV promoter, into Chinese Hamster Ovary (CHO) CHO DG44 cells.

The pDG vector is a modified version of pcDNA3 encoding the DHFR selectable marker with an attenuated promoter to increase selection pressure for the plasmid. Plasmid DNA (200 µg) was prepared using QIAGEN HISPEED® maxiprep kits, and purified plasmid was linearized at a unique AscI site (New England Biolabs, Ipswich, Mass. Catalog #R0558), purified by phenol extraction (Sigma-Aldrich, St. Louis, Mo.), ethanol precipitated, washed, and resuspended in EX-CELLO 302 tissue culture media, (Catalog #14324, SAFC/Sigma Aldrich, St. Louis, Mo.). Salmon sperm DNA (Sigma-Aldrich, St. Louis, Mo.) was added as carrier DNA just prior to phenol extraction and ethanol precipitation. Plasmid and carrier DNA were coprecipitated, and the 400 µg was used to transfect $2 \times 10^7$ CHO DG44 cells by electroporation.

For transfection, CHO DG44 cells were grown to logarithmic phase in EX-CELL® 302 media (Catalog #13424C, SAFC Biosciences, St. Louis, Mo.) containing glutamine (4 mM), pyruvate, recombinant insulin (1 µg/ml), penicillin-streptomycin, and 2×DMEM nonessential amino acids (all from Life Technologies, Grand Island, N.Y.), hereafter referred to as "EX-CELL 302 complete" media. Media for untransfected cells and cells to be transfected also contained HT (diluted from a 100× solution of hypoxanthine and thymidine) (Invitrogen/Life Technologies, Grand Island, N.Y.). Electroporations were performed at 280 volts, 950 microFarads, using a BioRad (Hercules, Calif.) GENEPULSER® electroporation unit with capacitance extender. Electroporation was performed in 0.4 cm gap sterile, disposable cuvettes. Electroporated cells were incubated for 5 minutes after electroporation prior to transfer of culture to non-selective EX-CELL 302 complete media in T75 flasks.

Transfected cells were allowed to recover overnight in non-selective media prior to selective plating in 96 well flat bottom plates (Costar) at varying serial dilutions ranging from 250 cells/well (2500 cells/ml) to 2000 cells/well (20,000 cells/ml). Culture media for cell cloning was EX-CELL 302 complete media containing 50 nM methotrexate. Transfection plates were fed at five day intervals with 80 µl fresh media. After the first couple of feedings, media was removed and replaced with fresh media. Plates were monitored and individual wells with clones were fed until clonal outgrowth became close to confluent, after which clones were expanded into 24 well dishes containing 1 ml media. Aliquots of the culture supernatants from the original 96 well plate were harvested to a second 96 well plate prior to transfer and expansion of the cells in 24 well plates. This second plate was frozen until ELISA analysis to estimate IgG concentrations.

Screening Culture Supernatants for Production Levels of Recombinant Fusion Proteins Once clonal outgrowth of initial transfectants was sufficient, serial dilutions of culture supernatants from master wells were thawed and the dilutions screened for expression of Ig fusion protein by use of an IgG sandwich ELISA. Briefly, NUNC MAXISORP® plates were coated overnight at 4° C. with 2 μg/ml F(ab'2) goat anti-human IgG (Jackson Immunoresearch, West Grove, Pa.; Catalog #109-006-098) in PBS. Plates were blocked in PBS/3% BSA, and serial dilutions of culture supernatants incubated at room temperature for 2-3 hours or overnight at 4° C. Plates were washed three times in PBS/0.05% Tween 20, and incubated with horseradish peroxidase conjugated F(ab'2)goat anti-human IgG (Jackson Immunoresearch, West Grove, Pa., Catalog #109-036-098) at 1:7500-1:10,000 in PBS/0.5% BSA, for 1-2 hours at room temperature. Plates were washed five times in PBS/0.05% Tween 20, and binding detected with SUREBLUE RESERVE™ TMB substrate (KPL Labs, Gaithersburg, Md.; catalog #53-00-02). Reactions were stopped by addition of equal volume of 1N HCl, and absorbance per well on each plate was read at 450 nm on a SYNERGY™ HT plate reader (Biotek, Winooski, Vt.). Concentrations were estimated by comparing the OD450 of the dilutions of culture supernatants to a standard curve generated using serial dilutions of a known standard, a protein A purified human IgG fusion protein with an Ig tail identical to that of the THER clones. Data was collected and analyzed using GEN5™ software (Biotek, Winooski, Vt.) and Microsoft Office EXCEL® spreadsheet software.

The results of initial screening of the CHO transfectants are summarized in Table 6 and FIGS. 4A-4E and 5A-5C. Table 6 shows a summary of the number of clones screened, the range of expression levels observed from initial 96-well cultures, and the expression observed from initial T25 and/or 24 well spent cultures. FIGS. 4A-4E show a series of columnar graphs representing the production levels obtained from each CHO clone of a transfection series. The clones from the THER0, THER2, THER4, THER6, and THER4RNA2 transfections are displayed as a group in each of the five panels shown. Each clone was screened at least once by IgG sandwich ELISA to assess expression level of the fusion protein. FIGS. 5A-5C show three panels showing the results of 6 and 10 day assays of fusion protein expression from the CHO transfectants with the highest expression after initial screening. Six and ten day assays were performed by setting up 5 ml cultures at 1×10⁵ viable cells/ml (5×10⁵ initial inoculum) in T25 flasks. The cultures were grown for six days after which a 1 ml aliquot was removed and live and dead cells counted. Cells were then centrifuged and the culture supernatants saved for further analysis by IgG sandwich ELISA and other analyses. The remainder of the cultures were incubated for a further four days until day 10, and the cells counted for cell number, viability, and a supernatant sample harvested for IgG sandwich ELISA. The results are tabulated in columnar form for each clone as shown in the graphs for cell number at day 6 and day 10, viability, and concentration of fusion protein.

TABLE 6

Expression of ApoA1-IgG fusion proteins in stably transfected CHO DG44 cells

| Construct | Clones Screened | 96 well sups expression range (μg/ml) | Spent T25 top producer (μg/ml) | 6/10 day assay on top clones (μg/ml) |
|---|---|---|---|---|
| THER0 | 45 | 0-46.5 | 135 | 60/230 |
| THER2 | 135 | 0-36 | 145 | 45/125 |
| THER4 | 237 | 0-76 | 165 | 70/200 |
| THER6 | 192 | 0-57 | 145 | 85/250 |
| THER4RNA2 | 50 | 0-45 | 90 | 50/118 |

The clones with the highest production of the fusion protein were expanded into T25 and then T75 flasks to provide adequate numbers of cells for freezing and for scaling up production of the fusion protein. Production levels were further increased in cultures from the four best clones by progressive amplification in methotrexate-containing culture media. At each successive passage of cells, the EX-CELL 302 complete media contained an increased concentration of methotrexate, such that only the cells that amplified the DHFR plasmid could survive. Media for transfections under selective amplification contained varying levels of methotrexate (Sigma-Aldrich) as selective agent, ranging from 50 nM to 1 μM, depending on the degree of amplification achieved.

Purification of Fusion Proteins from Culture Supernatants

Supernatants were collected from spent CHO cell cultures expressing the Apo A-1-lnk-mthIgG1 construct, filtered through 0.2 μm PES express filters (Nalgene, Rochester, N.Y.) and subjected to gravity flow affinity chromatography over a Protein A-agarose (IPA 300 crosslinked agarose, or IPA 400HC crosslinked agarose) column (Repligen, Waltham, Mass.). The column was conditioned with 0.1M citrate buffer, pH2.2, then supernatant adjusted to pH 8.0 with 0.5M NHCO₃, and loaded by gravity flow to allow binding of the fusion proteins. Columns were then washed with several column volumes column wash buffer (90 mM Tris-Base, 150 mM NaCl, 0.05% sodium azide, pH 8.7) or Dulbecco's modified PBS, pH 7.4 prior to elution. Bound protein was eluted using 0.1 M citrate buffer, pH 3.2. Fractions (0.8-0.9 ml) were collected into 0.2 ml 0.5M NaCO₃—NaHCO₃ buffer to neutralize each fraction. Protein concentration of aliquots (2 μl) from each fraction were determined at 280 nM using a Nanodrop (Wilmington Del.) microsample spectrophotometer, with blank determination using 0.1 M citrate buffer, pH 3.2, 0.5M NaCO₃ at a 10:1 v:v ratio. Fractions containing fusion protein were pooled, and buffer exchange performed by dialysis using Spectrum Laboratories G2 (Ranch Dominguez, Calif., Catalog #G235057, Fisher Scientific catalog #08-607-007) FLOAT-A-LYZER® units (MWCO 20 kDa) against D-PBS (Hyclone, ThermoFisher Scientific, Dallas, Tex.), pH 7.4. Dialysis was performed in sterile, 2.2 liter Corning roller bottles at 4° C. overnight.

After dialysis, protein was filtered using 0.2 μM filter units, and aliquots tested for endotoxin contamination using PYROTELL® LAL gel clot system single test vials (STV) (Catalog #G2006, Associates of Cape Cod, East Falmouth, Mass.). The predicted OD 280 of a 1 mg/ml solution of the THER4 fusion protein was determined to be 1.19 (mature protein without either the signal peptide or the 6 amino acid propeptide) or 1.27 (including the 6 amino acid propeptide) using the protein analysis tools in the VECTOR NTI® Version 11.5 Software package (Informax, North Bethesda, Md.) and the predicted cleavage site from the online ExPASy protein analysis tools. It is unclear whether the fusion protein secreted from the CHO cells is homogeneous with regard to complete cleavage of the propeptide from the recombinant molecules. The OD280 for each purified fusion protein was corrected using these tools.

Reducing and Nonreducing SDS-PAGE Analysis of apo A-1 Ig Fusion Proteins

Purified fusion proteins were analyzed by electrophoresis on SDS-Polyacrylamide 4-12% Bis-Tris NuPAGE® gels (Life Technologies, Grand Island, N.Y.). Fusion protein samples were heated at 72° C. for 10 minutes in LDS sample buffer with and without reduction of disulfide bonds and applied to 4-12% BIS-Tris gels (Catalog #NP0301, LIFE Technologies, Grand Island, N.Y.). Five micrograms of each purified protein was loaded on the gels. The proteins were visualized after electrophoresis by IMPERIAL™ protein staining (Pierce Imperial Protein Stain Reagent, Catalog #24615, ThermoFisher Scientific/Pierce, Rockford, Ill.), and destaining in distilled water. Molecular weight markers were included on the same gel (KALEIDOSCOPE™ Prestained Standards, Catalog #161-0324, Bio-Rad, Hercules, Calif.). The results from representative nonreducing and reducing gels are shown in FIGS. 6A and 6B, respectively. Lanes are as follows from left to right: Lane #1—KALEIDOSCOPE prestained MW markers; Lane #2—THER0; Lane #3—THER2; Lane #4—THER4; Lane #5—THER6; Lane #6—THER4RNA2; Lane #7—KALEIDOSCOPE Prestained MW markers. Approximate molecular weights are indicated on the figures.

Again, the linker length difference between the different fusion proteins is evident on both the reducing and nonreducing gels, with the THER0 protein running at just over 50 kDa. The absence of hinge disulfides is evident by the similar mobility for each protein when electrophoresed under reducing or nonreducing conditions.

Native Gel Electrophoresis of apo A-1 IgG Fusion Proteins

The protein A purified fusion proteins were subjected to native PAGE analysis. BLUE Native PAGE gels were run using 4-16% Bis-Tris NativePAGE™ gels (Life Technologies/ThermoFisher) with cathode and anode buffers prepared according to manufacturer's instructions. Samples (4.5 µg each fusion protein) were prepared without heating, using 4× sample buffer, without detergents. Gels were run for 30 minutes at 150 volts, followed by 1 hour at 180 volts, and the final hour at 220 volts. Gels were washed in distilled water and incubated for two hours in IMPERIAL™ Protein stain. Gels were extensively destained overnight with repeated washes in distilled water to remove the blue dye present in the cathode buffer used for running the gels. FIG. 7 shows a representative native gel using these conditions. Molecular weight markers were GE Healthcare high molecular weight calibration markers, a mixture of six large, multicomponent proteins, resuspended in the loading buffer used for samples, again without added detergents. Samples were loaded as follows: Lane #1—ORENCIA® (abatacept; CTLA4hIgG); Lane #2—anti-mouse CD40 monoclonal antibody 1C10; Lane #3—THER4RNA2; Lane #4—GE Healthcare High MW calibration markers; Lane #5—THER6; Lane #6—THER4; Lane #7—THER2; Lane #8—THER0; Lane #9—GE Healthcare high MW markers; Lane #10—Athens Research Apo A-1.

The native ApoA1-IgG fusion proteins run at an approximate molecular weight somewhere between the 140 and 233 kDa markers and with a similar mobility as ORENCIA® (abatacept), a CTLA4Ig fusion protein with the same human IgG1 Fc domain. The THER4RNase bispecific fusion protein did not stain well with the IMPERIAL stain possibly due to the highly basic composition of the RNase domain, but appears to migrate in a more diffuse pattern with the predominate visible band migrating between the 233 and 440 kDa standards.

Example 5: Use of an IgG/Apo A-1 Sandwich ELISA to Assess Binding of THER Apo A-1 Fusion Proteins An antigen binding ELISA was performed to assess the ability of Ig fusion proteins, captured by immobilized anti-human IgG (Fc-specific) to bind to and be detected by a horseradish peroxidase conjugated antibody specific for human apolipoprotein A-1. High protein-binding, 96-well ELISA plates (NUNC MAXISORP® plates, ThermoFisher Scientific) were coated with 1.5 kg/ml goat anti-human IgG (Jackson Immunoresearch). Plates were blocked overnight at 4° C. with PBS/3% BSA. Serial dilutions of each THER fusion protein, starting at 5 µg/ml, were incubated overnight at 4° C. The plate was washed three times and then incubated with horseradish peroxidase conjugated anti-human apolipoprotein A-1 (ThermoFisher Scientific, catalog #PAI-28965) diluted 1:1500. Plates were incubated at room temperature for 2 hours. Plates were washed four times, then SUREBLUE RESERVE™ TMB substrate (Catalog #: 53-00-02, KPL, Gaithersburg, Md.) was added to the plate at 80 µl/well. Development was stopped by addition of 80 µl/well 1N HCl. Samples were read at 450 nm using a SYNERGY™ HT Biotek plate reader (Biotek Instruments, Winooski, Vt.) and data analyzed using GEN5™ 2.0 software.

FIG. 8 shows the results from a representative Apo A-1 binding ELISA. OD450 is plotted versus concentration of fusion protein. THER 0, 2, 4, 6, and THER4RNA2 fusion proteins all exhibited similar dose-response curves, indicating that the molecules can each be captured by binding to the Ig tail and detected by binding of the Apo A-1 domain to the antibody targeted to human Apo A-1. Human apolipoprotein A-1 (Athens Research & Technology, catalog #16-16-120101) was included as a control and was not captured by the anti-human Fc specific antibody. At higher concentrations, the molecule showed weak binding by the antibody targeted to Apo A-1, indicating that the Apo A-1 may have bound weakly to the plastic without capture by the anti-Fc antibody.

Example 6: Expression and Testing of an RNase Bifunctional Enzyme Lipid Transport Fusion Molecule For the Apo A-1 IgG RNase fusion protein (THER4RNA2), RNase activity was assayed to determine whether fusion of the enzyme to the carboxyl end of the fusion construct interfered with ability of the molecule to digest RNA. FIGS. 9 and 10 show the results of an RNASEALERT™ assay (IDT, Coralville, Iowa) performed using the fluorescence and kinetic assay functions of the SYNERGY™ HT plate reader. RNASEALERT™ Substrate is a synthetic RNA oligonucleotide that has a fluorescein (R) on one end and a dark quencher (Q) on the other end. When intact, the substrate has little or no fluorescence, but when cleaved by an RNase, the substrate fluoresces green (490 nm excitation, 520 nm emission) and can be detected with the appropriately equipped fluorescence plate reader. A positive signal in this assay shows increasing fluorescence signal over time due to cleavage of the substrate by RNase present in the sample(s). Microplates were incubated with RNASEALERT substrate (a fixed concentration of 20 pmol/µl), 1× RNASEALERT buffer, and fusion protein or enzyme controls dilutions added to each well of a 96 well plate. Enzyme activity assays were performed in triplicate for each sample, and the kinetic assay allowed to proceed for 45 minutes, with successive readings every 60 seconds. The increasing fluorescence at each time point is displayed for each well as a trace of RFU/well as a function of time in FIG. 9. Serial dilutions of enzyme/fusion protein included 20 pmol/µl, 13.4 pmol/µl, 8.9 pmol/µl, 6 pmol/µl, 4 pmol/µl, 2.7 pmol/µl, 1.8 pmol/µl, and no enzyme. RNase A (Ambion/ThermoFisher, catalog #AM2270) was included as a positive control, and THER4 (apo A-1-lnk26-hIgG) was included as a negative control for comparing to the THER4RNA2 fusion protein. Overlays of the traces generated using the 4 pmol/µl enzyme are shown in FIG. 10. Two replicates of the RNaseA, THER4RNA2, and THER4, are shown. All enzymes are at 4 pmol/µl and the substrate is present at 20 pmol/µl.

Example 7: Measurement of Cholesterol Efflux to Fusion Protein Acceptors

Using two separate assays, THER0, THER2, THER4, THER6, and THER4RNA2 fusion proteins were assessed for their ability to act as acceptor molecules for reverse cholesterol transport from pre-loaded monocyte/macrophage mammalian cell lines. The first assay used the human monocytic/macrophage cell line THP-1 and a fluorescently labeled derivative of cholesterol, BODIPY-cholesterol or TOPFLUOR-cholesterol (cholesterol compound with fluorescent boron dipyrromethene difluoride linked to sterol carbon-24) (Avanti Polar Lipids, Alabaster, Ala.). The THP-1 cells were grown in RPMI with 4 mM glutamine, 10% FBS and maintained in mid-logarithmic growth prior to plating. The protocol was adapted from the procedures outlined in Sankaranararyanan et al. (*J. Lipid Res.* 52:2332-2340, 2011) and Zhang et al. (*ASSAY and Drug Development Technologies:* 136-146, 2011). Cells were harvested and plated to 96-well flat bottom tissue culture plates at $2\times10^6$ cells/ml or $2\times10^5$ cells/well in 100 µl RPMI media containing 33 ng/ml PMA. Cells were maintained in culture for 36-48 hours to allow for differentiation to occur prior to the assay. Culture media was aspirated and plates were washed in 1×PBS. Labeling media consisting of the following components (Phenol Red free RPMI with media supplements, 0.2% FBS, with ACAT inhibitor at 2 µg/ml, Sandoz 58-035 (Sigma-Aldrich, St. Louis Mo.), LXR agonist TO-901317 at 2.5 µM (Sigma-Aldrich, St. Louis, Mo.), 35 ng/ml PMA (Sigma-Aldrich, St. Louis, Mo.), and 1.25 mM methyl beta-cyclodextrin (Sigma-Aldrich, St. Louis, Mo.), 50 uM cholesterol (Sigma-Aldrich, St. Louis, Mo., and 25 µM TOPFLUOR cholesterol (Avanti Polar Lipids, Alabaster, Ala.) was added at a volume of 100 µl/well and incubated at 37 C, 5% CO2 for 10-12 hours. Equilibration media, RPMI complete with 10% FBS, 33 ng/ml PMA (100 ul/well), was added to each well and incubated for 8 hours prior to incubation with acceptors. Labeling/equilibration media was aspirated from plates, and plates were washed twice with 200 µl/well PBS+0.15% BSA. Efflux acceptor reagents were added to individual wells in efflux buffer and incubated for two hours prior to assay. Acceptors were added to efflux buffer at concentrations ranging from 100 nM to 500 nM, depending on the assay. Efflux buffer was phenol red-free RPMI with growth supplements and 0.15% BSA. Samples were run in sets of 6-12 per condition/acceptor, and a minimum of five replicates used for statistical analysis. APO A-1 was run as a positive control, and efflux media alone was used as the background negative control (baseline efflux). The efflux reaction was allowed to proceed for two hours, after which culture media was harvested to black, flat bottom 96-well plates (media reading). Cell lysates were prepared by addition of 100 ul 0.1 N NaOH to each well of the efflux plate, and incubation for 15 minutes on a plate shaker at 4° C. Cell lysates were transferred to black, 96-well plates (lysate reading), and fluorescence for media and lysate samples measured using a SYNERGY™ HT plate reader with excitation at 485 nm and emission at 528 nm. Efflux was calculated as the ratio of the fluorescence measurements: (media/(media+lysate)×100). The specific efflux was calculated by subtracting the baseline readings of the samples with no acceptor present from the total efflux/sample for each tested acceptor. Data analysis was performed using GraphPad Prism v 4.0 Software (San Diego, Calif.). The assay results are shown in FIG. 11.

The second assay used the mouse macrophage cell line J774A.1 (ATCC, Manassas, Va.) to assess reverse cholesterol transport (RCT) using a radioactive derivative of cholesterol, [$^3$H]-cholesterol as described by Sankaranararyanan et al. (*J. Lipid Res.* 52:2332-2340, 2011) and Yancey et al. (*J. Lipid Res.* 45:337-346, 2004). Briefly, J774 cells ($3.5\times10^5$ per well in 24 well plates) were incubated for 24 hours in 0.25 ml RPMI media supplemented with 5% FBS, ACAT inhibitor Sandoz 58-035 (2 µg/ml), and 4 µCi/ml of [$^3$H]-cholesterol. ACAT inhibitor was present at all times during the assay. Cells were equilibrated 16-24 hours in media with or without cAMP (0.3 mM) prior to incubation with acceptors. The presence of cAMP upregulates the ABCA1 molecule. Labeled cells were washed in media containing 1% BSA, then acceptor molecules were added at 50, 100 and 200 nM in MEM-HEPES media and incubated for 4 hours prior to measurements. All treatments were performed in triplicate. The [$^3$H] cholesterol in 100 µl of the media was then measured by liquid scintillation counting. The percentage efflux is based on the total [$^3$H]cholesterol present in the cells before the efflux incubation ($t_0$ sample). To measure the [$^3$H]cholesterol present in the cells, the cell lipids were extracted by incubating the cell monolayers overnight in isopropanol. After lipid extraction, the total [$^3$H]cholesterol present in the lipid extract was measured by liquid scintillation counting. Data analysis was performed using GraphPad Prism software 4.0 (San Diego, Calif.). The assay results are shown in FIG. 12.

Example 8: Construction of a PON1 Bifunctional Enzyme Lipid Transport Fusion Molecule In addition to the apoA-1-IgG-RNase expression constructs described above, additional molecules which physically link the ApoA-1 phospholipid transport function to the active sites of other enzyme domains are constructed. One such molecule contains a segment corresponding to human paraoxanase 1 (PON1), with nucleotide and encoded amino acid sequences as shown in SEQ ID NO:11 and SEQ ID NO:12, respectively. This arylesterase enzyme is present in human serum exclusively associated with high density lipoprotein (HDL), and inhibits oxidation of low density lipoprotein molecules. This protection from oxidation also inhibits development of vascular and coronary diseases. The mature protein form of PON1 is unique in that it retains its amino terminal signal peptide after secretion (amino acid residues 1 to 15 of SEQ ID NO:12, encoded by nucleotide residues 1 to 45 of SEQ ID NO:11). Expression of a mutant form of PON1 with a cleavable amino terminus demonstrated that PON1 associates with lipoproteins through its amino terminus by binding to phospholipids directly rather than first binding to ApoA-1. See Sorenson et al., *Arteriosclerosis, Thrombosis, and Vascular Biology* 19:2214-2225, 1999. Removal of the signal sequence was found to eliminate binding of the PON1 moiety to phospholipids, proteoliposomes, and serum lipoproteins. Additionally, in the absence of phospholipid, wild-type PON1 does not bind directly to ApoA-1. See Sorenson et al., supra. These PON1 signal sequence mutants showed reduced enzyme activity, possibly due to inability to bind the optimal phospholipid substrates. Nevertheless, a recombinant, active form of human PON1 has been expressed in bacteria that is missing this signal sequence. See Stevens et al., *Proc. Natl. Acad. Sci. USA* 105:12780-12784, 2008. The presence of ApoA-1 does appear to stabilize arylesterase activity of the enzyme.

Removal of the amino terminal signal sequence of PON1 (and thereby the phospholipid binding moiety) and substitution of this region with human apoA-1-lnk-IgG directly links the enzyme activity with the phospholipid binding domain of ApoA-1, stabilizing the arylesterase enzyme activity while providing the optimal substrates bound to the ApoA-1 domain. Such a molecule still traffics and is transported with the phospholipids bound by ApoA-1 and retains enzyme activity due to replacement of the signal sequence domain with an alternative phospholipid binding domain. In addition, a bifunctional molecule fusing these two domains exhibits improved expression and facilitates targeting of the PON1 activity to the choroid plexus through active binding of apo A-1. PON1 has been expressed at the carboxyl terminus of an insulin receptor targeted antibody (see Boado et al., *Mol. Pharm.* 5:1037-1043, 2008; Boado et al., *Biotechnology and Bioengineering* 108:186-196, 2011); however, the amino terminal signal peptide was included in this fusion protein. The fusion gene and protein described here provides a novel method of PON1 fusion protein expression, eliminating the requirement for the signal peptide by a direct physical coupling of the truncated enzyme to the apo A-1 domain, thereby preserving and stabilizing both the binding function and arylesterase activity of PON1.

Sequences for the fusion gene and protein are shown in SEQ ID NO:27 and SEQ ID NO:28 for THER4PON1 (nucleotide and amino acid sequences, respectively) and in SEQ ID NO:37 and SEQ ID NO:38 for THER2PON1 (nucleotide and amino acid sequences, respectively). Similar fusion genes and proteins contain alternative linker forms of ApoA-1 fused to the hIgG1-linker-PON1 segment(s). The PON1 sequences within the THER4PON1 and THER2PON1 molecules correspond to the Q192 allele for human PON1.

Alternative forms of PON1 are also used to construct bifunctional fusion molecules linking PON1 to Apo A-1. A sequence polymorphism that affects enzyme activity for different substrates is present at position 192 of the PON1 sequence. See Steven et al., supra. The amino acid at this position may be glutamine (Q) or arginine (R) in humans, or a lysine (K) in rabbits. The arginine allele at position 192 has been reported to have a higher catalytic activity in vitro and in vivo. Similarly, the rabbit form of PON1 with a lysine at position 192 has been reported to have a more stable catalytic activity in vitro and in vivo (see Steven et al., supra; Richter et al., *Circulation Cardiovascular Genetics* 1:147-152, 2008). These alternative PON1 sequences are shown in SEQ ID NO:41 (nucleotide) and SEQ ID NO:42 (amino acid) for the PON1 Q192K form, and SEQ ID NO:43 (nucleotide) and SEQ ID NO:44 (amino acid) for the PON1 Q192R form. The fusion construct between these alternate PON1 forms and the THER4 sequence (apoA-1(g4s)4hIgG-NLG-...) is designated as THER4PON1 Q192K (nucleotide and amino acid sequences shown in SEQ ID NO:45 and SEQ ID NO:46, respectively) or THER4PON1 Q192R (nucleotide and amino acid sequences shown in SEQ ID NO:47 and SEQ ID NO:48, respectively), depending on the polymorphism present in the PON1 sequence at amino acid 192 of the PON1 sequence (or at amino acid 720 of the THER4PON1Q variants shown in SEQ ID NO:46 and SEQ ID NO:48). Similarly, a THER2 form of the fusion gene/protein is indicated as THER2PON1 Q192K or THER2PON1Q192R. For all of these fusion constructs, the PON1 amino terminal signal sequence (amino acids 1-15 of SEQ ID NO:12) is removed.

Bispecific Enzyme Lipoprotein Transfer Proteins comprising PON1 are screened for arylesterase/PON1 activity using the nontoxic substrates 4-(chloromethyl)phenyl acetate (CMPA) and phenyl acetate (see Richter et al., supra). These substrates are preferable for screening activity since the substrate and reaction product are relatively nontoxic compared to organophosphate pesticides. The CMPA substrate (Sigma-Aldrich, Inc. St Louis, Mo.) is incubated with serial dilutions of fusion protein and rates of CMPA hydrolysis assayed at 280 nm for 4 minutes at 25° C. using ultraviolet transparent 96-well plates (Costar, Cambridge, Mass.). Dilutions are run in triplicate or quadruplicate and substrate concentration fixed at 3 mmol/L in 20 mM Tris-HCl (pH 8.0), 1.0 mM $CaCl_2$. Similarly, arylesterase assays are performed on phenyl acetate as substrate. The rates of PA hydrolysis are measured at 270 nm, for 4 minutes under both high and low salt conditions.

Example 9: Construction of a PAFAH or CETP Bifunctional Enzyme Lipid Transport Fusion Molecule In addition to the apoA-1-IgG-RNase and apoA-1-IgG-PON1 expression constructs described above, additional molecules which physically link the ApoA-1 phospholipid transport function to the active sites of other enzyme domains are constructed.

One such molecule contains a segment corresponding to human PAFAH (lipoprotein-associated phospholipase A2, human phospholipase A2 group VII, platelet activating factor acetyl hydrolase), with nucleotide and encoded amino acid sequences as shown in SEQ ID NO:31 and SEQ ID NO:32, respectively (see also GenBank accession number NM_005084 (transcript variant 1)). The PAFAH amino acid sequence is encoded by nucleotides 270 to 1592 of SEQ ID NO:31, with the STOP codon at nucleotides 1593 to 1595. The fusion gene and protein are designed fusing the PAFAH coding sequence at the carboxyl end of the human IgG with the N-linked glycosylation linker inserted between the two molecules. The THER4PAFAH nucleotide and encoded amino acid sequences are shown as SEQ ID NO:33 and SEQ ID NO:34, respectively. The PAFAH sequence without the 21 amino acid signal peptide (MVPPKLHVLFCLCGCLAV-VYP; residues 1-21 of SEQ ID NO:32) is fused to the NLG linker at amino acid position 544 in SEQ ID NO 34.

Another such molecule contains a segment corresponding to human CETP or cholesteryl ester transfer protein (CETP), transcript variant 1, with nucleotide and encoded amino acid sequences as shown in SEQ ID NO:29 and SEQ ID NO:30, respectively (see also GenBank accession number NM_000078). The CETP protein is encoded by nucleotides 58 to 1537 of SEQ ID NO:29. The fusion gene and protein are designed fusing the CETP coding sequence at the carboxyl end of the human IgG with the N-linked glycosylation linker inserted between the two molecules. The THER4CETP (or human apo A-1-(g4s)4-hIgG-NLG-CETP) nucleotide and encoded amino acid sequences are shown as SEQ ID NO:39 and SEQ ID NO:40, respectively. The nucleotides (57-107 of SEQ ID NO 29) encoding the signal peptide (amino acids 1-17 of SEQ ID NO 30) are removed in order to create the fusion gene between the NLG linker sequence and the CETP mature peptide. The fusion junction between these two protein domains is located at amino acid 544 of SEQ ID NO 40.

Example 10: Construction and Expression of PON1 Bifunctional Enzyme Lipid Transport Fusion Molecules THER4PON1 (also referred to herein as "T4P1") and other ApoA1-lnk-IgG-PON1 fusion gene variants were constructed by using THER4RNA2 as a recipient for substitution mutations, removing the RNase containing cassette and replacing it with different variants of the PON1 sequence. PON1 cDNA constructs were designed in cassette form, synthesized by PCR amplification, and the sequences assembled by subcloning using engineered restriction sites incorporated into the molecule design. Once cassettes were assembled in the desired configuration, fusion gene constructs were assembled in pUC-based vectors and final restriction fragments encoding the fusion genes were subcloned into the mammalian expression vector pDG. Briefly, HindIII+XbaI or EcoRV flanking restriction sites were used for removal of each expression gene from the vector, subfragments isolated by gel electrophoresis, DNA extracted using QIAquick purification columns, and eluted in 30 microliters EB buffer. Fragments were ligated into HindIII+XbaI or EcoRV digested pDG vector, and ligation reactions transformed into NEB 5-alpha, chemically competent bacteria. Clones were inoculated into 3 ml LB broth with 100 µg/ml ampicillin, grown at 37° C. overnight with shaking at 200 rpm, and plasmid DNA was prepared using the QIAGEN spin plasmid miniprep kits according to manufacturer's instructions. Sequencing primers were obtained from IDT Integrated DNA Technologies (Coralville, Iowa) and included the following:

```
pdgF-2:
                            (SEQ ID NO: 16)
5'-ggttttggcagtacatcaatgg-3';

pdgR-2:
                            (SEQ ID NO: 17)
5'-ctattgtcttcccaatcctccc-3';

higgras:
                            (SEQ ID NO: 18)
5'-accttgcacttgtactcctt-3'.
```

For sequencing constructs, plasmid DNA (800 ng) and sequencing primers (25 pmol, or 5 µl of a 5 pmol/µl stock) were mixed and submitted for DNA sequencing by GENEWIZ (South Plainfield, N.J.). Chromatograms were then analyzed, sequences assembled into contigs, and sequence verified using Vector Nti Advance 11.5 software (Life Technologies, Grand Island, N.Y.). Clones with the correct sequence were then amplified and plasmid DNA was used for transient transfection of HEK293T cells using Polyfect reagent (QIAGEN, Valencia, Calif.), according to manufacturer's instructions. Transfection media was changed after 24 hours to a low fluorescence, phenol red free media, FLUOROBRITE™ DMEM (Life Technologies, Grand Island, N.Y.), containing growth supplements (glutamine, pyruvate, non-essential amino acids, and pen/strep), but no serum. Serum-free transfection supernatants were harvested after 48-72 hours. Proteins were analyzed by SDS PAGE, Western blotting, and ELISA analysis. In addition, for proteins expressed at sufficient levels as determined by ELISA, undiluted and serial dilutions of culture supernatants were filter-sterilized and used in further functional assays.

Culture supernatants from transient and stable transfections were used directly for further analysis; in general, 10 µl of each serum-free culture supernatant from transfected cells was loaded onto gels in 1×LDS sample buffer (Life Technologies, Grand Island, N.Y.). For reducing gels, sample reducing agent was added to 1/10 final volume. Samples were heated at 72° C. for 10 minutes and loaded on NuPAGE® 4-12% Bis-Tris gels (Life Technologies/ThermoFisher Scientific, Grand Island, N.Y.). Gels were subjected to electrophoresis in 1× NuPAGE® MOPS SDS-PAGE running buffer (NP0001, Life Technologies/ThermoFisher) at 180 volts for 1.5 hours, and proteins transferred to nitrocellulose using the XCell II™ Blot Module (Catalog #E1002/EI9051, Life Technologies/ThermoFisher, Grand Island, N.Y.) at 30 volts for 1 hour. Blots were blocked overnight at 4° C. in PBS containing 5% nonfat milk Blots were incubated with 1:100,000× dilution of horseradish peroxidase conjugated goat anti-human IgG (Jackson Immunoresearch, Catalog #109-036-098, Lot #122301). Blots were washed three times for 30 minutes each in PBS/0.05% Tween 20 and were developed in ThermoScientific ECL reagent (Catalog #32106) for 1 minute. Blots were analyzed using a ProteinSimple fluorescence imager, and images were saved and analyzed with Adobe Photoshop software.

FIG. 13 shows Western Blot analysis of culture supernatants from representative 293T transient transfections. Prior to transfection, 293T cells were plated to 60 mm dishes at a density of 1.5×10e$^6$ cells/plate and grown overnight. Transfection media was prepared according to manufacturer's directions using Polyfect transfection reagent (QIAGEN, Valencia, Calif.). Positive and negative controls (THER4 and mock transfection/no DNA, respectively) were included in each transfection series. Three different ApoA1-lnk-hIgG-PON1 plasmids encoding sequence variants (THER4PON1 192Q, THER4PON1 192R, and THER4PON1 192K) were transfected in addition to the THER4 plasmid and the mock transfection. Supernatant samples (10 µl) were loaded onto 4-12% Bis-Tris gels in 1× reducing LDS sample buffer in the order listed from left to right: mock transfection, THER4, THER4PON1 192Q, THER4PON1 192R, THER4PON1 192K, and Precision Plus Kaleidoscope molecular weight markers (BioRad, Hercules, Calif.). The lanes with the ApoA1-lnk-hIgG-PON1 fusion proteins contain a single band migrating at approximately 105 kDa.

Stable transfection of ApoA1-lnk-hIgG-PON1 fusion protein expression plasmids was performed by electroporation of a selectable, amplifiable plasmid, pDG, containing the constructs under the control of the CMV promoter, into Chinese Hamster Ovary (CHO) CHO DG44 cells. Plasmid DNA (200 µg) was prepared using QIAGEN HISPEED® maxiprep kits, and purified plasmid was linearized at a unique AscI site (New England Biolabs, Ipswich, Mass. Catalog #R0558), purified by phenol extraction (Sigma-Aldrich, St. Louis, Mo.), ethanol precipitated, washed, and resuspended in EX-CELLO 302 tissue culture media, (Catalog #14324, SAFC/Sigma Aldrich, St. Louis, Mo.). Salmon sperm DNA (Sigma-Aldrich, St. Louis, Mo.) was added as carrier DNA just prior to phenol extraction and ethanol precipitation. Plasmid and carrier DNA were coprecipitated, and the 400 µg was used to transfect $2 \times 10^7$ CHO DG44 cells by electroporation.

For transfection, CHO DG44 cells were grown to logarithmic phase in EX-CELL 302 complete media (see Example 4). Media for untransfected cells and cells to be transfected also contained HT (diluted from a 100× solution of hypoxanthine and thymidine) (Invitrogen/Life Technologies, Grand Island, N.Y.). Electroporations were performed at 280 volts, 950 microFarads, using a BioRad (Hercules, Calif.) GENEPULSER® electroporation unit with capacitance extender. Electroporation was performed in 0.4 cm gap sterile, disposable cuvettes. Electroporated cells were incubated for 5 minutes after electroporation prior to transfer of culture to non-selective EX-CELL 302 complete media in T75 flasks.

Transfected cells were allowed to recover overnight in non-selective media prior to selective plating in 96 well flat bottom plates (Costar) at varying serial dilutions ranging from 250 cells/well (2500 cells/ml) to 2000 cells/well (20,000 cells/ml). Culture media for cell cloning was EX-CELL 302 complete media containing 50 nM methotrexate. Transfection plates were fed at five day intervals with 80 µl fresh media. After the first couple of feedings, media was removed and replaced with fresh media. Plates were monitored and individual wells with clones were fed until clonal outgrowth became close to confluent, after which clones were expanded into 24 well dishes containing 1 ml media. Aliquots of the culture supernatants from the original 96 well plate were also harvested and frozen for later ELISA analysis to estimate IgG concentrations.

Screening Culture Supernatants for Production Levels of Recombinant Fusion Proteins Once clonal outgrowth of initial transfectants was sufficient, serial dilutions of culture supernatants from master wells were thawed and the dilutions screened for expression of Ig fusion protein by use of an IgG sandwich ELISA. Briefly, NUNC MAXISORP® plates were coated overnight at 4° C. with 2 µg/ml F(ab'2) goat anti-human IgG (Jackson Immunoresearch, West Grove, Pa.; Catalog #109-006-098) in PBS. Plates were blocked in PBS/3% BSA, and serial dilutions of culture supernatants incubated at room temperature for 2-3 hours or overnight at 4° C. Plates were washed three times in PBS/0.05% Tween 20, and incubated with horseradish peroxidase conjugated F(ab'2)goat anti-human IgG (Jackson Immunoresearch, West Grove, Pa., Catalog #109-036-098) at 1:7500-1:10,000 in PBS/0.5% BSA, for 1-2 hours at room temperature. Plates were washed five times in PBS/0.05% Tween 20, and binding detected with SUREBLUE RESERVE™ TMB substrate (SeraCare, Gaithersburg, Md.). Reactions were stopped by addition of equal volume of 1N HCl, and absorbance per well on each plate was read at 450 nm on a SYNERGY™ HT plate reader (Biotek, Winooski, Vt.). Concentrations were estimated by comparing the OD450 of the dilutions of culture supernatants to a standard curve generated using serial dilutions of a known standard, a protein A purified human IgG fusion protein with an Ig tail identical to that of the clones. Data was collected and analyzed using GEN5™ software (Biotek, Winooski, Vt.) and Microsoft Office EXCEL® (Microsoft, Redmond, Wash.) spreadsheet software and GraphPad Prism 4.0 (GraphPad Software, La Jolla, Calif.).

For the THER4PON1 variants, 75-100 clones from each transfection were screened for expression level. The expression level of the best clones ranged from 7.5-35 µg/ml in the initial 96 well culture supernatants. Clones with the highest level of expression were expanded up in Excell302 selective media and cell samples (approximately $1-2 \times 10^6$ cells) frozen in liquid nitrogen. In addition, cultures were grown for ten days and culture supernatants from spent cultures were harvested by centrifugation, culture media filtered, and pH adjusted with sodium carbonate/bicarbonate solution to pH 8.0. Proteins from transfected CHO cells were purified by protein A affinity chromatography, using a modified purification strategy to preserve protein function. A modified strategy was necessary for affinity chromatography of the THER4PON1 fusion proteins, since both the apo A-1 and the PON1 specificities are sensitive to pH and to divalent cation conditions. Culture supernatants were incubated in sterile 50 ml conical tubes with approximately 1.0 ml protein A slurry (Repligen, Waltham, Mass.), per tube, with gentle rotation at 4° C., for 24-48 hours. Protein A slurry was harvested from each tube by centrifugation at 2400 rpm for 10 minutes, and culture media removed to a separate bottle. Slurry was sometimes incubated with a second batch of culture supernatant for another 24-48 hours, with gentle rotation at 4° C. Tubes were then centrifuged at 2400 rpm, 10 minutes at 4° C. prior to removal of culture supernatants to secondary container. The protein A resin was gently mixed in remaining culture supernatant and transferred and loaded into presterilized, acid washed econocolums (Bio-RAD, Hercules, Calif.) fitted with a two way stopcock. Columns were then washed in several column volumes Pierce/ThermoFisher (Rockville, Ill.) gentle antigen/antibody binding buffer, pH 8.0, allowing the buffer to drip through columns by gravity flow. Bound fusion proteins eluted with gentle antigen/antibody elution buffer pH 6.6, (Pierce/ThermoFisher, Rockville Ill.). Eluted fractions (1.0 ml/tube) were collected into microfuge tubes and aliquots from each fraction assessed for protein level using a Nanodrop 2.0 (ThermoFisher, Waltham, Mass.) spectrophotometer. Positive fractions were pooled and dialyzed in FLOAT-A-LYZER® dialysis units with a molecular weight cutoff of 10 kilodaltons (Spectrum Labs/Repligen, Rancho Dominguez, Calif.). Dialysis buffer contained 0.9% NaCl, 2.5 mM HEPES buffer, 1 mM $CaCl_2$, and 5 mM sodium bicarbonate, pH 7.5. Dialysis was performed at 4° C., in sterile roller bottles containing 2 liters buffer. A second round of dialysis was performed in the same volume buffer. Proteins were harvested after dialysis, concentrated using Millipore Sigma (Burlington, Mass.) Amicon centrifugal concentrators, and sterile filtered through 0.2 µm PES syringe filter units. Protein concentrations were then determined from the OD280 assayed using a Nanodrop spectrophotometer with dialysis buffer as a blank. Once THER4PON1 fusion molecules were purified, they were assessed by SDS-PAGE analysis, Western blotting, and in further functional assays.

Example 11: Measurement of PON1 Enzyme Activity in THER4PON1 192 Sequence Variants PON1 has multiple enzyme activities. Here, enzyme activity was screened by two different assays; a fluorescent kinetic assay which measures phosphotriesterase activity associated with organophosphate pesticides, while the second assay assesses the arylesterase activity of the enzyme.
Phosphotriesterase Activity FIG. 14 shows the results of a PON1 functional assay for the phosphotriesterase activity using culture supernatants from transfected clones of three THER4PON1 sequence variants as test enzymes: THER4PON1 (also referred herein as "THER4PON1 192Q" or "T4P1-192Q"), THER4PON1 Q192R (also referred to herein as "THER4PON1 192R" or "T4P1-192R"), and THER4PON1 Q192K (also referred to herein as "THER4PON1 192K" or "T4P1-192K") (see Examples 8 and 10). The data were generated using a commercially available kit from Molecular Probes/Life Technologies, the EnzChek paraoxonase assay kit E33702, (ThermoFisher). This kit provides a sensitive, less toxic, homogeneous fluorometric assay (excitation/emission maxima ~360/450 nm) for the organophosphatase activity of paraoxonase and is based on the hydrolysis of a proprietary, fluorogenic organophosphate analog as substrate. Enzyme assays were set up with the stock solutions provided, and with serial dilutions of a positive control PON1 enzyme provided with the kit reagents, or with serial dilutions of dialyzed, filtered CHO culture supernatants of the three different sequence variants of ApoA1-lnk-hIgG-PON1 fusion proteins as test enzymes. The relative fluorescence units produced as a function of time were determined for each reaction using a fixed concentration of substrate and serial dilutions of the different enzyme supernatants. Enzyme kinetics were measured using a SYNERGY™ HT fluorescence plate reader (BioTek, Winooski, Vt.), and the data was analyzed using GEN5™ software. The data shown demonstrate that the T4P1 192 sequence variants all exhibit organophosphatase activity detectable in unconcentrated, filtered cell culture supernatants after transfection.

Each THER4PON1 192 sequence variant was purified from spent CHO culture supernatants using a modified protein A purification strategy as described previously. The EnzCheck paraoxonase assay was then repeated with purified protein to better assess the specific activity of the fusion proteins. Serial dilutions of the purified T4P1-192Q, T4P1-192R, T4P1-192K, and THER4 were prepared and transferred to appropriate wells of 96 well, black microplates. Similar dilution series were also prepared for the fluorescence reference standard and the organophosphatase positive control enzyme provided with the kit. Organophosphatase substrate was prepared according to the kit instructions and aliquots added to each well of the assay except for the fluorescence reference wells. For these assays, the concentration of organophosphate substrate was kept fixed for every reaction. After addition of substrate, plates were transferred to a SYNERGY™ HT plate reader at 37° C., with excitation 360 nm and emission 460 nm settings. Serial dilutions of the control and test enzymes were assessed for the RFU generated during a 60 minute kinetic assay, with readings every 60 seconds (1 min). The RFU as a function of time was assessed relative to the fluorescent reference standard readings and to serial dilutions of the organophosphatase positive control supplied with the kit. Inclusion of the fluorescence reference standard permitted proper setting of the reader gains and sensitivity settings, and generation of a standard curve for estimation of activity per unit volumes. The graph shown in FIG. 15 displays relative fluorescence units plotted as a function of time (HH:MM:SS), comparing the activity profiles of the control organophosphatase enzyme at two different dilutions (50 mU and 20 mU) to that of the T4P1-192K, T4P1-192R, and T4P1-192Q molecules at 415 nM, or to that of the THER4 molecule at 715 nM. The equation of the line fit to the stand curve was determined and used to convert the fluorescence measures to the nmol of fluorescent product. The 30 minute time point was used for these calculations. The U/L estimates of the activity for the test proteins and the positive controls were 1688 U/L for T4P1-192Q, 3943 U/L for T4P1-192R, 10840 U/L for T4P1-192K, and 1600-11900 U/L for the organophosphatase positive control dilution series from 10 mU to 100 mU.

Arylesterase Activity

In addition to assessment of the paraoxonase fusion proteins for organophosphatase activity, the arylesterase activity was also measured using conversion of phenyl acetate (Sigma-Aldrich) to phenol. Purified fusion proteins were diluted in enzyme assay buffer, 20 mM Tris-HCl (pH 7.5), 2 mM $CaCl_2$ to 80 µg/ml (2× enzyme for each dilution). Two-fold serial dilutions were then made of the T4P1-192Q, T4P1-192R, and T4P1-192K variants and of the THER4 fusion protein, using the same buffer to create a dilution series of each molecule. The serial dilutions of enzyme were used in assays with a constant amount of 5 mM phenyl acetate as substrate (10 mM stock, diluted 2×) to determine the optimal amount of enzyme to be used with serial dilutions of substrate. A kinetic enzyme assay was performed by aliquoting 50 µl/well each serial dilution of enzyme into a 96 well UV transparent plate (Greiner BioOne, Catalog #655 801), followed by addition of 50 µl 2× substrate solution containing 10 mM phenyl acetate, to give a final concentration of 5 mM. The conversion of substrate was monitored by measuring the OD at 270 nm at 60 second intervals for 20 minutes. For each well, a kinetic curve was generated reflecting the rate of substrate conversion. FIG. 16 shows representative results of the arylesterase analysis using the THER4PON1 192Q, 192R, and 192K molecules and the THER4 negative control as test enzymes for conversion of the phenyl acetate substrate to phenol and acetic acid. T4P1-192Q and T4P1-192R have similar kinetics under these conditions of low salt, although the 192Q form converted the substrate more efficiently than the 192R variant. The T4P1-192K variant at the same concentration (208 nM) exhibits a much higher enzyme efficiency than either of the 192Q and 192R forms. At lower concentrations (104 nM), this variant looked more similar to the other two forms, but still showed the highest activity. The THER4 fusion protein without PON1 did not generate a signal for conversion of the phenyl acetate substrate in this assay. For each T4P1 variant, the enzyme concentration which generated a kinetics curve most closely approximating linearity was used as the enzyme concentration in a second assay, keeping enzyme concentration fixed while varying the amount of substrate. Serial dilutions of phenyl acetate substrate were then made from 0.5 mM to 20 mM with a fixed concentration of fusion protein as enzyme in order to further characterize the enzyme kinetics for these molecules.

Example 12: In Vivo Analysis of the Pharmacokinetics of THER4PON1 192R in Wild-Type Mice A PK study was performed on the THER4PON1 192R protein to determine the rate of clearance of the molecule in vivo. This study was performed in wild-type C57BL/6 mice using intravenous (IV) injection of the test materials. THER4PON1 192R protein (see Examples 8 and 10) was purified by a modified protein A purification strategy, followed by testing of the purified proteins prior to the in vivo study.

C57BL/6 mice (5 mice per group) were injected intravenously with 200 µg/mouse fusion protein in a volume of 0.1 ml or with vehicle in a single bolus injection. Mice were then sacrificed at 1 hour, 6 hours, 24 hours, 72 hours, 7 days, and 14 days after injection. Plasma was harvested from each mouse at these time points and assessed by sandwich ELISA for levels of the human fusion protein. Trial ELISAs were performed with wild-type mouse sera spiked with human fusion protein in order to determine the parameters for testing the treated samples. Fusion protein levels were screened by a sandwich ELISA using anti-human IgG to capture the molecules (2.0 μg/ml in D-PBS) from mouse plasma, and using either an HRP-conjugated anti-human IgG (Jackson Immunoresearch, Catalog #109-036-098 at 1:7500) or HRP-conjugated anti-human APO A-1 (ThermoFisher Scientific, Catalog #PA1-28965 at 1:1500) antibody for detection. ELISA plates were washed with 1×D-PBS containing 0.05% Tween-20 between each step. SeraCare (Milford, Mass.; Catalog #5120-0076) SUREBLUE RESERVE™ TMB 1-component microwell peroxidase substrate (85 μl/well) was used for visualization, and reactions stopped by the addition of 1N HCl. ELISA plates were analyzed on a SYNERGY™ HT plate reader at wavelengths of 450 and 630 nm. Raw data was imported into GraphPad Prism 4 for analysis.

FIG. 17 shows results of the PK analysis of the purified ApoA1-lnk-hIgG-PON1 fusion protein after injection into wild-type mice. The data shown summarize the plasma levels of the THER4PON1 192R variant in wild-type mice at the indicated time points after injection. Also shown is the absence of signal from five mice injected with vehicle alone. The dot plot graph summarizes the concentration estimates for each individual mouse. Each dot represents the estimate for a single mouse. These concentration estimates were generated from the ELISA data using serial dilutions and replicates of each plasma sample compared to a standard curve created from serial dilutions of the purified, uninjected treatment molecule. Five animals were assessed for presence of the T4P1-192R purified protein in plasma per time point. The data show that low levels of the fusion protein are still detectable in mouse plasma after 14 days. The dot plot displays the concentration data as a function of time using a linear scale. A similar dot plot can be generated that displays the same data using a logarithmic scale for the concentration estimates. In this case, the dot plot generates a curve that more closely approximates linearity, but still departs from it. The pharmacokinetics exhibit second order or higher behavior, suggesting a rapid initial loss due to localization in the periphery, followed by a more gradual decrease due to metabolism. This more complex curve suggests a two compartment or higher process of elimination. The THER4PON1 variants are expected to interact with HDL, FcR, and possibly other apolipoprotein targets in addition to the substrate targets for PON1, so that much of the initial bolus may localize to sites in the periphery. Other systemic reservoirs including monocytes may bind to the THER4PON1 192R variant, resulting in a rapid decrease in circulating plasma levels during the first few hours after injection.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A polynucleotide encoding a fusion polypeptide, wherein the fusion polypeptide comprises, from an amino-terminal position to a carboxyl-terminal position, ApoA1-L1-D-L2-P, wherein:
   ApoA1 is a first polypeptide segment comprising an amino acid sequence having at least 97% sequence identity with amino acid residues 19-267 or 25-267 of SEQ ID NO:2, wherein said first polypeptide segment has cholesterol efflux activity;
   L1 is a first polypeptide linker comprising at least 5 amino acid residues;
   D is an immunoglobulin Fc region;
   L2 is a second polypeptide linker; and
   P is a paraoxonase having at least 98% sequence identity with amino acid residues 16-355 of SEQ ID NO:12, amino acid residues 16-355 of SEQ ID NO:42, or amino acid residues 16-355 of SEQ ID NO:44,
   wherein the encoded fusion polypeptide comprises an amino acid sequence having at least 99% sequence identity with (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48.

2. The polynucleotide of claim 1, wherein the first polypeptide segment has the amino acid sequence shown in residues 19-267 or 25-267 of SEQ ID NO:2.

3. The polynucleotide of claim 1, wherein L1 comprises at least 16 amino acid residues.

4. The polynucleotide of claim 1, wherein L1 consists of from 10 to 31 amino acid residues.

5. The polynucleotide of claim 1, wherein L1 comprises two or more tandem repeats of the amino acid sequence of SEQ ID NO:15.

6. The polynucleotide of claim 1, wherein the Fc region is a human γ1 Fc variant in which residues C220, C226, and C229, according to EU numbering for human IgG heavy chain constant region, are each replaced by serine.

7. The polynucleotide of claim 6, wherein residue P238, according to EU numbering for human IgG heavy chain constant region, is replaced by serine.

8. The polynucleotide of claim 7, wherein residue P331, according to EU numbering for human IgG heavy chain constant region, is replaced by serine.

9. The polynucleotide of claim 1, wherein L2 has the amino acid sequence shown in residues 526-543 of SEQ ID NO:28.

10. The polynucleotide of claim 1, wherein the paraoxonase has the amino acid sequence shown in residues 16-355 of SEQ ID NO:12, residues 16-355 of SEQ ID NO:42, or residues 16-355 of SEQ ID NO:44.

11. The polynucleotide of claim 1, wherein the encoded fusion polypeptide comprises the amino acid sequence shown in
   (i) residues 19-883 or 25-883 of SEQ ID NO:28,
   (ii) residues 19-873 or 25-873 of SEQ ID NO:38,
   (iii) residues 19-883 or 25-883 of SEQ ID NO:46, or
   (iv) residues 19-883 or 25-883 of SEQ ID NO:48.

12. A method of making a fusion polypeptide, the method comprising:
   (1) culturing a mammalian cell into which has been introduced an expression vector comprising the following operably linked elements:
   (a) a transcription promoter;
   (b) a DNA segment encoding a fusion polypeptide, wherein the fusion polypeptide comprises, from an amino-terminal position to a carboxyl-terminal position, ApoA1-L1-D-L2-P, wherein:
   ApoA1 is a first polypeptide segment comprising an amino acid sequence having at least 97% sequence identity with amino acid residues 19-267 or 25-267 of SEQ ID NO:2, wherein said first polypeptide segment has cholesterol efflux activity;
   L1 is a first polypeptide linker comprising at least 5 amino acid residues;
   D is an immunoglobulin Fc region;
   L2 is a second polypeptide linker; and
   P is a paraoxonase having at least 98% sequence identity with amino acid residues 16-355 of SEQ ID NO:12, amino acid residues 16-355 of SEQ ID NO:42, or amino acid residues 16-355 of SEQ ID NO:44; wherein the encoded fusion polypeptide comprises an amino acid sequence having at least 99% sequence identity with (i) residues 19-883 or 25-883 of SEQ ID NO:28, (ii) residues 19-873 or 25-873 of SEQ ID NO:38, (iii) residues 19-883 or 25-883 of SEQ ID NO:46, or (iv) residues 19-883 or 25-883 of SEQ ID NO:48; and (c) a transcription terminator, wherein the cell expresses the DNA segment and the encoded fusion polypeptide is produced; and (2) recovering the fusion polypeptide.

13. The method of claim 12, wherein the human Fc region is a γ1 Fc variant comprising one or more amino acid substitutions relative to a wild-type human γ1 Fc region sequence.

14. The method of claim 12, wherein the paraoxonase has the amino acid sequence shown in residues 16-355 of SEQ ID NO:12, residues 16-355 of SEQ ID NO:42, or residues 16-355 of SEQ ID NO:44.

15. The method of claim 12, wherein the encoded fusion polypeptide comprises the amino acid sequence shown in
(i) residues 19-883 or 25-883 of SEQ ID NO:28,
(ii) residues 19-873 or 25-873 of SEQ ID NO:38,
(iii) residues 19-883 or 25-883 of SEQ ID NO:46, or
(iv) residues 19-883 or 25-883 of SEQ ID NO:48.

16. The method of claim 12, wherein the encoded fusion polypeptide is produced in the cell and recovered as a dimeric protein.

* * * * *

SEQUENCE LISTING

```
<160> NUMBER OF SEQ ID NOS: 59

<210> SEQ ID NO 1
<211> LENGTH: 1602
<212> TYPE: DNA
<213> ORGANISM: Artificial
<220> FEATURE:
<223> OTHER INFORMATION: hWTAPO1-(g4s)4-mthIgG DNA

<400> SEQUENCE: 1
gttaagcttg ccaccatgaa agctgcggtg ctgaccttgg ccgtgctctt cctgacgggg      60
agccaggctc ggcatttctg gcagcaagat gaaccccccc agagcccctg ggatcgagtg     120
aaggacctgg ccactgtgta cgtggatgtg ctcaaagaca gcggcagaga ctatgtgtcc     180
cagtttgaag gctccgcctt gggaaaacag ctaaacctaa agctccttga caactgggac     240
agcgtgacct ccaccttcag caagctgcgc gaacagctcg gccctgtgac ccaggagttc     300
tgggataacc tggaaaagga gacagagggc ctgaggcagg agatgagcaa ggatctggag     360
gaggtgaagg ccaaggtgca gccctacctg gacgacttcc agaagaagtg gcaggaggag     420
atggagctct accgccagaa ggtggagccg ctgcgcgcag agctccaaga gggcgcgcgc     480
cagaagctgc acgagctgca agagaagctg agcccactgg gcgaggagat gcgcgaccgc     540
gcgcgcgccc atgtggacgc gctgcgcacg catctggccc cctacagcga cgagctgcgc     600
cagcgcttgg ccgcgcgcct tgaggctctc aaggagaacg gcggcgccag actggccgag     660
taccacgcca aggccaccga gcatctgagc acgctcagcg agaaggccaa gcccgcgctc     720
gaggacctcc gccaaggcct gctgcccgtg ctggagagct tcaaggtcag cttcctgagc     780
gctctcgagg agtacactaa gaagctcaac acccaagatc tctccggagg aggtggctca     840
```

```
ggtggtggag gatctggagg aggtgggagt ggtggaggtg gttctaccgg tctcgagccc    900
aaatcttctg acaaaactca cacatctcca ccgtccccag cacctgaact cctgggagga    960
tcgtcagtct tcctcttccc cccaaaaccc aaggacaccc tcatgatctc ccggacccct   1020
gaggtcacat gcgtggtggt ggacgtgagc cacgaagacc ctgaggtcaa gttcaactgg   1080
tacgtggacg gcgtggaggt gcataatgcc aagacaaagc cgcgggagga gcagtacaac   1140
agcacgtacc gtgtggtcag cgtcctcacc gtcctgcacc aggactggct gaatggcaag   1200
gagtacaagt gcaaggtctc caacaaagcc ctcccagcct ccatcgagaa aaccatctcc   1260
aaagccaaag gcagccccg agaaccacag gtgtacaccc tgcccccatc ccgggatgag   1320
ctgaccaaga accaggtcag cctgacctgc ctggtcaaag gcttctatcc cagcgacatc   1380
gccgtggagt gggagagcaa tgggcagccg gagaacaact acaagaccac gcctcccgtg   1440
ctggactccg acggctcctt cttcctctac agcaagctca ccgtggacaa gagcaggtgg   1500
cagcagggga acgtcttctc atgctccgtg atgcatgagg ctctgcacaa ccactacacg   1560
cagaagagcc tctctctctc tccgggtaaa tgataatcta ga                      1602
```

<210> SEQ ID NO 2
<211> LENGTH: 525
<212> TYPE: PRT
<213> ORGANISM: Artificial
<220> FEATURE:
<223> OTHER INFORMATION: hWTAPO1-(g4s)4-mthIgG
<220> FEATURE:
<221> NAME/KEY: SIGNAL
<222> LOCATION: (1)..(18)

<400> SEQUENCE: 2

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
```

```
        210              215              220
Ser Thr Leu Ser Glu Lys Ala Lys Pro Ala Leu Glu Asp Leu Arg Gln
225              230              235              240

Gly Leu Leu Pro Val Leu Glu Ser Phe Lys Val Ser Phe Leu Ser Ala
            245              250              255

Leu Glu Glu Tyr Thr Lys Lys Leu Asn Thr Gln Asp Leu Ser Gly Gly
                260              265              270

Gly Gly Ser Gly Gly Gly Gly Ser Gly Gly Gly Gly Ser Gly Gly Gly
            275              280              285

Gly Ser Thr Gly Leu Glu Pro Lys Ser Ser Asp Lys Thr His Thr Ser
    290              295              300

Pro Pro Ser Pro Ala Pro Glu Leu Leu Gly Gly Ser Ser Val Phe Leu
305              310              315              320

Phe Pro Pro Lys Pro Lys Asp Thr Leu Met Ile Ser Arg Thr Pro Glu
                325              330              335

Val Thr Cys Val Val Val Asp Val Ser His Glu Asp Pro Glu Val Lys
                340              345              350

Phe Asn Trp Tyr Val Asp Gly Val Glu Val His Asn Ala Lys Thr Lys
                355              360              365

Pro Arg Glu Glu Gln Tyr Asn Ser Thr Tyr Arg Val Val Ser Val Leu
370              375              380

Thr Val Leu His Gln Asp Trp Leu Asn Gly Lys Glu Tyr Lys Cys Lys
385              390              395              400

Val Ser Asn Lys Ala Leu Pro Ala Ser Ile Glu Lys Thr Ile Ser Lys
                405              410              415

Ala Lys Gly Gln Pro Arg Glu Pro Gln Val Tyr Thr Leu Pro Pro Ser
            420              425              430

Arg Asp Glu Leu Thr Lys Asn Gln Val Ser Leu Thr Cys Leu Val Lys
                435              440              445

Gly Phe Tyr Pro Ser Asp Ile Ala Val Glu Trp Glu Ser Asn Gly Gln
450              455              460

Pro Glu Asn Asn Tyr Lys Thr Thr Pro Pro Val Leu Asp Ser Asp Gly
465              470              475              480

Ser Phe Phe Leu Tyr Ser Lys Leu Thr Val Asp Lys Ser Arg Trp Gln
                485              490              495

Gln Gly Asn Val Phe Ser Cys Ser Val Met His Glu Ala Leu His Asn
                500              505              510

His Tyr Thr Gln Lys Ser Leu Ser Leu Ser Pro Gly Lys
            515              520              525

<210> SEQ ID NO 3
<211> LENGTH: 2052
<212> TYPE: DNA
<213> ORGANISM: Artificial
<220> FEATURE:
<223> OTHER INFORMATION: hWTAPO1-(g4s)4-mthIgG-hRNase1 DNA

<400> SEQUENCE: 3
gttaagcttg ccaccatgaa agctgcggtg ctgaccttgg ccgtgctctt cctgacgggg      60
agccaggctc ggcatttctg cagcaagat gaaccccccc agagccctg ggatcgagtg      120 aaggacctgg ccactgtgta cgtggatgtg ctcaaagaca gcggcagaga ctatgtgtcc     180
cagtttgaag gctccgcctt gggaaaacag ctaaacctaa agctccttga caactgggac     240
agcgtgacct ccaccttcag caagctgcgc gaacagctcg gccctgtgac ccaggagttc     300
```

```
tgggataacc tggaaaagga cagagagggc ctgaggcagg agatgagcaa ggatctggag    360
gaggtgaagg ccaaggtgca gccctacctg gacgacttcc agaagaagtg caggaggag    420
atggagctct accgccagaa ggtggagccg ctgcgcgcag agctccaaga gggcgcgcgc    480
cagaagctgc acgagctgca agagaagctg agcccactgg cgaggagat gcgcgaccgc    540
gcgcgcgccc atgtggacgc gctgcgcacg catctggccc cctacagcga cgagctgcgc    600
cagcgcttgg ccgcgcgcct tgaggctctc aaggagaacg gcggcgccag actgccgag    660
taccacgcca aggccaccga gcatctgagc acgctcagcg agaaggccaa gcccgcgctc    720
gaggacctcc gccaaggcct gctgcccgtg ctggagagct tcaaggtcag cttcctgagc    780
gctctcgagg agtacactaa gaagctcaac acccaagatc tctccggagg aggtggctca    840
ggtggtggag gatctggagg aggtgggagt ggtggaggtg gttctaccgg tctcgagccc    900
aaatcttctg acaaaactca cacatctcca ccgtccccag cacctgaact cctgggagga    960
tcgtcagtct tcctcttccc cccaaaaccc aaggacaccc tcatgatctc ccggaccccct   1020
gaggtcacat gcgtggtggt ggacgtgagc cacgaagacc ctgaggtcaa gttcaactgg   1080
tacgtggacg gcgtggaggt gcataatgcc aagacaaagc cgcgggagga gcagtacaac   1140
agcacgtacc gtgtggtcag cgtcctcacc gtcctgcacc aggactggct gaatggcaag   1200
gagtacaagt gcaaggtctc caacaaagcc ctcccagcct ccatcgagaa aaccatctcc   1260
aaagccaaag gcagccccg agaaccacag gtgtacaccc tgcccccatc ccgggatgag   1320
ctgaccaaga accaggtcag cctgacctgc ctggtcaaag gcttctatcc cagcgacatc   1380
gccgtggagt gggagagcaa tgggcagccg gagaacaact acaagaccac gcctcccgtg   1440
ctggactccg acggctcctt cttcctctac agcaagctca ccgtggacaa gagcaggtgg   1500
cagcagggga acgtcttctc atgctccgtg atgcatgagg ctctgcacaa ccactacacg   1560
cagaagagcc tctctctctc tccgggtaaa gtcgacggag ctagcagccc cgtgaacgtg   1620
agcagcccca gcgtgcagga tatcccttcc ctgggcaaga atcccgggc caagaaattc   1680
cagcggcagc atatggactc agacagttcc cccagcagca gctccaccta ctgtaaccaa   1740
atgatgaggc gccggaatat gacacagggg cggtgcaaac cagtgaacac ctttgtgcac   1800
gagcccctgg tagatgtcca gaatgtctgt ttccaggaaa aggtcacctg caagaacggg   1860
cagggcaact gctacaagag caactccagc atgcacatca gagactgccg cctgacaaac   1920
ggctccaggt acccccaactg tgcataccgg accagcccga aggagagaca catcattgtg   1980
gcctgtgaag ggagcccata tgtgccagtc cactttgatg cttctgtgga ggactctacc   2040
taataatcta ga                                                       2052
```

<210> SEQ ID NO 4
<211> LENGTH: 675
<212> TYPE: PRT
<213> ORGANISM: Artificial
<220> FEATURE:
<223> OTHER INFORMATION: hWTAPO1-(g4s)4-mthIgG-hRNase1

<400> SEQUENCE: 4

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

```
Ser Gly Arg Asp Tyr Val Ser Gln Phe Glu Gly Ser Ala Leu Gly Lys
 50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Ser Gly Gly Gly Gly Ser Gly Gly Gly Ser Gly Gly
        275                 280                 285

Gly Ser Thr Gly Leu Glu Pro Lys Ser Ser Asp Lys Thr His Thr Ser
290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Ser Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Asp Glu Leu Thr Lys Asn Gln Val Ser Leu Thr Cys Leu Val Lys
        435                 440                 445

Gly Phe Tyr Pro Ser Asp Ile Ala Val Glu Trp Glu Ser Asn Gly Gln
450                 455                 460

Pro Glu Asn Asn Tyr Lys Thr Thr Pro Pro Val Leu Asp Ser Asp Gly
```

|  | 465 |  |  |  | 470 |  |  |  | 475 |  |  |  | 480 |
|---|---|---|---|---|---|---|---|---|---|---|---|---|---|

Ser Phe Phe Leu Tyr Ser Lys Leu Thr Val Asp Lys Ser Arg Trp Gln
                        485                 490                 495

Gln Gly Asn Val Phe Ser Cys Ser Val Met His Glu Ala Leu His Asn
            500                 505                 510

His Tyr Thr Gln Lys Ser Leu Ser Leu Ser Pro Gly Lys Val Asp Gly
                515                 520                 525

Ala Ser Ser Pro Val Asn Val Ser Ser Pro Ser Val Gln Asp Ile Pro
530                 535                 540

Ser Leu Gly Lys Glu Ser Arg Ala Lys Lys Phe Gln Arg Gln His Met
545                 550                 555                 560

Asp Ser Asp Ser Ser Pro Ser Ser Ser Thr Tyr Cys Asn Gln Met
                565                 570                 575

Met Arg Arg Arg Asn Met Thr Gln Gly Arg Cys Lys Pro Val Asn Thr
            580                 585                 590

Phe Val His Glu Pro Leu Val Asp Val Gln Asn Val Cys Phe Gln Glu
                595                 600                 605

Lys Val Thr Cys Lys Asn Gly Gln Gly Asn Cys Tyr Lys Ser Asn Ser
        610                 615                 620

Ser Met His Ile Thr Asp Cys Arg Leu Thr Asn Gly Ser Arg Tyr Pro
625                 630                 635                 640

Asn Cys Ala Tyr Arg Thr Ser Pro Lys Glu Arg His Ile Ile Val Ala
                645                 650                 655

Cys Glu Gly Ser Pro Tyr Val Pro Val His Phe Asp Ala Ser Val Glu
                660                 665                 670

Asp Ser Thr
        675

<210> SEQ ID NO 5
<211> LENGTH: 414
<212> TYPE: DNA
<213> ORGANISM: Homo sapiens

<400> SEQUENCE: 5
gatatccctt ccctgggcaa ggaatcccgg gccaagaaat tccagcggca gcatatggac      60
tcagacagtt ccccccagcag cagctccacc tactgtaacc aaatgatgag gcgccggaat     120
atgacacagg ggcggtgcaa accagtgaac acctttgtgc acgagcccct ggtagatgtc     180
cagaatgtct gtttccagga aaaggtcacc tgcaagaacg ggcagggcaa ctgctacaag     240
agcaactcca gcatgcacat cacagactgc cgcctgacaa acggctccag gtaccccaac     300
tgtgcatacc ggaccagccc gaaggagaga cacatcattg tggcctgtga agggagccca     360
tatgtgccag tccactttga tgcttctgtg gaggactcta cctaataatc taga            414

<210> SEQ ID NO 6
<211> LENGTH: 134
<212> TYPE: PRT
<213> ORGANISM: Homo sapiens

<400> SEQUENCE: 6

Asp Ile Pro Ser Leu Gly Lys Glu Ser Arg Ala Lys Lys Phe Gln Arg
1               5                   10                  15

Gln His Met Asp Ser Asp Ser Ser Pro Ser Ser Ser Thr Tyr Cys
            20                  25                  30

Asn Gln Met Met Arg Arg Arg Asn Met Thr Gln Gly Arg Cys Lys Pro
        35                  40                  45

Val Asn Thr Phe Val His Glu Pro Leu Val Asp Val Gln Asn Val Cys
 50                  55                  60

Phe Gln Glu Lys Val Thr Cys Lys Asn Gly Gln Gly Asn Cys Tyr Lys
 65                  70                  75                  80

Ser Asn Ser Ser Met His Ile Thr Asp Cys Arg Leu Thr Asn Gly Ser
                 85                  90                  95

Arg Tyr Pro Asn Cys Ala Tyr Arg Thr Ser Pro Lys Glu Arg His Ile
            100                 105                 110

Ile Val Ala Cys Glu Gly Ser Pro Tyr Val Pro Val His Phe Asp Ala
        115                 120                 125

Ser Val Glu Asp Ser Thr
    130

<210> SEQ ID NO 7
<211> LENGTH: 462
<212> TYPE: DNA
<213> ORGANISM: Artificial
<220> FEATURE:
<223> OTHER INFORMATION: 3-NLG-WThRNase1 DNA

<400> SEQUENCE: 7
gtcgacggag ctagcagccc cgtgaacgtg agcagcccca gcgtgcagga tatcccttcc      60
ctgggcaagg aatcccgggc caagaaattc agcggcagc atatggactc agacagttcc     120
cccagcagca gctccaccta ctgtaaccaa atgatgaggc gccggaatat gacacagggg     180
cggtgcaaac cagtgaacac ctttgtgcac gagcccctgg tagatgtcca gaatgtctgt     240
ttccaggaaa aggtcacctg caagaacggg cagggcaact gctacaagag caactccagc     300
atgcacatca cagactgccg cctgacaaac ggctccaggt accccaactg tgcataccgg     360
accagcccga aggagagaca catcattgtg gcctgtgaag ggagcccata tgtgccagtc     420
cactttgatg cttctgtgga ggactctacc taataatcta ga                       462

<210> SEQ ID NO 8
<211> LENGTH: 150
<212> TYPE: PRT
<213> ORGANISM: Artificial
<220> FEATURE:
<223> OTHER INFORMATION: 3-NLG-WThRNase1

<400> SEQUENCE: 8

Val Asp Gly Ala Ser Ser Pro Val Asn Val Ser Ser Pro Ser Val Gln
 1               5                  10                  15

Asp Ile Pro Ser Leu Gly Lys Glu Ser Arg Ala Lys Lys Phe Gln Arg
             20                  25                  30

Gln His Met Asp Ser Asp Ser Pro Ser Ser Ser Thr Tyr Cys
         35                  40                  45

Asn Gln Met Met Arg Arg Arg Asn Met Thr Gln Gly Arg Cys Lys Pro
 50                  55                  60

Val Asn Thr Phe Val His Glu Pro Leu Val Asp Val Gln Asn Val Cys
 65                  70                  75                  80

Phe Gln Glu Lys Val Thr Cys Lys Asn Gly Gln Gly Asn Cys Tyr Lys
                 85                  90                  95

Ser Asn Ser Ser Met His Ile Thr Asp Cys Arg Leu Thr Asn Gly Ser
            100                 105                 110

Arg Tyr Pro Asn Cys Ala Tyr Arg Thr Ser Pro Lys Glu Arg His Ile
        115                 120                 125

```
Ile Val Ala Cys Glu Gly Ser Pro Tyr Val Pro Val His Phe Asp Ala
    130                 135                 140

Ser Val Glu Asp Ser Thr
145                 150

<210> SEQ ID NO 9
<211> LENGTH: 97
<212> TYPE: DNA
<213> ORGANISM: Artificial
<220> FEATURE:
<223> OTHER INFORMATION: (g4s)5 linker DNA

<400> SEQUENCE: 9
agatctctcc ggaggaggtg gctcaggtgg tggaggatct ggaggaggtg gctcaggtgg    60
tggaggatct ggaggaggtg ggagtaccgg tctcgag                             97

<210> SEQ ID NO 10
<211> LENGTH: 32
<212> TYPE: PRT
<213> ORGANISM: Artificial
<220> FEATURE:
<223> OTHER INFORMATION: (g4s)5 linker

<400> SEQUENCE: 10

Asp Leu Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Thr Gly Leu Glu
            20                  25                  30

<210> SEQ ID NO 11
<211> LENGTH: 1099
<212> TYPE: DNA
<213> ORGANISM: Homo sapiens

<400> SEQUENCE: 11
atggcgaagc tgattgcgct caccctcttg gggatgggac tggcactctt caggaaccac    60
cagtcttctt accaaacacg acttaatgct ctccgagagg tacaacccgt agaacttcct   120
aactgtaatt tagttaaagg aatcgaaact ggctctgaag acttggagat actgcctaat   180
ggactggctt tcattagctc tggattaaag tatcctggaa taaagagctt caaccccaac   240
agtcctggaa aaatacttct gatggacctg aatgaagaag atccaacagt gttggaattg   300
gggatcactg gaagtaaatt tgatgtatct tcatttaacc ctcatgggat tagcacattc   360
acagatgaag ataatgccat gtacctcctg gtggtgaacc atccagatgc caagtccaca   420
gtggagttgt ttaaatttca agaagaagaa aaatcgcttt tgcatctaaa aaccatcaga   480
cataaacttc tgcctaattt gaatgatatt gttgctgtgg acctgagcca cttttatggc   540
acaaatgatc actatttttct tgaccctac ttacaatcct gggagatgta tttgggttta   600
gcgtggtcgt atgttgtcta ctatagtcca agtgaagttc gagtggtggc agaaggattt   660
gattttgcta atggaatcaa catttcaccc gatggcaagt atgtctatat agctgagttg   720
ctggctcata gattcatgt gtatgaaaag catgctaatt ggactttaac tccattgaag   780
tcccttgact taatacccct cgtggataac atatctgtgg atcctgagac aggagacctt   840
tgggttggat gccatcccaa tggcatgaaa atcttcttct atgactcaga gaatcctcct   900
gcatcagagg tgcttcgaat ccagaacatt ctaacagaag aacctaaagt gacacaggtt   960
tatgcagaaa atggcacagt gttgcaaggc agtacagttg cctctgtgta caaagggaaa  1020
ctgctgattg gcacagtgtt tcacaaagct ctttactgtg agctctaaca gaccgatttg  1080
```
cacccatgcc atagaaact                                                1099

<210> SEQ ID NO 12
<211> LENGTH: 355
<212> TYPE: PRT
<213> ORGANISM: Homo sapiens
<220> FEATURE:
<221> NAME/KEY: SIGNAL
<222> LOCATION: (1)..(15)

<400> SEQUENCE: 12

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

```
Cys Glu Leu
        355

<210> SEQ ID NO 13
<211> LENGTH: 525
<212> TYPE: PRT
<213> ORGANISM: Artificial
<220> FEATURE:
<223> OTHER INFORMATION: hWTAPO1-(g4s)4-mthIgG with proline at Eu
      position 331 in Fc region

<400> SEQUENCE: 13

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Gly Ser Gly Gly Gly Gly Ser Gly Gly Gly
        275                 280                 285

Gly Ser Thr Gly Leu Glu Pro Lys Ser Ser Asp Lys Thr His Thr Ser
    290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Lys
```

```
                340             345             350
Phe Asn Trp Tyr Val Asp Gly Val Glu Val His Asn Ala Lys Thr Lys
            355             360             365

Pro Arg Glu Glu Gln Tyr Asn Ser Thr Tyr Arg Val Val Ser Val Leu
            370             375             380

Thr Val Leu His Gln Asp Trp Leu Asn Gly Lys Glu Tyr Lys Cys Lys
385             390             395             400

Val Ser Asn Lys Ala Leu Pro Ala Pro Ile Glu Lys Thr Ile Ser Lys
            405             410             415

Ala Lys Gly Gln Pro Arg Glu Pro Gln Val Tyr Thr Leu Pro Pro Ser
            420             425             430

Arg Asp Glu Leu Thr Lys Asn Gln Val Ser Leu Thr Cys Leu Val Lys
            435             440             445

Gly Phe Tyr Pro Ser Asp Ile Ala Val Glu Trp Glu Ser Asn Gly Gln
            450             455             460

Pro Glu Asn Asn Tyr Lys Thr Thr Pro Pro Val Leu Asp Ser Asp Gly
465             470             475             480

Ser Phe Phe Leu Tyr Ser Lys Leu Thr Val Asp Lys Ser Arg Trp Gln
            485             490             495

Gln Gly Asn Val Phe Ser Cys Ser Val Met His Glu Ala Leu His Asn
            500             505             510

His Tyr Thr Gln Lys Ser Leu Ser Leu Ser Pro Gly Lys
            515             520             525

<210> SEQ ID NO 14
<211> LENGTH: 675
<212> TYPE: PRT
<213> ORGANISM: Artificial
<220> FEATURE:
<223> OTHER INFORMATION: hWTAPO1-(g4s)4-mthIgG-hRNase1 with proline at
      Eu position 331 in Fc region

<400> SEQUENCE: 14

Met Lys Ala Ala Val Leu Thr Leu Ala Val Leu Phe Leu Thr Gly Ser
1               5               10              15

Gln Ala Arg His Phe Trp Gln Gln Asp Glu Pro Pro Gln Ser Pro Trp
            20              25              30

Asp Arg Val Lys Asp Leu Ala Thr Val Tyr Val Asp Val Leu Lys Asp
            35              40              45

Ser Gly Arg Asp Tyr Val Ser Gln Phe Glu Gly Ser Ala Leu Gly Lys
        50              55              60

Gln Leu Asn Leu Lys Leu Leu Asp Asn Trp Asp Ser Val Thr Ser Thr
65              70              75              80

Phe Ser Lys Leu Arg Glu Gln Leu Gly Pro Val Thr Gln Glu Phe Trp
            85              90              95

Asp Asn Leu Glu Lys Glu Thr Glu Gly Leu Arg Gln Glu Met Ser Lys
            100             105             110

Asp Leu Glu Glu Val Lys Ala Lys Val Gln Pro Tyr Leu Asp Asp Phe
            115             120             125

Gln Lys Lys Trp Gln Glu Glu Met Glu Leu Tyr Arg Gln Lys Val Glu
        130             135             140

Pro Leu Arg Ala Glu Leu Gln Glu Gly Ala Arg Gln Lys Leu His Glu
145             150             155             160

Leu Gln Glu Lys Leu Ser Pro Leu Gly Glu Glu Met Arg Asp Arg Ala
            165             170             175
```

-continued

```
Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Ser Gly Gly Gly Ser Gly Gly Gly
        275                 280                 285

Gly Ser Thr Gly Leu Glu Pro Lys Ser Ser Asp Lys Thr His Thr Ser
    290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
    370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Pro Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Asp Glu Leu Thr Lys Asn Gln Val Ser Leu Thr Cys Leu Val Lys
        435                 440                 445

Gly Phe Tyr Pro Ser Asp Ile Ala Val Glu Trp Glu Ser Asn Gly Gln
    450                 455                 460

Pro Glu Asn Asn Tyr Lys Thr Thr Pro Pro Val Leu Asp Ser Asp Gly
465                 470                 475                 480

Ser Phe Phe Leu Tyr Ser Lys Leu Thr Val Asp Lys Ser Arg Trp Gln
                485                 490                 495

Gln Gly Asn Val Phe Ser Cys Ser Val Met His Glu Ala Leu His Asn
            500                 505                 510

His Tyr Thr Gln Lys Ser Leu Ser Leu Ser Pro Gly Lys Val Asp Gly
        515                 520                 525

Ala Ser Ser Pro Val Asn Val Ser Ser Pro Ser Val Gln Asp Ile Pro
    530                 535                 540

Ser Leu Gly Lys Glu Ser Arg Ala Lys Lys Phe Gln Arg Gln His Met
545                 550                 555                 560

Asp Ser Asp Ser Ser Pro Ser Ser Ser Thr Tyr Cys Asn Gln Met
                565                 570                 575

Met Arg Arg Arg Asn Met Thr Gln Gly Arg Cys Lys Pro Val Asn Thr
            580                 585                 590

Phe Val His Glu Pro Leu Val Asp Val Gln Asn Val Cys Phe Gln Glu
```

```
                595                 600                 605
    Lys Val Thr Cys Lys Asn Gly Gln Gly Asn Cys Tyr Lys Ser Asn Ser
        610                 615                 620

Ser Met His Ile Thr Asp Cys Arg Leu Thr Asn Gly Ser Arg Tyr Pro
    625                 630                 635                 640

Asn Cys Ala Tyr Arg Thr Ser Pro Lys Glu Arg His Ile Ile Val Ala
                    645                 650                 655

Cys Glu Gly Ser Pro Tyr Val Pro Val His Phe Asp Ala Ser Val Glu
                    660                 665                 670

Asp Ser Thr
            675

<210> SEQ ID NO 15
<211> LENGTH: 5
<212> TYPE: PRT
<213> ORGANISM: Artificial
<220> FEATURE:
<223> OTHER INFORMATION: linker

<400> SEQUENCE: 15

Gly Gly Gly Gly Ser
1               5

<210> SEQ ID NO 16
<211> LENGTH: 22
<212> TYPE: DNA
<213> ORGANISM: Artificial
<220> FEATURE:
<223> OTHER INFORMATION: sequencing primer

<400> SEQUENCE: 16
ggttttggca gtacatcaat gg                                               22

<210> SEQ ID NO 17
<211> LENGTH: 22
<212> TYPE: DNA
<213> ORGANISM: Artificial
<220> FEATURE:
<223> OTHER INFORMATION: sequencing primer

<400> SEQUENCE: 17
ctattgtctt cccaatcctc cc                                               22

<210> SEQ ID NO 18
<211> LENGTH: 20
<212> TYPE: DNA
<213> ORGANISM: Artificial
<220> FEATURE:
<223> OTHER INFORMATION: sequencing primer

<400> SEQUENCE: 18
accttgcact tgtactcctt                                                  20

<210> SEQ ID NO 19
<211> LENGTH: 1531
<212> TYPE: DNA
<213> ORGANISM: Artificial
<220> FEATURE:
<223> OTHER INFORMATION: THER0 DNA (apo A-1-(lnk2)-mthIgG; apo
      A-1-mthIgG)

<400> SEQUENCE: 19
gttaagcttg ccaccatgaa agctgcggtg ctgaccttgg ccgtgctctt cctgacgggg      60
```

-continued

```
agccaggctc ggcatttctg gcagcaagat gaaccccccc agagcccctg ggatcgagtg    120
aaggacctgg ccactgtgta cgtggatgtg ctcaaagaca gcggcagaga ctatgtgtcc    180
cagtttgaag gctccgcctt gggaaaacag ctaaacctaa agctccttga caactgggac    240
agcgtgacct ccaccttcag caagctgcgc gaacagctcg ccctgtgac ccaggagttc     300 tgggataacc tggaaaagga cagagggc ctgaggcagg agatgagcaa ggatctggag      360
gaggtgaagg ccaaggtgca gccctacctg gacgacttcc agaagaagtg caggaggag    420 atggagctct accgccagaa ggtggagccg ctgcgcgcag agctccaaga gggcgcgcgc    480
cagaagctgc acgagctgca agagaagctg agcccactgg gcgaggagat gcgcgaccgc    540
gcgcgcgccc atgtggacgc gctgcgcacg catctggccc cctacagcga cgagctgcgc    600
cagcgcttgg ccgcgcgcct tgaggctctc aaggagaacg gcggcgccag actggccgag    660
taccacgcca aggccaccga gcatctgagc acgctcagcg agaaggccaa gcccgcgctc    720
gaggacctcc gccaaggcct gctgcccgtg ctggagagct tcaaggtcag cttcctgagc    780
gctctcgagg agtacactaa gaagctcaac acccaagatc tcgagcccaa atcttctgac    840
aaaactcaca catctccacc gtccccagca cctgaactcc tgggaggatc gtcagtcttc    900 ctcttcccc caaaacccaa ggacaccctc atgatctccc ggaccctga ggtcacatgc      960 gtggtggtgg acgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtctcca caaagccct cccagcctcc atcgagaaaa ccatctccaa agccaaaggg    1200
cagccccgag aaccacaggt gtacaccctg cccccatccc gggatgagct gaccaagaac   1260
caggtcagcc tgacctgcct ggtcaaaggc ttctatccca gcgacatcgc cgtggagtgg   1320
gagagcaatg ggcagccgga gaacaactac aagaccacgc ctcccgtgct ggactccgac   1380
ggctccttct tcctctacag caagctcacc gtggacaaga gcaggtggca gcaggggaac   1440
gtcttctcat gctccgtgat gcatgaggct ctgcacaacc actacacgca gaagagcctc   1500
tctctctctc cgggtaaatg ataatctaga a                                   1531
```

<210> SEQ ID NO 20
<211> LENGTH: 501
<212> TYPE: PRT
<213> ORGANISM: Artificial
<220> FEATURE:
<223> OTHER INFORMATION: THER0 polypeptide (apo A-1-(lnk2)-mthIgG; apo A-1-mthIgG)

<400> SEQUENCE: 20

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95
```

-continued

Asp Asn Leu Glu Lys Glu Thr Glu Gly Leu Arg Gln Glu Met Ser Lys
        100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
        130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
            245                 250                 255

Leu Glu Glu Tyr Thr Lys Lys Leu Asn Thr Gln Asp Leu Glu Pro Lys
        260                 265                 270

Ser Ser Asp Lys Thr His Thr Ser Pro Ser Pro Ala Pro Glu Leu
        275                 280                 285

Leu Gly Gly Ser Ser Val Phe Leu Phe Pro Pro Lys Pro Lys Asp Thr
        290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
            325                 330                 335

Glu Val His Asn Ala Lys Thr Lys Pro Arg Glu Glu Gln Tyr Asn Ser
        340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
370                 375                 380

Ser Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
            405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
        450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
            485                 490                 495

Leu Ser Pro Gly Lys
        500

<210> SEQ ID NO 21
<211> LENGTH: 1573
<212> TYPE: DNA
<213> ORGANISM: Artificial
<220> FEATURE:
<223> OTHER INFORMATION: THER2 DNA (apo A-1-(lnk16)-mthIgG; apo A-1-(g4s)2-mthIgG)

<400> SEQUENCE: 21

| | |
|---|---|
| gttaagcttg ccaccatgaa agctgcggtg ctgaccttgg ccgtgctctt cctgacgggg | 60 |
| agccaggctc ggcatttctg gcagcaagat gaaccccccc agagccctg ggatcgagtg | 120 |
| aaggacctgg ccactgtgta cgtggatgtg ctcaaagaca gcggcagaga ctatgtgtcc | 180 |
| cagtttgaag gctccgcctt gggaaaacag ctaaacctaa agctccttga caactgggac | 240 |
| agcgtgacct ccaccttcag caagctgcgc aacagctcg ccctgtgac ccaggagttc | 300 |
| tgggataacc tggaaaagga cagagggc ctgaggcagg agatgagcaa ggatctggag | 360 |
| gaggtgaagg ccaaggtgca gccctacctg gacgacttcc agaagaagtg gcaggaggag | 420 |
| atggagctct accgccagaa ggtggagccg ctgcgcgcag agctccaaga gggcgcgcgc | 480 |
| cagaagctgc acgagctgca agagaagctg agcccactgg gcgaggagat gcgcgaccgc | 540 |
| gcgcgcgccc atgtggacgc gctgcgcacg catctggccc cctacagcga cgagctgcgc | 600 |
| cagcgcttgg ccgcgcgcct tgaggctctc aaggagaacg gcggcgccag actggccgag | 660 |
| taccacgcca aggccaccga gcatctgagc acgctcagcg agaaggccaa gcccgcgctc | 720 |
| gaggacctcc gccaaggcct gctgcccgtg ctggagagct tcaaggtcag cttcctgagc | 780 |
| gctctcgagg agtacactaa gaagctcaac acccaagatc tctccggagg aggtggctca | 840 |
| ggaggaggtg ggagtaccgg tctcgagccc aaatcttctg acaaaactca cacatctcca | 900 |
| ccgtccccag cacctgaact cctgggagga tcgtcagtct tcctcttccc cccaaaaccc | 960 |
| aaggacaccc tcatgatctc ccggacccct gaggtcacat gcgtggtggt ggacgtgagc | 1020 |
| cacgaagacc ctgaggtcaa gttcaactgg tacgtggacg gcgtggaggt gcataatgcc | 1080 |
| aagacaaagc cgcgggagga gcagtacaac agcacgtacc gtgtggtcag cgtcctcacc | 1140 |
| gtcctgcacc aggactggct gaatggcaag gagtacaagt gcaaggtctc caacaaagcc | 1200 |
| ctcccagcct ccatcgagaa aaccatctcc aaagccaaag gcagccccg agaaccacag | 1260 |
| gtgtacaccc tgcccccatc ccgggatgag ctgaccaaga accaggtcag cctgacctgc | 1320 |
| ctggtcaaag gcttctatcc cagcgacatc gccgtggagt gggagagcaa tgggcagccg | 1380 |
| gagaacaact acaagaccac gcctcccgtg ctggactccg acggctcctt cttcctctac | 1440 |
| agcaagctca ccgtggacaa gagcaggtgg cagcagggga acgtcttctc atgctccgtg | 1500 |
| atgcatgagg ctctgcacaa ccactacacg cagaagagcc tctctctctc tccgggtaaa | 1560 |
| tgataatcta gaa | 1573 |

<210> SEQ ID NO 22
<211> LENGTH: 515
<212> TYPE: PRT
<213> ORGANISM: Artificial
<220> FEATURE:
<223> OTHER INFORMATION: THER2 polypeptide (apo A-1-(lnk16)-mthIgG; apo A-1-(g4s)2-mthIgG)

<400> SEQUENCE: 22

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp

```
            20                  25                  30
Asp Arg Val Lys Asp Leu Ala Thr Val Tyr Val Asp Val Leu Lys Asp
            35                  40                  45
Ser Gly Arg Asp Tyr Val Ser Gln Phe Glu Gly Ser Ala Leu Gly Lys
            50                  55                  60
Gln Leu Asn Leu Lys Leu Leu Asp Asn Trp Asp Ser Val Thr Ser Thr
 65                  70                  75                  80
Phe Ser Lys Leu Arg Glu Gln Leu Gly Pro Val Thr Gln Glu Phe Trp
                    85                  90                  95
Asp Asn Leu Glu Lys Glu Thr Glu Gly Leu Arg Gln Glu Met Ser Lys
                    100                 105                 110
Asp Leu Glu Glu Val Lys Ala Lys Val Gln Pro Tyr Leu Asp Asp Phe
                    115                 120                 125
Gln Lys Lys Trp Gln Glu Met Glu Leu Tyr Arg Gln Lys Val Glu
                    130                 135                 140
Pro Leu Arg Ala Glu Leu Gln Glu Gly Ala Arg Gln Lys Leu His Glu
145                 150                 155                 160
Leu Gln Glu Lys Leu Ser Pro Leu Gly Glu Glu Met Arg Asp Arg Ala
                    165                 170                 175
Arg Ala His Val Asp Ala Leu Arg Thr His Leu Ala Pro Tyr Ser Asp
                    180                 185                 190
Glu Leu Arg Gln Arg Leu Ala Ala Arg Leu Glu Ala Leu Lys Glu Asn
                    195                 200                 205
Gly Gly Ala Arg Leu Ala Glu Tyr His Ala Lys Ala Thr Glu His Leu
                    210                 215                 220
Ser Thr Leu Ser Glu Lys Ala Lys Pro Ala Leu Glu Asp Leu Arg Gln
225                 230                 235                 240
Gly Leu Leu Pro Val Leu Glu Ser Phe Lys Val Ser Phe Leu Ser Ala
                    245                 250                 255
Leu Glu Glu Tyr Thr Lys Lys Leu Asn Thr Gln Asp Leu Ser Gly Gly
                    260                 265                 270
Gly Gly Ser Gly Gly Gly Gly Ser Thr Gly Leu Glu Pro Lys Ser Ser
                    275                 280                 285
Asp Lys Thr His Thr Ser Pro Pro Ser Pro Ala Pro Glu Leu Leu Gly
                    290                 295                 300
Gly Ser Ser Val Phe Leu Phe Pro Pro Lys Pro Lys Asp Thr Leu Met
305                 310                 315                 320
Ile Ser Arg Thr Pro Glu Val Thr Cys Val Val Val Asp Val Ser His
                    325                 330                 335
Glu Asp Pro Glu Val Lys Phe Asn Trp Tyr Val Asp Gly Val Glu Val
                    340                 345                 350
His Asn Ala Lys Thr Lys Pro Arg Glu Glu Gln Tyr Asn Ser Thr Tyr
                    355                 360                 365
Arg Val Val Ser Val Leu Thr Val Leu His Gln Asp Trp Leu Asn Gly
                    370                 375                 380
Lys Glu Tyr Lys Cys Lys Val Ser Asn Lys Ala Leu Pro Ala Ser Ile
385                 390                 395                 400
Glu Lys Thr Ile Ser Lys Ala Lys Gly Gln Pro Arg Glu Pro Gln Val
                    405                 410                 415
Tyr Thr Leu Pro Pro Ser Arg Asp Glu Leu Thr Lys Asn Gln Val Ser
                    420                 425                 430
Leu Thr Cys Leu Val Lys Gly Phe Tyr Pro Ser Asp Ile Ala Val Glu
                    435                 440                 445
```

```
Trp Glu Ser Asn Gly Gln Pro Glu Asn Asn Tyr Lys Thr Thr Pro Pro
            450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys
        515

<210> SEQ ID NO 23
<211> LENGTH: 1633
<212> TYPE: DNA
<213> ORGANISM: Artificial
<220> FEATURE:
<223> OTHER INFORMATION: THER6 DNA (apo A-1-(lnk36)-mthIgG; apo
      A-1-(g4s)6-mthIgG)

<400> SEQUENCE: 23
```

| | | | | | |
|---|---|---|---|---|---|
| gttaagcttg | ccaccatgaa | agctgcggtg | ctgaccttgg | ccgtgctctt | cctgacgggg | 60 |
| agccaggctc | ggcatttctg | gcagcaagat | gaaccccccc | agagcccctg | ggatcgagtg | 120 |
| aaggacctgg | ccactgtgta | cgtggatgtg | ctcaaagaca | gcggcagaga | ctatgtgtcc | 180 |
| cagtttgaag | gctccgcctt | gggaaaacag | ctaaacctaa | agctccttga | caactgggac | 240 |
| agcgtgacct | ccaccttcag | caagctgcgc | gaacagctcg | ccctgtgac | ccaggagttc | 300 |
| tgggataacc | tggaaaagga | gacagagggc | ctgaggcagg | agatgagcaa | ggatctggag | 360 |
| gaggtgaagg | ccaaggtgca | gccctacctg | gacgacttcc | agaagaagtg | gcaggaggag | 420 |
| atggagctct | accgccagaa | ggtggagcgc | ctgcgcgcag | agctccaaga | gggcgcgcgc | 480 |
| cagaagctgc | acgagctgca | agagaagctg | agcccactgg | gcgaggagat | gcgcgaccgc | 540 |
| gcgcgcgccc | atgtggacgc | gctgcgcacg | catctggccc | cctacagcga | cgagctgcgc | 600 |
| cagcgcttgg | ccgcgcgcct | tgaggctctc | aaggagaacg | gcggcgccag | actggccgag | 660 |
| taccacgcca | aggccaccga | gcatctgagc | acgctcagcg | agaaggccaa | gcccgcgctc | 720 |
| gaggacctcc | gccaaggcct | gctgcccgtg | ctggagagct | tcaaggtcag | cttcctgagc | 780 |
| gctctcgagg | agtacactaa | gaagctcaac | acccaagatc | tctccggagg | aggtggctca | 840 |
| ggtggtggag | gatctggagg | aggtgggagt | ggtggaggtg | gttctggagg | aggtggtagt | 900 |
| ggaggtggag | gttctaccgg | tctcgagccc | aaatcttctg | acaaaactca | cacatctcca | 960 |
| ccgtccccag | cacctgaact | cctgggagga | tcgtcagtct | tcctcttccc | cccaaaaccc | 1020 |
| aaggacaccc | tcatgatctc | ccggacccct | gaggtcacat | gcgtggtggt | ggacgtgagc | 1080 |
| cacgaagacc | ctgaggtcaa | gttcaactgg | tacgtggacg | gcgtggaggt | gcataatgcc | 1140 |
| aagacaaagc | cgcgggagga | gcagtacaac | agcacgtacc | gtgtggtcag | cgtcctcacc | 1200 |
| gtcctgcacc | aggactggct | gaatggcaag | gagtacaagt | gcaaggtctc | caacaaagcc | 1260 |
| ctcccagcct | ccatcgagaa | aaccatctcc | aaagccaaag | gcagccccg | agaaccacag | 1320 |
| gtgtacaccc | tgcccccatc | ccgggatgag | ctgaccaaga | accaggtcag | cctgacctgc | 1380 |
| ctggtcaaag | gcttctatcc | cagcgacatc | gccgtggagt | gggagagcaa | tgggcagccg | 1440 |
| gagaacaact | acaagaccac | gcctcccgtg | ctggactccg | acggctcctt | cttcctctac | 1500 |
| agcaagctca | ccgtggacaa | gagcaggtgg | cagcagggga | acgtcttctc | atgctccgtg | 1560 |

```
atgcatgagg ctctgcacaa ccactacacg cagaagagcc tctctctctc tccgggtaaa    1620
tgataatcta gaa                                                        1633
```

<210> SEQ ID NO 24
<211> LENGTH: 535
<212> TYPE: PRT
<213> ORGANISM: Artificial
<220> FEATURE:
<223> OTHER INFORMATION: THER6 polypeptide (apo A-1-(lnk36)-mthIgG; apo A-1-(g4s)6-mthIgG)

<400> SEQUENCE: 24

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Gly Ser Gly Gly Gly Gly Ser Gly Gly Gly
        275                 280                 285

Gly Ser Gly Gly Gly Gly Ser Gly Gly Gly Gly Ser Thr Gly Leu Glu
    290                 295                 300

Pro Lys Ser Ser Asp Lys Thr His Thr Ser Pro Pro Ser Pro Ala Pro
305                 310                 315                 320

Glu Leu Leu Gly Gly Ser Ser Val Phe Leu Phe Pro Pro Lys Pro Lys
                325                 330                 335

Asp Thr Leu Met Ile Ser Arg Thr Pro Glu Val Thr Cys Val Val Val
```

```
              340             345             350
Asp Val Ser His Glu Asp Pro Glu Val Lys Phe Asn Trp Tyr Val Asp
            355                 360                 365
Gly Val Glu Val His Asn Ala Lys Thr Lys Pro Arg Glu Glu Gln Tyr
        370                 375                 380
Asn Ser Thr Tyr Arg Val Ser Val Leu Thr Val Leu His Gln Asp
385                 390                 395                 400
Trp Leu Asn Gly Lys Glu Tyr Lys Cys Lys Val Ser Asn Lys Ala Leu
                405                 410                 415
Pro Ala Ser Ile Glu Lys Thr Ile Ser Lys Ala Lys Gly Gln Pro Arg
            420                 425                 430
Glu Pro Gln Val Tyr Thr Leu Pro Pro Ser Arg Asp Glu Leu Thr Lys
        435                 440                 445
Asn Gln Val Ser Leu Thr Cys Leu Val Lys Gly Phe Tyr Pro Ser Asp
    450                 455                 460
Ile Ala Val Glu Trp Glu Ser Asn Gly Gln Pro Glu Asn Asn Tyr Lys
465                 470                 475                 480
Thr Thr Pro Pro Val Leu Asp Ser Asp Gly Ser Phe Phe Leu Tyr Ser
                485                 490                 495
Lys Leu Thr Val Asp Lys Ser Arg Trp Gln Gln Gly Asn Val Phe Ser
            500                 505                 510
Cys Ser Val Met His Glu Ala Leu His Asn His Tyr Thr Gln Lys Ser
        515                 520                 525
Leu Ser Leu Ser Pro Gly Lys
    530                 535

<210> SEQ ID NO 25
<211> LENGTH: 1588
<212> TYPE: DNA
<213> ORGANISM: Artificial
<220> FEATURE:
<223> OTHER INFORMATION: THER3 DNA (apo A-1-(lnk21)-mthIgG; apo
      A-1-(g4s)3-mthIgG)

<400> SEQUENCE: 25
gttaagcttg ccaccatgaa agctgcggtg ctgaccttgg ccgtgctctt cctgacgggg      60
agccaggctc ggcatttctg cagcaagat gaaccccccc agagcccctg ggatcgagtg     120
aaggacctgg ccactgtgta cgtggatgtg ctcaaagaca gcggcagaga ctatgtgtcc     180
cagtttgaag gctccgcctt gggaaaacag ctaaacctaa agctccttga caactgggac     240
agcgtgacct ccaccttcag caagctgcgc gaacagctcg gccctgtgac ccaggagttc     300
tgggataacc tggaaaagga gacagagggc ctgaggcagg agatgagcaa ggatctggag     360
gaggtgaagg ccaaggtgca gcctacctg gacgacttcc agaagaagtg gcaggaggag     420
atggagctct accgccagaa ggtggagccg ctgcgcgcag agctccaaga gggcgcgcgc     480
cagaagctgc acgagctgca agagaagctg agcccactgg gcgaggagat gcgcgaccgc     540
gcgcgcgccc atgtggacgc gctgcgcacg catctggccc cctacagcga cgagctgcgc     600
cagcgcttgg ccgcgcgcct tgaggctctc aaggagaacg gcggcgccag actggccgag     660
taccacgcca aggccaccga gcatctgagc acgctcagcg agaaggccaa gcccgcgctc     720
gaggacctcc gccaaggcct gctgccgtg ctggagagct tcaaggtcag cttcctgagc     780
gctctcgagg agtacactaa gaagctcaac acccaagatc tctcaggtgg tggaggatct     840
ggaggaggtg ggagtggtgg aggtggttct accggtctcg agcccaaatc ttctgacaaa     900
```

```
actcacacat ctccaccgtc cccagcacct gaactcctgg gaggatcgtc agtcttcctc    960
ttccccccaa aacccaagga caccctcatg atctcccgga cccctgaggt cacatgcgtg   1020
gtggtggacg tgagccacga agaccctgag gtcaagttca actggtacgt ggacggcgtg   1080
gaggtgcata atgccaagac aaagccgcgg gaggagcagt acaacagcac gtaccgtgtg   1140
gtcagcgtcc tcaccgtcct gcaccaggac tggctgaatg gcaaggagta caagtgcaag   1200
gtctccaaca aagccctccc agcctccatc gagaaaacca tctccaaagc caagggcag    1260
ccccgagaac cacaggtgta caccctgccc ccatcccggg atgagctgac caagaaccag   1320
gtcagcctga cctgcctggt caaaggcttc tatcccagcg acatcgccgt ggagtgggag   1380
agcaatgggc agccggagaa caactacaag accacgcctc ccgtgctgga ctccgacggc   1440
tccttcttcc tctacagcaa gctcaccgtg gacaagagca ggtggcagca ggggaacgtc   1500
ttctcatgct ccgtgatgca tgaggctctg cacaaccact acacgcagaa gagcctctct   1560
ctctctccgg gtaaatgata atctagaa                                     1588
```

<210> SEQ ID NO 26
<211> LENGTH: 520
<212> TYPE: PRT
<213> ORGANISM: Artificial
<220> FEATURE:
<223> OTHER INFORMATION: THER3 polypeptide (apo A-1-(lnk21)-mthIgG; apo A-1-(g4s)3-mthIgG)

<400> SEQUENCE: 26

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240
```

Gly Leu Leu Pro Val Leu Glu Ser Phe Lys Val Ser Phe Leu Ser Ala
            245                 250                 255

Leu Glu Glu Tyr Thr Lys Lys Leu Asn Thr Gln Asp Leu Ser Gly Gly
            260                 265                 270

Gly Gly Ser Gly Gly Gly Gly Ser Gly Gly Gly Gly Ser Thr Gly Leu
            275                 280                 285

Glu Pro Lys Ser Ser Asp Lys Thr His Thr Ser Pro Pro Ser Pro Ala
        290                 295                 300

Pro Glu Leu Leu Gly Gly Ser Ser Val Phe Leu Phe Pro Pro Lys Pro
305                 310                 315                 320

Lys Asp Thr Leu Met Ile Ser Arg Thr Pro Glu Val Thr Cys Val Val
                325                 330                 335

Val Asp Val Ser His Glu Asp Pro Glu Val Lys Phe Asn Trp Tyr Val
                340                 345                 350

Asp Gly Val Glu Val His Asn Ala Lys Thr Lys Pro Arg Glu Glu Gln
            355                 360                 365

Tyr Asn Ser Thr Tyr Arg Val Val Ser Val Leu Thr Val Leu His Gln
        370                 375                 380

Asp Trp Leu Asn Gly Lys Glu Tyr Lys Cys Lys Val Ser Asn Lys Ala
385                 390                 395                 400

Leu Pro Ala Ser Ile Glu Lys Thr Ile Ser Lys Ala Lys Gly Gln Pro
                405                 410                 415

Arg Glu Pro Gln Val Tyr Thr Leu Pro Pro Ser Arg Asp Glu Leu Thr
            420                 425                 430

Lys Asn Gln Val Ser Leu Thr Cys Leu Val Lys Gly Phe Tyr Pro Ser
        435                 440                 445

Asp Ile Ala Val Glu Trp Glu Ser Asn Gly Gln Pro Glu Asn Asn Tyr
450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
            500                 505                 510

Ser Leu Ser Leu Ser Pro Gly Lys
        515                 520

<210> SEQ ID NO 27
<211> LENGTH: 2677
<212> TYPE: DNA
<213> ORGANISM: Artificial
<220> FEATURE:
<223> OTHER INFORMATION: THER4PON1 DNA

<400> SEQUENCE: 27
gttaagcttg ccaccatgaa agctgcggtg ctgaccttgg ccgtgctctt cctgacgggg      60
agccaggctc ggcatttctg gcagcaagat gaaccccccc agagcccctg ggatcgagtg     120
aaggacctgg ccactgtgta cgtggatgtg ctcaaagaca gcggcagaga ctatgtgtcc     180
cagtttgaag gctccgcctt ggaaaaacag ctaaacctaa agctccttga caactgggac     240
agcgtgacct ccaccttcag caagctgcgc gaacagctcg gccctgtgac ccaggagttc     300
tgggataacc tggaaaagga gacagagggc ctgaggcagg agatgagcaa ggatctggag     360
gaggtgaagg ccaaggtgca gccctacctg gacgacttcc agaagaagtg gcaggaggag     420

| | |
|---|---|
| atggagctct accgccagaa ggtggagccg ctgcgcgcag agctccaaga gggcgcgcgc | 480 |
| cagaagctgc acgagctgca agagaagctg agcccactgg gcgaggagat gcgcgaccgc | 540 |
| gcgcgcgccc atgtggacgc gctgcgcacg catctggccc cctacagcga cgagctgcgc | 600 |
| cagcgcttgg ccgcgcgcct tgaggctctc aaggagaacg gcggcgccag actggccgag | 660 |
| taccacgcca aggccaccga gcatctgagc acgctcagcg agaaggccaa gcccgcgctc | 720 |
| gaggacctcc gccaaggcct gctgcccgtg ctggagagct tcaaggtcag cttcctgagc | 780 |
| gctctcgagg agtacactaa gaagctcaac acccaagatc tctccggagg aggtggctca | 840 |
| ggtggtggag gatctggagg aggtgggagt ggtggaggtg gttctaccgg tctcgagccc | 900 |
| aaatcttctg acaaaactca cacatctcca ccgtccccag cacctgaact cctgggagga | 960 |
| tcgtcagtct tcctcttccc cccaaaaccc aaggacaccc tcatgatctc ccggacccct | 1020 |
| gaggtcacat gcgtggtggt ggacgtgagc cacgaagacc ctgaggtcaa gttcaactgg | 1080 |
| tacgtggacg gcgtggaggt gcataatgcc aagacaaagc cgcgggagga gcagtacaac | 1140 |
| agcacgtacc gtgtggtcag cgtcctcacc gtcctgcacc aggactggct gaatggcaag | 1200 |
| gagtacaagt gcaaggtctc caacaaagcc ctcccagcct ccatcgagaa aaccatctcc | 1260 |
| aaagccaaag ggcagccccg agaaccacag gtgtacaccc tgcccccatc ccgggatgag | 1320 |
| ctgaccaaga accaggtcag cctgacctgc ctggtcaaag gcttctatcc cagcgacatc | 1380 |
| gccgtggagt gggagagcaa tgggcagccg gagaacaact acaagaccac gcctcccgtg | 1440 |
| ctggactccg acggctcctt cttcctctac agcaagctca ccgtggacaa gagcaggtgg | 1500 |
| cagcagggga acgtcttctc atgctccgtg atgcatgagg ctctgcacaa ccactacacg | 1560 |
| cagaagagcc tctctctctc tccgggtaaa gtcgacggag ctagcagccc cgtgaacgtg | 1620 |
| agcagcccca gcgtgcagga tatcctcttc aggaaccacc agtcttctta ccaaacacga | 1680 |
| cttaatgctc tccgagaggt acaacccgta gaacttccta actgtaattt agttaaagga | 1740 |
| atcgaaactg gctctgaaga cttggagata ctgcctaatg gactggcttt cattagctct | 1800 |
| ggattaaagt atcctggaat aaagagcttc aaccccaaca gtcctggaaa atacttctg | 1860 |
| atggacctga tgaagaaga tccaacagtg ttggaattgg ggatcactgg aagtaaattt | 1920 |
| gatgtatctt catttaaccc tcatgggatt agcacattca cagatgaaga taatgccatg | 1980 |
| tacctcctgg tggtgaacca tccagatgcc aagtccacag tggagttgtt taaatttcaa | 2040 |
| gaagaagaaa aatcgctttt gcatctaaaa accatcagac ataaacttct gcctaatttg | 2100 |
| aatgatattg ttgctgtggg acctgagcac ttttatggca caaatgatca ctatttttctt | 2160 |
| gaccccctact tacaatcctg ggagatgtat ttgggtttag cgtggtcgta tgttgtctac | 2220 |
| tatagtccaa gtgaagttcg agtggtggca gaaggatttg attttgctaa tggaatcaac | 2280 |
| atttcacccg atggcaagta tgtctatata gctgagttgc tggctcataa gattcatgtg | 2340 |
| tatgaaaagc atgctaattg gactttaact ccattgaagt cccttgactt taataccctc | 2400 |
| gtggataaca tatctgtgga tcctgagaca ggagaccttt gggttggatg ccatcccaat | 2460 |
| ggcatgaaaa tcttcttcta tgactcagag aatcctcctg catcagaggt gcttcgaatc | 2520 |
| cagaacattc taacagaaga acctaaagtg acacaggttt atgcagaaaa tggcacagtg | 2580 |
| ttgcaaggca gtacagttgc ctctgtgtac aaagggaaac tgctgattgg cacagtgttt | 2640 |
| cacaaagctc tttactgtga gctctaataa tctagaa | 2677 |

<210> SEQ ID NO 28
<211> LENGTH: 883

<212> TYPE: PRT
<213> ORGANISM: Artificial
<220> FEATURE:
<223> OTHER INFORMATION: THER4PON1 polypeptide

<400> SEQUENCE: 28

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Gly Ser Gly Gly Gly Gly Ser Gly Gly Gly
        275                 280                 285

Gly Ser Thr Gly Leu Glu Pro Lys Ser Ser Asp Lys Thr His Thr Ser
    290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
    370                 375                 380
```

```
Thr Val Leu His Gln Asp Trp Leu Asn Gly Lys Glu Tyr Lys Cys Lys
385                 390                 395                 400
Val Ser Asn Lys Ala Leu Pro Ala Ser Ile Glu Lys Thr Ile Ser Lys
            405                 410                 415
Ala Lys Gly Gln Pro Arg Glu Pro Gln Val Tyr Thr Leu Pro Pro Ser
        420                 425                 430
Arg Asp Glu Leu Thr Lys Asn Gln Val Ser Leu Thr Cys Leu Val Lys
            435                 440                 445
Gly Phe Tyr Pro Ser Asp Ile Ala Val Glu Trp Glu Ser Asn Gly Gln
        450                 455                 460
Pro Glu Asn Asn Tyr Lys Thr Thr Pro Pro Val Leu Asp Ser Asp Gly
465                 470                 475                 480
Ser Phe Phe Leu Tyr Ser Lys Leu Thr Val Asp Lys Ser Arg Trp Gln
            485                 490                 495
Gln Gly Asn Val Phe Ser Cys Ser Val Met His Glu Ala Leu His Asn
        500                 505                 510
His Tyr Thr Gln Lys Ser Leu Ser Leu Ser Pro Gly Lys Val Asp Gly
        515                 520                 525
Ala Ser Ser Pro Val Asn Val Ser Ser Pro Ser Val Gln Asp Ile Leu
530                 535                 540
Phe Arg Asn His Gln Ser Ser Tyr Gln Thr Arg Leu Asn Ala Leu Arg
545                 550                 555                 560
Glu Val Gln Pro Val Glu Leu Pro Asn Cys Asn Leu Val Lys Gly Ile
                565                 570                 575
Glu Thr Gly Ser Glu Asp Leu Glu Ile Leu Pro Asn Gly Leu Ala Phe
            580                 585                 590
Ile Ser Ser Gly Leu Lys Tyr Pro Gly Ile Lys Ser Phe Asn Pro Asn
        595                 600                 605
Ser Pro Gly Lys Ile Leu Leu Met Asp Leu Asn Glu Glu Asp Pro Thr
610                 615                 620
Val Leu Glu Leu Gly Ile Thr Gly Ser Lys Phe Asp Val Ser Ser Phe
625                 630                 635                 640
Asn Pro His Gly Ile Ser Thr Phe Thr Asp Glu Asp Asn Ala Met Tyr
                645                 650                 655
Leu Leu Val Val Asn His Pro Asp Ala Lys Ser Thr Val Glu Leu Phe
            660                 665                 670
Lys Phe Gln Glu Glu Lys Ser Leu Leu His Leu Lys Thr Ile Arg
        675                 680                 685
His Lys Leu Leu Pro Asn Leu Asn Asp Ile Val Ala Val Gly Pro Glu
690                 695                 700
His Phe Tyr Gly Thr Asn Asp His Tyr Phe Leu Asp Pro Tyr Leu Gln
705                 710                 715                 720
Ser Trp Glu Met Tyr Leu Gly Leu Ala Trp Ser Tyr Val Val Tyr Tyr
                725                 730                 735
Ser Pro Ser Glu Val Arg Val Val Ala Glu Gly Phe Asp Phe Ala Asn
            740                 745                 750
Gly Ile Asn Ile Ser Pro Asp Gly Lys Tyr Val Tyr Ile Ala Glu Leu
        755                 760                 765
Leu Ala His Lys Ile His Val Tyr Glu Lys His Ala Asn Trp Thr Leu
        770                 775                 780
Thr Pro Leu Lys Ser Leu Asp Phe Asn Thr Leu Val Asp Asn Ile Ser
785                 790                 795                 800
Val Asp Pro Glu Thr Gly Asp Leu Trp Val Gly Cys His Pro Asn Gly
```

|  | 805 |  |  |  | 810 |  |  |  | 815 |  |  |
|---|---|---|---|---|---|---|---|---|---|---|---|

Met Lys Ile Phe Phe Tyr Asp Ser Glu Asn Pro Pro Ala Ser Glu Val
            820                 825                 830

Leu Arg Ile Gln Asn Ile Leu Thr Glu Glu Pro Lys Val Thr Gln Val
        835                 840                 845

Tyr Ala Glu Asn Gly Thr Val Leu Gln Gly Ser Thr Val Ala Ser Val
    850                 855                 860

Tyr Lys Gly Lys Leu Leu Ile Gly Thr Val Phe His Lys Ala Leu Tyr
865                 870                 875                 880

Cys Glu Leu

```
<210> SEQ ID NO 29
<211> LENGTH: 1717
<212> TYPE: DNA
<213> ORGANISM: Homo sapiens

<400> SEQUENCE: 29
atatacgggc tccaggctga acggctcggg ccacttacac accactgcct gataaccatg      60
ctggctgcca cagtcctgac cctggccctg ctgggcaatg cccatgcctg ctccaaaggc     120
acctcgcacg aggcaggcat cgtgtgccgc atcaccaagc tgccctcct ggtgttgaac      180 cacgagactg ccaaggtgat ccagaccgcc ttccagcgag ccagctaccc agatatcacg     240
ggcgagaagg ccatgatgct ccttggccaa gtcaagtatg ggttgcacaa catccagatc     300
agccacttgt ccatcgccag cagccaggtg gagctggtgg aagccaagtc cattgatgtc     360
tccattcaga acgtgtctgt ggtcttcaag gggaccctga gtatggcta caccactgcc     420 tggtggctgg gtattgatca gtccattgac ttcgagatcg actctgccat tgacctccag     480
atcaacacac agctgacctg tgactctggt agagtgcgga ccgatgcccc tgactgctac     540
ctgtctttcc ataagctgct cctgcatctc aaggggagc gagagcctgg gtggatcaag     600
cagctgttca caatttcat ctccttcacc ctgaagctgg tcctgaaggg acagatctgc     660
aaagagatca acgtcatctc taacatcatg gccgattttg tccagacaag ggctgccagc     720 atccttttcag atggagacat tggggtggac atttccctga caggtgatcc cgtcatcaca     780
gcctcctacc tggagtccca tcacaagggt catttcatct acaagaatgt ctcagaggac     840
ctccccctcc ccaccttctc gcccacactg ctggggact cccgcatgct gtacttctgg     900
ttctctgagc gagtcttcca ctcgctggcc aaggtagctt tccaggatgg ccgcctcatg     960
ctcagcctga tggagacga gttcaaggca gtgctggaga cctggggctt caacaccaac    1020
caggaaatct tccaagaggt tgtcggcggc ttccccagcc aggcccaagt caccgtccac    1080
tgcctcaaga tgcccaagat ctcctgccaa aacaagggag tcgtggtcaa ttcttcagtg    1140
atggtgaaat tcctctttcc acgcccagac cagcaacatt ctgtagctta cattttgaa    1200 gaggatatcg tgactaccgt ccaggcctcc tattctaaga aaaagctctt cttaagcctc    1260
ttggatttcc agattacacc aaagactgtt ccaacttga ctgagagcag ctccgagtcc     1320
gtccagagct tcctgcagtc aatgatcacc gctgtgggca tccctgaggt catgtctcgg    1380
ctcgaggtag tgtttacagc cctcatgaac agcaaaggcg tgagcctctt cgacatcatc    1440
aaccctgaga ttatcactcg agatggcttc ctgctgctgc agatggactt tggcttccct    1500
gagcacctgc tggtggattt cctccagagc ttgagctaga agtctccaag gaggtcggga    1560
tggggcttgt agcagaaggc aagcaccagg ctcacagctg gaaccctggt gtctcctcca    1620
gcgtggtgga agttgggtta ggagtacgga gatggagatt ggctcccaac tcctccctat    1680
```
cctaaaggcc cactggcatt aaagtgctgt atccaag                    1717

<210> SEQ ID NO 30
<211> LENGTH: 493
<212> TYPE: PRT
<213> ORGANISM: Homo sapiens

<400> SEQUENCE: 30

Met Leu Ala Ala Thr Val Leu Thr Leu Ala Leu Leu Gly Asn Ala His
1               5                   10                  15

Ala Cys Ser Lys Gly Thr Ser His Glu Ala Gly Ile Val Cys Arg Ile
            20                  25                  30

Thr Lys Pro Ala Leu Leu Val Leu Asn His Glu Thr Ala Lys Val Ile
        35                  40                  45

Gln Thr Ala Phe Gln Arg Ala Ser Tyr Pro Asp Ile Thr Gly Glu Lys
    50                  55                  60

Ala Met Met Leu Leu Gly Gln Val Lys Tyr Gly Leu His Asn Ile Gln
65                  70                  75                  80

Ile Ser His Leu Ser Ile Ala Ser Ser Gln Val Glu Leu Val Glu Ala
                85                  90                  95

Lys Ser Ile Asp Val Ser Ile Gln Asn Val Ser Val Val Phe Lys Gly
            100                 105                 110

Thr Leu Lys Tyr Gly Tyr Thr Thr Ala Trp Trp Leu Gly Ile Asp Gln
        115                 120                 125

Ser Ile Asp Phe Glu Ile Asp Ser Ala Ile Asp Leu Gln Ile Asn Thr
    130                 135                 140

Gln Leu Thr Cys Asp Ser Gly Arg Val Arg Thr Asp Ala Pro Asp Cys
145                 150                 155                 160

Tyr Leu Ser Phe His Lys Leu Leu His Leu Gln Gly Glu Arg Glu
                165                 170                 175

Pro Gly Trp Ile Lys Gln Leu Phe Thr Asn Phe Ile Ser Phe Thr Leu
            180                 185                 190

Lys Leu Val Leu Lys Gly Gln Ile Cys Lys Glu Ile Asn Val Ile Ser
        195                 200                 205

Asn Ile Met Ala Asp Phe Val Gln Thr Arg Ala Ala Ser Ile Leu Ser
    210                 215                 220

Asp Gly Asp Ile Gly Val Asp Ile Ser Leu Thr Gly Asp Pro Val Ile
225                 230                 235                 240

Thr Ala Ser Tyr Leu Glu Ser His His Lys Gly His Phe Ile Tyr Lys
                245                 250                 255

Asn Val Ser Glu Asp Leu Pro Leu Pro Thr Phe Ser Pro Thr Leu Leu
            260                 265                 270

Gly Asp Ser Arg Met Leu Tyr Phe Trp Phe Ser Glu Arg Val Phe His
        275                 280                 285

Ser Leu Ala Lys Val Ala Phe Gln Asp Gly Arg Leu Met Leu Ser Leu
    290                 295                 300

Met Gly Asp Glu Phe Lys Ala Val Leu Glu Thr Trp Gly Phe Asn Thr
305                 310                 315                 320

Asn Gln Glu Ile Phe Gln Glu Val Gly Gly Phe Pro Ser Gln Ala
                325                 330                 335

Gln Val Thr Val His Cys Leu Lys Met Pro Lys Ile Ser Cys Gln Asn
            340                 345                 350

Lys Gly Val Val Val Asn Ser Ser Val Met Val Lys Phe Leu Phe Pro
        355                 360                 365

```
Arg Pro Asp Gln Gln His Ser Val Ala Tyr Thr Phe Glu Glu Asp Ile
    370                 375                 380

Val Thr Thr Val Gln Ala Ser Tyr Ser Lys Lys Leu Phe Leu Ser
385                 390                 395                 400

Leu Leu Asp Phe Gln Ile Thr Pro Lys Thr Val Ser Asn Leu Thr Glu
                405                 410                 415

Ser Ser Ser Glu Ser Val Gln Ser Phe Leu Gln Ser Met Ile Thr Ala
            420                 425                 430

Val Gly Ile Pro Glu Val Met Ser Arg Leu Glu Val Val Phe Thr Ala
        435                 440                 445

Leu Met Asn Ser Lys Gly Val Ser Leu Phe Asp Ile Ile Asn Pro Glu
    450                 455                 460

Ile Ile Thr Arg Asp Gly Phe Leu Leu Leu Gln Met Asp Phe Gly Phe
465                 470                 475                 480

Pro Glu His Leu Leu Val Asp Phe Leu Gln Ser Leu Ser
                485                 490

<210> SEQ ID NO 31
<211> LENGTH: 1880
<212> TYPE: DNA
<213> ORGANISM: Homo sapiens

<400> SEQUENCE: 31
gggtcggggc cacaaggccg cgctaggcgg acccaggaca cagcccgcgc gcagcccacc      60
cgcccgccgc ctgccagagc tgctcggccc gcagccaggg ggacagcggc tggtcggagg     120
ctcgcagtgc tgtcggcgag aagcagtcgg gtttggagcg cttgggtcgc gttggtgcgc     180
ggtggaacgc gcccagggac cccagttccc gcgagcagct ccgcgccgcg cctgagagac     240
taagctgaaa ctgctgctca gctcccaaga tggtgccacc caaattgcat gtgcttttct     300
gcctctgcgg ctgcctggct gtggtttatc cttttgactg caatacata aatcctgttg      360 cccatatgaa atcatcagca tgggtcaaca aaatacaagt actgatggct gctgcaagct     420
ttggccaaac taaaatcccc cggggaaatg ggccttattc cgttggttgt acagacttaa     480
tgtttgatca cactaataag ggcaccttct tgcgtttata ttatccatcc aagataatg     540 atcgccttga cacccttttgg atcccaaata agaatatttt tgggtgtctt agcaaatttc   600
ttggaacaca ctggcttatg gcaacatttt tgaggttact ctttggttca atgacaactc    660
ctgcaaactg gaattcccct ctgaggcctg gtgaaaaata tccacttgtt gttttttctc   720
atggtcttgg ggcattcagg acactttatt ctgctattgg cattgacctg gcatctcatg    780
ggtttatagt tgctgctgta gaacacagag atagatctgc atctgcaact tactatttca    840
aggaccaatc tgctgcagaa ataggggaca agtcttggct ctaccttaga accctgaaac    900
aagaggagga gacacatata cgaaatgagc aggtacggca agagcaaaaa gaatgttccc    960
aagctctcag tctgattctt gacattgatc atggaaagcc agtgaagaat gcattagatt   1020
taaagtttga tatggaacaa ctgaaggact ctattgatag ggaaaaaata gcagtaattg   1080
gacattcttt tggtggagca acggttatc agactcttag tgaagatcag agattccagat   1140 gtggtattgc cctggatgca tggatgtttc cactgggtga tgaagtatat tccagaattc   1200
ctcagccctt tctttttate aactctgaat atttccaata tcctgctaat atcataaaaa   1260
tgaaaaaatg ctactcacct gataaagaaa gaaagatgat tacaatcagg ggttcagtcc   1320
accagaattt tgctgacttc acttttgcaa ctggcaaaat aattggacac atgctcaaat   1380
```

-continued

```
taaagggaga catagattca aatgtagcta ttgatcttag caacaaagct tcattagcat    1440
tcttacaaaa gcatttagga cttcataaag attttgatca gtgggactgc ttgattgaag    1500
gagatgatga gaatcttatt ccagggacca acattaacac aaccaatcaa cacatcatgt    1560
tacagaactc ttcaggaata gagaaataca attaggatta aaataggttt tttaaaagtc    1620
ttgtttcaaa actgtctaaa attatgtgtg tgtgtgtgtg tgtgtgtgtg tgtgtgagag    1680
agagagagag agagagagag agagagagag agaattttaa tgtattttcc caaaggactc    1740
atattttaaa atgtaggcta tactgtaatc gtgattgaag cttggactaa gaatttttc     1800 cctttagatg taaagaaaga atacagtata caatattcaa aaaaaaaaaa aaaaaaaaa     1860 aaaaaaaaaa aaaaaaaaa                                                 1880
```

<210> SEQ ID NO 32
<211> LENGTH: 441
<212> TYPE: PRT
<213> ORGANISM: Homo sapiens

<400> SEQUENCE: 32

```
Met Val Pro Pro Lys Leu His Val Leu Phe Cys Leu Cys Gly Cys Leu
1               5                   10                  15

Ala Val Val Tyr Pro Phe Asp Trp Gln Tyr Ile Asn Pro Val Ala His
                20                  25                  30

Met Lys Ser Ser Ala Trp Val Asn Lys Ile Gln Val Leu Met Ala Ala
            35                  40                  45

Ala Ser Phe Gly Gln Thr Lys Ile Pro Arg Gly Asn Gly Pro Tyr Ser
        50                  55                  60

Val Gly Cys Thr Asp Leu Met Phe Asp His Thr Asn Lys Gly Thr Phe
65                  70                  75                  80

Leu Arg Leu Tyr Tyr Pro Ser Gln Asp Asn Asp Arg Leu Asp Thr Leu
                85                  90                  95

Trp Ile Pro Asn Lys Glu Tyr Phe Trp Gly Leu Ser Lys Phe Leu Gly
            100                 105                 110

Thr His Trp Leu Met Gly Asn Ile Leu Arg Leu Leu Phe Gly Ser Met
        115                 120                 125

Thr Thr Pro Ala Asn Trp Asn Ser Pro Leu Arg Pro Gly Glu Lys Tyr
    130                 135                 140

Pro Leu Val Val Phe Ser His Gly Leu Gly Ala Phe Arg Thr Leu Tyr
145                 150                 155                 160

Ser Ala Ile Gly Ile Asp Leu Ala Ser His Gly Phe Ile Val Ala Ala
                165                 170                 175

Val Glu His Arg Asp Arg Ser Ala Ser Ala Thr Tyr Tyr Phe Lys Asp
            180                 185                 190

Gln Ser Ala Ala Glu Ile Gly Asp Lys Ser Trp Leu Tyr Leu Arg Thr
        195                 200                 205

Leu Lys Gln Glu Glu Glu Thr His Ile Arg Asn Glu Gln Val Arg Gln
    210                 215                 220

Arg Ala Lys Glu Cys Ser Gln Ala Leu Ser Leu Ile Leu Asp Ile Asp
225                 230                 235                 240

His Gly Lys Pro Val Lys Asn Ala Leu Asp Leu Lys Phe Asp Met Glu
                245                 250                 255

Gln Leu Lys Asp Ser Ile Asp Arg Glu Lys Ile Ala Val Ile Gly His
            260                 265                 270

Ser Phe Gly Gly Ala Thr Val Ile Gln Thr Leu Ser Glu Asp Gln Arg
        275                 280                 285
```

```
Phe Arg Cys Gly Ile Ala Leu Asp Ala Trp Met Phe Pro Leu Gly Asp
    290                 295                 300
Glu Val Tyr Ser Arg Ile Pro Gln Pro Leu Phe Ile Asn Ser Glu
305                 310                 315                 320
Tyr Phe Gln Tyr Pro Ala Asn Ile Ile Lys Met Lys Lys Cys Tyr Ser
                325                 330                 335
Pro Asp Lys Glu Arg Lys Met Ile Thr Ile Arg Gly Ser Val His Gln
            340                 345                 350
Asn Phe Ala Asp Phe Thr Phe Ala Thr Gly Lys Ile Ile Gly His Met
        355                 360                 365
Leu Lys Leu Lys Gly Asp Ile Asp Ser Asn Val Ala Ile Asp Leu Ser
    370                 375                 380
Asn Lys Ala Ser Leu Ala Phe Leu Gln Lys His Leu Gly Leu His Lys
385                 390                 395                 400
Asp Phe Asp Gln Trp Asp Cys Leu Ile Glu Gly Asp Asp Glu Asn Leu
                405                 410                 415
Ile Pro Gly Thr Asn Ile Asn Thr Thr Asn Gln His Ile Met Leu Gln
            420                 425                 430
Asn Ser Ser Gly Ile Glu Lys Tyr Asn
        435                 440

<210> SEQ ID NO 33
<211> LENGTH: 2907
<212> TYPE: DNA
<213> ORGANISM: Artificial
<220> FEATURE:
<223> OTHER INFORMATION: THER4PAFAH DNA

<400> SEQUENCE: 33
gttaagcttg ccaccatgaa agctgcggtg ctgaccttgg ccgtgctctt cctgacgggg      60
agccaggctc ggcatttctg gcagcaagat gaaccccccc agagcccctg ggatcgagtg     120
aaggacctgg ccactgtgta cgtggatgtg ctcaaagaca gcggcagaga ctatgtgtcc     180
cagtttgaag ctccgccttg ggaaaaacag ctaaacctaa agctccttga caactgggac     240
agcgtgacct ccaccttcag caagctgcgc gaacagctcg ccctgtgac ccaggagttc     300 tgggataacc tggaaaagga gacagagggc ctgaggcagg agatgagcaa ggatctggag     360
gaggtgaagg ccaaggtgca gccctacctg gacgacttcc agaagaagtg caggaggag     420 atggagctct accgccagaa ggtggagccg ctgcgcgcag agctccaaga gggcgcgcgc     480
cagaagctgc acgagctgca agagaagctg agcccactgg gcgaggagat gcgcgaccgc     540
gcgcgcgccc atgtggacgc gctgcgcacg catctggccc cctacagcga cgagctgcgc     600
cagcgcttgg ccgcgcgcct tgaggctctc aaggagaacg gcggcgccag actggccgag     660
taccacgcca aggccaccga gcatctgagc acgctcagcg agaaggccaa gcccgcgctc     720
gaggacctcc gccaaggcct gctgcccgtg ctggagagct tcaaggtcag cttcctgagc     780
gctctcgagg agtacactaa gaagctcaac acccaagatc tctccggagg aggtggctca     840
ggtggtggag gatctggagg aggtgggagt ggtggaggtg gttctaccgg tctcgagccc     900
aaatcttctg acaaaactca cacatctcca cgtccccag cacctgaact cctgggagga     960
tcgtcagtct tcctcttccc cccaaaaccc aaggacaccc tcatgatctc ccggacccct    1020
gaggtcacat gcgtggtggt ggacgtgagc cacgaagacc ctgaggtcaa gttcaactgg    1080
tacgtggacg gcgtggaggt gcataatgcc aagacaaagc cgcgggagga gcagtacaac    1140
```

| | | | |
|---|---|---|---|
| agcacgtacc gtgtggtcag cgtcctcacc gtcctgcacc aggactggct gaatggcaag | 1200 |
| gagtacaagt gcaaggtctc caacaaagcc ctcccagcct ccatcgagaa aaccatctcc | 1260 |
| aaagccaaag gcagccccg agaaccacag gtgtacaccc tgcccccatc ccgggatgag | 1320 |
| ctgaccaaga accaggtcag cctgacctgc ctggtcaaag gcttctatcc cagcgacatc | 1380 |
| gccgtggagt gggagagcaa tgggcagccg gagaacaact acaagaccac gcctcccgtg | 1440 |
| ctggactccg acggctcctt cttcctctac agcaagctca ccgtggacaa gagcaggtgg | 1500 |
| cagcagggga acgtcttctc atgctccgtg atgcatgagg ctctgcacaa ccactacacg | 1560 |
| cagaagagcc tctctctctc tccgggtaaa gtcgacggag ctagcagccc cgtgaacgtg | 1620 |
| agcagcccca gcgtgcagga tatctttgac tggcaataca taaatcctgt tgcccatatg | 1680 |
| aaatcatcag catgggtcaa caaaatacaa gtactgatgg ctgctgcaag ctttggccaa | 1740 |
| actaaaatcc cccggggaaa tgggccttat tccgttggtt gtacagactt aatgtttgat | 1800 |
| cacactaata agggcacctt cttgcgttta tattatccat cccaagataa tgatcgcctt | 1860 |
| gacacccttt ggatcccaaa taagaatat ttttgggtc ttagcaaatt tcttggaaca | 1920 |
| cactggctta tgggcaacat tttgaggtta ctctttggtt caatgacaac tcctgcaaac | 1980 |
| tggaattccc ctctgaggcc tggtgaaaaa tatccacttg ttgttttttc tcatggtctt | 2040 |
| ggggcattca ggacactta ttctgctatt ggcattgacc tggcatctca tgggtttata | 2100 |
| gttgctgctg tagaacacag agatagatct gcatctgcaa cttactattt caaggaccaa | 2160 |
| tctgctgcag aaatagggga caagtcttgg ctctaccta gaaccctgaa acaagaggag | 2220 |
| gagacacata tacgaaatga gcaggtacgg caaagagcaa agaatgttc ccaagctctc | 2280 |
| agtctgattc ttgacattga tcatggaaag ccagtgaaga atgcattaga tttaaagttt | 2340 |
| gatatggaac aactgaagga ctctattgat agggaaaaaa tagcagtaat tggacattct | 2400 |
| tttggtggag caacggttat tcagactctt agtgaagatc agagattcag atgtggtatt | 2460 |
| gccctggatg catggatgtt tccactgggt gatgaagtat attccagaat tcctcagccc | 2520 |
| ctcttttta tcaactctga atatttccaa tatcctgcta atatcataaa aatgaaaaaa | 2580 |
| tgctactcac ctgataaaga aagaaagatg attacaatca ggggttcagt ccaccagaat | 2640 |
| tttgctgact tcacttttgc aactggcaaa ataattggac acatgctcaa attaaaggga | 2700 |
| gacatagatt caaatgtagc tattgatctt agcaacaaag cttcattagc attcttacaa | 2760 |
| aagcatttag gacttcataa agattttgat cagtgggact gcttgattga aggagatgat | 2820 |
| gagaatctta ttccagggac caacattaac acaaccaatc aacacatcat gttacagaac | 2880 |
| tcttcaggaa tagagaaata caattag | 2907 |

<210> SEQ ID NO 34
<211> LENGTH: 963
<212> TYPE: PRT
<213> ORGANISM: Artificial
<220> FEATURE:
<223> OTHER INFORMATION: THER4PAFAH polypeptide

<400> SEQUENCE: 34

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

-continued

```
Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Ser Gly Gly Gly Ser Gly Gly Gly
        275                 280                 285

Gly Ser Thr Gly Leu Glu Pro Lys Ser Ser Asp Lys Thr His Thr Ser
    290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
    370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Ser Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Asp Glu Leu Thr Lys Asn Gln Val Ser Leu Thr Cys Leu Val Lys
        435                 440                 445

Gly Phe Tyr Pro Ser Asp Ile Ala Val Glu Trp Glu Ser Asn Gly Gln
    450                 455                 460

Pro Glu Asn Asn Tyr Lys Thr Thr Pro Pro Val Leu Asp Ser Asp Gly
```

```
                465                 470                 475                 480
        Ser Phe Phe Leu Tyr Ser Lys Leu Thr Val Asp Lys Ser Arg Trp Gln
                        485                 490                 495

Gln Gly Asn Val Phe Ser Cys Ser Val Met His Glu Ala Leu His Asn
                        500                 505                 510

His Tyr Thr Gln Lys Ser Leu Ser Leu Ser Pro Gly Lys Val Asp Gly
                        515                 520                 525

Ala Ser Ser Pro Val Asn Val Ser Ser Pro Ser Val Gln Asp Ile Phe
        530                 535                 540

Asp Trp Gln Tyr Ile Asn Pro Val Ala His Met Lys Ser Ser Ala Trp
        545                 550                 555                 560

Val Asn Lys Ile Gln Val Leu Met Ala Ala Ser Phe Gly Gln Thr
                        565                 570                 575

Lys Ile Pro Arg Gly Asn Gly Pro Tyr Ser Val Gly Cys Thr Asp Leu
                        580                 585                 590

Met Phe Asp His Thr Asn Lys Gly Thr Phe Leu Arg Leu Tyr Tyr Pro
                        595                 600                 605

Ser Gln Asp Asn Asp Arg Leu Asp Thr Leu Trp Ile Pro Asn Lys Glu
                        610                 615                 620

Tyr Phe Trp Gly Leu Ser Lys Phe Leu Gly Thr His Trp Leu Met Gly
        625                 630                 635                 640

Asn Ile Leu Arg Leu Leu Phe Gly Ser Met Thr Thr Pro Ala Asn Trp
                        645                 650                 655

Asn Ser Pro Leu Arg Pro Gly Glu Lys Tyr Pro Leu Val Val Phe Ser
                        660                 665                 670

His Gly Leu Gly Ala Phe Arg Thr Leu Tyr Ser Ala Ile Gly Ile Asp
                        675                 680                 685

Leu Ala Ser His Gly Phe Ile Val Ala Ala Val Glu His Arg Asp Arg
        690                 695                 700

Ser Ala Ser Ala Thr Tyr Tyr Phe Lys Asp Gln Ser Ala Ala Glu Ile
        705                 710                 715                 720

Gly Asp Lys Ser Trp Leu Tyr Leu Arg Thr Leu Lys Gln Glu Glu Glu
                        725                 730                 735

Thr His Ile Arg Asn Glu Gln Val Arg Gln Arg Ala Lys Glu Cys Ser
                        740                 745                 750

Gln Ala Leu Ser Leu Ile Leu Asp Ile Asp His Gly Lys Pro Val Lys
                        755                 760                 765

Asn Ala Leu Asp Leu Lys Phe Asp Met Glu Gln Leu Lys Asp Ser Ile
        770                 775                 780

Asp Arg Glu Lys Ile Ala Val Ile Gly His Ser Phe Gly Gly Ala Thr
        785                 790                 795                 800

Val Ile Gln Thr Leu Ser Glu Asp Gln Arg Phe Arg Cys Gly Ile Ala
                        805                 810                 815

Leu Asp Ala Trp Met Phe Pro Leu Gly Asp Glu Val Tyr Ser Arg Ile
                        820                 825                 830

Pro Gln Pro Leu Phe Phe Ile Asn Ser Glu Tyr Phe Gln Tyr Pro Ala
                        835                 840                 845

Asn Ile Ile Lys Met Lys Lys Cys Tyr Ser Pro Asp Lys Glu Arg Lys
                        850                 855                 860

Met Ile Thr Ile Arg Gly Ser Val His Gln Asn Phe Ala Asp Phe Thr
        865                 870                 875                 880

Phe Ala Thr Gly Lys Ile Ile Gly His Met Leu Lys Leu Lys Gly Asp
                        885                 890                 895
```

Ile Asp Ser Asn Val Ala Ile Asp Leu Ser Asn Lys Ala Ser Leu Ala
         900                 905                 910

Phe Leu Gln Lys His Leu Gly Leu His Lys Asp Phe Asp Gln Trp Asp
         915                 920                 925

Cys Leu Ile Glu Gly Asp Asp Glu Asn Leu Ile Pro Gly Thr Asn Ile
         930                 935                 940

Asn Thr Thr Asn Gln His Ile Met Leu Gln Asn Ser Ser Gly Ile Glu
945                 950                 955                 960

Lys Tyr Asn

<210> SEQ ID NO 35
<211> LENGTH: 801
<212> TYPE: DNA
<213> ORGANISM: Homo sapiens

<400> SEQUENCE: 35
atgaaagctg cggtgctgac cttggccgtg ctcttcctga cggggagcca ggctcggcat      60
ttctggcagc aagatgaacc cccccagagc ccctgggatc gagtgaagga cctggccact     120
gtgtacgtgg atgtgctcaa agacagcggc agagactatg tgtcccagtt tgaaggctcc     180
gccttgggaa aacagctaaa cctaaagctc cttgacaact gggacagcgt gacctccacc     240
ttcagcaagc tgcgcgaaca gctcggcccct gtgacccagg agttctggga taacctggaa     300
aaggagacag agggcctgag gcaggagatg agcaaggatc tggaggaggt gaaggccaag     360
gtgcagccct acctggacga cttccagaag agtggcagg aggagatgga gctctaccgc     420
cagaaggtgg agccgctgcg cgcagagctc aagagggcg cgcgccagaa gctgcacgag     480
ctgcaagaga agctgagccc actgggcgag gagatgcgcg accgcgcgcg cgcccatgtg     540
gacgcgctgc gcacgcatct ggcccctac agcgacgagc tgcgccagcg cttggccgcg     600
cgccttgagg ctctcaagga aacggcggc gccagactgg ccgagtacca cgccaaggcc     660
accgagcatc tgagcacgct cagcgagaag gccaagcccg cgctcgagga cctccgccaa     720
ggcctgctgc ccgtgctgga gagcttcaag gtcagcttcc tgagcgctct cgaggagtac     780
actaagaagc tcaacaccca a                                               801

<210> SEQ ID NO 36
<211> LENGTH: 267
<212> TYPE: PRT
<213> ORGANISM: Homo sapiens

<400> SEQUENCE: 36

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
    115                 120                 125

Gln Lys Lys Trp Gln Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 37
<211> LENGTH: 2647
<212> TYPE: DNA
<213> ORGANISM: Artificial
<220> FEATURE:
<223> OTHER INFORMATION: THER2PON1 DNA

<400> SEQUENCE: 37

```
gttaagcttg ccaccatgaa agctgcggtg ctgaccttgg ccgtgctctt cctgacgggg      60
agccaggctc ggcatttctg gcagcaagat gaaccccccc agagcccctg ggatcgagtg     120
aaggacctgg ccactgtgta cgtggatgtg ctcaaagaca gcggcagaga ctatgtgtcc     180
cagtttgaag gctccgcctt gggaaaaacag ctaaacctaa agctccttga caactgggac     240
agcgtgacct ccaccttcag caagctgcgc gaacagctcg ccctgtgac ccaggagttc     300
tgggataacc tggaaaagga gacagagggc ctgaggcagg agatgagcaa ggatctggag     360
gaggtgaagg ccaaggtgca gccctacctg gacgacttcc agaagaagtg gcaggaggag     420
atggagctct accgccagaa ggtggagccg ctgcgcgcag agctccaaga gggcgcgcgc     480
cagaagctgc acgagctgca agagaagctg agcccactgg gcgaggagat gcgcgaccgc     540
gcgcgcgccc atgtggacgc gctgcgcacg catctggccc cctacagcga cgagctgcgc     600
cagcgcttgg ccgcgcgcct tgaggctctc aaggagaacg gcggcgccag actggccgag     660
taccacgcca aggccaccga gcatctgagc acgctcagcg agaaggccaa gcccgcgctc     720
gaggacctcc gccaaggcct gctgcccgtg ctggagagct tcaaggtcag cttcctgagc     780
gctctcgagg agtacactaa gaagctcaac acccaagatc tctccggagg aggtggctca     840
ggaggaggtg ggagtaccgg tctcgagccc aaatcttctg acaaaactca cacatctcca     900
ccgtccccag cacctgaact cctggggagga tcgtcagtct tcctcttccc cccaaaaccc     960
aaggacaccc tcatgatctc ccggacccct gaggtcacat gcgtggtggt ggacgtgagc    1020
cacgaagacc ctgaggtcaa gttcaactgg tacgtggacg gcgtggaggt gcataatgcc    1080
aagacaaagc cgcgggagga gcagtacaac agcacgtacc gtgtggtcag cgtcctcacc    1140
```

```
gtcctgcacc aggactggct gaatggcaag gagtacaagt gcaaggtctc caacaaagcc    1200
ctcccagcct ccatcgagaa aaccatctcc aaagccaaag ggcagccccg agaaccacag    1260
gtgtacaccc tgcccccatc ccgggatgag ctgaccaaga accaggtcag cctgacctgc    1320
ctggtcaaag gcttctatcc cagcgacatc gccgtggagt gggagagcaa tgggcagccg    1380
gagaacaact acaagaccac gcctcccgtg ctggactccg acggctcctt cttcctctac    1440
agcaagctca ccgtggacaa gagcaggtgg cagcagggga acgtcttctc atgctccgtg    1500
atgcatgagg ctctgcacaa ccactacacg cagaagagcc tctctctctc tccgggtaaa    1560
gtcgacggag ctagcagccc cgtgaacgtg agcagcccca gcgtgcagga tatcctcttc    1620
aggaaccacc agtcttctta ccaaacacga cttaatgctc tccgagaggt acaacccgta    1680
gaacttccta actgtaattt agttaaagga atcgaaactg ctctgaaga cttggagata    1740 ctgcctaatg gactggcttt cattagctct ggattaaagt atcctggaat aaagagcttc    1800 aacccccaaca gtcctggaaa atacttctg atggacctga atgaagaaga tccaacagtg    1860
ttggaattgg ggatcactgg aagtaaattt gatgtatctt catttaaccc tcatgggatt    1920
agcacattca cagatgaaga taatgccatg tacctcctgg tggtgaacca tccagatgcc    1980
aagtccacag tggagttgtt taaatttcaa gaagaagaaa atcgcttttt gcatctaaaa    2040
accatcagac ataaacttct gcctaatttg aatgatattg ttgctgtggg acctgagcac    2100
ttttatggca caaatgatca ctattttctt gacccctact acaatcctg ggagatgtat    2160 ttgggtttag cgtggtcgta tgttgtctac tatagtccaa gtgaagttcg agtggtggca    2220
gaaggatttg attttgctaa tggaatcaac atttcacccg atggcaagta tgtctatata    2280
gctgagttgc tggctcataa gattcatgtg tatgaaaagc atgctaattg gactttaact    2340
ccattgaagt cccttgactt taataccctc gtggataaca tatctgtgga tcctgagaca    2400
ggagaccttt gggttggatg ccatcccaat ggcatgaaaa tcttcttcta tgactcagag    2460
aatcctcctg catcagaggt gcttcgaatc cagaacattc taacagaaga acctaaagtg    2520
acacaggttt atgcagaaaa tggcacagtg ttgcaaggca gtacagttgc ctctgtgtac    2580
aaagggaaac tgctgattgg cacagtgttt cacaaagctc tttactgtga gctctaataa    2640
tctagaa                                                              2647
```

<210> SEQ ID NO 38
<211> LENGTH: 873
<212> TYPE: PRT
<213> ORGANISM: Artificial
<220> FEATURE:
<223> OTHER INFORMATION: THER2PON1 polypeptide

<400> SEQUENCE: 38

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95
```

-continued

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
            115                 120                 125

Gln Lys Lys Trp Gln Glu Met Glu Leu Tyr Arg Gln Lys Val Glu
            130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
            195                 200                 205

Gly Gly Ala Arg Leu Ala Glu Tyr His Ala Lys Ala Thr Glu His Leu
            210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Ser Thr Gly Leu Glu Pro Lys Ser Ser
            275                 280                 285

Asp Lys Thr His Thr Ser Pro Ser Pro Ala Pro Glu Leu Leu Gly
            290                 295                 300

Gly Ser Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
            355                 360                 365

Arg Val Val Ser Val Leu Thr Val Leu His Gln Asp Trp Leu Asn Gly
            370                 375                 380

Lys Glu Tyr Lys Cys Lys Val Ser Asn Lys Ala Leu Pro Ala Ser Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Asp Glu Leu Thr Lys Asn Gln Val Ser
            420                 425                 430

Leu Thr Cys Leu Val Lys Gly Phe Tyr Pro Ser Asp Ile Ala Val Glu
            435                 440                 445

Trp Glu Ser Asn Gly Gln Pro Glu Asn Asn Tyr Lys Thr Thr Pro Pro
            450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

```
Pro Gly Lys Val Asp Gly Ala Ser Pro Val Asn Val Ser Ser Pro
            515                 520                 525

Ser Val Gln Asp Ile Leu Phe Arg Asn His Gln Ser Ser Tyr Gln Thr
530                 535                 540

Arg Leu Asn Ala Leu Arg Glu Val Gln Pro Val Glu Leu Pro Asn Cys
545                 550                 555                 560

Asn Leu Val Lys Gly Ile Glu Thr Gly Ser Glu Asp Leu Glu Ile Leu
                565                 570                 575

Pro Asn Gly Leu Ala Phe Ile Ser Ser Gly Leu Lys Tyr Pro Gly Ile
            580                 585                 590

Lys Ser Phe Asn Pro Asn Ser Pro Gly Lys Ile Leu Leu Met Asp Leu
        595                 600                 605

Asn Glu Glu Asp Pro Thr Val Leu Glu Leu Gly Ile Thr Gly Ser Lys
610                 615                 620

Phe Asp Val Ser Ser Phe Asn Pro His Gly Ile Ser Thr Phe Thr Asp
625                 630                 635                 640

Glu Asp Asn Ala Met Tyr Leu Leu Val Val Asn His Pro Asp Ala Lys
                645                 650                 655

Ser Thr Val Glu Leu Phe Lys Phe Gln Glu Glu Glu Lys Ser Leu Leu
            660                 665                 670

His Leu Lys Thr Ile Arg His Lys Leu Leu Pro Asn Leu Asn Asp Ile
        675                 680                 685

Val Ala Val Gly Pro Glu His Phe Tyr Gly Thr Asn Asp His Tyr Phe
690                 695                 700

Leu Asp Pro Tyr Leu Gln Ser Trp Glu Met Tyr Leu Gly Leu Ala Trp
705                 710                 715                 720

Ser Tyr Val Val Tyr Tyr Ser Pro Ser Glu Val Arg Val Val Ala Glu
                725                 730                 735

Gly Phe Asp Phe Ala Asn Gly Ile Asn Ile Ser Pro Asp Gly Lys Tyr
            740                 745                 750

Val Tyr Ile Ala Glu Leu Leu Ala His Lys Ile His Val Tyr Glu Lys
        755                 760                 765

His Ala Asn Trp Thr Leu Thr Pro Leu Lys Ser Leu Asp Phe Asn Thr
770                 775                 780

Leu Val Asp Asn Ile Ser Val Asp Pro Glu Thr Gly Asp Leu Trp Val
785                 790                 795                 800

Gly Cys His Pro Asn Gly Met Lys Ile Phe Phe Tyr Asp Ser Glu Asn
                805                 810                 815

Pro Pro Ala Ser Glu Val Leu Arg Ile Gln Asn Ile Leu Thr Glu Glu
            820                 825                 830

Pro Lys Val Thr Gln Val Tyr Ala Glu Asn Gly Thr Val Leu Gln Gly
        835                 840                 845

Ser Thr Val Ala Ser Val Tyr Lys Gly Lys Leu Leu Ile Gly Thr Val
850                 855                 860

Phe His Lys Ala Leu Tyr Cys Glu Leu
865                 870

<210> SEQ ID NO 39
<211> LENGTH: 3084
<212> TYPE: DNA
<213> ORGANISM: Artificial
<220> FEATURE:
<223> OTHER INFORMATION: THER4CETP DNA

<400> SEQUENCE: 39
```

| | |
|---|---|
| gttaagcttg ccaccatgaa agctgcggtg ctgaccttgg ccgtgctctt cctgacgggg | 60 |
| agccaggctc ggcatttctg gcagcaagat gaaccccccc agagcccctg ggatcgagtg | 120 |
| aaggacctgg ccactgtgta cgtggatgtg ctcaaagaca gcggcagaga ctatgtgtcc | 180 |
| cagtttgaag gctccgcctt gggaaaacag ctaaacctaa agctccttga caactgggac | 240 |
| agcgtgacct ccaccttcag caagctgcgc gaacagctcg gccctgtgac ccaggagttc | 300 |
| tgggataacc tggaaaagga gacagagggc ctgaggcagg atgagcaa ggatctggag | 360 |
| gaggtgaagg ccaaggtgca gccctacctg gacgacttcc agaagaagtg gcaggaggag | 420 |
| atggagctct accgccagaa ggtggagccg ctgcgcgcag agctccaaga gggcgcgcgc | 480 |
| cagaagctgc acgagctgca agagaagctg agcccactgg gcgaggagat gcgcgaccgc | 540 |
| gcgcgcgccc atgtggacgc gctgcgcacg catctggccc cctacagcga cgagctgcgc | 600 |
| cagcgcttgg ccgcgcgcct tgaggctctc aaggagaacg gcggcgccag actggccgag | 660 |
| taccacgcca aggccaccga gcatctgagc acgctcagcg agaaggccaa gcccgcgctc | 720 |
| gaggacctcc gccaaggcct gctgcccgtg ctggagagct tcaaggtcag cttcctgagc | 780 |
| gctctcgagg agtacactaa gaagctcaac acccaagatc tctccggagg aggtggctca | 840 |
| ggtggtggag gatctggagg aggtgggagt ggtggaggtg gttctaccgg tctcgagccc | 900 |
| aaatcttctg acaaaactca cacatctcca ccgtccccag cacctgaact cctgggagga | 960 |
| tcgtcagtct tcctcttccc cccaaaaccc aaggacaccc tcatgatctc ccggacccct | 1020 |
| gaggtcacat gcgtggtggt ggacgtgagc cacgaagacc ctgaggtcaa gttcaactgg | 1080 |
| tacgtggacg gcgtggaggt gcataatgcc aagacaaagc cgcgggagga gcagtacaac | 1140 |
| agcacgtacc gtgtggtcag cgtcctcacc gtcctgcacc aggactggct gaatggcaag | 1200 |
| gagtacaagt gcaaggtctc caacaaagcc ctcccagcct ccatcgagaa aaccatctcc | 1260 |
| aaagccaaag ggcagccccg agaaccacag gtgtacaccc tgcccccatc ccgggatgag | 1320 |
| ctgaccaaga accaggtcag cctgacctgc ctggtcaaag gcttctatcc cagcgacatc | 1380 |
| gccgtggagt gggagagcaa tgggcagccg gagaacaact acaagaccac gcctcccgtg | 1440 |
| ctggactccg acggctcctt cttcctctac agcaagctca ccgtggacaa gagcaggtgg | 1500 |
| cagcagggga acgtcttctc atgctccgtg atgcatgagg ctctgcacaa ccactacacg | 1560 |
| cagaagagcc tctctctctc tccgggtaaa gtcgacggag ctagcagccc cgtgaacgtg | 1620 |
| agcagcccca gcgtgcagga tatctgctcc aaaggcacct cgcacgaggc aggcatcgtg | 1680 |
| tgccgcatca ccaagcctgc cctcctggtg ttgaaccacg agactgccaa ggtgatccag | 1740 |
| accgccttcc agcgagccag ctacccagat atcacgggcg agaaggccat gatgctcctt | 1800 |
| ggccaagtca gtatgggttt gcacaacatc cagatcagcc acttgtccat cgccagcagc | 1860 |
| caggtggagc tggtggaagc caagtccatt gatgtctcca ttcagaacgt gtctgtggtc | 1920 |
| ttcaagggga ccctgaagta tggctacacc actgcctggt ggctgggtat tgatcagtcc | 1980 |
| attgacttcg agatcgactc tgccattgac ctccagatca cacacagct gacctgtgac | 2040 |
| tctggtagag tgcggaccga tgcccctgac tgctacctgt cttt ccataa gctgctcctg | 2100 |
| catctccaag gggagcgaga gcctgggtgg atcaagcagc tgttcacaaa tttcatctcc | 2160 |
| ttcaccctga gctggtcct gaagggacag atctgcaaag atcaacgt catctctaac | 2220 |
| atcatgccg attttgtcca gacaagggct gccagcatcc tttcagatgg agacattggg | 2280 |
| gtggacattt ccctgacagg tgatcccgtc atcacagcct cctacctgga gtcccatcac | 2340 |
| aagggtcatt tcatctacaa gaatgtctca gaggacctcc ccctccccac cttctcgccc | 2400 |

```
acactgctgg gggactcccg catgctgtac ttctggttct ctgagcgagt cttccactcg   2460
ctggccaagg tagcttttcca ggatggccgc ctcatgctca gcctgatggg agacgagttc   2520
aaggcagtgc tggagacctg gggcttcaac accaaccagg aaatcttcca agaggttgtc   2580
ggcggcttcc ccagccaggc ccaagtcacc gtccactgcc tcaagatgcc caagatctcc   2640
tgccaaaaca agggagtcgt ggtcaattct tcagtgatgg tgaaattcct ctttccacgc   2700
ccagaccagc aacattctgt agcttacaca tttgaagagg atatcgtgac taccgtccag   2760
gcctcctatt ctaagaaaaa gctcttctta agcctcttgg atttccagat tacaccaaag   2820 actgttttcca acttgactga gagcagctcc gagtccgtcc agagcttcct gcagtcaatg   2880
atcaccgctg tgggcatccc tgaggtcatg tctcggctcg aggtagtgtt tacagccctc   2940
atgaacagca aaggcgtgag cctcttcgac atcatcaacc ctgagattat cactcgagat   3000
ggcttcctgc tgctgcagat ggactttggc ttccctgagc acctgctggt ggatttcctc   3060
cagagcttga gctaataatc taga                                          3084
```

<210> SEQ ID NO 40
<211> LENGTH: 1019
<212> TYPE: PRT
<213> ORGANISM: Artificial
<220> FEATURE:
<223> OTHER INFORMATION: THER4CETP polypeptide

<400> SEQUENCE: 40

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240
```

-continued

Gly Leu Leu Pro Val Leu Glu Ser Phe Lys Val Ser Phe Leu Ser Ala
            245                 250                 255

Leu Glu Glu Tyr Thr Lys Lys Leu Asn Thr Gln Asp Leu Ser Gly Gly
            260                 265                 270

Gly Gly Ser Gly Gly Gly Gly Ser Gly Gly Gly Ser Gly Gly Gly
            275                 280                 285

Gly Ser Thr Gly Leu Glu Pro Lys Ser Ser Asp Lys Thr His Thr Ser
290                     295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
            325                 330                 335

Val Thr Cys Val Val Val Asp Val Ser His Glu Asp Pro Glu Val Lys
            340                 345                 350

Phe Asn Trp Tyr Val Asp Gly Val Glu Val His Asn Ala Lys Thr Lys
            355                 360                 365

Pro Arg Glu Glu Gln Tyr Asn Ser Thr Tyr Arg Val Val Ser Val Leu
            370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Ser Ile Glu Lys Thr Ile Ser Lys
            405                 410                 415

Ala Lys Gly Gln Pro Arg Glu Pro Gln Val Tyr Thr Leu Pro Pro Ser
            420                 425                 430

Arg Asp Glu Leu Thr Lys Asn Gln Val Ser Leu Thr Cys Leu Val Lys
            435                 440                 445

Gly Phe Tyr Pro Ser Asp Ile Ala Val Glu Trp Glu Ser Asn Gly Gln
450                 455                 460

Pro Glu Asn Asn Tyr Lys Thr Thr Pro Pro Val Leu Asp Ser Asp Gly
465                 470                 475                 480

Ser Phe Phe Leu Tyr Ser Lys Leu Thr Val Asp Lys Ser Arg Trp Gln
            485                 490                 495

Gln Gly Asn Val Phe Ser Cys Ser Val Met His Glu Ala Leu His Asn
            500                 505                 510

His Tyr Thr Gln Lys Ser Leu Ser Leu Ser Pro Gly Lys Val Asp Gly
            515                 520                 525

Ala Ser Ser Pro Val Asn Val Ser Ser Pro Ser Val Gln Asp Ile Cys
530                 535                 540

Ser Lys Gly Thr Ser His Glu Ala Gly Ile Val Cys Arg Ile Thr Lys
545                 550                 555                 560

Pro Ala Leu Leu Val Leu Asn His Glu Thr Ala Lys Val Ile Gln Thr
            565                 570                 575

Ala Phe Gln Arg Ala Ser Tyr Pro Asp Ile Thr Gly Glu Lys Ala Met
            580                 585                 590

Met Leu Leu Gly Gln Val Lys Tyr Gly Leu His Asn Ile Gln Ile Ser
            595                 600                 605

His Leu Ser Ile Ala Ser Ser Gln Val Glu Leu Val Glu Ala Lys Ser
            610                 615                 620

Ile Asp Val Ser Ile Gln Asn Val Ser Val Val Phe Lys Gly Thr Leu
625                 630                 635                 640

Lys Tyr Gly Tyr Thr Thr Ala Trp Trp Leu Gly Ile Asp Gln Ser Ile
            645                 650                 655

-continued

Asp Phe Glu Ile Asp Ser Ala Ile Asp Leu Gln Ile Asn Thr Gln Leu
            660                 665                 670

Thr Cys Asp Ser Gly Arg Val Arg Thr Asp Ala Pro Asp Cys Tyr Leu
        675                 680                 685

Ser Phe His Lys Leu Leu Leu His Leu Gln Gly Glu Arg Glu Pro Gly
    690                 695                 700

Trp Ile Lys Gln Leu Phe Thr Asn Phe Ile Ser Phe Thr Leu Lys Leu
705                 710                 715                 720

Val Leu Lys Gly Gln Ile Cys Lys Glu Ile Asn Val Ile Ser Asn Ile
                725                 730                 735

Met Ala Asp Phe Val Gln Thr Arg Ala Ala Ser Ile Leu Ser Asp Gly
            740                 745                 750

Asp Ile Gly Val Asp Ile Ser Leu Thr Gly Asp Pro Val Ile Thr Ala
        755                 760                 765

Ser Tyr Leu Glu Ser His His Lys Gly His Phe Ile Tyr Lys Asn Val
    770                 775                 780

Ser Glu Asp Leu Pro Leu Pro Thr Phe Ser Pro Thr Leu Leu Gly Asp
785                 790                 795                 800

Ser Arg Met Leu Tyr Phe Trp Phe Ser Glu Arg Val Phe His Ser Leu
                805                 810                 815

Ala Lys Val Ala Phe Gln Asp Gly Arg Leu Met Leu Ser Leu Met Gly
            820                 825                 830

Asp Glu Phe Lys Ala Val Leu Glu Thr Trp Gly Phe Asn Thr Asn Gln
        835                 840                 845

Glu Ile Phe Gln Glu Val Gly Gly Phe Pro Ser Gln Ala Gln Val
    850                 855                 860

Thr Val His Cys Leu Lys Met Pro Lys Ile Ser Cys Gln Asn Lys Gly
865                 870                 875                 880

Val Val Val Asn Ser Ser Val Met Val Lys Phe Leu Phe Pro Arg Pro
                885                 890                 895

Asp Gln Gln His Ser Val Ala Tyr Thr Phe Glu Glu Asp Ile Val Thr
            900                 905                 910

Thr Val Gln Ala Ser Tyr Ser Lys Lys Lys Leu Phe Leu Ser Leu Leu
        915                 920                 925

Asp Phe Gln Ile Thr Pro Lys Thr Val Ser Asn Leu Thr Glu Ser Ser
    930                 935                 940

Ser Glu Ser Val Gln Ser Phe Leu Gln Ser Met Ile Thr Ala Val Gly
945                 950                 955                 960

Ile Pro Glu Val Met Ser Arg Leu Glu Val Val Phe Thr Ala Leu Met
                965                 970                 975

Asn Ser Lys Gly Val Ser Leu Phe Asp Ile Ile Asn Pro Glu Ile Ile
            980                 985                 990

Thr Arg Asp Gly Phe Leu Leu Leu Gln Met Asp Phe Gly Phe Pro Glu
        995                 1000                1005

His Leu Leu Val Asp Phe Leu Gln Ser Leu Ser
    1010                1015

<210> SEQ ID NO 41
<211> LENGTH: 1068
<212> TYPE: DNA
<213> ORGANISM: Artificial
<220> FEATURE:
<223> OTHER INFORMATION: human PON1 Q192K DNA

<400> SEQUENCE: 41

```
atggcgaagc tgattgcgct caccctcttg gggatgggac tggcactctt caggaaccac      60
cagtcttctt accaaacacg acttaatgct ctccgagagg tacaacccgt agaacttcct     120
aactgtaatt tagttaaagg aatcgaaact ggctctgaag acttggagat actgcctaat     180
ggactggctt tcattagctc tggattaaag tatcctggaa taaagagctt caaccccaac     240
agtcctggaa aaatacttct gatggacctg aatgaagaag atccaacagt gttggaattg     300
gggatcactg gaagtaaatt tgatgtatct tcatttaacc ctcatgggat tagcacattc     360
acagatgaag ataatgccat gtacctcctg gtggtgaacc atccagatgc aagtccaca      420
gtggagttgt ttaaatttca agaagaagaa aaatcgcttt tgcatctaaa aaccatcaga     480
cataaacttc tgcctaattt gaatgatatt gttgctgtgg gacctgagca cttttatggc     540
acaaatgatc actattttct tgaccccta  ttaaaatcct gggagatgta tttgggttta     600
gcgtggtcgt atgttgtcta ctatagtcca agtgaagttc gagtggtggc agaaggattt     660
gattttgcta atggaatcaa catttcaccc gatggcaagt atgtctatat agctgagttg     720
ctggctcata agattcatgt gtatgaaaag catgctaatt ggactttaac tccattgaag     780
tcccttgact ttaataccct cgtggataac atatctgtgg atcctgagac aggagacctt     840
tgggttggat gccatcccaa tggcatgaaa atcttcttct atgactcaga gaatcctcct     900
gcatcagagg tgcttcgaat ccagaacatt ctaacagaag aacctaaagt gacacaggtt     960
tatgcagaaa atggcacagt gttgcaaggc agtacagttg cctctgtgta caagggaaa    1020
ctgctgattg gcacagtgtt tcacaaagct ctttactgtg agctctaa                 1068
```

<210> SEQ ID NO 42
<211> LENGTH: 355
<212> TYPE: PRT
<213> ORGANISM: Artificial
<220> FEATURE:
<223> OTHER INFORMATION: human PON1 Q192K polypeptide

<400> SEQUENCE: 42

```
Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175
```

```
His Phe Tyr Gly Thr Asn Asp His Tyr Phe Leu Asp Pro Tyr Leu Lys
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
        290                 295                 300

Leu Arg Ile Gln Asn Ile Leu Thr Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 43
<211> LENGTH: 1065
<212> TYPE: DNA
<213> ORGANISM: Homo sapiens

<400> SEQUENCE: 43
atggcgaagc tgattgcgct caccctcttg gggatgggac tggcactctt caggaaccac      60
cagtcttctt accaaacacg acttaatgct ctccgagagg tacaacccgt agaacttcct     120
aactgtaatt tagttaaagg aatcgaaact ggctctgaag acttggagat actgcctaat     180
ggactggctt tcattagctc tggattaaag tatcctggaa taagagcttc aaccccaac     240 agtcctggaa aaatacttct gatggacctg aatgaagaag atccaacagt gttggaattg     300
gggatcactg gaagtaaatt tgatgtatct tcatttaacc ctcatgggat tagcacattc     360
acagatgaag ataatgccat gtacctcctg gtggtgaacc atccagatgc caagtccaca     420
gtggagttgt ttaaatttca agaagaagaa aaatcgcttt tgcatctaaa aaccatcaga     480
cataaacttc tgcctaattt gaatgatatt gttgctgtgg acctgagcac tttttatggc     540
acaaatgatc actattttct tgacccctac ttaagatcct gggagatgta tttgggttta     600
gcgtggtcgt atgttgtcta ctatagtcca agtgaagttc gagtggtggc agaaggattt     660
gattttgcta atggaatcaa catttcaccc gatggcaagt atgtctatat agctgagttg     720
ctggctcata gattcatgt gtatgaaaag catgctaatt ggactttaac tccattgaag     780
tcccttgact taatacccct cgtggataac atatctgtgg atcctgagac aggagacctt     840
tgggttggat gccatcccaa tggcatgaaa atcttcttct atgactcaga gaatcctcct     900
gcatcagagg tgcttcgaat ccagaacatt ctaacagaag aacctaaagt gacacaggtt     960
tatgcagaaa atggcacagt gttgcaaggc agtacagttg cctctgtgta caagggaaa    1020 ctgctgattg gcacagtgtt tcacaaagct ctttactgtg agctc                     1065
```

<210> SEQ ID NO 44
<211> LENGTH: 355
<212> TYPE: PRT
<213> ORGANISM: Homo sapiens

<400> SEQUENCE: 44

```
Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Arg
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355
```

-continued

<210> SEQ ID NO 45
<211> LENGTH: 2677
<212> TYPE: DNA
<213> ORGANISM: Artificial
<220> FEATURE:
<223> OTHER INFORMATION: THER4PON1 Q192K DNA

<400> SEQUENCE: 45

| | |
|---|---:|
| gttaagcttg ccaccatgaa agctgcggtg ctgaccttgg ccgtgctctt cctgacgggg | 60 |
| agccaggctc ggcatttctg gcagcaagat gaaccccccc agagcccctg ggatcgagtg | 120 |
| aaggacctgg ccactgtgta cgtggatgtg ctcaaagaca gcggcagaga ctatgtgtcc | 180 |
| cagtttgaag gctccgcctt gggaaaacag ctaaacctaa agctccttga caactgggac | 240 |
| agcgtgacct ccaccttcag caagctgcgc aacagctcg ccctgtgac ccaggagttc | 300 |
| tgggataacc tggaaaagga gacagagggc ctgaggcagg agatgagcaa ggatctggag | 360 |
| gaggtgaagg ccaaggtgca gccctacctg gacgacttcc agaagaagtg gcaggaggag | 420 |
| atggagctct accgccagaa ggtggagccg ctgcgcgcag agctccaaga gggcgcgcgc | 480 |
| cagaagctgc acgagctgca agagaagctg agcccactgg gcgaggagat gcgcgaccgc | 540 |
| gcgcgcgccc atgtggacgc gctgcgcacg catctggccc cctacagcga cgagctgcgc | 600 |
| cagcgcttgg ccgcgcgcct tgaggctctc aaggagaacg gcggcgccag actggccgag | 660 |
| taccacgcca aggccaccga gcatctgagc acgctcagcg agaaggccaa gcccgcgctc | 720 |
| gaggacctcc gccaaggcct gctgcccgtg ctggagagct tcaaggtcag cttcctgagc | 780 |
| gctctcgagg agtacactaa gaagctcaac acccaagatc tctccggagg aggtggctca | 840 |
| ggtggtggag gatctggagg aggtgggagt ggtggaggtg gttctaccgg tctcgagccc | 900 |
| aaatcttctg acaaaactca cacatctcca ccgtccccag cacctgaact cctgggagga | 960 |
| tcgtcagtct tcctcttccc cccaaaaccc aaggacaccc tcatgatctc ccggacccct | 1020 |
| gaggtcacat gcgtggtggt ggacgtgagc cacgaagacc ctgaggtcaa gttcaactgg | 1080 |
| tacgtggacg gcgtggaggt gcataatgcc aagacaaagc cgcgggagga gcagtacaac | 1140 |
| agcacgtacc gtgtggtcag cgtcctcacc gtcctgcacc aggactggct gaatggcaag | 1200 |
| gagtacaagt gcaaggtctc caacaaagcc ctcccagcct ccatcgagaa aaccatctcc | 1260 |
| aaagccaaag gcagccccg agaaccacag gtgtacaccc tgcccccatc ccgggatgag | 1320 |
| ctgaccaaga accaggtcag cctgacctgc ctggtcaaag gcttctatcc cagcgacatc | 1380 |
| gccgtggagt gggagagcaa tgggcagccg gagaacaact acaagaccac gcctcccgtg | 1440 |
| ctggactccg acggctcctt cttcctctac agcaagctca ccgtggacaa gagcaggtgg | 1500 |
| cagcagggga acgtcttctc atgctccgtg atgcatgagg ctctgcacaa ccactacacg | 1560 |
| cagaagagcc tctctctctc tccgggtaaa gtcgacggag ctagcagccc cgtgaacgtg | 1620 |
| agcagcccca gcgtgcagga tatcctcttc aggaaccacc agtcttctta ccaaacacga | 1680 |
| cttaatgctc tccgagaggt acaacccgta gaacttccta actgtaattt agttaaagga | 1740 |
| atcgaaactg ctctgaaga cttggagata ctgcctaatg gactggcttt cattagctct | 1800 |
| ggattaaagt atcctggaat aaagagcttc aaccccaaca gtcctggaaa aatacttctg | 1860 |
| atggacctga tgaagaaga tccaacagtg ttggaattgg ggatcactgg aagtaaatttc | 1920 |
| gatgtatctt catttaaccc tcatgggatt agcacattca cagatgaaga taatgccatg | 1980 |
| tacctcctgg tggtgaacca tccagatgcc aagtccacag tggagttgtt taaatttcaa | 2040 |
| gaagaagaaa atcgcttttt gcatctaaaa accatcagac ataaacttct gcctaatttg | 2100 |

-continued

```
aatgatattg ttgctgtggg acctgagcac ttttatggca caaatgatca ctattttctt      2160 gaccectact taaaatcctg ggagatgtat ttgggtttag cgtggtcgta tgttgtctac      2220
tatagtccaa gtgaagttcg agtggtggca aaggatttg attttgctaa tggaatcaac       2280
atttcacccg atggcaagta tgtctatata gctgagttgc tggctcataa gattcatgtg      2340
tatgaaaagc atgctaattg gactttaact ccattgaagt ccettgactt taatacccte      2400 gtggataaca tatctgtgga tcctgagaca ggagaccttt gggttggatg ccatcccaat      2460
ggcatgaaaa tcttcttcta tgactcagag aatcctcctg catcagaggt gcttcgaatc      2520
cagaacattc taacagaaga acctaaagtg acacaggttt atgcagaaaa tggcacagtg      2580
ttgcaaggca gtacagttgc ctctgtgtac aaagggaaac tgctgattgg cacagtgttt      2640
cacaaagctc tttactgtga gctctaataa tctagaa                              2677
```

<210> SEQ ID NO 46
<211> LENGTH: 883
<212> TYPE: PRT
<213> ORGANISM: Artificial
<220> FEATURE:
<223> OTHER INFORMATION: THER4PON1 Q192K polypeptide

<400> SEQUENCE: 46

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
        130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
            195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
```

```
                260                 265                 270
Gly Gly Ser Gly Gly Gly Ser Gly Gly Gly Ser Gly Gly
            275                 280                 285
Gly Ser Thr Gly Leu Glu Pro Lys Ser Ser Asp Lys Thr His Thr Ser
            290                 295                 300
Pro Pro Ser Pro Ala Pro Glu Leu Leu Gly Gly Ser Ser Val Phe Leu
305                 310                 315                 320
Phe Pro Pro Lys Pro Lys Asp Thr Leu Met Ile Ser Arg Thr Pro Glu
                325                 330                 335
Val Thr Cys Val Val Val Asp Val Ser His Glu Asp Pro Glu Val Lys
            340                 345                 350
Phe Asn Trp Tyr Val Asp Gly Val Glu Val His Asn Ala Lys Thr Lys
                355                 360                 365
Pro Arg Glu Glu Gln Tyr Asn Ser Thr Tyr Arg Val Val Ser Val Leu
            370                 375                 380
Thr Val Leu His Gln Asp Trp Leu Asn Gly Lys Glu Tyr Lys Cys Lys
385                 390                 395                 400
Val Ser Asn Lys Ala Leu Pro Ala Ser Ile Glu Lys Thr Ile Ser Lys
                405                 410                 415
Ala Lys Gly Gln Pro Arg Glu Pro Gln Val Tyr Thr Leu Pro Pro Ser
            420                 425                 430
Arg Asp Glu Leu Thr Lys Asn Gln Val Ser Leu Thr Cys Leu Val Lys
                435                 440                 445
Gly Phe Tyr Pro Ser Asp Ile Ala Val Glu Trp Glu Ser Asn Gly Gln
            450                 455                 460
Pro Glu Asn Asn Tyr Lys Thr Thr Pro Pro Val Leu Asp Ser Asp Gly
465                 470                 475                 480
Ser Phe Phe Leu Tyr Ser Lys Leu Thr Val Asp Lys Ser Arg Trp Gln
                485                 490                 495
Gln Gly Asn Val Phe Ser Cys Ser Val Met His Glu Ala Leu His Asn
            500                 505                 510
His Tyr Thr Gln Lys Ser Leu Ser Leu Ser Pro Gly Lys Val Asp Gly
                515                 520                 525
Ala Ser Ser Pro Val Asn Val Ser Ser Pro Ser Val Gln Asp Ile Leu
            530                 535                 540
Phe Arg Asn His Gln Ser Ser Tyr Gln Thr Arg Leu Asn Ala Leu Arg
545                 550                 555                 560
Glu Val Gln Pro Val Glu Leu Pro Asn Cys Asn Leu Val Lys Gly Ile
                565                 570                 575
Glu Thr Gly Ser Glu Asp Leu Glu Ile Leu Pro Asn Gly Leu Ala Phe
            580                 585                 590
Ile Ser Ser Gly Leu Lys Tyr Pro Gly Ile Lys Ser Phe Asn Pro Asn
                595                 600                 605
Ser Pro Gly Lys Ile Leu Leu Met Asp Leu Asn Glu Glu Asp Pro Thr
            610                 615                 620
Val Leu Glu Leu Gly Ile Thr Gly Ser Lys Phe Asp Val Ser Ser Phe
625                 630                 635                 640
Asn Pro His Gly Ile Ser Thr Phe Thr Asp Glu Asp Asn Ala Met Tyr
                645                 650                 655
Leu Leu Val Val Asn His Pro Asp Ala Lys Ser Thr Val Glu Leu Phe
            660                 665                 670
Lys Phe Gln Glu Glu Glu Lys Ser Leu Leu His Leu Lys Thr Ile Arg
                675                 680                 685
```

His Lys Leu Leu Pro Asn Leu Asn Asp Ile Val Ala Val Gly Pro Glu
690                 695                 700

His Phe Tyr Gly Thr Asn Asp His Tyr Phe Leu Asp Pro Tyr Leu Lys
705                 710                 715                 720

Ser Trp Glu Met Tyr Leu Gly Leu Ala Trp Ser Tyr Val Val Tyr Tyr
                725                 730                 735

Ser Pro Ser Glu Val Arg Val Val Ala Glu Gly Phe Asp Phe Ala Asn
            740                 745                 750

Gly Ile Asn Ile Ser Pro Asp Gly Lys Tyr Val Tyr Ile Ala Glu Leu
        755                 760                 765

Leu Ala His Lys Ile His Val Tyr Glu Lys His Ala Asn Trp Thr Leu
770                 775                 780

Thr Pro Leu Lys Ser Leu Asp Phe Asn Thr Leu Val Asp Asn Ile Ser
785                 790                 795                 800

Val Asp Pro Glu Thr Gly Asp Leu Trp Val Gly Cys His Pro Asn Gly
                805                 810                 815

Met Lys Ile Phe Phe Tyr Asp Ser Glu Asn Pro Pro Ala Ser Glu Val
            820                 825                 830

Leu Arg Ile Gln Asn Ile Leu Thr Glu Glu Pro Lys Val Thr Gln Val
        835                 840                 845

Tyr Ala Glu Asn Gly Thr Val Leu Gln Gly Ser Thr Val Ala Ser Val
850                 855                 860

Tyr Lys Gly Lys Leu Leu Ile Gly Thr Val Phe His Lys Ala Leu Tyr
865                 870                 875                 880

Cys Glu Leu

<210> SEQ ID NO 47
<211> LENGTH: 2677
<212> TYPE: DNA
<213> ORGANISM: Artificial
<220> FEATURE:
<223> OTHER INFORMATION: THER4PON1 Q192R DNA

<400> SEQUENCE: 47
gttaagcttg ccaccatgaa agctgcggtg ctgaccttgg ccgtgctctt cctgacgggg      60
agccaggctc ggcatttctg gcagcaagat gaaccccccc agagcccctg ggatcgagtg     120
aaggacctgg ccactgtgta cgtggatgtg ctcaaagaca gcggcagaga ctatgtgtcc     180
cagtttgaag ctccgccttg gaaaaacag ctaaacctaa agctccttga caactgggac      240
agcgtgacct ccaccttcag caagctgcgc gaacagctcg ccctgtgac ccaggagttc      300 tgggataacc tggaaaagga cacagagggc ctgaggcagg agatgagcaa ggatctggag     360
gaggtgaagg ccaaggtgca gccctacctg gacgacttcc agaagaagtg gcaggaggag     420
atggagctct accgccagaa ggtggagccg ctgcgcgcag agctccaaga gggcgcgcgc     480
cagaagctgc acgagctgca agagaagctg agcccactgg gcgaggagat gcgcgaccgc     540
gcgcgcgccc atgtggacgc gctgcgcacg catctggccc cctacagcga cgagctgcgc     600
cagcgcttgg ccgcgcgcct tgaggctctc aaggagaacg gcggcgccag actggccgag     660
taccacgcca aggccaccga gcatctgagc acgctcagcg agaaggccaa gcccgcgctc     720
gaggacctcc gccaaggcct gctgcccgtg ctggagagct tcaaggtcag cttcctgagc     780
gctctcgagg agtacactaa gaagctcaac acccaagatc tctccggagg aggtggctca     840
ggtggtggag gatctggagg aggtgggagt ggtggaggtg gttctaccgg tctcgagccc     900

```
aaatcttctg acaaaactca cacatctcca ccgtccccag cacctgaact cctgggagga    960
tcgtcagtct tcctcttccc cccaaaaccc aaggacaccc tcatgatctc ccggaccccct   1020
gaggtcacat gcgtggtggt ggacgtgagc cacgaagacc ctgaggtcaa gttcaactgg   1080
tacgtggacg gcgtggaggt gcataatgcc aagacaaagc cgcgggagga gcagtacaac   1140
agcacgtacc gtgtggtcag cgtcctcacc gtcctgcacc aggactggct gaatggcaag   1200
gagtacaagt gcaaggtctc caacaaagcc ctcccagcct ccatcgagaa aaccatctcc   1260
aaagccaaag ggcagccccg agaaccacag gtgtacaccc tgcccccatc ccgggatgag   1320
ctgaccaaga accaggtcag cctgacctgc ctggtcaaag gcttctatcc cagcgacatc   1380
gccgtggagt gggagagcaa tgggcagccg gagaacaact acaagaccac gcctcccgtg   1440
ctggactccg acggctcctt cttcctctac agcaagctca ccgtggacaa gagcaggtgg   1500
cagcagggga acgtcttctc atgctccgtg atgcatgagg ctctgcacaa ccactacacg   1560
cagaagagcc tctctctctc tccgggtaaa gtcgacggag ctagcagccc cgtgaacgtg   1620
agcagccccca gcgtgcagga tatcctcttc aggaaccacc agtcttctta ccaaacacga   1680
cttaatgctc tccgagaggt acaacccgta gaacttccta actgtaattt agttaaagga   1740
atcgaaactg ctctgaaga cttggagata ctgcctaatg gactggcttt cattagctct   1800
ggattaaagt atcctggaat aaagagcttc aaccccaaca gtcctggaaa aatacttctg   1860
atggacctga tgaagaaga tccaacagtg ttggaattgg ggatcactgg aagtaaattt   1920
gatgtatctt catttaaccc tcatgggatt agcacattca cagatgaaga taatgccatg   1980
tacctcctgg tggtgaacca tccagatgcc aagtccacag tggagttgtt taaatttcaa   2040
gaagaagaaa aatcgctttt gcatctaaaa accatcagac ataaaacttct gcctaatttg   2100
aatgatattg ttgctgtggg acctgagcac tttatggca caaatgatca ctatttcctt   2160
gaccctact aagatcctg ggagatgtat ttgggtttag cgtggtcgta tgttgtctac    2220
tatagtccaa gtgaagttcg agtggtggca gaaggatttg attttgctaa tggaatcaac   2280
atttcacccg atggcaagta tgtctatata gctgagttgc tggctcataa gattcatgtg   2340
tatgaaaagc atgctaattg gactttaact ccattgaagt cccttgactt taataccctc   2400
gtggataaca tatctgtgga tcctgagaca ggagaccttt gggttggatg ccatccccaat   2460
ggcatgaaaa tcttcttcta tgactcagag aatcctcctg catcagaggt gcttcgaatc   2520
cagaacattc taacagaaga acctaaagtg acacaggttt atgcagaaaa tggcacagtg   2580
ttgcaaggca gtacagttgc ctctgtgtac aaagggaaac tgctgattgg cacagtgttt   2640
cacaaagctc tttactgtga gctctaataa tctagaa                          2677
```

<210> SEQ ID NO 48
<211> LENGTH: 883
<212> TYPE: PRT
<213> ORGANISM: Artificial
<220> FEATURE:
<223> OTHER INFORMATION: THER4PON1 Q192R polypeptide

<400> SEQUENCE: 48

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45
```

-continued

```
Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Ser Gly Gly Gly Ser Gly Gly Gly
        275                 280                 285

Gly Ser Thr Gly Leu Glu Pro Lys Ser Ser Asp Lys Thr His Thr Ser
    290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
    370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Ser Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Asp Glu Leu Thr Lys Asn Gln Val Ser Leu Thr Cys Leu Val Lys
        435                 440                 445

Gly Phe Tyr Pro Ser Asp Ile Ala Val Glu Trp Glu Ser Asn Gly Gln
    450                 455                 460

Pro Glu Asn Asn Tyr Lys Thr Thr Pro Pro Val Leu Asp Ser Asp Gly
```

```
            465                 470                 475                 480
        Ser Phe Phe Leu Tyr Ser Lys Leu Thr Val Asp Lys Ser Arg Trp Gln
                        485                 490                 495
        Gln Gly Asn Val Phe Ser Cys Ser Val Met His Glu Ala Leu His Asn
                        500                 505                 510
        His Tyr Thr Gln Lys Ser Leu Ser Leu Ser Pro Gly Lys Val Asp Gly
                        515                 520                 525
        Ala Ser Ser Pro Val Asn Val Ser Ser Pro Ser Val Gln Asp Ile Leu
                        530                 535                 540
        Phe Arg Asn His Gln Ser Ser Tyr Gln Thr Arg Leu Asn Ala Leu Arg
        545                 550                 555                 560
        Glu Val Gln Pro Val Glu Leu Pro Asn Cys Asn Leu Val Lys Gly Ile
                            565                 570                 575
        Glu Thr Gly Ser Glu Asp Leu Glu Ile Leu Pro Asn Gly Leu Ala Phe
                        580                 585                 590
        Ile Ser Ser Gly Leu Lys Tyr Pro Gly Ile Lys Ser Phe Asn Pro Asn
                        595                 600                 605
        Ser Pro Gly Lys Ile Leu Leu Met Asp Leu Asn Glu Glu Asp Pro Thr
                        610                 615                 620
        Val Leu Glu Leu Gly Ile Thr Gly Ser Lys Phe Asp Val Ser Ser Phe
        625                 630                 635                 640
        Asn Pro His Gly Ile Ser Thr Phe Thr Asp Glu Asp Asn Ala Met Tyr
                            645                 650                 655
        Leu Leu Val Val Asn His Pro Asp Ala Lys Ser Thr Val Glu Leu Phe
                        660                 665                 670
        Lys Phe Gln Glu Glu Lys Ser Leu Leu His Leu Lys Thr Ile Arg
                        675                 680                 685
        His Lys Leu Leu Pro Asn Leu Asn Asp Ile Val Ala Val Gly Pro Glu
                        690                 695                 700
        His Phe Tyr Gly Thr Asn Asp His Tyr Phe Leu Asp Pro Tyr Leu Arg
        705                 710                 715                 720
        Ser Trp Glu Met Tyr Leu Gly Leu Ala Trp Ser Tyr Val Val Tyr Tyr
                            725                 730                 735
        Ser Pro Ser Glu Val Arg Val Val Ala Glu Gly Phe Asp Phe Ala Asn
                        740                 745                 750
        Gly Ile Asn Ile Ser Pro Asp Gly Lys Tyr Val Tyr Ile Ala Glu Leu
                        755                 760                 765
        Leu Ala His Lys Ile His Val Tyr Glu Lys His Ala Asn Trp Thr Leu
                        770                 775                 780
        Thr Pro Leu Lys Ser Leu Asp Phe Asn Thr Leu Val Asp Asn Ile Ser
        785                 790                 795                 800
        Val Asp Pro Glu Thr Gly Asp Leu Trp Val Gly Cys His Pro Asn Gly
                            805                 810                 815
        Met Lys Ile Phe Phe Tyr Asp Ser Glu Asn Pro Pro Ala Ser Glu Val
                        820                 825                 830
        Leu Arg Ile Gln Asn Ile Leu Thr Glu Glu Pro Lys Val Thr Gln Val
                        835                 840                 845
        Tyr Ala Glu Asn Gly Thr Val Leu Gln Gly Ser Thr Val Ala Ser Val
                        850                 855                 860
        Tyr Lys Gly Lys Leu Leu Ile Gly Thr Val Phe His Lys Ala Leu Tyr
        865                 870                 875                 880
        Cys Glu Leu
```

<210> SEQ ID NO 49
<211> LENGTH: 82
<212> TYPE: DNA
<213> ORGANISM: Artificial
<220> FEATURE:
<223> OTHER INFORMATION: (gly4ser)4 linker DNA

<400> SEQUENCE: 49
agatctctcc ggaggaggtg gctcaggtgg tggaggatct ggaggaggtg ggagtggtgg    60
aggtggttct accggtctcg ag    82

<210> SEQ ID NO 50
<211> LENGTH: 26
<212> TYPE: PRT
<213> ORGANISM: Artificial
<220> FEATURE:
<223> OTHER INFORMATION: (gly4ser)4 linker

<400> SEQUENCE: 50

Asp Leu Ser Gly Gly Gly Gly Ser Gly Gly Gly Ser Gly Gly Gly
1               5                   10                  15

Gly Ser Gly Gly Gly Gly Ser Thr Gly Leu
            20                  25

<210> SEQ ID NO 51
<211> LENGTH: 112
<212> TYPE: DNA
<213> ORGANISM: Artificial
<220> FEATURE:
<223> OTHER INFORMATION: (gly4ser)6 linker DNA

<400> SEQUENCE: 51
agatctctcc ggaggaggtg gctcaggtgg tggaggatct ggaggaggtg ggagtggtgg    60
aggtggttct ggaggaggtg gtagtggagg tggaggttct accggtctcg ag    112

<210> SEQ ID NO 52
<211> LENGTH: 36
<212> TYPE: PRT
<213> ORGANISM: Artificial
<220> FEATURE:
<223> OTHER INFORMATION: (gly4ser)6 linker

<400> SEQUENCE: 52

Asp Leu Ser Gly Gly Gly Gly Ser Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Thr Gly Leu
        35

<210> SEQ ID NO 53
<211> LENGTH: 93
<212> TYPE: DNA
<213> ORGANISM: Artificial
<220> FEATURE:
<223> OTHER INFORMATION: (gly4ser)5 linker DNA

<400> SEQUENCE: 53
gatctctccg gaggaggtgg ctcaggtggt ggaggatctg gaggaggtgg gagtggtgga    60
ggtggttctg gaggaggtgg tagtaccggt ctc    93

<210> SEQ ID NO 54

```
<211> LENGTH: 31
<212> TYPE: PRT
<213> ORGANISM: Artificial
<220> FEATURE:
<223> OTHER INFORMATION: (gly4ser)5 linker

<400> SEQUENCE: 54

Asp Leu Ser Gly Gly Gly Gly Ser Gly Gly Gly Ser Gly Gly Gly
1               5                   10                  15

Gly Ser Gly Gly Gly Gly Ser Gly Gly Gly Ser Thr Gly Leu
            20                  25                  30

<210> SEQ ID NO 55
<211> LENGTH: 396
<212> TYPE: DNA
<213> ORGANISM: Homo sapiens

<400> SEQUENCE: 55
aaggaatccc gggccaagaa attccagcgg cagcatatgg actcagacag ttcccccagc    60
agcagctcca cctactgtaa ccaaatgatg aggcgccgga atatgacaca ggggcggtgc   120
aaaccagtga acacctttgt gcacgagccc ctggtagatg tccagaatgt ctgtttccag   180
gaaaaggtca cctgcaagaa cgggcagggc aactgctaca agagcaactc cagcatgcac   240
atcacagact gccgcctgac aaacggctcc aggtacccca actgtgcata ccggaccagc   300
ccgaaggaga gacacatcat tgtggcctgt gaagggagcc catatgtgcc agtccacttt   360
gatgcttctg tggaggactc tacctaataa tctaga                             396

<210> SEQ ID NO 56
<211> LENGTH: 128
<212> TYPE: PRT
<213> ORGANISM: Homo sapiens

<400> SEQUENCE: 56

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

<210> SEQ ID NO 57
<211> LENGTH: 2041
<212> TYPE: DNA
<213> ORGANISM: Artificial
<220> FEATURE:
<223> OTHER INFORMATION: hWTAPO1-(g4s)4-mthIgG-hRNase1 DNA

<400> SEQUENCE: 57
gttaagcttg ccaccatgaa agctgcggtg ctgaccttgg ccgtgctctt cctgacgggg    60
```

```
agccaggctc ggcatttctg gcagcaagat gaaccccccc agagcccctg ggatcgagtg      120
aaggacctgg ccactgtgta cgtggatgtg ctcaaagaca gcggcagaga ctatgtgtcc      180
cagtttgaag gctccgcctt gggaaaacag ctaaacctaa agctccttga caactgggac      240
agcgtgacct ccaccttcag caagctgcgc gaacagctcg ccctgtgac ccaggagttc       300 tgggataacc tggaaaagga cagagggc ctgaggcagg agatgagcaa ggatctggag        360
gaggtgaagg ccaaggtgca gccctacctg gacgacttcc agaagaagtg caggaggag      420 atggagctct accgccagaa ggtggagccg ctgcgcgcag agctccaaga gggcgcgcgc      480
cagaagctgc acgagctgca agagaagctg agcccactgg gcgaggagat gcgcgaccgc      540
gcgcgcgccc atgtggacgc gctgcgcacg catctggccc cctacagcga cgagctgcgc      600
cagcgcttgg ccgcgcgcct tgaggctctc aaggagaacg gcggcgccag actgccgag       660 taccacgcca aggccaccga gcatctgagc acgctcagcg agaaggccaa gcccgcgctc      720
gaggacctcc gccaaggcct gctgcccgtg ctggagagct tcaaggtcag cttcctgagc      780
gctctcgagg agtacactaa gaagctcaac acccaagatc tctccggagg aggtggctca      840
ggtggtggag gatctggagg aggtgggagt ggtggaggtg gttctaccgg tctcgagccc      900
aaatcttctg acaaaactca cacatctcca ccgtcccag cacctgaact cctgggagga       960
tcgtcagtct tcctcttccc cccaaaaccc aaggacaccc tcatgatctc ccggacccct     1020
gaggtcacat gcgtggtggt ggacgtgagc cacgaagacc ctgaggtcaa gttcaactgg     1080
tacgtggacg gcgtggaggt gcataatgcc aagacaaagc cgcgggagga gcagtacaac     1140
agcacgtacc gtgtggtcag cgtcctcacc gtcctgcacc aggactggct gaatggcaag     1200
gagtacaagt gcaaggtctc caacaaagcc ctcccagcct ccatcgagaa aaccatctcc     1260
aaagccaaag ggcagccccg agaaccacag gtgtacaccc tgcccccatc ccgggatgag     1320
ctgaccaaga accaggtcag cctgacctgc ctggtcaaag gcttctatcc cagcgacatc     1380
gccgtggagt gggagagcaa tgggcagccg gagaacaact acaagaccac gcctcccgtg     1440
ctggactccg acggctcctt cttcctctac agcaagctca ccgtggacaa gagcaggtgg     1500 cagcaggga acgtcttctc atgctccgtg atgcatgagg ctctgcacaa ccactacacg      1560
cagaagagcc tctctctctc tccgggtaaa gtcgacggag ctagcagccc cgtgaacgtg     1620
agcagcccca cgtgcagga tatcaaggaa tcccgggcca agaaattcca gcggcagcat      1680
atggactcag acagttcccc cagcagcagc tccacctact gtaaccaaat gatgaggcgc     1740
cggaatatga cacaggggcg gtgcaaacca gtgaacacct tgtgcacga gcccctggta      1800 gatgtccaga atgtctgttt ccaggaaaag gtcacctgca agaacgggca gggcaactgc     1860
tacaagagca actccagcat gcacatcaca gactgccgcc tgacaaacgg ctccaggtac     1920
cccaactgtg cataccggac cagcccgaag gagagacaca tcattgtggc ctgtgaaggg     1980
agcccatatg tgccagtcca ctttgatgct tctgtggagg actctaccta ataatctaga     2040
a                                                                    2041
```

<210> SEQ ID NO 58
<211> LENGTH: 671
<212> TYPE: PRT
<213> ORGANISM: Artificial
<220> FEATURE:
<223> OTHER INFORMATION: hWTAPO1-(g4s)4-mthIgG-hRNase1

<400> SEQUENCE: 58

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Asp Leu Ser Gly Gly
            260                 265                 270

Gly Gly Ser Gly Gly Gly Ser Gly Gly Gly Ser Gly Gly Gly
        275                 280                 285

Gly Ser Thr Gly Leu Glu Pro Lys Ser Ser Asp Lys Thr His Thr Ser
    290                 295                 300

Pro Pro Ser Pro Ala Pro Glu Leu Leu Gly Gly Ser Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Lys
            340                 345                 350

Phe Asn Trp Tyr Val Asp Gly Val Glu Val His Asn Ala Lys Thr Lys
        355                 360                 365

Pro Arg Glu Glu Gln Tyr Asn Ser Thr Tyr Arg Val Val Ser Val Leu
    370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Ser Ile Glu Lys Thr Ile Ser Lys
                405                 410                 415

Ala Lys Gly Gln Pro Arg Glu Pro Gln Val Tyr Thr Leu Pro Pro Ser
```

```
                420                 425                 430
Arg Asp Glu Leu Thr Lys Asn Gln Val Ser Leu Thr Cys Leu Val Lys
            435                 440                 445

Gly Phe Tyr Pro Ser Asp Ile Ala Val Glu Trp Glu Ser Asn Gly Gln
    450                 455                 460

Pro Glu Asn Asn Tyr Lys Thr Thr Pro Pro Val Leu Asp Ser Asp Gly
465                 470                 475                 480

Ser Phe Phe Leu Tyr Ser Lys Leu Thr Val Asp Lys Ser Arg Trp Gln
            485                 490                 495

Gln Gly Asn Val Phe Ser Cys Ser Val Met His Glu Ala Leu His Asn
        500                 505                 510

His Tyr Thr Gln Lys Ser Leu Ser Leu Ser Pro Gly Lys Val Asp Gly
    515                 520                 525

Ala Ser Ser Pro Val Asn Val Ser Ser Pro Ser Val Gln Asp Ile Lys
530                 535                 540

Glu Ser Arg Ala Lys Lys Phe Gln Arg Gln His Met Asp Ser Asp Ser
545                 550                 555                 560

Ser Pro Ser Ser Ser Ser Thr Tyr Cys Asn Gln Met Met Arg Arg Arg
            565                 570                 575

Asn Met Thr Gln Gly Arg Cys Lys Pro Val Asn Thr Phe Val His Glu
        580                 585                 590

Pro Leu Val Asp Val Gln Asn Val Cys Phe Gln Glu Lys Val Thr Cys
    595                 600                 605

Lys Asn Gly Gln Gly Asn Cys Tyr Lys Ser Asn Ser Ser Met His Ile
610                 615                 620

Thr Asp Cys Arg Leu Thr Asn Gly Ser Arg Tyr Pro Asn Cys Ala Tyr
625                 630                 635                 640

Arg Thr Ser Pro Lys Glu Arg His Ile Ile Val Ala Cys Glu Gly Ser
            645                 650                 655

Pro Tyr Val Pro Val His Phe Asp Ala Ser Val Glu Asp Ser Thr
        660                 665                 670

<210> SEQ ID NO 59
<211> LENGTH: 671
<212> TYPE: PRT
<213> ORGANISM: Artificial
<220> FEATURE:
<223> OTHER INFORMATION: hWTAPO1-(g4s)4-mthIgG-hRNase1 with proline at
      Eu position 331 in Fc region

<400> SEQUENCE: 59

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110
```

-continued

```
Asp Leu Glu Glu Val Lys Ala Lys Val Gln Pro Tyr Leu Asp Asp Phe
            115                 120                 125
Gln Lys Lys Trp Gln Glu Glu Met Glu Leu Tyr Arg Gln Lys Val Glu
130                 135                 140
Pro Leu Arg Ala Glu Leu Gln Glu Gly Ala Arg Gln Lys Leu His Glu
145                 150                 155                 160
Leu Gln Glu Lys Leu Ser Pro Leu Gly Glu Glu Met Arg Asp Arg Ala
                165                 170                 175
Arg Ala His Val Asp Ala Leu Arg Thr His Leu Ala Pro Tyr Ser Asp
            180                 185                 190
Glu Leu Arg Gln Arg Leu Ala Ala Arg Leu Glu Ala Leu Lys Glu Asn
            195                 200                 205
Gly Gly Ala Arg Leu Ala Glu Tyr His Ala Lys Ala Thr Glu His Leu
210                 215                 220
Ser Thr Leu Ser Glu Lys Ala Lys Pro Ala Leu Glu Asp Leu Arg Gln
225                 230                 235                 240
Gly Leu Leu Pro Val Leu Glu Ser Phe Lys Val Ser Phe Leu Ser Ala
                245                 250                 255
Leu Glu Glu Tyr Thr Lys Lys Leu Asn Thr Gln Asp Leu Ser Gly Gly
            260                 265                 270
Gly Gly Ser Gly Gly Gly Ser Gly Gly Gly Ser Gly Gly Gly
            275                 280                 285
Gly Ser Thr Gly Leu Glu Pro Lys Ser Ser Asp Lys Thr His Thr Ser
290                 295                 300
Pro Pro Ser Pro Ala Pro Glu Leu Leu Gly Gly Ser Ser Val Phe Leu
305                 310                 315                 320
Phe Pro Pro Lys Pro Lys Asp Thr Leu Met Ile Ser Arg Thr Pro Glu
                325                 330                 335
Val Thr Cys Val Val Asp Val Ser His Glu Asp Pro Glu Val Lys
            340                 345                 350
Phe Asn Trp Tyr Val Asp Gly Val Glu Val His Asn Ala Lys Thr Lys
            355                 360                 365
Pro Arg Glu Glu Gln Tyr Asn Ser Thr Tyr Arg Val Val Ser Val Leu
370                 375                 380
Thr Val Leu His Gln Asp Trp Leu Asn Gly Lys Glu Tyr Lys Cys Lys
385                 390                 395                 400
Val Ser Asn Lys Ala Leu Pro Ala Pro Ile Glu Lys Thr Ile Ser Lys
                405                 410                 415
Ala Lys Gly Gln Pro Arg Glu Pro Gln Val Tyr Thr Leu Pro Pro Ser
            420                 425                 430
Arg Asp Glu Leu Thr Lys Asn Gln Val Ser Leu Thr Cys Leu Val Lys
            435                 440                 445
Gly Phe Tyr Pro Ser Asp Ile Ala Val Glu Trp Glu Ser Asn Gly Gln
450                 455                 460
Pro Glu Asn Asn Tyr Lys Thr Thr Pro Pro Val Leu Asp Ser Asp Gly
465                 470                 475                 480
Ser Phe Phe Leu Tyr Ser Lys Leu Thr Val Asp Lys Ser Arg Trp Gln
                485                 490                 495
Gln Gly Asn Val Phe Ser Cys Ser Val Met His Glu Ala Leu His Asn
            500                 505                 510
His Tyr Thr Gln Lys Ser Leu Ser Leu Ser Pro Gly Lys Val Asp Gly
            515                 520                 525
Ala Ser Ser Pro Val Asn Val Ser Ser Pro Ser Val Gln Asp Ile Lys
```

```
                530                 535                 540
Glu Ser Arg Ala Lys Lys Phe Gln Arg Gln His Met Asp Ser Asp Ser
545                 550                 555                 560

Ser Pro Ser Ser Ser Ser Thr Tyr Cys Asn Gln Met Met Arg Arg Arg
                565                 570                 575

Asn Met Thr Gln Gly Arg Cys Lys Pro Val Asn Thr Phe Val His Glu
            580                 585                 590

Pro Leu Val Asp Val Gln Asn Val Cys Phe Gln Glu Lys Val Thr Cys
        595                 600                 605

Lys Asn Gly Gln Gly Asn Cys Tyr Lys Ser Asn Ser Ser Met His Ile
    610                 615                 620

Thr Asp Cys Arg Leu Thr Asn Gly Ser Arg Tyr Pro Asn Cys Ala Tyr
625                 630                 635                 640

Arg Thr Ser Pro Lys Glu Arg His Ile Ile Val Ala Cys Glu Gly Ser
            645                 650                 655

Pro Tyr Val Pro Val His Phe Asp Ala Ser Val Glu Asp Ser Thr
        660                 665                 670
```